(12) United States Patent
Takashima et al.

(10) Patent No.: US 9,120,748 B2
(45) Date of Patent: *Sep. 1, 2015

(54) FLUORANTHENE COMPOUND, ORGANIC ELECTROLUMINESCENCE DEVICE USING THE SAME, AND SOLUTION CONTAINING ORGANIC ELECTROLUMINESCENCE MATERIAL

(75) Inventors: Yoriyuki Takashima, Chiba (JP); Masakazu Funahashi, Chiba (JP); Kiyoshi Ikeda, Chiba (JP); Chishio Hosokawa, Chiba (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 523 days.

This patent is subject to a terminal disclaimer.

(21) Appl. No.: 11/932,100

(22) Filed: Oct. 31, 2007

(65) Prior Publication Data
US 2009/0015144 A1    Jan. 15, 2009

(30) Foreign Application Priority Data

Nov. 15, 2006  (JP) ................................. 2006-308640
Feb. 28, 2007  (JP) ................................. 2007-050373

(51) Int. Cl.

| | | |
|---|---|---|
| *H01L 51/50* | (2006.01) | |
| *C07D 209/86* | (2006.01) | |
| *C07C 13/62* | (2006.01) | |
| *C07C 13/72* | (2006.01) | |
| *C07C 22/08* | (2006.01) | |
| *C07C 25/22* | (2006.01) | |
| *C07C 43/267* | (2006.01) | |
| *C07C 49/784* | (2006.01) | |
| *C07C 205/12* | (2006.01) | |
| *C07C 211/54* | (2006.01) | |
| *C07C 211/58* | (2006.01) | |
| *C07C 211/60* | (2006.01) | |
| *C07C 255/50* | (2006.01) | |
| *C07C 255/52* | (2006.01) | |
| *C07C 321/30* | (2006.01) | |
| *C07D 307/91* | (2006.01) | |
| *C07F 7/08* | (2006.01) | |
| *C09K 11/06* | (2006.01) | |
| *H01L 51/00* | (2006.01) | |

(52) U.S. Cl.
CPC .............. *C07D 209/86* (2013.01); *C07C 13/62* (2013.01); *C07C 13/72* (2013.01); *C07C 22/08* (2013.01); *C07C 25/22* (2013.01); *C07C 43/267* (2013.01); *C07C 49/784* (2013.01); *C07C 205/12* (2013.01); *C07C 211/54* (2013.01); *C07C 211/58* (2013.01); *C07C 211/60* (2013.01); *C07C 255/50* (2013.01); *C07C 255/52* (2013.01); *C07C 321/30* (2013.01); *C07D 307/91* (2013.01); *C07F 7/0809* (2013.01); *C09K 11/06* (2013.01); *H01L 51/0055* (2013.01); *H01L 51/0094* (2013.01); *C07C 2101/14* (2013.01); *C07C 2103/18* (2013.01); *C07C 2103/20* (2013.01); *C07C 2103/24* (2013.01); *C07C 2103/26* (2013.01); *C07C 2103/48* (2013.01); *C07C 2103/50* (2013.01); *C07C 2103/52* (2013.01); *C07C 2103/54* (2013.01); *C07C 2103/94* (2013.01); *C09K 2211/1011* (2013.01); *C09K 2211/1014* (2013.01); *C09K 2211/1029* (2013.01); *C09K 2211/1044* (2013.01); *C09K 2211/1048* (2013.01); *C09K 2211/1059* (2013.01); *C09K 2211/1088* (2013.01); *H01L 51/006* (2013.01); *H01L 51/0058* (2013.01); *H01L 51/0067* (2013.01)

(58) Field of Classification Search
USPC .................. 428/690, 917; 313/504, 505, 506; 257/40, E51.05, E51.036, E51.032; 585/27
See application file for complete search history.

(56) References Cited

U.S. PATENT DOCUMENTS

| | | | |
|---|---|---|---|
| 6,803,120 B2 * | 10/2004 | Fukuoka et al. ............... | 428/690 |
| 7,097,917 B1 | 8/2006 | Fujita et al. | |
| 2005/0222417 A1 | 10/2005 | Brown et al. | |
| 2005/0244645 A1 | 11/2005 | Ionkin et al. | |
| 2006/0238110 A1 | 10/2006 | Shirai et al. | |
| 2007/0072002 A1 | 3/2007 | Kim et al. | |

(Continued)

FOREIGN PATENT DOCUMENTS

| | | |
|---|---|---|
| EP | 2049616 A1 | 4/2009 |
| JP | 10-189247 | 7/1998 |

(Continued)

OTHER PUBLICATIONS

U.S. Appl. No. 11/928,907, filed Oct. 30, 2007, Yumiko Mizuki, et al.

(Continued)

Primary Examiner — Gregory Clark
(74) Attorney, Agent, or Firm — Oblon, McClelland, Maier & Neustadt, L.L.P.

(57) ABSTRACT

A fluoranthene compound with a specified asymmetric structure; an organic EL device which is composed of one or more organic compound layers including at least one emitting layer sandwiched between a pair of electrodes, wherein at least one of the organic compound layers contains at least one kind of the fluoranthene compound; and a solution containing a material for the organic EL which is composed of the fluoranthene compound as the material for the organic EL and a solvent. An organic electroluminescence (EL) device having a superior luminance of light emission, an enhanced efficiency of light emission, and a prolonged lifetime and a compound realizing the device are provided.

7 Claims, 7 Drawing Sheets

(56) References Cited

U.S. PATENT DOCUMENTS

| | | |
|---|---|---|
| 2007/0243411 A1 | 10/2007 | Takashima |
| 2008/0071122 A1 | 3/2008 | Inoue |
| 2009/0121625 A1 | 5/2009 | Ohrui et al. |
| 2010/0308718 A1 | 12/2010 | Kubota et al. |

FOREIGN PATENT DOCUMENTS

| | | | |
|---|---|---|---|
| JP | 2001-267078 | 9/2001 | |
| JP | 2001-1351783 | 12/2001 | |
| JP | 2001-1351784 | 12/2001 | |
| JP | 2002-25774 | 1/2002 | |
| JP | 2002-25776 A | 1/2002 | |
| JP | 2002-025777 * | 1/2002 | ............ C09K 11/06 |
| JP | 2003-272866 | 9/2003 | |
| JP | 2004-2351 | 1/2004 | |
| JP | 2004002351 A | 1/2004 | |
| JP | 2004-303488 A | 10/2004 | |
| JP | 2005-68087 | 3/2005 | |
| JP | 2005-93134 | 4/2005 | |
| JP | 2005-093135 | 4/2005 | |
| JP | 2005-100782 | 4/2005 | |
| JP | 2005-108552 | 4/2005 | |
| JP | 2005-108556 | 4/2005 | |
| JP | 2005-235633 | 9/2005 | |
| JP | 2005-272805 | 10/2005 | |
| JP | 2006-151930 | 6/2006 | |
| JP | 2006-151931 | 6/2006 | |
| WO | WO 2007/100010 A1 | 9/2007 | |
| WO | WO 2007/125809 A1 | 11/2007 | |
| WO | WO 2008/016166 A1 | 2/2008 | |

OTHER PUBLICATIONS

U.S. Appl. No. 11/928,276, filed Oct. 30, 2007, Yoriyuki Takashima.
Japanese Office Action dated Aug. 14, 2012 in corresponding Japanese Office Action 2008-544106 (3 pp.).
Japanese Office Action dated Dec. 4, 2012, in corresponding Japanese Patent Application No. JP 2008-544106, with English Abstract (4 pp.).
European Office Action dated Feb. 21, 2014 in corresponding European Patent Application No. 07 830 854.1, 7pp.
Supplementary European Search Report mailed Aug. 19, 2011, in European Patent Application No. 07 83 0854, filed Oct. 30, 2007.

* cited by examiner

FLUORANTHENE COMPOUND, ORGANIC ELECTROLUMINESCENCE DEVICE USING THE SAME, AND SOLUTION CONTAINING ORGANIC ELECTROLUMINESCENCE MATERIAL

TECHNICAL FIELD

The present invention relates to a fluoranthene compound, an organic electroluminescence (EL) device using the fluoranthene compound and a solution containing a material for the organic EL. Particularly, it relates to an organic EL device with a superior luminance of light emission, an enhanced efficiency of light emission, and a prolonged lifetime; and further, relates to both the fluoranthene compound and a solution containing a material for the organic EL, practical as a light emitting material and applicable to the organic EL device.

BACKGROUND ART

An organic EL device is a spontaneous light emitting device which utilizes the phenomenon that a fluorescent substance emits light by energy of recombination of holes injected from an anode and electrons injected from a cathode when an electric field is applied.

The organic EL device is composed of a pair of electrodes consisting of an anode and a cathode, and an organic emitting layer disposed between the electrodes.

The organic emitting layer is constituted of a lamination of layers having each function, for example, nominated from the anode side, such as a hole injecting layer/a hole transporting layer/an emitting layer/an electron transporting layer/an electron injecting layer.

As a light emitting material in the emitting layer, materials emitting light with colors of light emission of each color (for example, red, green, blue) are developed.

For example, Patent Document 1 and Patent Document 2 disclose fluoranthene compounds as light emitting materials that emit blue light.

However, there were problems in the fluoranthene compounds disclosed in Patent Document 1 and Patent Document 2 that the efficiency of light emission and the lifetime are not sufficient yet.

Patent Document 1: JP 10-189247A
Patent Document 2: JP 2005-068087A

DISCLOSURE OF THE INVENTION

Problems to be Solved by the Invention

The present invention has been made to overcome the above problems and has an object of providing an organic EL device with a superior luminance of light emission, an enhanced efficiency of light emission, and a prolonged lifetime, and an object of providing a compound realizing the EL device.

Means for Solving the Problem

As a result of intensive researches and studies to achieve the above object by the present inventors, it was found that an employment of a fluoranthene compound having an asymmetric structure represented by the following general formula (1) as a light emitting material provides the EL device with a superior luminance of light emission, an enhanced efficiency of light emission, and a prolonged lifetime, resultantly completing the present invention.

Namely, the present invention provides a fluoranthene compound represented by the following general formula (1):

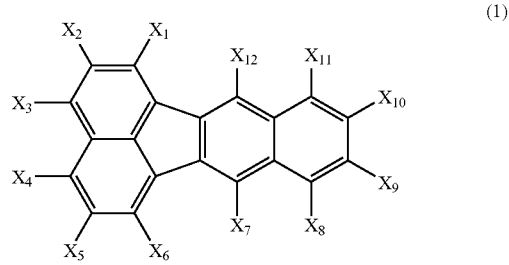

(1)

(In the formula, $X_1$, $X_2$, $X_5$ to $X_6$ and $X_8$ to $X_{11}$ each independently represents one member selected from a hydrogen atom, a substituted or unsubstituted aryl group having 5 to 50 carbon atoms forming a ring, a substituted or unsubstituted heteroaryl group having 5 to 50 atoms forming a ring, a substituted or unsubstituted alkyl group having 1 to 50 carbon atoms, a substituted or unsubstituted cycloalkyl group having 3 to 50 carbon atoms, a substituted or unsubstituted alkoxy group having 1 to 50 carbon atoms, a substituted or unsubstituted aralkyl group having 1 to 50 carbon atoms, a substituted or unsubstituted aryloxy group having 5 to 50 atoms forming a ring, a substituted or unsubstituted arylthio group having 5 to 50 atoms forming a ring, a substituted or unsubstituted alkoxycarbonyl group having 2 to 50 carbon atoms, an amino group substituted by a substituted or unsubstituted aryl group having 5 to 50 carbon atoms forming a ring, a halogen group, a cyano group, a nitro group, a hydroxy group, a silyl group and a carboxy group.

$X_3$ represents one member selected from a substituted or unsubstituted aryl group having 5 to 50 atoms forming a ring, a substituted or unsubstituted heteroaxyl group having 5 to 50 atoms forming a ring, a substituted or unsubstituted alkyl group having 1 to 50 carbon atoms, a substituted or unsubstituted cycloalkyl group having 3 to 50 carbon atoms, a substituted or unsubstituted alkoxy group having 1 to 50 carbon atoms, a substituted or unsubstituted aralkyl group having 1 to 50 carbon atoms, a substituted or unsubstituted aryloxy group having 5 to 50 atoms forming a ring, a substituted or unsubstituted arylthio group having 5 to 50 atoms forming a ring, a substituted or unsubstituted alkoxycarbonyl group having 2 to 50 carbon 10 atoms, an amino group substituted by a substituted or unsubstituted aryl group having 5 to 50 carbon atoms forming a ring, a halogen group, a cyano group, a nitro group, a hydroxy group, a silyl group and a carboxy group.

$X_4$ represents one member selected from a hydrogen atom,
a substituted or unsubstituted alkyl group having 1 to 50 carbon atoms,
a substituted or unsubstituted cycloalkyl group having 3 to 50 carbon atoms,
a substituted or unsubstituted alkoxy group having 1 to 50 carbon atoms,
a substituted or unsubstituted aralkyl group having 1 to 50 carbon atoms,
a substituted or unsubstituted aryloxy group having 5 to 50 atoms forming a ring,
a substituted or unsubstituted arylthio group having 5 to 50 atoms forming a ring,
a substituted or unsubstituted alkoxycarbonyl group having 2 to 50 carbon atoms,
an amino group substituted by a substituted or unsubstituted aryl group having 5 to 50 carbon atoms forming a ring,
a halogen group, a cyano group, a nitro group, a hydroxy group, a silyl group and a carboxy group.

$X_7$ and $X_{12}$ each independently represents one member selected from a substituted or unsubstituted aryl group having 5 to 50 atoms forming a ring,
a substituted or unsubstituted heteroaryl group having 5 to 50 atoms forming a ring,
a substituted or unsubstituted alkyl group having 1 to 50 carbon atoms,
a substituted or unsubstituted cycloalkyl group having 3 to 50 carbon atoms,
a substituted or unsubstituted alkoxy group having 1 to 50 carbon atoms,
a substituted or unsubstituted aralkyl group having 1 to 50 carbon atoms,
a substituted or unsubstituted aryloxy group having 5 to 50 atoms forming a ring,
a substituted or unsubstituted arylthio group having 5 to 50 atoms forming a ring,
a substituted or unsubstituted alkoxycarbonyl group having 2 to 50 carbon atoms, and
an amino group substituted by a substituted or unsubstituted aryl group having 5 to 50 carbon atoms forming a ring.

Further, in $X_1$ to $X_3$ and $X_5$ to $X_{12}$, each neighboring substituent may be bonded to each other to form a saturated or unsaturated cyclic structure; which cyclic structure may be substituted; with the proviso that none of $X_1$ to $X_3$ and $X_5$ to $X_{12}$ contains benzo[k]fluoranthene skeleton.

However, $X_3$ and $X_4$ are different from each other.)

Further, the present invention provides an organic EL device which is composed of one or more organic compound layers including at least one emitting layer sandwiched between a pair of electrodes, wherein at least one of the organic compound layers contains at least one kind of the fluoranthene compound.

Furthermore, the present invention provides a solution containing a material for the organic EL including the fluoranthene compound as the material for the organic EL and a solvent.

Effect of the Invention

The organic EL device employing the fluoranthene compound of the present invention has a superior luminance of light emission, an enhanced efficiency of light emission, and a prolonged lifetime.

PREFERRED EMBODIMENT TO CARRY OUT THE INVENTION

Figure 1:
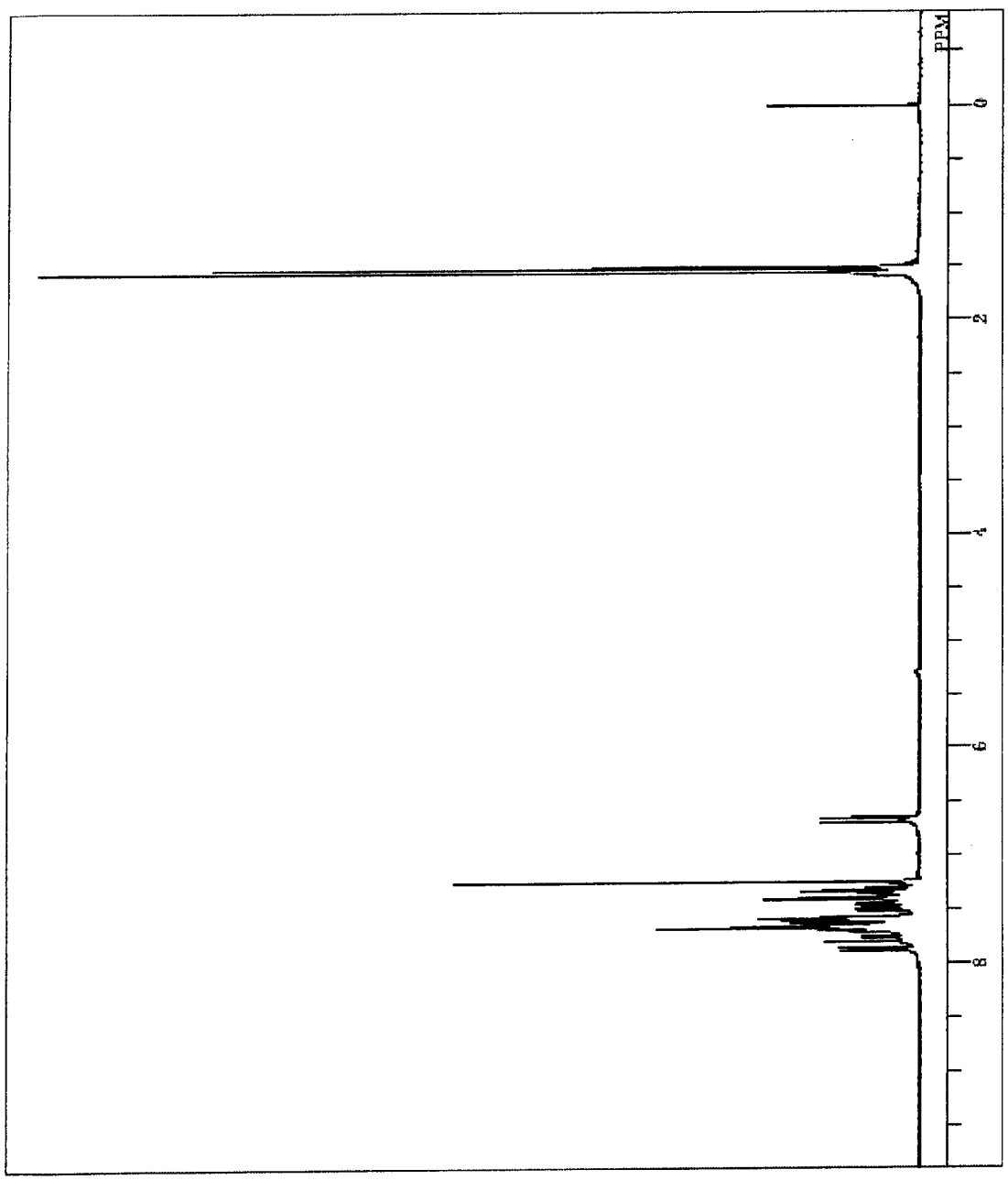
FIG. 1 is a diagram showing $^1$H-NMR spectrum of Compound 1-2, which is obtained in Synthesis Example 1.

The present invention provides a fluoranthene compound represented by the following general formula (1);

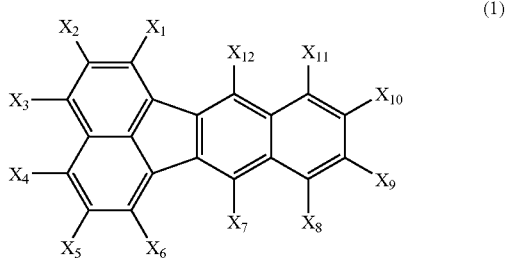

(1)

In the general formula (1), $X_1$, $X_2$, $X_5$ to $X_6$ and $X_8$ to $X_{11}$ each independently represents one member selected from a hydrogen atom, a substituted or unsubstituted aryl group having 5 to 50 carbon atoms forming a ring, a substituted or unsubstituted heteroaryl group having 5 to 50 atoms forming a ring, a substituted or unsubstituted alkyl group having 1 to 50 carbon atoms, a substituted or unsubstituted cycloalkyl group having 3 to 50 carbon atoms, a substituted or unsubstituted alkoxy group having 1 to 50 carbon atoms, a substituted or unsubstituted aralkyl group having 1 to 50 carbon atoms, a substituted or unsubstituted aryloxy group having 5 to 50 atoms forming a ring, a substituted or unsubstituted arylthio group having 5 to 50 atoms forming a ring, a substituted or unsubstituted alkoxycarbonyl group having 2 to 50 carbon atoms, an amino group substituted by a substituted or unsubstituted aryl group having 5 to 50 carbon atoms forming a ring, a halogen group, a cyano group, a nitro group, a hydroxy group, a silyl group and a carboxy group.

$X_3$ represents one member selected from a substituted or unsubstituted aryl group having 5 to 50 atoms forming a ring, a substituted or unsubstituted heteroaryl group having 5 to 50 atoms forming a ring, a substituted or unsubstituted alkyl group having 1 to 50 carbon atoms, a substituted or unsubstituted cycloalkyl group having 3 to 50 carbon atoms, a substituted or unsubstituted alkoxy group having 1 to 50 carbon atoms, a substituted or unsubstituted aralkyl group having 1 to 50 carbon atoms, a substituted or unsubstituted aryloxy group having 5 to 50 atoms forming a ring, a substituted or unsubstituted arylthio group having 5 to 50 atoms forming a ring, a substituted or unsubstituted alkoxycarbonyl group having 2 to 50 carbon atoms, an amino group substituted by a substituted or unsubstituted aryl group having 5 to 50 carbon atoms forming a ring, a halogen group, a cyano group, a nitro group, a hydroxy group, a silyl group and a carboxy group.

$X_4$ represents one member selected from a hydrogen atom, a. substituted or unsubstituted alkyl group having 1 to 50 carbon atoms, a substituted or unsubstituted cycloalkyl group having 3 to 50 carbon atoms, a substituted or unsubstituted alkoxy group having 1 to 50 carbon atoms, a substituted or unsubstituted aralkyl group having 1 to 50 carbon atoms, a substituted or unsubstituted aryloxy group having 5 to 50 atoms forming a ring, a substituted or unsubstituted arylthio group having 5 to 50 atoms forming a ring, a substituted or unsubstituted alkoxycarbonyl group having 2 to 50 carbon atoms, an amino group substituted by a substituted or unsubstituted aryl group having 5 to 50 carbon atoms forming a ring, a halogen group, a cyan group, a nitro group, a hydroxy group, a silyl group and a carboxy group.

$X_7$ and. $X_{12}$ each independently represents one member selected from a substituted or unsubstituted aryl group having 5 to 50 atoms forming a ring, a substituted or unsubstituted heteroaryl group having 5 to 50 atoms forming a ring, a substituted or unsubstituted alkyl group having 1 to 50 carbon atoms, a substituted or unsubstituted cycloalkyl group having 3 to 50 carbon atoms, a substituted or unsubstituted alkoxy group having 1 to 50 carbon atoms, a substituted or unsubstituted aralkyl group having 1 to 50 carbon atoms, a substituted or unsubstituted aryloxy group having 5 to 50 atoms forming a ring, a substituted or unsubstituted arylthio group having 5 to 50 atoms forming a ring, a substituted or unsubstituted alkoxycarbonyl group having 2 to 50 carbon atoms, and an amino group substituted by a substituted or unsubstituted aryl group having 5 to 50 carbon atoms forming a ring.

Further, in $X_1$ to $X_3$ and $X_5$ to $X_{12}$, each neighboring substituent may be bonded to each other to form a saturated or unsaturated cyclic structure; which cyclic structure may be substituted; with the proviso that none of $X_1$ to $X_3$ and $X_5$ to $X_{12}$ contains benzo[k]fluoranthene skeleton.

However, $X_3$ and $X_4$ are different from each other.

However, $X_3$ and $X_4$ are different from each other. The fact that $X_3$ and $X_4$ are different from each other prevents any association between compounds each other. Accordingly, when the above compound is employed in the EL device, the lifetime of the device will be prolonged and further; an efficiency of light emission will be enhanced.

Further, an asymmetric structure of a molecule will decrease a vapor deposition temperature in producing the device in accordance with a vapor deposition process.

Furthermore, the asymmetric structure of the molecule will enable to elevate solubility into a solvent. Therefore, the EL device employing the compound can be produced in accordance with a coating process.

Examples of the substituted or unsubstituted aryl group having 5 to 50 carbon atoms forming a ring represented by $X_1$ to $X_{12}$ include phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methylbiphenylyl group, 4"-t-butyl-p-terphenyl-4-yl group, etc.

Preferable example is a substituted or unsubstituted aryl group having 6 to 20 atoms forming a ring.

Examples of the substituted or unsubstituted heteroaryl group having 5 to 50 atoms forming a ring represented by $X_1$ to $X_{12}$ include 1-pyrrolyl group, 2-pyrrolyl group, 3-pyrrolyl group, pyrazinyl group, 2-pyridinyl group, 3-pyridinyl group, 4-pyridinyl group, 1-indolyl group, 2-indolyl group, 3-indolyl group, 4-indolyl group, 5-indolyl group, 6-indolyl group, 7-indolyl group, 1-isoindolyl group, 2-isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzofuranyl group, quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxalinyl group, 5-quinoxalinyl group, 6-quinoxalinyl group, 1-carbazolyl group, 2-carbazolyl group, 3-carbazolyl group, 4-carbazolyl group, 9-carbazolyl group, 1-phenanthridinyl group, 2-phenanthridinyl group, 3-phenanthridinyl group, 4-phenanthridinyl group, 6-phenanthridinyl group, 7-phenanthridinyl group, 8-phenanthridinyl group, 9-phenanthridinyl group, 10-phenanthridinyl group, 1-acridinyl group, 2-acridinyl group, 3-acridinyl group, 4-acridinyl group, 9-acridinyl group, 1,7-phenanthroline-2-yl group, 1,7-phenanthroline-3-yl group, 1,7-phenanthroline-4-yl group, 1,7-phenanthroline-5-yl group, 1,7-phenanthroline-6-yl group, 1,7-phenanthroline-8-yl group, 1,7-phenanthroline-9-yl group, 1,7-phenanthroline-10-yl group, 1,8-phenanthroline-2-yl group, 1,8-phenanthroline-3-yl group, 1,8-phenanthroline-4-yl group, 1,8-phenanthroline-5-yl group, 1,8-phenanthroline-6-yl group, 1,8-phenanthroline-7-yl group, 1,8-phenanthroline-9-yl group, 1,8-phenanthroline-10-yl group, 1,9-phenanthroline-2-yl group, 1,9-phenanthroline-3-yl group, 1,9-phenanthroline-4-yl group, 1,9-phenanthroline-5-yl group, 1,9-phenanthroline-6-yl group, 1,9-phenanthroline-7-yl group, 1,9-phenanthroline-8-yl group, 1,9-phenanthroline-10-yl group, 1,10-phenanthroline-2-yl group, 1,10-phenanthroline-3-yl group, 1,10-phenanthroline-4-yl group, 1,10-phenanthroline-5-yl group, 2,9-phenanthroline-1-yl group, 2,9-phenanthroline-3-yl group, 2,9-phenanthroline-4-yl group, 2,9-phenanthroline-5-yl group, 2,9-phenanthroline-6-yl group, 2,9-phenanthroline-7-yl group, 2,9-phenanthroline-8-yl group, 2,9-phenanthroline-10-yl group, 2,8-phenanthroline-1-yl group, 2,8-phenanthroline-3-yl group, 2,8-phenanthroline-4-yl group, 2,8-phenanthroline-5-yl group, 2,8-phenanthroline-6-yl group, 2,8-phenanthroline-7-yl group, 2,8-phenanthroline-9-yl group, 2,8-phenanthroline-10-yl group, 2,7-phenanthroline-1-yl group, 2,7-phenanthroline-3-yl group, 2,7-phenanthroline-4-yl group, 2,7-phenanthroline-5-yl group, 2,7-phenanthroline-6-yl group, 2,7-phenanthroline-8-yl group, 2,7-phenanthroline-9-yl group, 2,7-phenanthroline-10-yl group, 1-phenazinyl group, 2-phenazinyl group, 1-phenothiazinyl group, 2-phenothiazinyl group, 3-phenothiazinyl group, 4-phenothiazinyl group, 10-phenothiazinyl group, 1-phenoxazinyl group, 2-phenoxazinyl group, 3-phenoxazinyl group, 4-phenoxazinyl group, 10-phenoxazinyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 2-methylpyrrole-1-yl group, 2-methylpyrrole-3-yl group, 2-methylpyrrole-4-yl group, 2-methylpyrrole-5-yl group, 3-methylpyrrole-1-yl group, 3-methylpyrrole-2-yl group, 3-methylpyrrole-4-yl group, 3-methylpyrrole-5-yl group, 2-t-butylpyrrole-4-yl group, 3-(2-phenylpropyl)pyrrole-1-yl group, 2-methyl-1 indolyl group, 4-methyl-1-indolyl group, 2-methyl-3-indolyl group, 4-methyl-3-indolyl group, 2-t-butyl-1-indolyl group, 4-t-butyl-1-indolyl group, 2-t-butyl-3-indolyl group, 4-t-butyl-3-indolyl group, etc.

Preferable example is a substituted or unsubstituted heteroaryl group having 5 to 20 atoms forming a ring.

Examples of the substituted or unsubstituted alkyl group having 1 to 50 carbon atoms represented by $X_1$ to $X_{12}$ include methyl group, ethyl group, propyl group, isopropyl group, n-butyl group, s-butyl group, isobutyl group, t-butyl group, n-pentyl group, n-hexyl group, n-heptyl group, n-octyl group, hydroxymethyl group, 1-hydroxyethyl group, 2-hydroxyethyl group, 2-hydroxyisobutyl group, 1,2-dihydroxyethyl group, 1,3-dihydroxyisopropyl group, 2,3-dihydroxy-t-butyl group, 1,2,3-trihydroxypropyl group, chloromethyl group, 1-chloroethyl group, 2-chloroethyl group, 2-chloroisobutyl group, 1,2-dichloroethyl group, 1,3-dichloroisopropyl group, 2,3-dichloro-t-butyl group, 1,2,3-trichloropropyl group, bromomethyl group, 1-bromoethyl group, 2-bromoethyl group, 2-bromoisobutyl group, 1,2-dibromoethyl group, 1,3-dibromoisopropyl group, 2,3-dibromo-t-butyl group, 1,2,3-tribromopropyl group, iodomethyl group, 1-iodoethyl group, 2-iodoethyl group, 2-iodoisobutyl group, 1,2-diiodoethyl group, 1,3-diiodoisopropyl group, 2,3-diiodo-t-butyl group, 1,2,3-triiodopropyl group, aminomethyl group, 1-aminoethyl group, 2-aminoethyl group, 2-aminoisobutyl group, 1,2-diaminoethyl group, 1,3-diaminoisopropyl group, 2,3-diamino-t-butyl group, 1,2,3-triaminopropyl group, cyanomethyl group, 1-cyanoethyl group, 2-cyanoethyl group, 2-cyanoisobutyl group, 1,2-dicyanoethyl group, 1,3-dicyanoisopropyl group, 2,3-dicyano-t-butyl group, 1,2,3-tricyanopropyl group, nitromethyl group, 1-nitroethyl group, 2-nitroethyl group, 2-nitroisobutyl group, 1,2-dinitroethyl group, 1,3-dinitroisopropyl group, 2,3-dinitro-t-butyl group, 1,2,3-trinitropropyl group, trifluoromethyl group, perfluoroethyl group, perfluoropropyl group, perfluorobutyl group, perfluoropentyl group, perfluorohexyl group, 1H, 1H-perfluoroethyl group, 1H, 1H-perfluoropropyl group, 1H, 1H-perfluorobutyl group, 1H,1H-perfluoropentyl group, 1H, 1H-perfluorohexyl group, etc.

Preferable example is a substituted or unsubstituted alkyl group having 1 to 20 carbon atoms.

Examples of the substituted or unsubstituted cycloalkyl group having 3 to 50 carbon atoms represented by $X_1$ to $X_{12}$ include cyclopropyl group, cyclobutyl group, cyclopentyl group, cyclohexyl group, 4-methylcyclohexyl group, 1-adamantyl group, 2-adamantyl group, 1-norbornyl group, 2-norbornyl group, etc.

Preferable example is a substituted or unsubstituted cycloalkyl group having 3 to 10 carbon atoms.

The substituted or substituted alkoxy group having 1 to 50 carbon atoms represented by $X_1$ to $X_{12}$ is a group expressed by —OY and examples of Y are the same as described about the foregoing alkyl group having 1 to 50 carbon atoms represented by $X_1$ to $X_{12}$.

Preferable example is a substituted or unsubstituted alkoxy group having 1 to 20 carbon atoms.

Examples of the substituted or unsubstituted aralkyl group having 1 to 50 carbon atoms represented by $X_1$ to $X_{12}$ include benzyl group, 1-phenylethyl group, 2-phenylethyl group, 1•phenylisopropyl group, 2-phenylisopropyl group, phenyl•t•butyl group, α•naphthylmethyl group, 1•α•naphthylethyl group, 2•α•naphthylmethyl group, 1•α•naphthylisopropyl group, 2•α•naphthylisopropyl group, β-naphthylmethyl group, 1-β-naphthylethyl group, 2-β-naphthylethyl group, 1-β-naphthylisopropyl group, 2•β•naphthylisopropyl group, 1-pyrrolylmethyl group, 2-(1-pyrrolyl)ethyl group, p-methylbenzyl group, m-methylbenzyl group, o-methylbenzyl group, p-chlorobenzyl group, m-chlorobenzyl group, o-chlorobenzyl group, p•bromobenzyl group, m-bromobenzyl group, o-bromobenzyl group, p-iodobenzyl group, m-ioclobenzyl group, o-iodoben.zyl group, p-hydroxybenzyl group, m-hydroxybenzyl group, o-hydroxybenzyl group, p-aminobenzyl group, m-aminobenzyl group, o-aminobenzyl group, p-nitrobenzyl group, m-nitrobenzyl group, o-nitrobenzyl group, p-cyanobenzyl group, m-cyanobenzyl group, o-cyanobenzyl group, 1-hydxoxy-2-phenylisopropyl group, 1•chloro-2-phenylisopropyl group, etc.

Preferable example is a substituted or unsubstituted aralkyl group having 7 to 20 carbon atoms.

The substituted or unsubstituted aryloxy group having 5 to 50 atoms forming a ring and the substituted or unsubstituted arylthio group having 5 to 50 atoms forming a ring both represented by $X_1$ to $X_{12}$ is a group expressed by —OY' and —SY" respectively and examples of Y' and Y" are the same as described about the foregoing substituted or unsubstituted aryl group having 5 to 50 carbon atoms forming a ring.

Preferable example is a substituted or unsubstituted aryloxy group having 5 to 20 atoms forming a ring.

The substituted or unsubstituted alkoxycarbonyl group having 2 to 50 carbon atoms represented by $X_1$ to $X_{12}$ is a group expressed by —COOZ and examples of Z are the same as described about the foregoing substituted or unsubstituted alkyl group having 1 to 50 carbon atoms.

Preferable example is a substituted or unsubstituted alkoxycarbonyl group having 1 to 20 carbon atoms.

The substituted or unsubstituted aryl group having 5 to 50 carbon atoms forming a ring in the amino group substituted by them represented by $X_1$ to $X_{12}$ are the same as described about the foregoing substituted or unsubstituted aryl group having 5 to 50 carbon atoms forming a ring.

Preferable example is an amino group substituted by a substituted or unsubstituted aryl group having 5 to 20 carbon atoms forming a ring.

Examples of the halogen atom represented by $X_1$ to $X_6$ and $X_8$ to $X_{11}$ include fluorine atom, chlorine atom, bromine atom, iodine atom, and so on, in which fluorine atom is preferable.

Examples of the silyl group represented by $X_1$ to $X_6$ and $X_8$ to $X_{11}$ include trimethylsilyl group, triethylsilyl group, t-butyldimethylsilyl group, vinyldimethylsilyl group, propyldimethylsilyl group, triphenylsilyl group, etc.

Examples of the substituent of the groups represented by the above $X_1$ to $X_{12}$ include halogen atoms, hydroxy group, nitro group, cyano group, alkyl groups, aryl groups, cycloalkyl groups, alkoxy groups, aromatic heterocyclic groups, aralkyl groups, aryloxy groups, arylthio groups, alkoxycarbonyl groups and carboxy group.

The saturated or unsaturated cyclic structure formed by neighboring substituents in $X_1$ to $X_{12}$ bonded each other is preferably a five-membered ring or a six-membered ring which may be substituted.

Examples of the ring structure include a cycloalkane having 4 to 12 carbon atoms such as cyclobutane, cyclopentane, cyclohexane, adamantane, norbornane, etc.; a cycloalkene having 4 to 12 carbon atoms such as cyclobutene, cyclopentene, cyclohexene, cycloheptene, cyclooctene, etc.; a cycloalkadiene having 6 to 12 carbon atoms such as cyclohexadiene, cyclohepta diene, cyclooctadiene, etc.; and an aromatic ring having 6 to 50 carbon atoms such as benzene, naphthalene, phenanthrene, anthracene, pyrene, chrysene, acenaphthylene, etc. Further, examples of the substituent include the same as the above description.

It is preferable for the fluoranthene compound of the present invention that $X_4$ in the general formula (1) is a hydrogen atom.

It is preferable for the fluoranthene compound of the present invention that $X_7$ and $X_{12}$ in the general formula (1) is a substituted or unsubstituted aryl group having 5 to 50 atoms forming a ring.

It is preferable for the fluoranthene compound of the present invention that $X_7$ and $X_{12}$ in the general formula (1) is a phenyl group.

It is preferable for the fluoranthene compound of the present invention that $X_1$, $X_2$, $X_4$ to $X_6$, and $X_5$ to $X_{11}$ in the general formula (1) are hydrogen atoms, and that $X_3$, $X_7$ and $X_{12}$ in the general formula (1) each independently represents a substituted or unsubstituted aryl group having 5 to 50 atoms forming a ring.

It is preferable for the fluoranthene compound of the present invention that $X_1$, $X_2$, $X_4$ to $X_6$, and $X_8$ to $X_{11}$ in the general formula (1) are hydrogen atoms, that $X_7$ and $X_{12}$ in the general formula (1) each independently represents a substituted or unsubstituted aryl group having 5 to 50 atoms forming a ring, and that $X_3$ represents $Ar_1$—$Ar_2$ ($Ar_1$ and $Ar_2$ each independently represents a substituted or unsubstituted aryl group having 5 to 50 atoms forming a ring respectively and further, $Ar_1$ and $Ar_2$ may bond each other to form a cyclic structure).

It is preferable for the fluoranthene compound of the present invention that $X_1$, $X_2$, $X_4$ to $X_6$, and $X_8$ to $X_{11}$ in the general formula (1) are hydrogen atoms, that $X_7$ and $X_{12}$ in the general formula (1) each independently represents a substituted or unsubstituted aryl group having 5 to 50 atoms forming a ring, and that $X_3$ represents $Ar_1$—$Ar_2$—$Ar_3$ ($Ar_1$, $Ar_2$ and $Ar_3$ each independently represents a substituted or unsubstituted aryl group having 5 to 50 atoms forming a ring respectively and further, $Ar_1$, $Ar_2$ and $Ar_3$ may bond each other to form a cyclic structure).

Specific examples of the fluoranthene compound represented by the general formula (1) of the present invention include the following compounds, though not limited thereto.

1-1

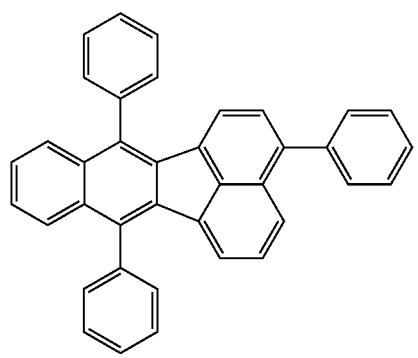

1-2

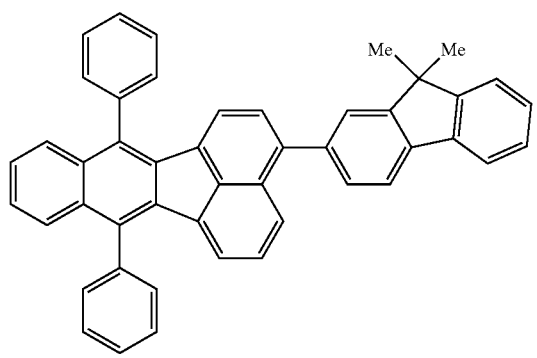

1-3

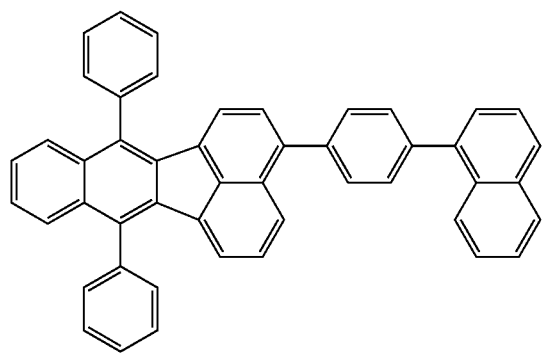

1-4

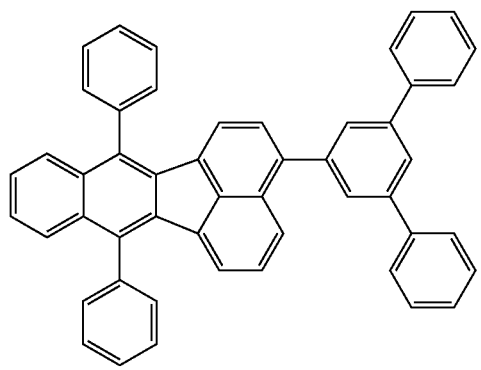

1-5

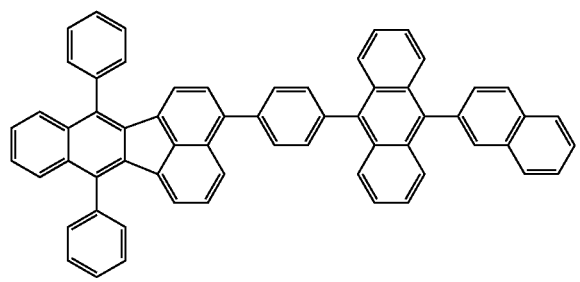

1-6

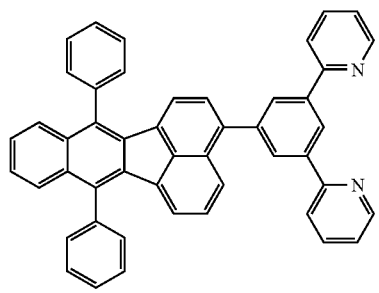

-continued
1-7
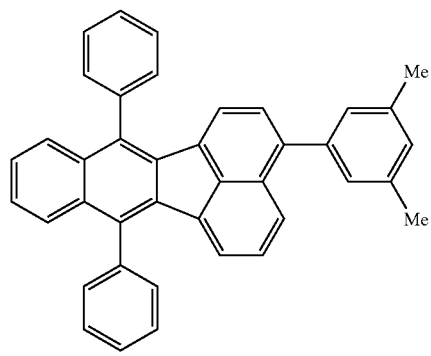
1-8
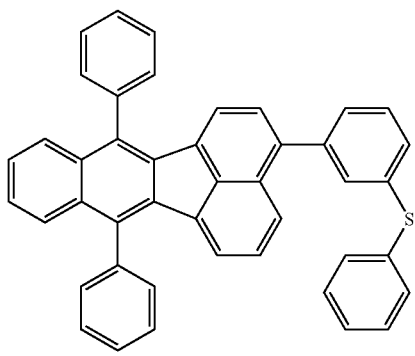
1-9
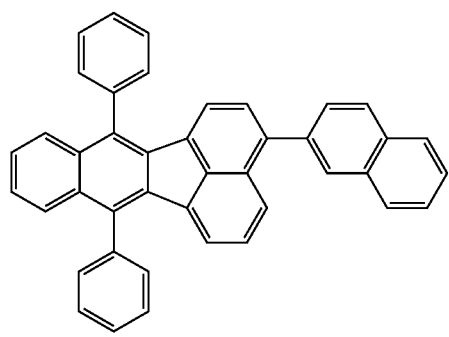
1-10
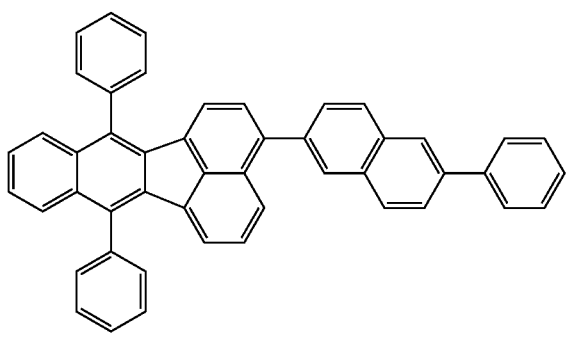
1-11
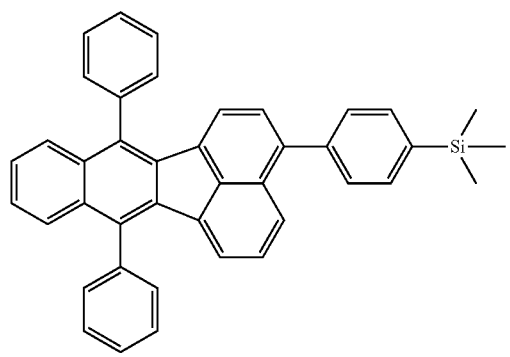
1-12
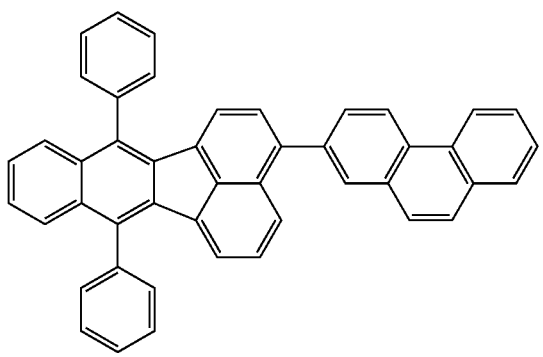
1-13
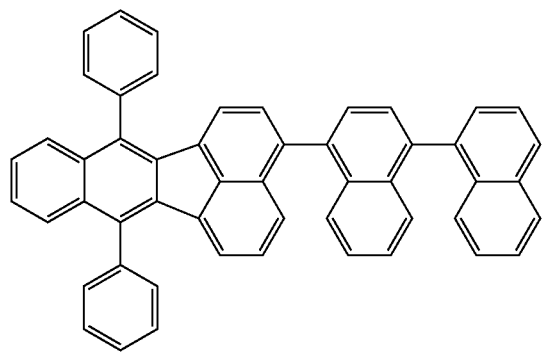
1-14
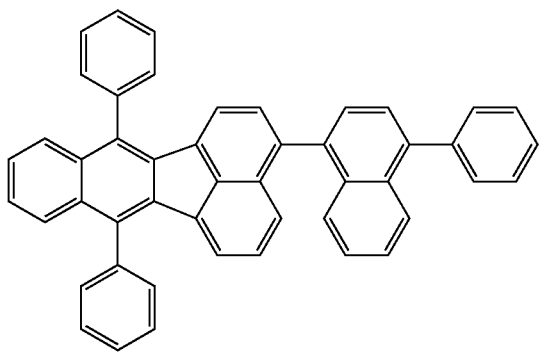

-continued
1-15
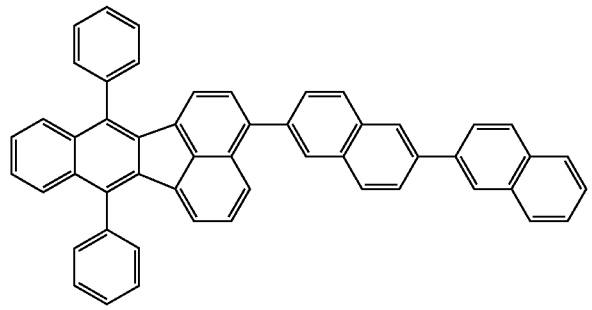
1-16
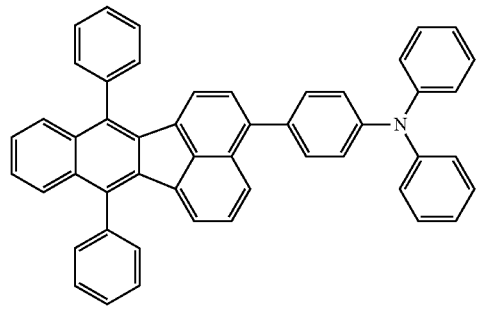
2-1
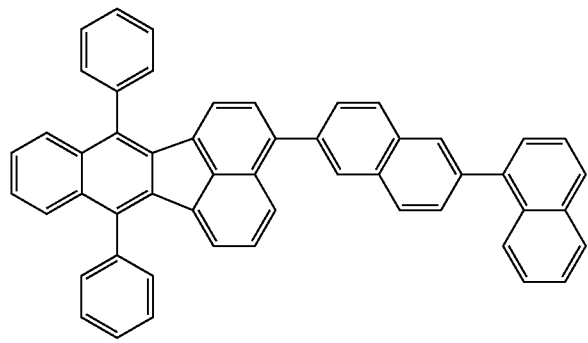
2-2
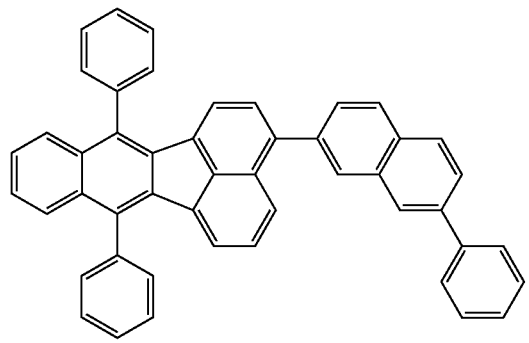
2-3
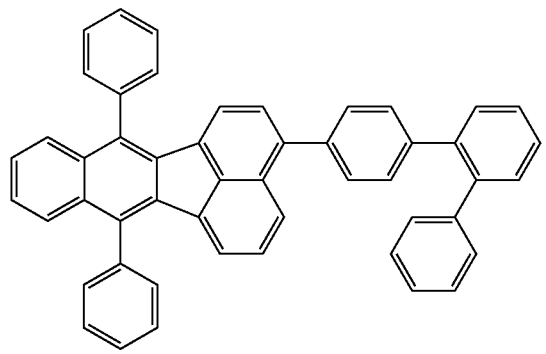
2-4
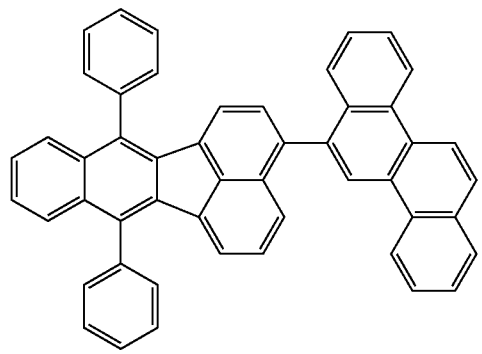
2-5
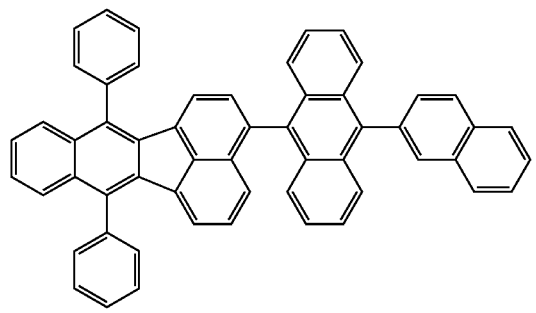
2-6
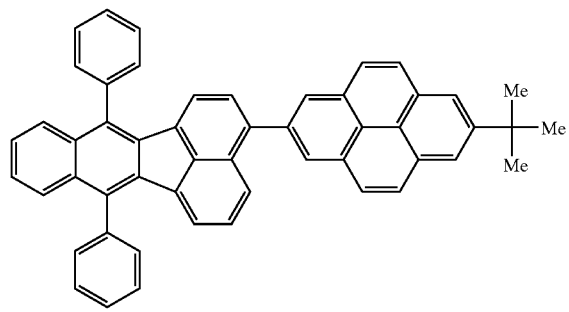

-continued
2-7
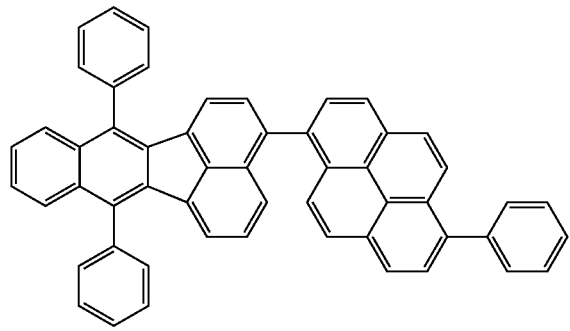
2-8
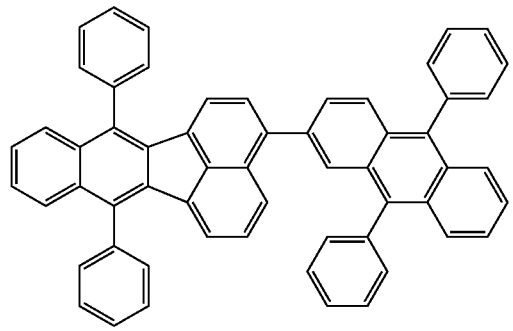
2-9
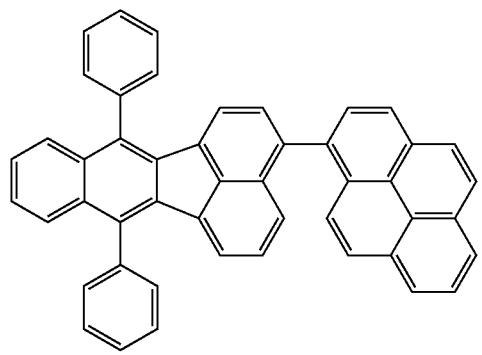
2-10
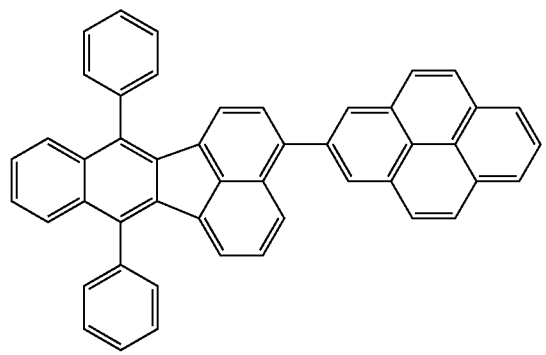
2-11
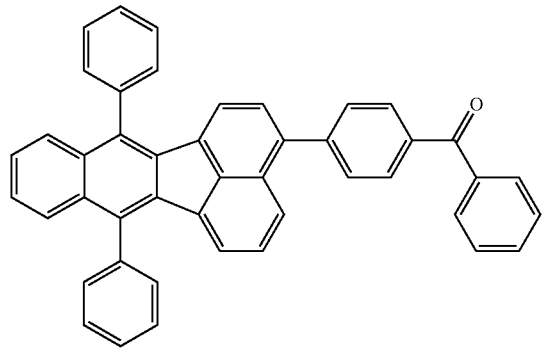
2-12
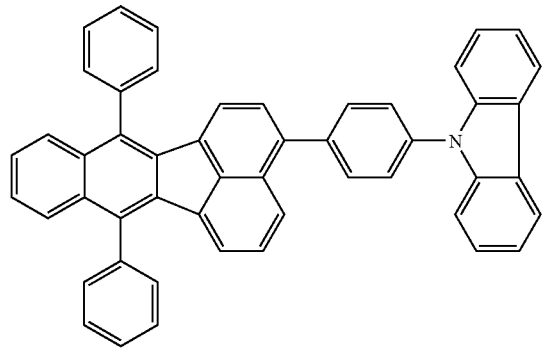
2-13
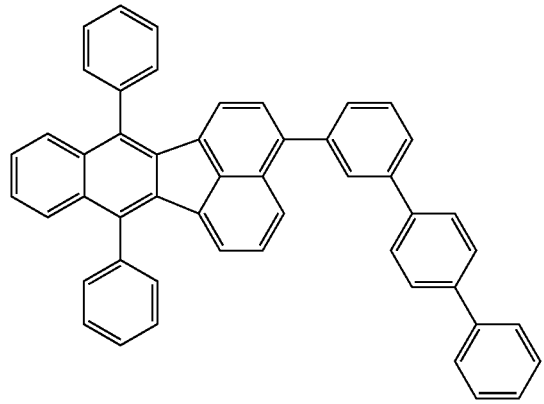
2-14
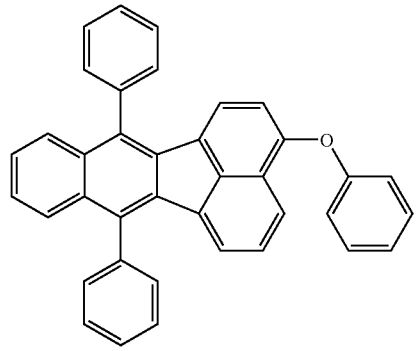

-continued
2-15
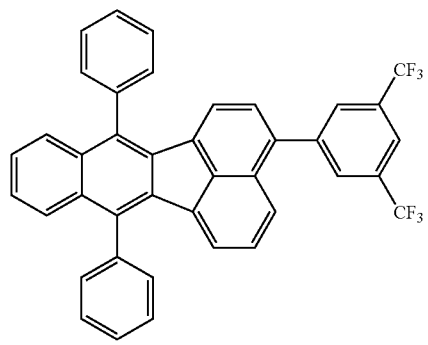
2-16
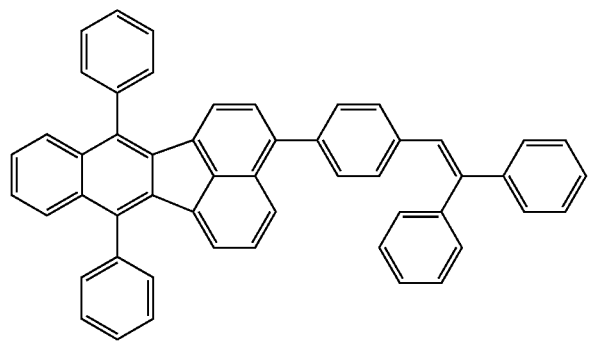
3-1
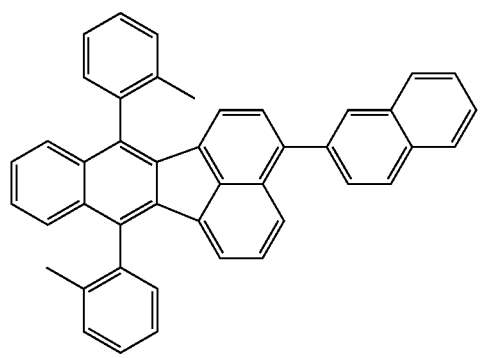
3-2
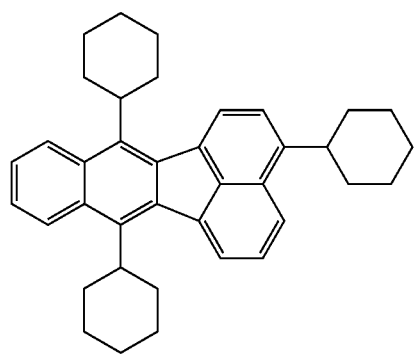
3-3
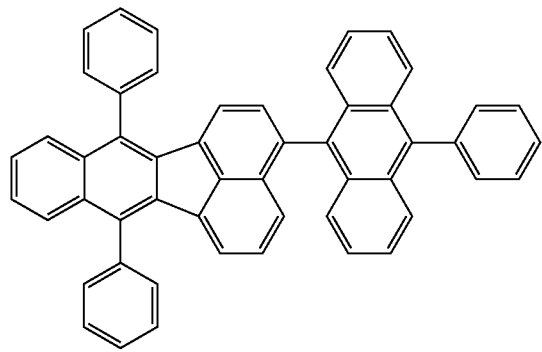
3-4
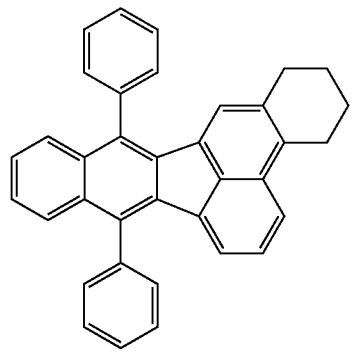
3-5
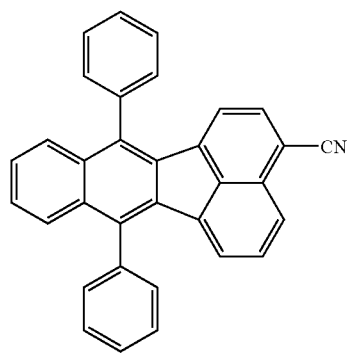
3-6
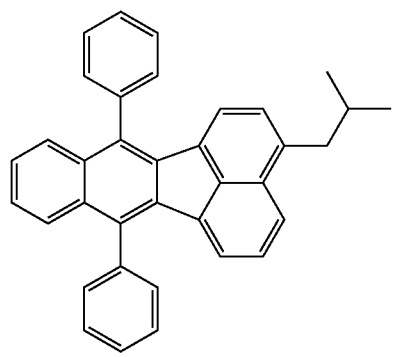

-continued
3-7
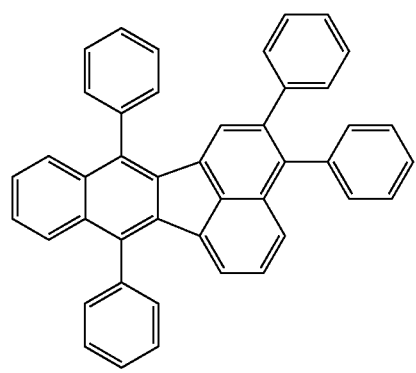
3-8
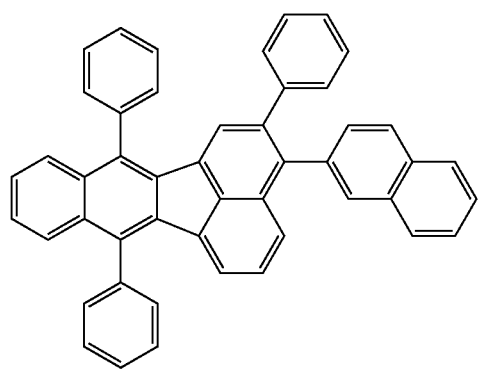
3-9
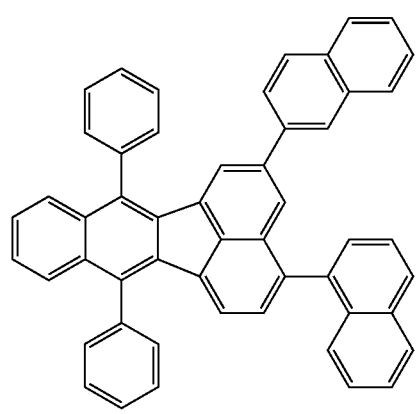
3-10
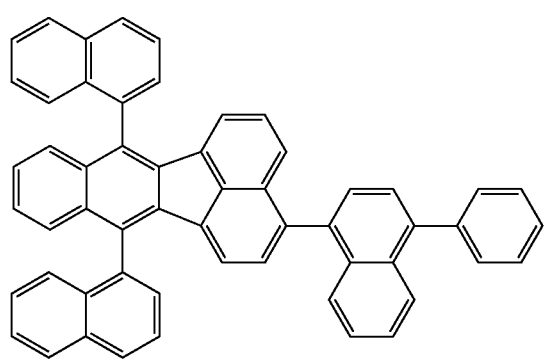
3-11
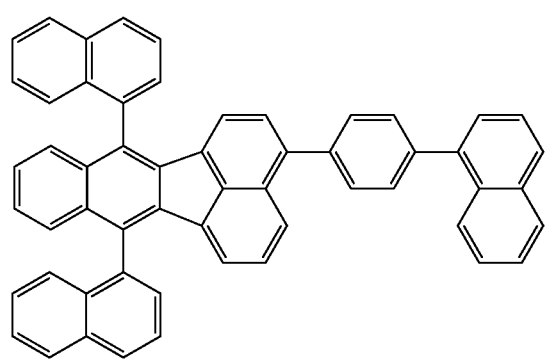
3-12
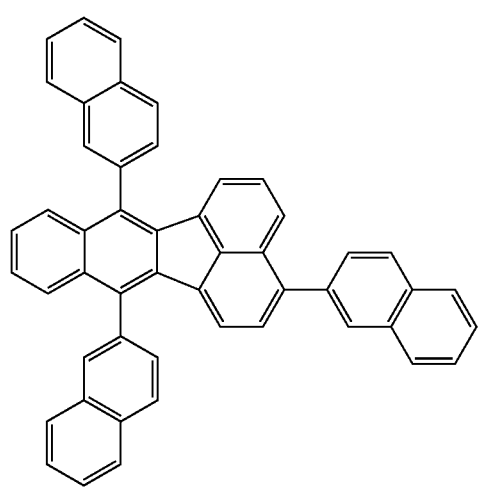

-continued
3-13
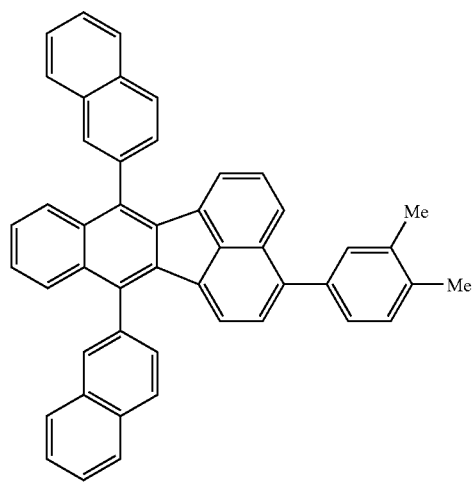
3-14
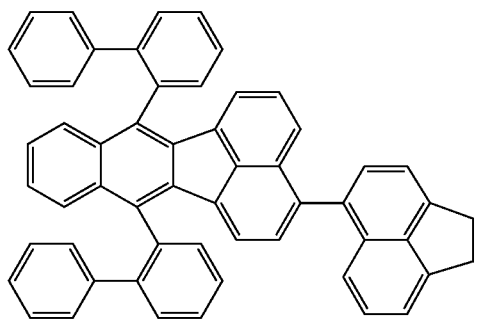
3-15
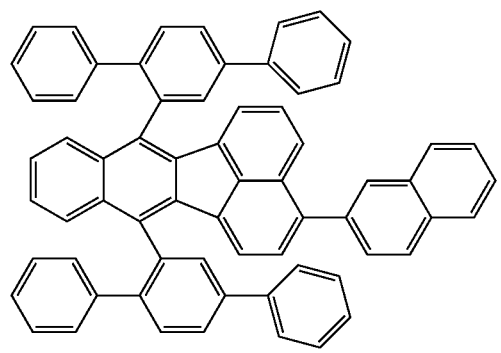
3-16
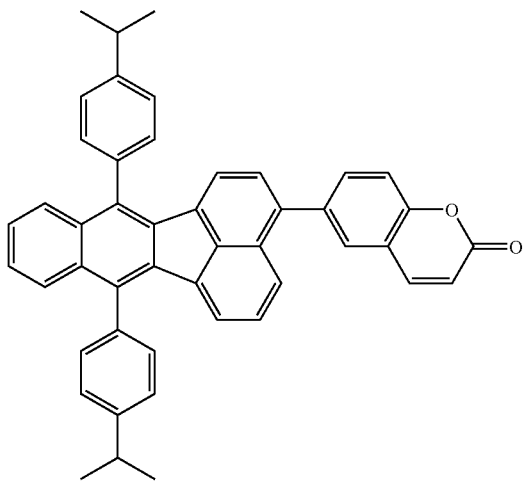
3-17
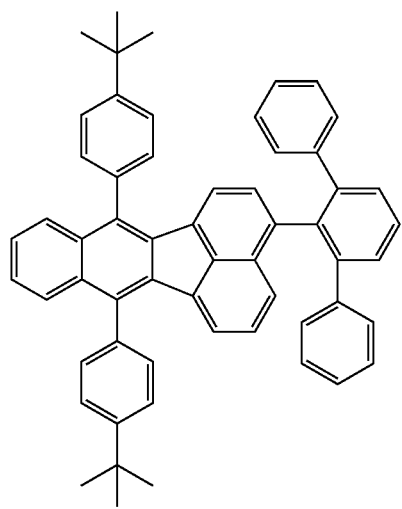
4-1
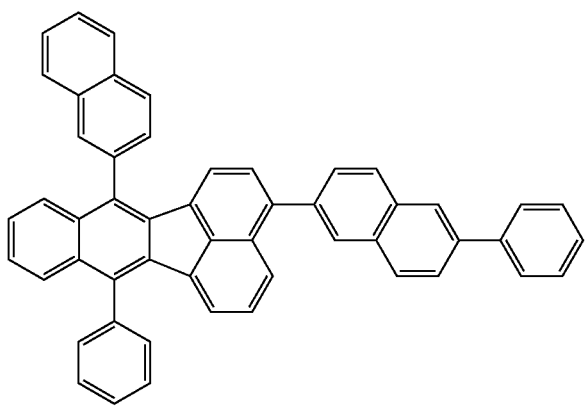

-continued
4-2
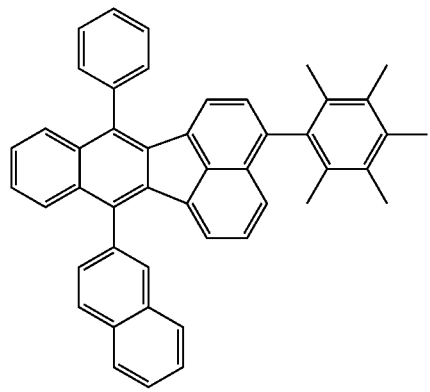
4-3
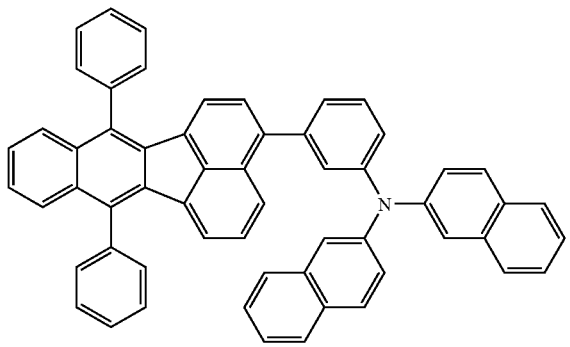
4-4
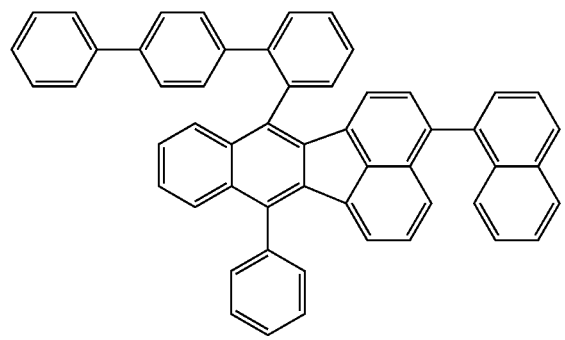
4-5
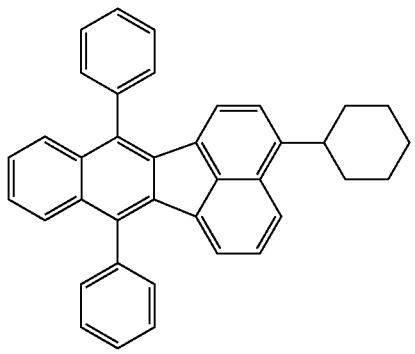
4-6
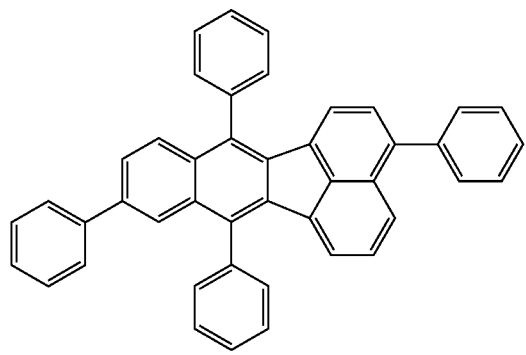
4-7
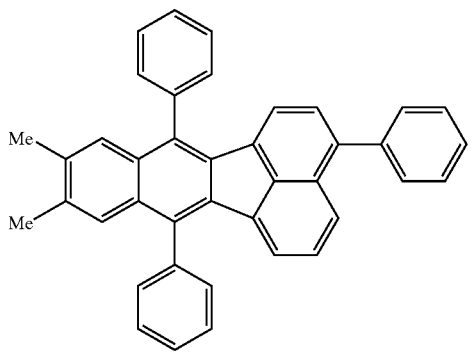
4-8
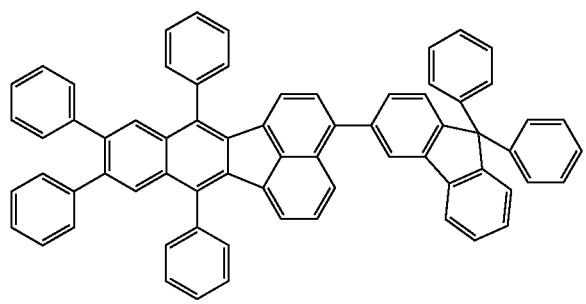
4-9
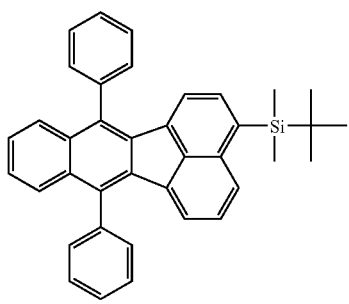

-continued
4-10
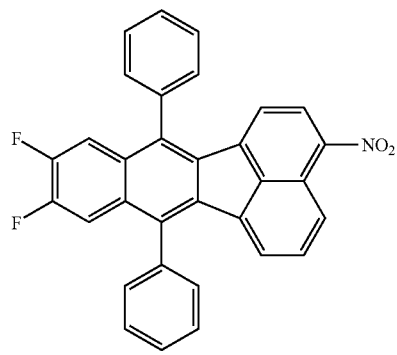
4-11
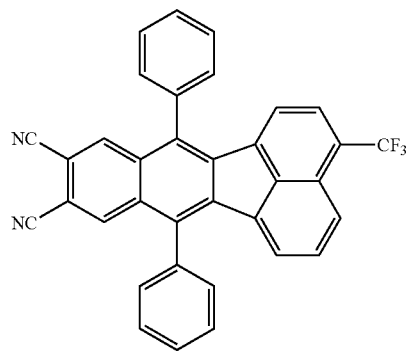
4-12
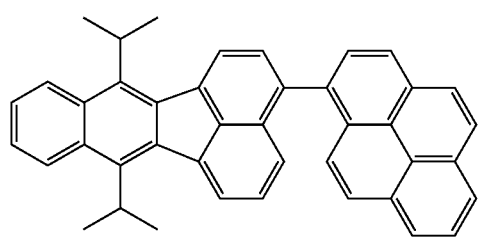
4-13
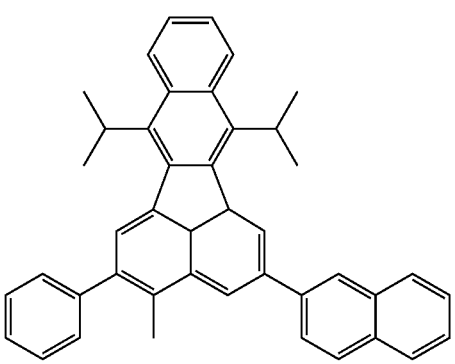
4-14
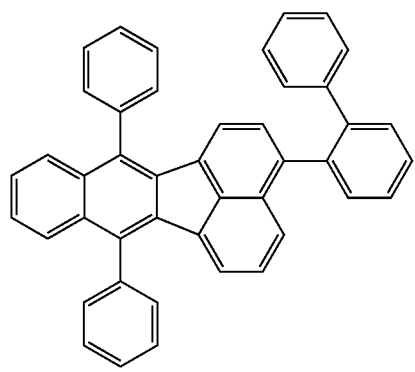
4-15
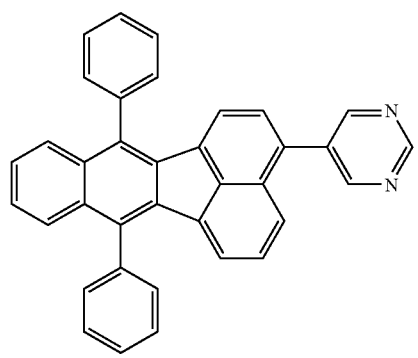
4-16
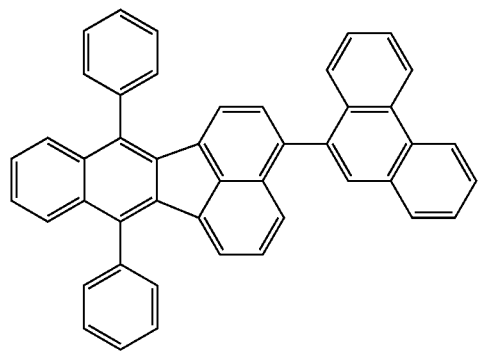
4-17
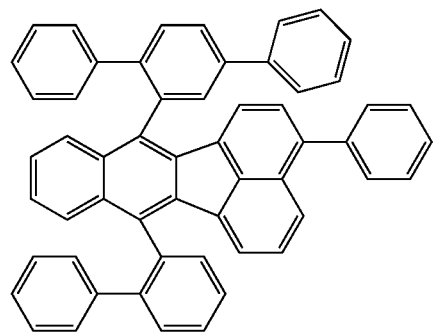

-continued
4-18
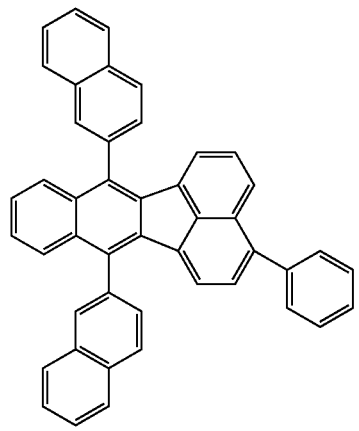
5-1
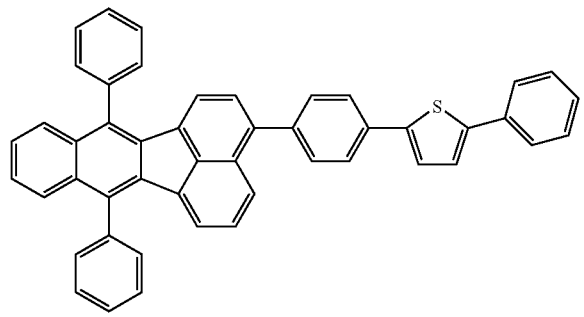
5-2
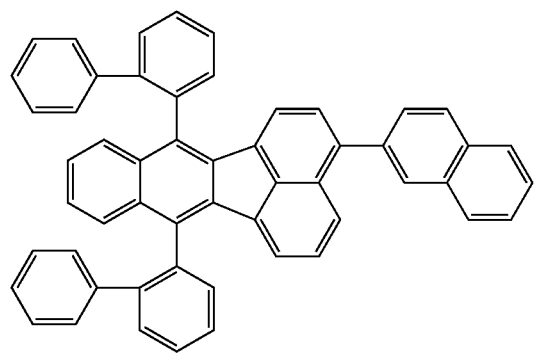
5-3
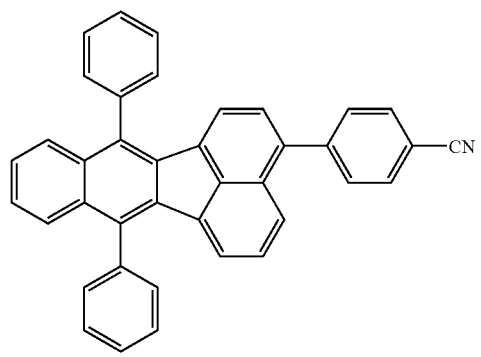
5-4
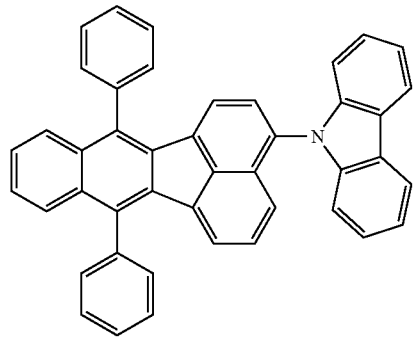
5-5
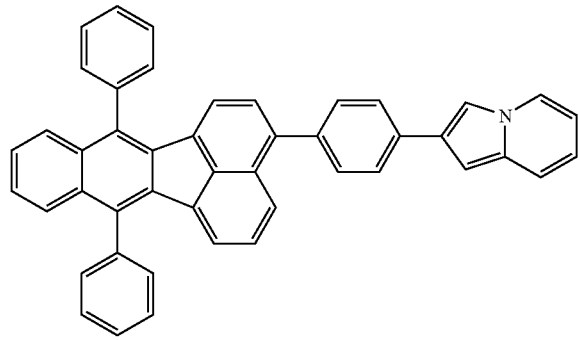
5-6
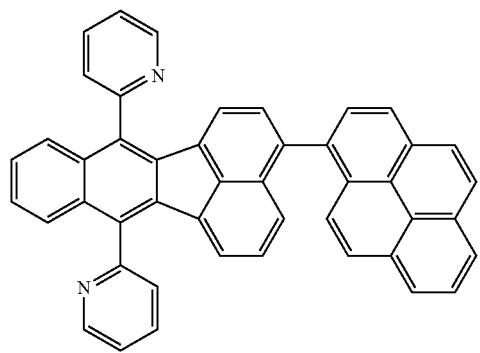
5-7
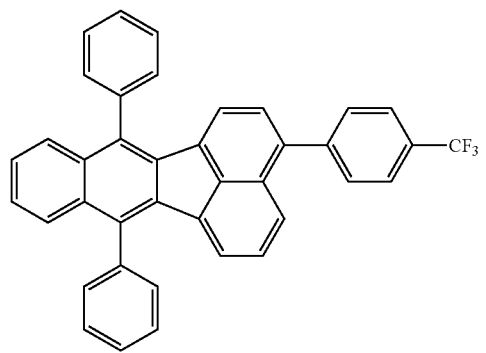

-continued
5-8
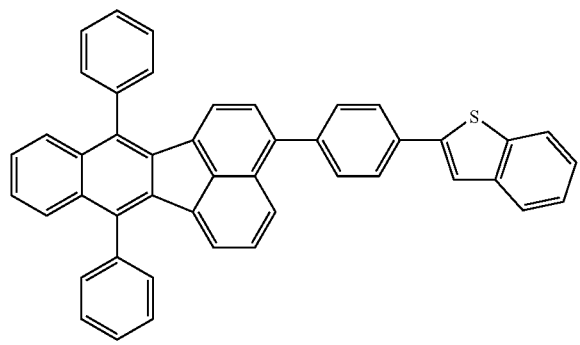
5-9
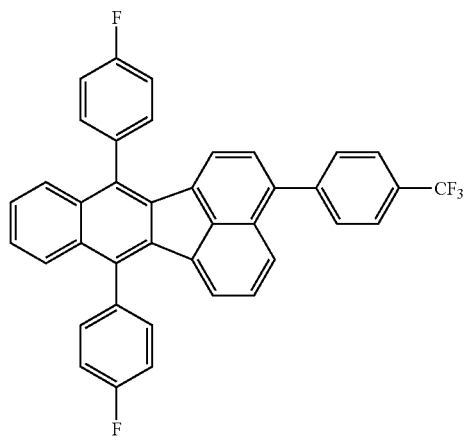
5-10
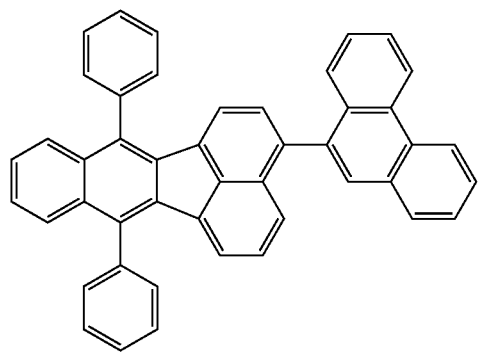
5-11
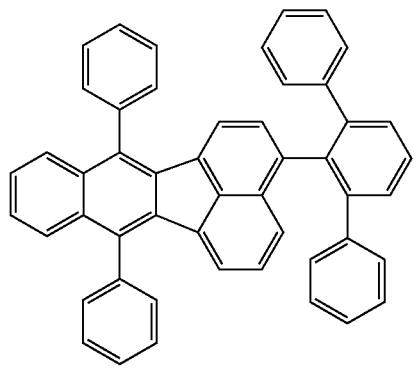
5-12
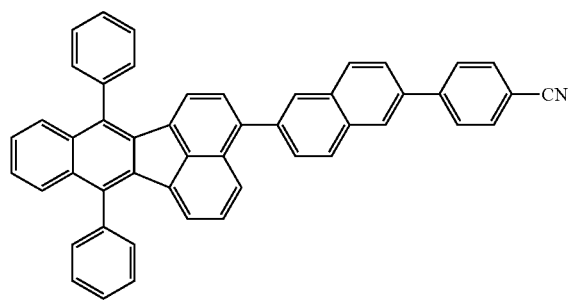
5-13
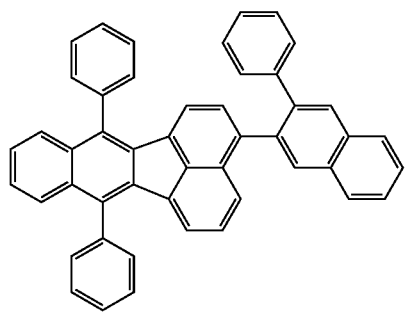
5-14
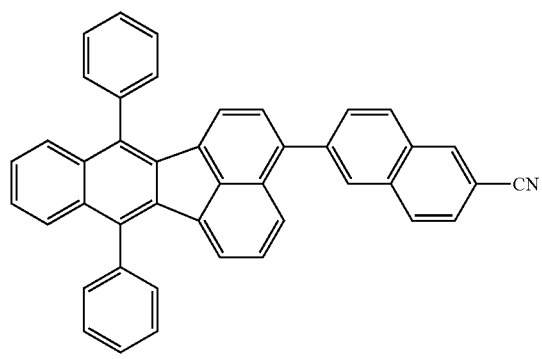
5-15
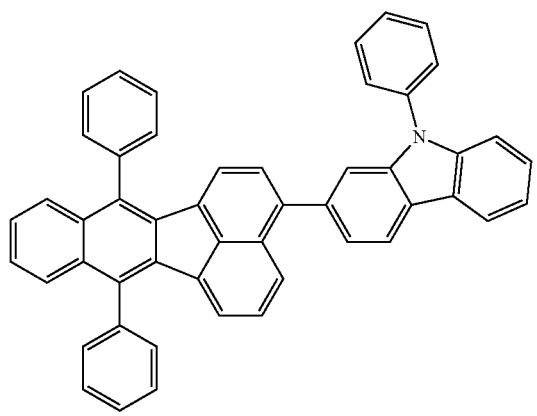

-continued
5-16
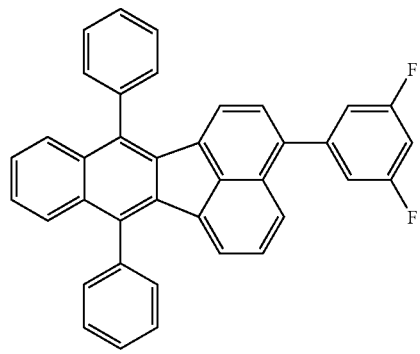
6-1
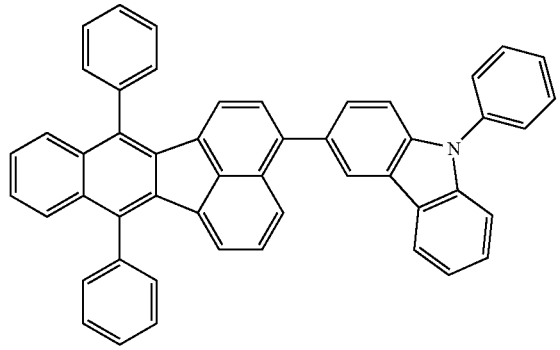
6-2
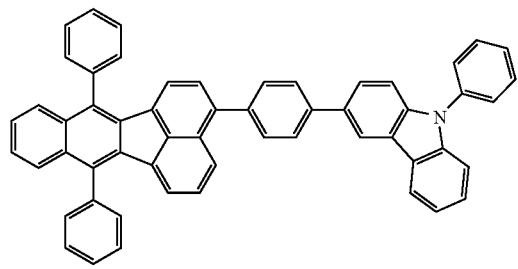
6-3
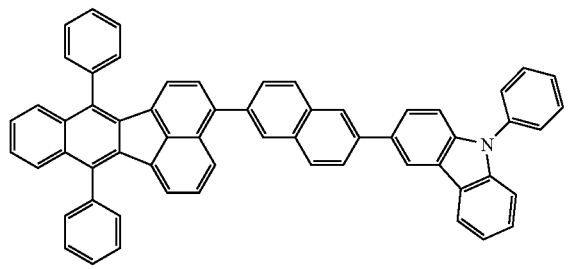
6-4
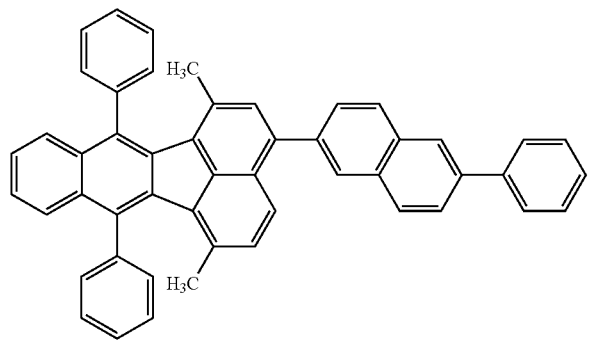
6-5
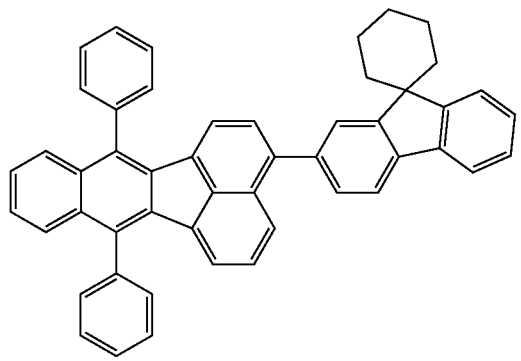
6-6
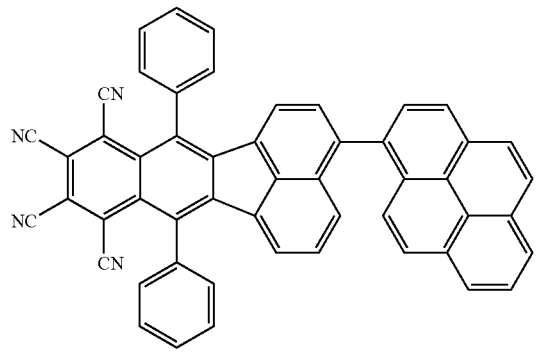
6-7
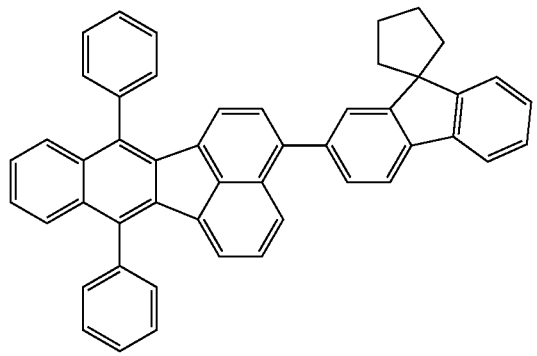

6-8
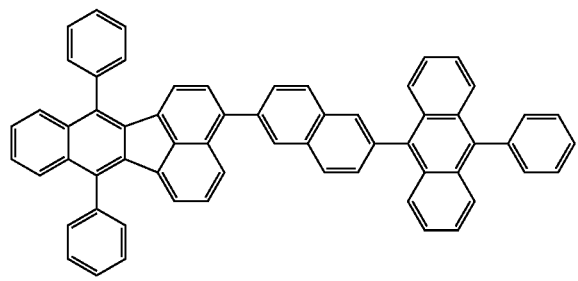
6-9
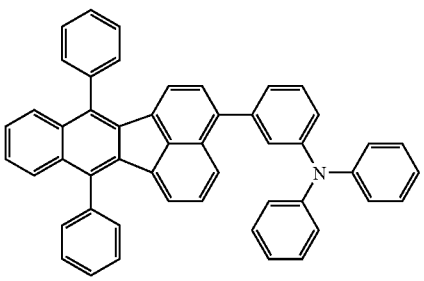
6-10
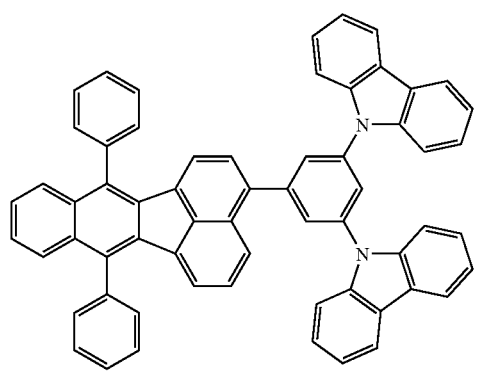
6-11
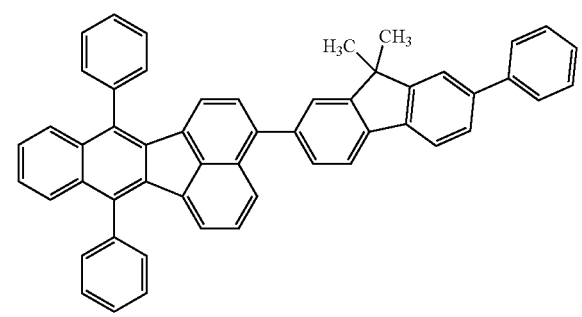
6-12
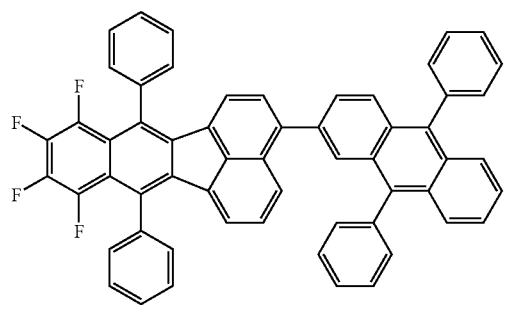
7-1
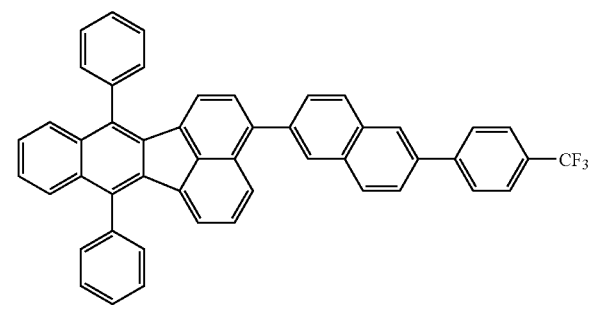
7-2
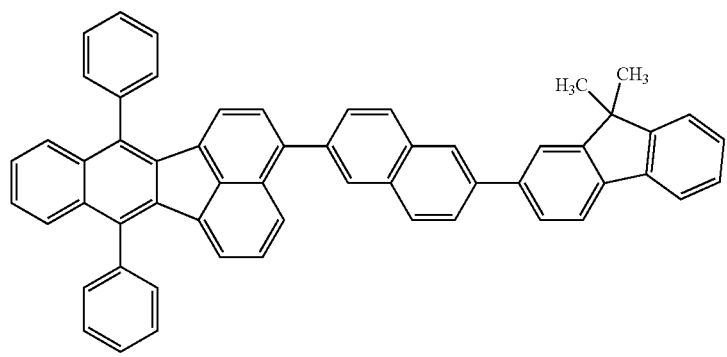

7-3
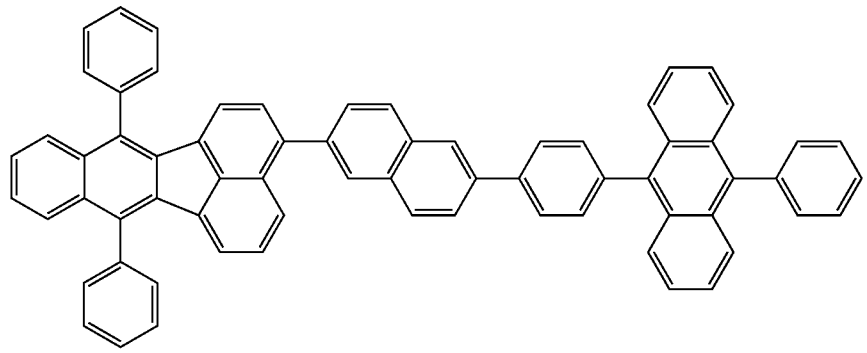
7-4
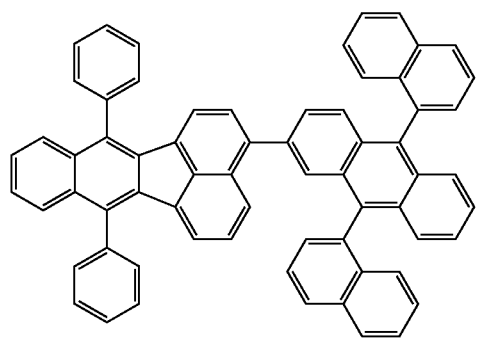
7-5
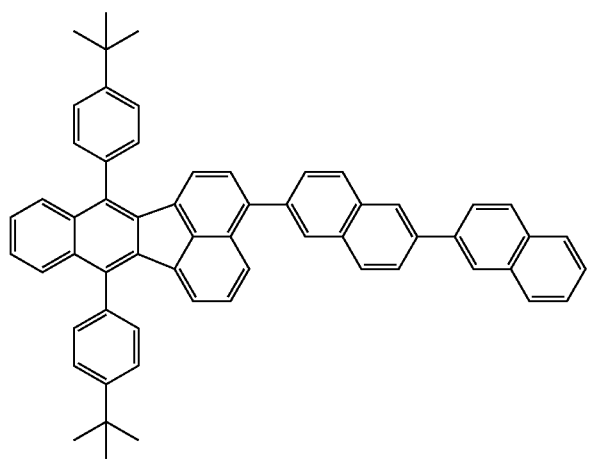
7-6
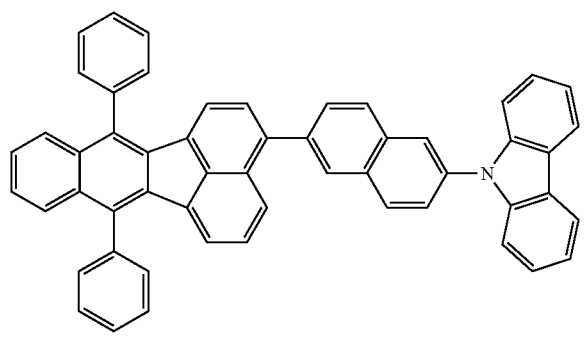
7-8
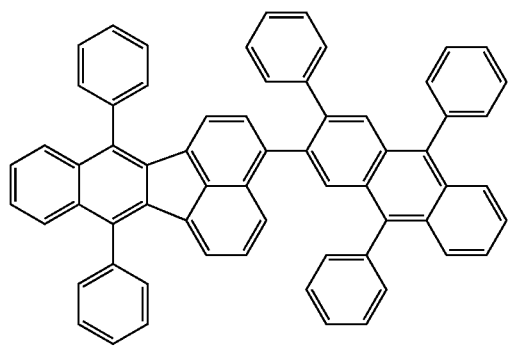
7-9
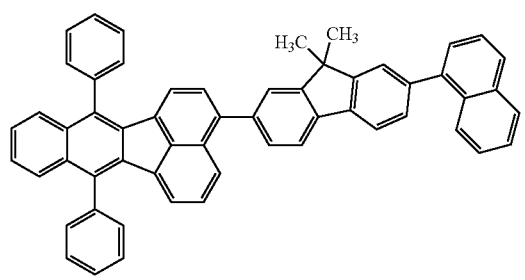
7-10
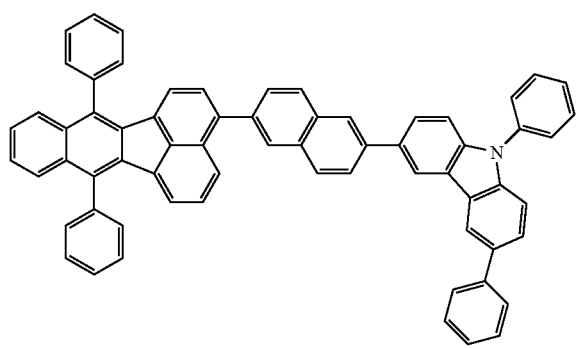

-continued
8-1
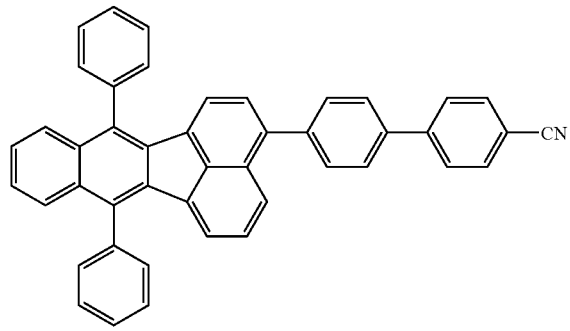
8-2
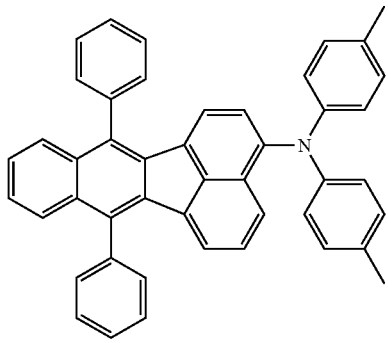
8-3
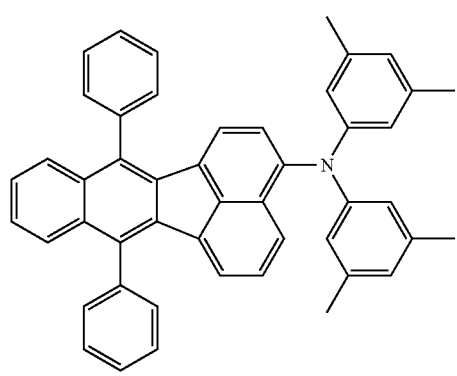
8-4
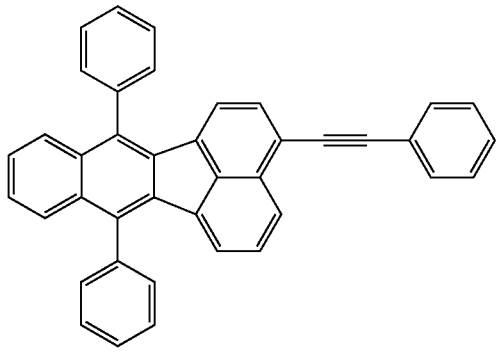
8-5
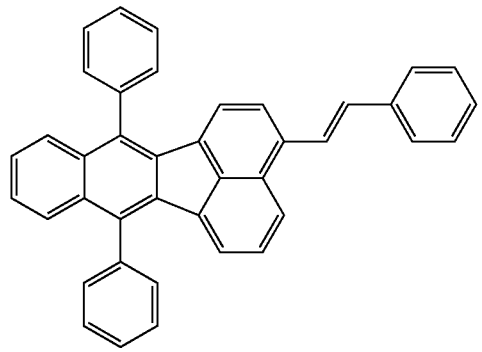
8-6
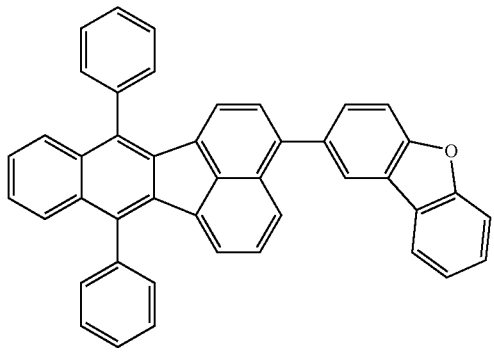
8-7
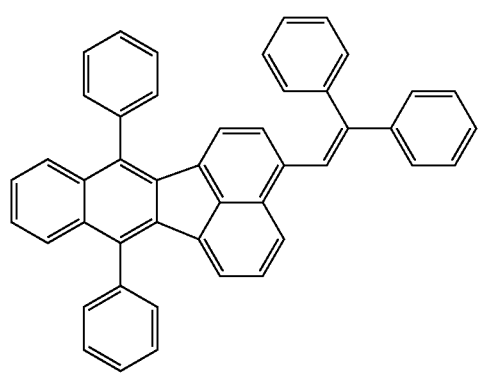
8-8
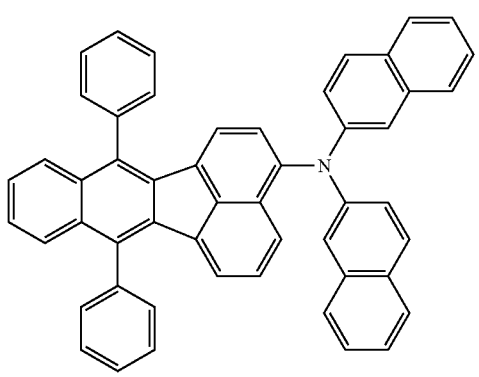

-continued
| 8-9 | 9-1 |
|---|---|
| 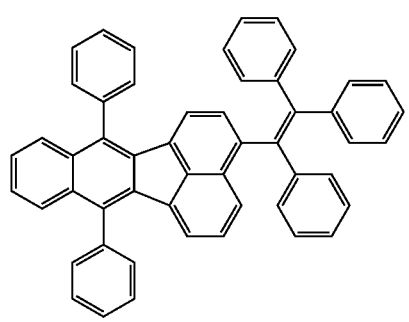 | 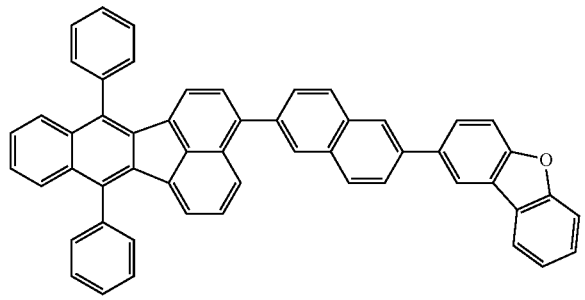 |
| 9-2 | 9-3 |
|---|---|
| 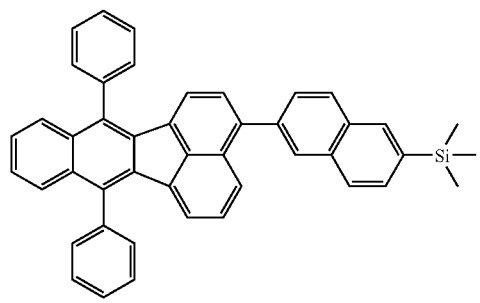 | 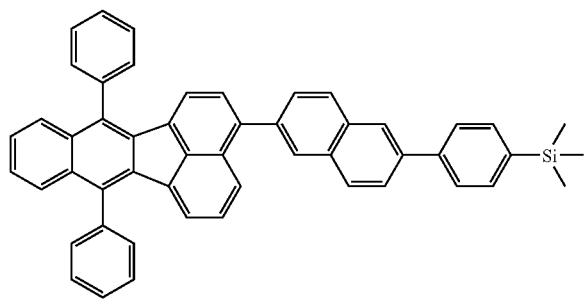 |
| 9-4 | 9-5 |
|---|---|
| 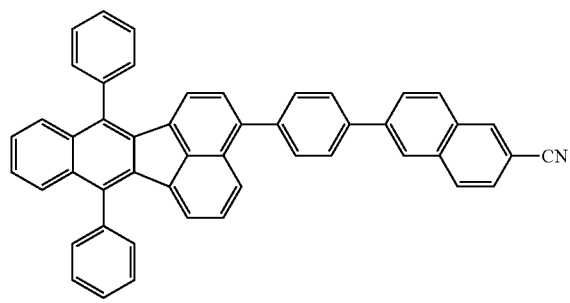 | 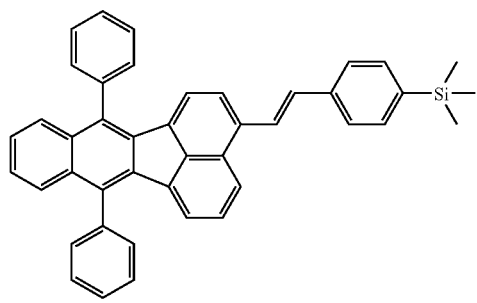 |
| 9-6 | 9-7 |
|---|---|
| 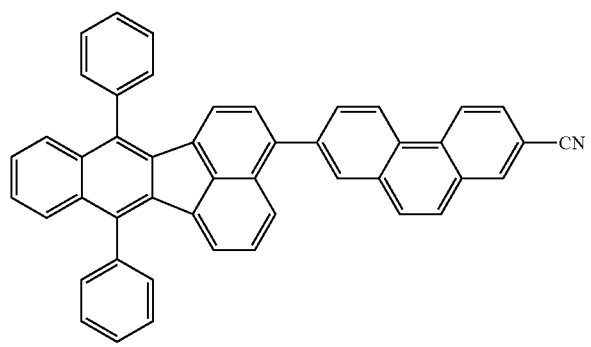 | 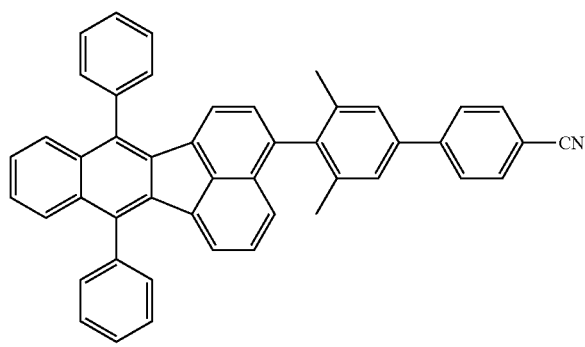 |

-continued
9-8
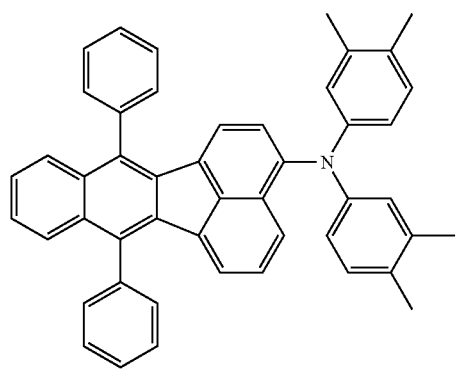
9-9
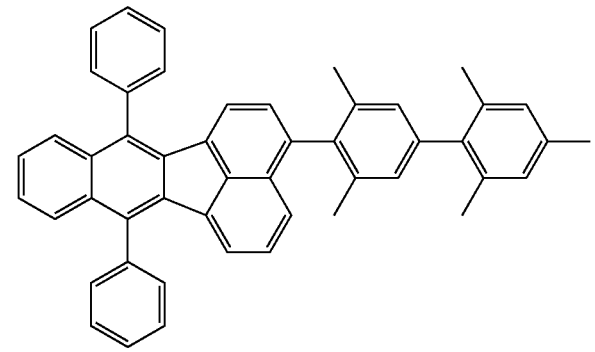
10-1
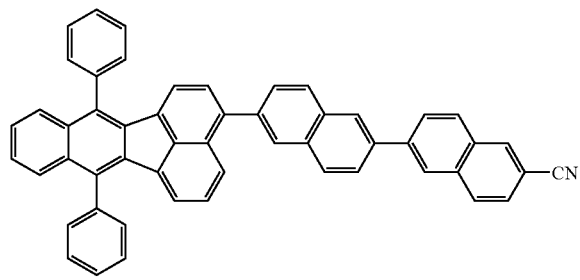
10-2
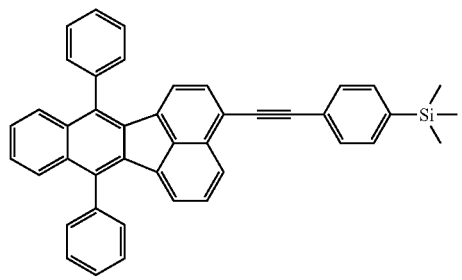
10-3
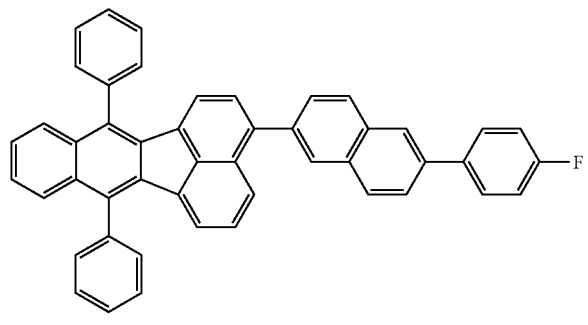
10-4
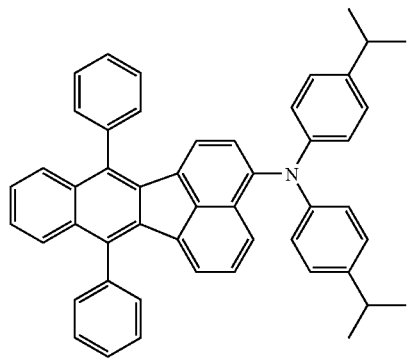
10-5
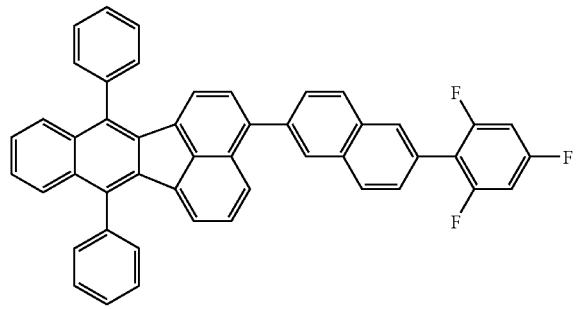
10-6
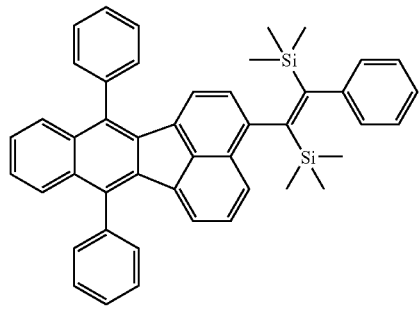

-continued
10-7
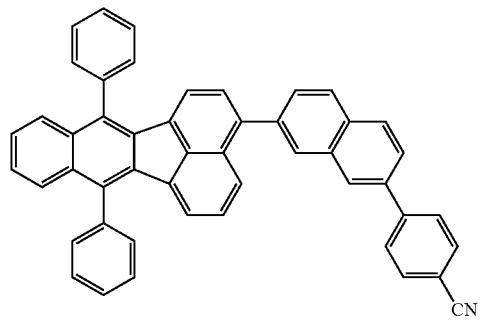
10-8
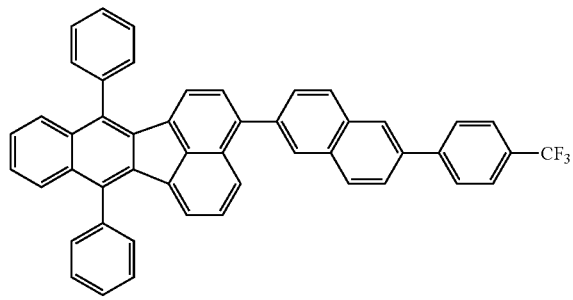
10-9
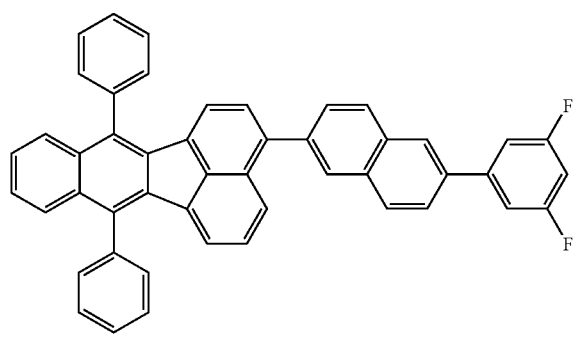
11-1
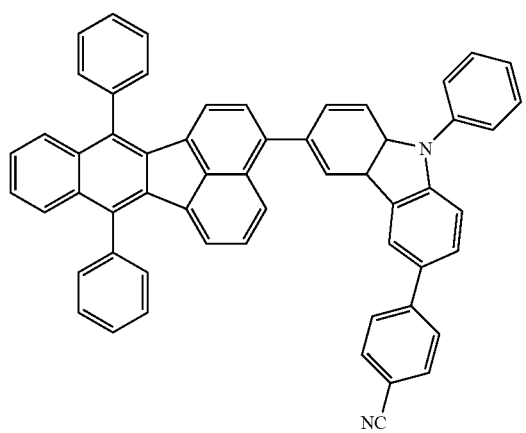
11-2
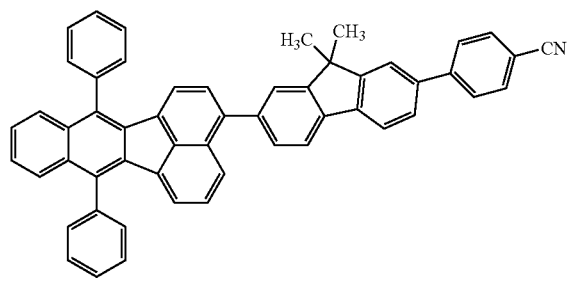
11-3
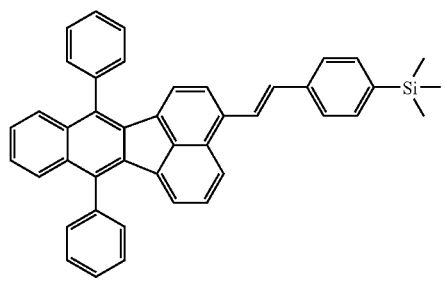
11-4
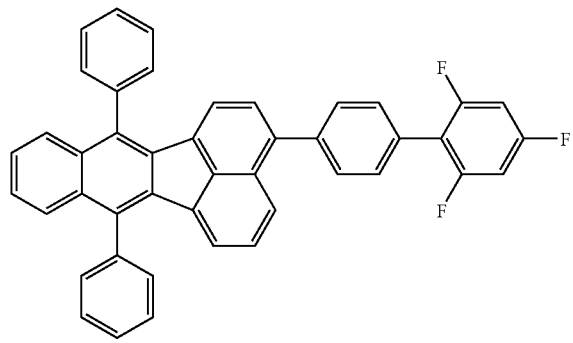
11-5
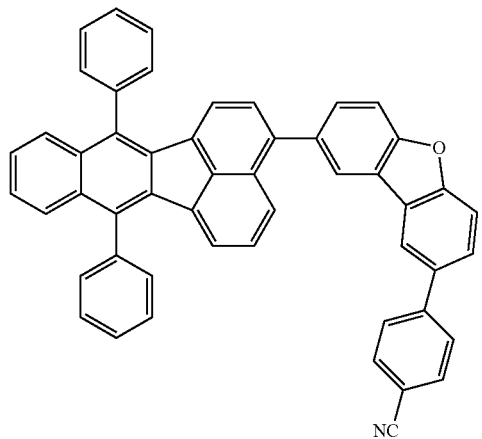

11-6
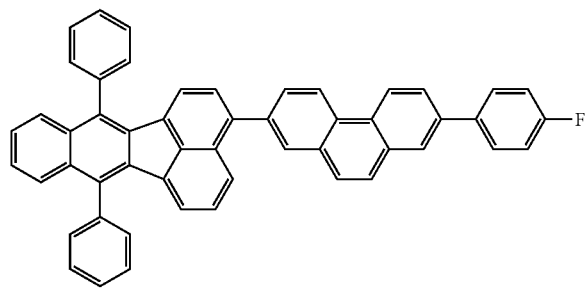

11-7
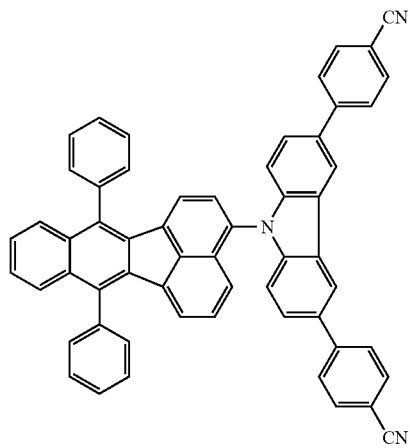

11-8
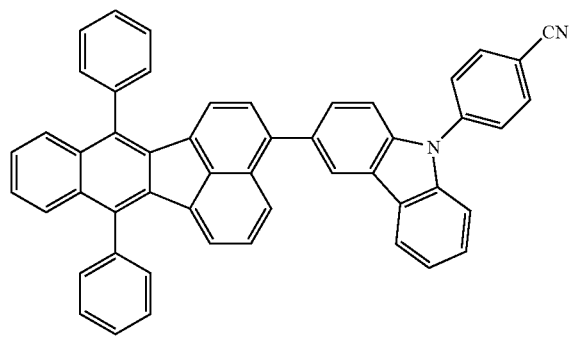

11-9
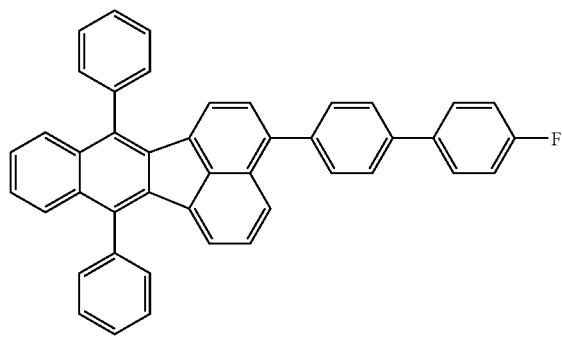

11-10
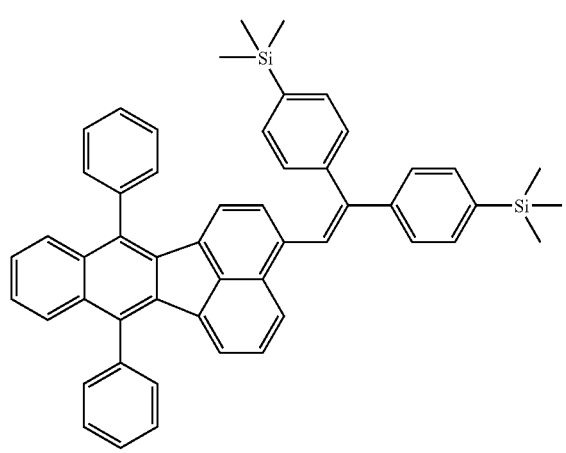

Preparation of the fluoranthene compound of the present invention is possible, for example, in accordance with the well-known preparation process described in J. Org. Chem. Chem., 62, 530, (1997), J. Am. Chem. Soc., 74, 1075, (1952), J. Am. Chem. Soc., 118, 2374, (1996), Tetrahedron, 22, 2957, (1966), Tetrahedron Lett., 38, 741, (1997), Indian. J. Chem. Sect. B, 39, 173, (2000), J. Phys. Chem. A, 106, 1961, (2002); and, for example, bromofluoranthene derivative is prepared by reacting isobenzofuran derivative and bromo acenaphthylene derivative, followed by dehydration treatment. Subsequently, those derivatives can be derived to the fluoranthene compound of the present invention in accordance with a carbon-carbon bond generation reaction (Suzuki reaction, Kumada-Tamao reaction, Still reaction, Sonogashira reaction, etc.), a carbon-nitrogen bond generation reaction (Buchwald-Hartwig reaction, etc.).

It is preferable for the aminodibenzofluorene derivative of the present invention to be used as a material for the organic EL device, more preferable to be used as a material for a light emitting material for the organic EL device, and particularly, further preferable to be used as a doping material for the organic EL device.

The present invention provides an organic EL device which is composed of one or more organic compound layers including at least one emitting layer sandwiched between a pair of electrodes, wherein at least one of the organic compound layers contains at least one kind of the fluoranthene compound of the present invention.

It is preferable for the organic EL device of the present invention that the above emitting layer contains at least one kind of the fluoranthene compound. In the organic EL device, the fluoranthene compound of the present invention is contained in the emitting layer in an amount of preferably from 0.01 to 20% by weight, more preferably from 0.5 to 20% by weight, particularly preferably from 8 to 20% by weight, and the most preferably from 15 to 20% by weight.

Further, in the case where the fluoranthene compound of the present invention is employed as the light emitting material for the organic EL device, it is preferable that the emitting layer contains at least one kind of the above fluoranthene compound and at least one kind selected from the compounds represented by the following general formulae (2a) to (2d), and that at least one kind selected from the compounds represented by the following general formulae (2a) to (2d) is a host material.

The general formulae (2a) to (2d) will be explained below.
General formula (2a):

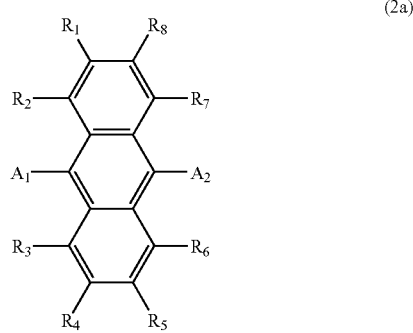

(2a)

(In the formula (2a), $A_1$ and $A_2$ each independently represents a group derived from a substituted or unsubstituted aromatic ring having 6 to 20 carbon atoms. The aromatic ring may be substituted by 1 or more substituents. The substituent is selected from a substituted or unsubstituted aryl group having 6 to 50 carbon atoms forming a ring, a substituted or unsubstituted alkyl group having 1 to 50 carbon atoms, a substituted or unsubstituted cycloalkyl group having 3 to 50 carbon atoms, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 atoms forming a ring, a substituted or unsubstituted arylthio group having 5 to 50 atoms forming a ring, a substituted or unsubstituted alkoxycarbonyl group having 1 to 50 carbon atoms, a substituted or unsubstituted silyl group, a carboxy group, a halogen atom, a cyano group, a nitro group and a hydroxy group. When the aromatic ring is substituted by 2 or more substituents, the substituents may be the same with or different from each other, and neighboring substituents may be bonded with each other to form a saturated or unsaturated cyclic structure.

$R_1$ to $R_8$ each independently represents one member selected from a hydrogen atom, a substituted or unsubstituted aryl group having 6 to 50 carbon atoms forming a ring, a substituted or unsubstituted heteroaryl group having 5 to 50 atoms forming a ring, a substituted or unsubstituted alkyl group having 1 to 50 carbon atoms, a substituted or unsubstituted cycloalkyl group having 3 to 50 carbon atoms, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 atoms forming a ring, a substituted or unsubstituted arylthio group having 5 to 50 atoms forming a ring, a substituted or unsubstituted alkoxycarbonyl group having 1 to 50 carbon atoms, a substituted or unsubstituted silyl group, a carboxy group, a halogen atom, a cyano group, a nitro group and a hydroxy group.)

In the general formula (2a), it is preferable that $A_1$ and $A_2$ are the groups which are different from each other.

It is preferable that in the above general formula (2a), at least one of $A_1$ and $A_2$ corresponds to a substituent with substituted or unsubstituted aromatic fused ring groups having 10 to 30 atoms forming a ring.

It is preferable that the substituted or unsubstituted fused ring group having 10 to 30 atoms forming a ring corresponds to a substituted or unsubstituted naphthalene ring.

Examples of the group derived from the substituted or unsubstituted aromatic ring having 6 to 20 carbon atoms forming a ring represented by $A_1$ and $A_2$ in the general formula 2(a) include phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methylbiphenylyl group, 4''-t-butyl-p-terphenyl-4-yl group, etc. Preferable examples are the groups derived from the substituted or unsubstituted aromatic ring having 10 to 14 carbon atoms forming a ring and in particular, 1-naphthyl group, 2-naphthyl group and 9-phenanthryl group.

Examples of the substituted or unsubstituted aryl group having 6 to 50 carbon atoms forming a ring as the substituent of the aromatic ring include phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methylbiphenylyl group, 4''-t-butyl-p-terphenyl-4-yl group, etc. Preferable examples are the substituted or unsubstituted aryl group having 6 to 18 carbon atoms forming a ring including particularly phenyl group, 1-naphthyl group, 2-naphthyl group, 9-phenanthryl group, 1-naphthacenyl group, 2-naphthacenyl group, 9-naphthacenyl group, 1-pyrenyl group, 2-pyrenyl group, 4-pyrenyl group, 2-biphenyl group, 3-biphenylyl group, 4-biphenylyl group, o-tolyl group, m-tolyl group, p-tolyl group, p-t-butylphenyl group.

In the general formula (2a), $A_1$ and $A_2$ each independently represents a substituted or unsubstituted aromatic ring group having 10 to 30 carbon atoms forming a ring (with the proviso that an anthracene residue is excluded). The substituents of $A_1$ and $A_2$ each independently corresponds to a hydrogen atom, a substituted or unsubstituted aromatic group having 6 to 50 carbon atoms forming a ring, a substituted or unsubstituted aromatic heterocyclic group having 5 to 50 atoms forming a ring, a substituted or unsubstituted alkyl group having 1 to 50 carbon atoms, a substituted or unsubstituted cycloalkyl group, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 atoms forming a ring, a substituted or unsubstituted arylthio group having 5 to 50 atoms forming a ring, a substituted or unsubstituted alkoxycarbonyl group having 1 to 50 carbon atoms, a substituted or unsubstituted silyl group, a carboxy group, a halogen atom, a cyano group, a nitro group and a hydroxy group.

Examples of the aromatic ring group having 10 to 30 carbon atoms forming a ring (with the proviso that an anthracene residue is excluded) represented by $A_1$ and $A_2$ in the general formula (2a) include a substituted or unsubstituted a-naphthyl group and β-naphthyl group, a substituted or unsubstituted phenanthrenyl group, a substituted or unsubstituted crycenyl group, a substituted or unsubstituted tetracenyl group, a substituted or unsubstituted pyrenyl group, a substituted or unsubstituted phenylnaphthyl group, a substituted or unsubstituted naphthylnaphthyl group, a substituted or unsubstituted naphthylphenyl group, a substituted or unsubstituted phenylpyrenyl group, a substituted or unsubstituted pyrenylphenyl group, a substituted or unsubstituted naphthylnaphthylnaphthyl group, a substituted or unsubstituted naphthylnaphthylphenyl group, a substituted or unsubstituted naphthylphenylphenyl group, a substituted or unsubstituted naphthylphenylnaphthyl group, a substituted or unsubstituted phenylnaphthylnaphthyl group, a substituted or unsubstituted phenylnaphthylphenyl group, a substituted or unsubstituted phenylphenylnaphthyl group, etc. Among those, the substituted or unsubstituted a-naphthyl group and β-naphthyl group, the substituted or unsubstituted phenylnaphthyl group, the substituted or unsubstituted naphthylnaphthyl group, or the substituted or unsubstituted naphthylphenyl group are preferable.

Examples of the substituted or unsubstituted aryl group having 6 to 50 carbon atoms forming a ring represented by $R_1$ to $R_8$ in the general formula (2a) include phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methylbiphenylyl group, 4"-t-butyl-p-terphenyl-4-yl group, etc.

Examples of the substituted or unsubstituted heteroaryl group having 5 to 50 carbon atoms forming a ring represented by $R_1$ to $R_8$ in the general formula (2a) include 1-pyrrolyl group, 2-pyrrolyl group, 3-pyrrolyl group, pyrazinyl group, 2-pyridinyl group, 3-pyridinyl group, 4-pyridinyl group, 1-indolyl group, 2-indolyl group, 3-indolyl group, 4-indolyl group, 5-indolyl group, 6-indolyl group, 7-indolyl group, 1-isoindolyl group, 2-isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzofuranyl group, quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxalinyl group, 5-quinoxalinyl group, 6-quinoxalinyl group, 1-carbazoryl group, 2-carbazoryl group, 3-carbazoryl group, 4-carbazoryl group, 9-carbazoryl group, 1-phenanthridinyl group, 2-phenanthridinyl group, 3-phenanthridinyl group, 4-phenanthridinyl group, 6-phenanthridinyl group, 7-phenanthridinyl group, 8-phenanthridinyl group, 9-phenanthridinyl group, 10-phenanthridinyl group, 1-acridinyl group, 2-acridinyl group, 3-acridinyl group, 4-acridinyl group, 9-acridinyl group, 1,7-phenanthroline-2-yl group, 1,7-phenanthroline-3-yl group, 1,7-phenanthroline-4-yl group, 1,7-phenanthroline-5-yl group, 1,7-phenanthroline-6-yl group, 1,7-phenanthroline-8-yl group, 1,7-phenanthroline-9-yl group, 1,7-phenanthroline-10-yl group, 1,8-phenanthroline-2-yl group, 1,8-phenanthroline-3-yl group, 1,8-phenanthroline-4-yl group, 1,8-phenanthroline-5-yl group, 1,8-phenanthroline-6-yl group, 1,8-phenanthroline-7-yl group, 1,8-phenanthroline-9-yl group, 1,8-phenanthroline-10-yl group, 1,9-phenanthroline-2-yl group, 1,9-phenanthroline-3-yl group, 1,9-phenanthroline-4-yl group, 1,9-phenanthroline-5-yl group, 1,9-phenanthroline-6-yl group, 1,9-phenanthroline-7-yl group, 1,9-phenanthroline-8-yl group, 1,9-phenanthroline-10-yl group, 1,10-phenanthroline-2-yl group, 1,10-phenanthroline-3-yl group, 1,10-phenanthroline-4-yl group, 1,10-phenanthroline-5-yl group, 2,9-phenanthroline-1-yl group, 2,9-phenanthroline-3-yl group, 2,9-phenanthroline-4-yl group, 2,9-phenanthroline-5-yl group, 2,9-phenanthroline-6-yl group, 2,9-phenanthroline-7-yl group, 2,9-phenanthroline-8-yl group, 2,9-phenanthroline-10-yl group, 2,8-phenanthroline-1-yl group, 2,8-phenanthroline-3-yl group, 2,8-phenanthroline-4-yl group, 2,8-phenanthroline-5-yl group, 2,8-phenanthroline-6-yl group, 2,8-phenanthroline-7-yl group, 2,8-phenanthroline-9-yl group, 2,8-phenanthroline-10-yl group, 2,7-phenanthroline-1-yl group, 2,7-phenanthroline-3-yl group, 2,7-phenanthroline-4-yl group, 2,7-phenanthroline-5-yl group, 2,7-phenanthroline-6-yl group, 2,7-phenanthroline-8-yl group, 2,7-phenanthroline-9-yl group, 2,7-phenanthroline-10-yl group, 1-phenazinyl group, 2-phenazinyl group, 1-phenothiazinyl group, 2-phenothiazinyl group, 3-phenothiazinyl group, 4-phenothiazinyl group, 10-phenothiazinyl group, 1-phenoxazinyl group, 2-phenoxazinyl group, 3-phenoxazinyl group, 4-phenoxazinyl group, 10-phenoxazinyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 2-methylpyrrole-1-yl group, 2-methylpyrrole-3-yl group, 2-methylpyrrole-4-yl group, 2-methylpyrrole-5-yl group, 3-methylpyrrole-1-yl group, 3-methylpyrrole-2-yl group, 3-methylpyrrole-4-yl group, 3-methylpyrrole-5-yl group, 2-t-butylpyrrole-4-yl group, 3-(2-phenylpropyl)pyrrole-1-yl group, 2-methyl-1-indolyl group, 4-methyl-1-indolyl group, 2-methyl-3-indolyl group, 4-methyl-3-indolyl group, 2-t-butyl-1-indolyl group, 4-t-butyl-1-indolyl group, 2-t-butyl-3-indolyl group, 4-t-butyl-3-indolyl group, etc.

Examples of the substituted or unsubstituted alkyl group having 1 to 50 carbon atoms represented by $R_1$ to $R_8$ in the general formula (2a) include methyl group, ethyl group, propyl group, isopropyl group, n-butyl group, s-butyl group, isobutyl group, t-butyl group, n-pentyl group, n-hexyl group, n-heptyl group, n-octyl group, hydroxymethyl group, 1-hydroxyethyl group, 2-hydroxyethyl group, 2-hydroxyisobutyl group, 1,2-dihydroxyethyl group, 1,3-dihydroxyisopropyl group, 2,3-dihydroxy-t-butyl group, 1,2,3-trihydroxypropyl group, chloromethyl group, 1-chloroethyl group, 2-chloroethyl group, 2-chloroisobutyl group, 1,2-dichloroethyl group, 1,3-dichloroisopropyl group, 2,3-dichloro-t-butyl group, 1,2,3-trichloropropyl group, bromomethyl group, 1-bromoethyl group, 2-bromoethyl group, 2-bromoisobutyl group, 1,2-dibromoethyl group, 1,3-dibromoisopropyl group, 2,3-dibromo-t-butyl group, 1,2,3-tribromopropyl group, iodomethyl group, 1-iodoethyl group, 2-iodoethyl group, 2-iodoisobutyl group, 1,2-diiodoethyl group, 1,3-diiodoisopropyl group, 2,3-diiodo-t-butyl group, 1,2,3-triiodopropyl group, aminomethyl group, 1-aminoethyl group, 2-aminoethyl group, 2-aminoisobutyl group, 1,2-diaminoethyl group, 1,3-diaminoisopropyl group, 2,3-diamino-t-butyl group, 1,2,3-triaminopropyl group, cyanomethyl group, 1-cyanoethyl group, 2-cyanoethyl group, 2-cyanoisobutyl group, 1,2-dicyanoethyl group, 1,3-dicyanoisopropyl group, 2,3-dicyano-t-butyl group, 1,2,3-tricyanopropyl group, nitromethyl group, 1-nitroethyl group, 2-nitroethyl group, 2-nitroisobutyl group, 1,2-dinitroethyl group, 1,3-dinitroisopropyl group, 2,3-dinitro-t-butyl group, 1,2,3-trinitropropyl group, etc.

Examples of the substituted or unsubstituted cycloalkyl group having 3 to 50 carbon atoms represented by $R_1$ to $R_8$ in the general formula (2a) and the substituent for the above aromatic ring include cyclopropyl group, cyclobutyl group, cyclopentyl group, cyclohexyl group, 4-methylcyclohexyl group, 1-adamantyl group, 2-adamantyl group, 1-norbornyl group, 2-norbornyl group, etc.

Examples of the substituted or unsubstituted alkoxy group having 1 to 50 carbon atoms represented by $R_1$ to $R_8$ in the general formula (2a) and the substituent for the above aromatic ring is a group expressed by —OY and examples of Y are the same as described about the foregoing substituted or unsubstituted alkyl group having 1 to 50 carbon atoms represented by $R_1$ to $R_8$ and as the substituent for the above aromatic groups.

Examples of the substituted or unsubstituted aralkyl group having 6 to 50 carbon atoms represented by $R_1$ to $R_8$ in the general formula (2a) and the substituent for the above aromatic ring include benzyl group, 1-phenylethyl group, 2-phenylethyl group, 1-phenylisopropyl group, 2-phenylisopropyl group, phenyl-t-butyl group, a-naphthylmethyl group, 1-a-naphthylethyl group, 2-a-naphthylethyl group, 1-a-naphthylisopropyl group, 2-a-naphthylisopropyl group, β-naphthylmethyl group, 1-β-naphthylethyl group, 2-β-naphthylethyl group, 1-β-naphthylisopropyl group, 2-β-naphthylisopropyl group, 1-pyrrolylmethyl group, 2-(1-pyrrolyl)ethyl group, p-methylbenzyl group, m-methylbenzyl group, o-methylbenzyl group, p-chlorobenzyl group, m-chlorobenzyl group, o-chlorobenzyl group, p-bromobenzyl group, m-bromobenzyl group, o-bromobenzyl group, p-iodobenzyl group, m-iodobenzyl group, o-iodobenzyl group, p-hydroxybenzyl group, m-hydroxybenzyl group, o-hydroxybenzyl group, p-aminobenzyl group, m-aminobenzyl group, o-aminobenzyl group, p-nitrobenzyl group, m-nitrobenzyl group, o-nitrobenzyl group, p-cyanobenzyl group, m-cyanobenzyl group, o-cyanobenzyl group, 1-hydroxy-2-phenylisopropyl group, 1-chloro-2-phenylisopropyl group, etc.

The substituted or unsubstituted aryloxy group having 5 to 50 atoms forming a ring and the substituted or unsubstituted arylthio group having 5 to 50 atoms forming a ring both represented by $R_1$ to $R_8$ in the general formula (2a) and the substituent for the above aromatic ring is a group expressed by —OY' and —SY'' respectively and examples of Y' and Y'' are the same as described about the foregoing substituted or unsubstituted aryl group having 5 to 50 atoms forming a ring.

The substituted or unsubstituted alkoxycarbonyl group having 1 to 50 carbon atoms represented by $R_1$ to $R_8$ in the general formula (2a) and the substituent for the above aromatic ring is a group expressed by —COOZ and examples of Z are the same as described about the foregoing substituted or unsubstituted alkyl group having 1 to 50 carbon atoms represented by $R_1$ to $R_8$ and as the substituent for the above aromatic groups.

Examples of the silyl group represented by $R_1$ to $R_8$ in the general formula (2a) and the substituent for the above aromatic ring include trimethylsilyl group, triethylsilyl group, t-butyldimethylsilyl group, vinyldimethylsilyl group, propyldimethylsilyl group, triphenylsilyl group, etc.

Examples of the halogen atom represented by $R_1$ to $R_8$ in the general formula (2a) and the substituent for the above aromatic ring include fluorine atom, chlorine atom, bromine atom, iodine atom, etc.

Examples of the substituent of the groups represented by the above $R_1$ to $R_8$ and the substituent for the above aromatic ring include halogen atoms, hydroxy groups, nitro groups, cyano groups, alkyl groups, aryl groups, cycloalkyl groups, alkoxy groups, aromatic heterocyclic groups, aralkyl groups, aryloxy groups, arylthio groups, alkoxycarbonyl groups and carboxy groups.

It is preferable that the anthracene derivative represented by the general formula (2a) corresponds to a compound having a structure shown by the following general formula (2a');

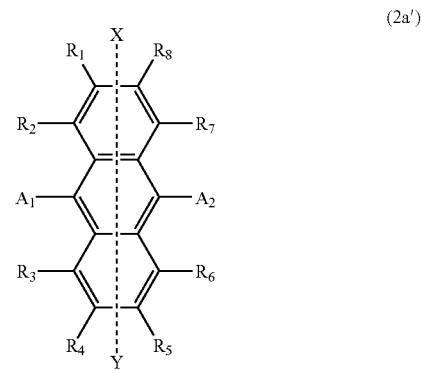

(2a')

(In the formula (2a'), $A_1, A_2$, and $R_1$ to $R_8$ each independently represents the same as about the general formula (2a), and the specific examples include the same as those described above; with the proviso that, in the general formula (2a'), the groups at 9- and 10-positions of the central anthracene are not symmetrical with respect to the X-Y axis.)

Specific examples of the anthracene derivative represented by the general formula (2a) employed for the organic EL device of the present invention include various kinds of publicly known anthracene derivative such as the anthracene derivative having two anthracene skeletons in its molecule which is shown in paragraphs of [0043] to [0063] of JP 2004-356033 A, the compound having a single anthracene skeleton in itself which is shown on pages 27 and 28 of International PCT publication WO 2005/061656 pamphlet, etc. Typical examples are shown below.
2a-1
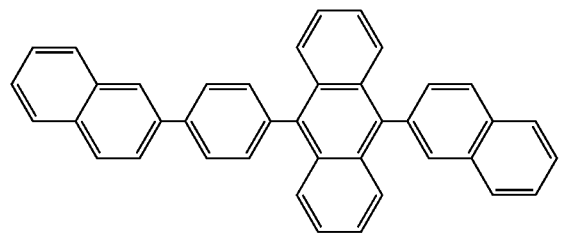
2a-2
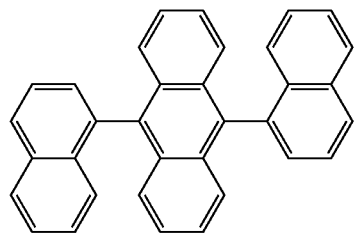
2a-3
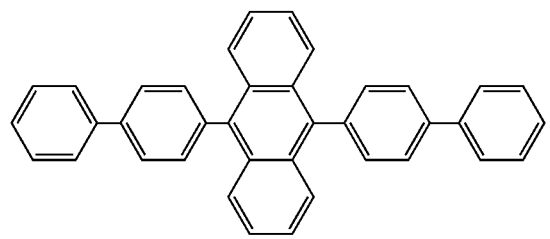
2a-4
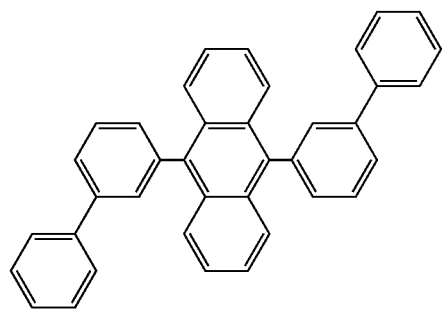
2a-5
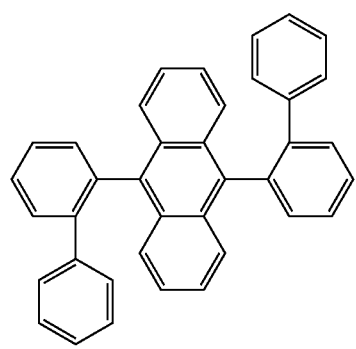
2a-6
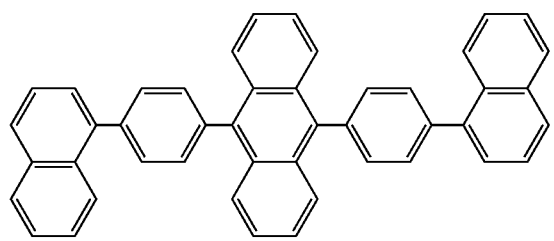
2a-7
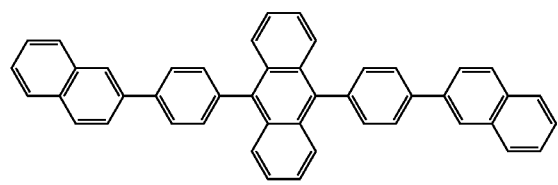
2a-8
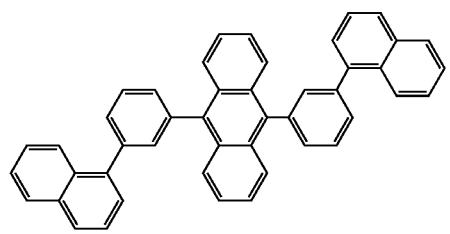
2a-9
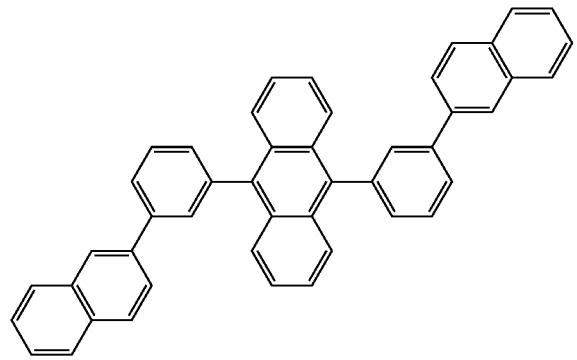
2a-10
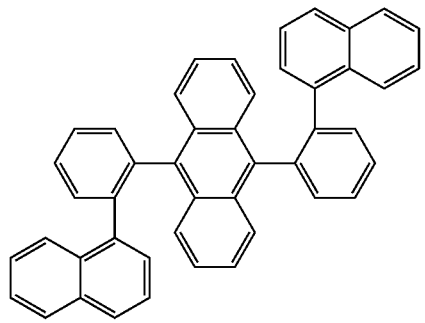

-continued
2a-11
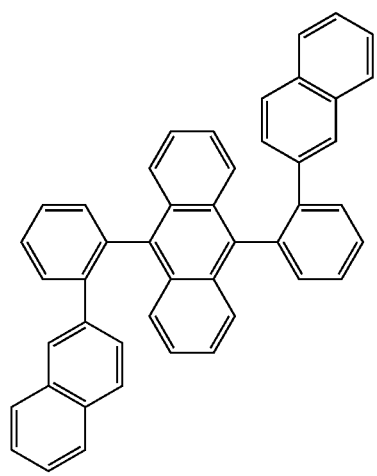
2a-12
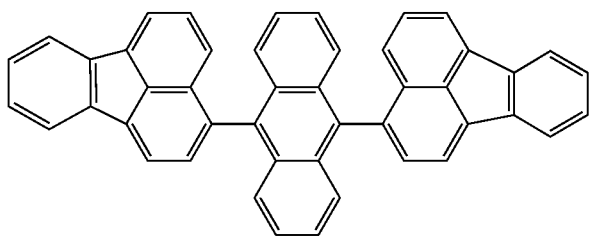
2a-13
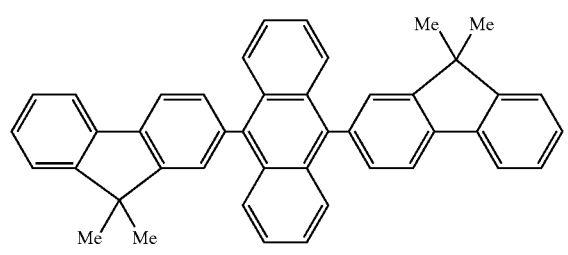
2a-14
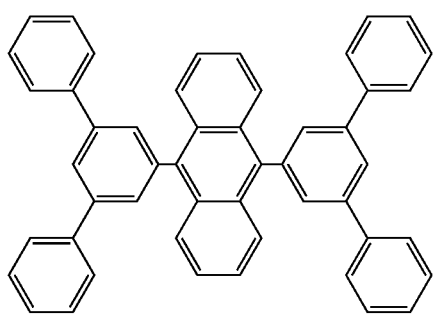
2a-15
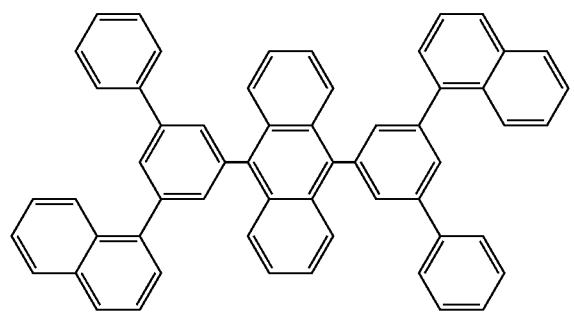
2a-16
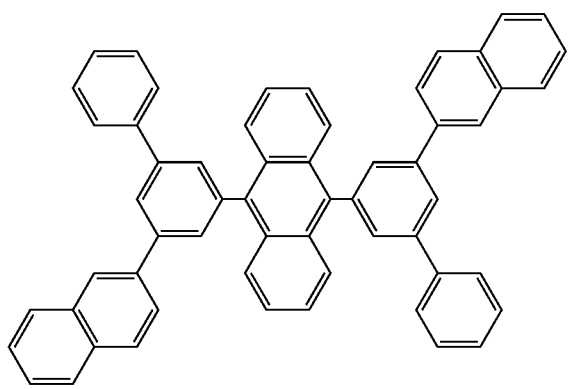
2a-17
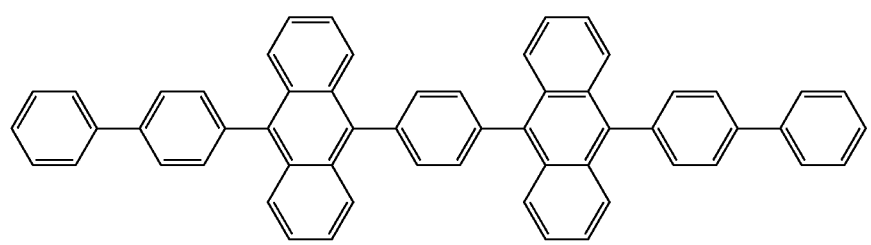

2a-18
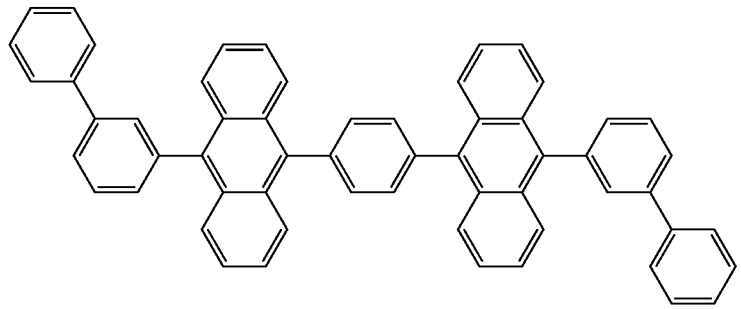
2a-19
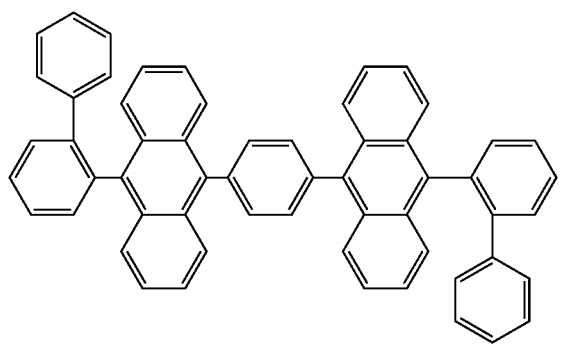
2a-20
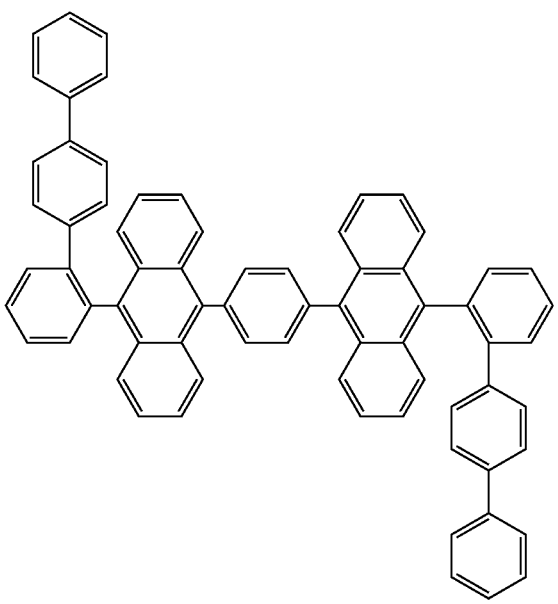
2a-21
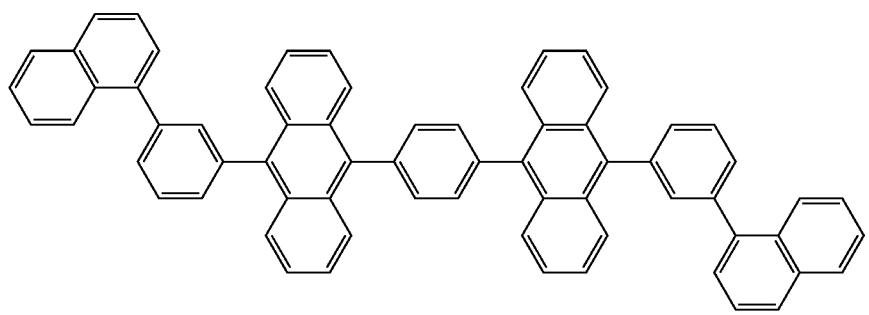
2a-22
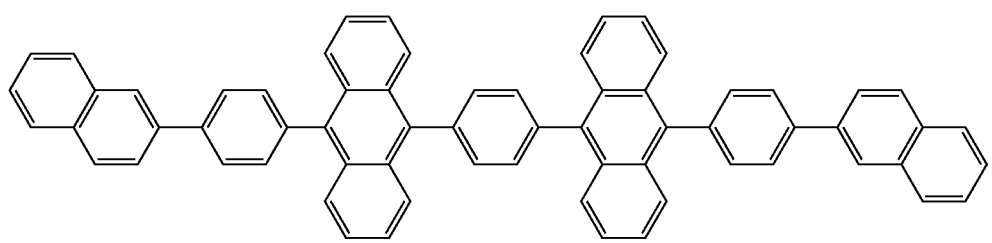

2a-23
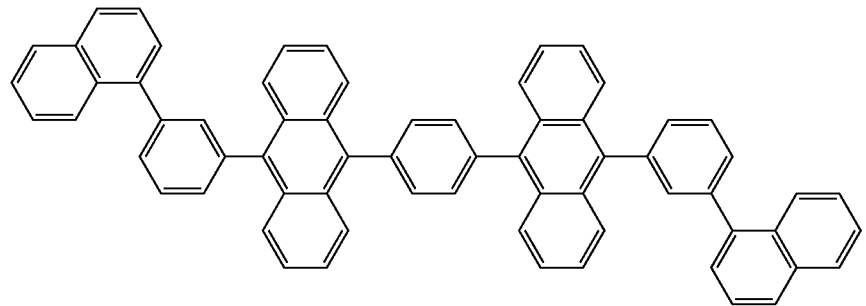
2a-24
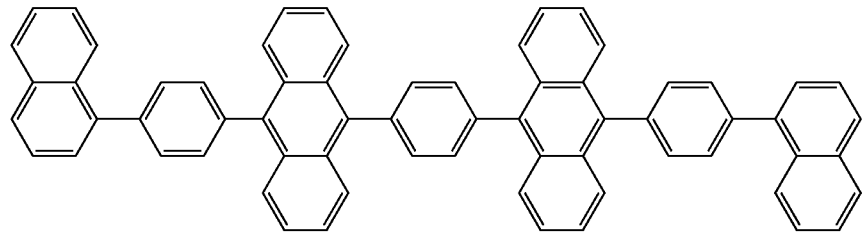
2a-25 2a-26
2a-27 2a-28
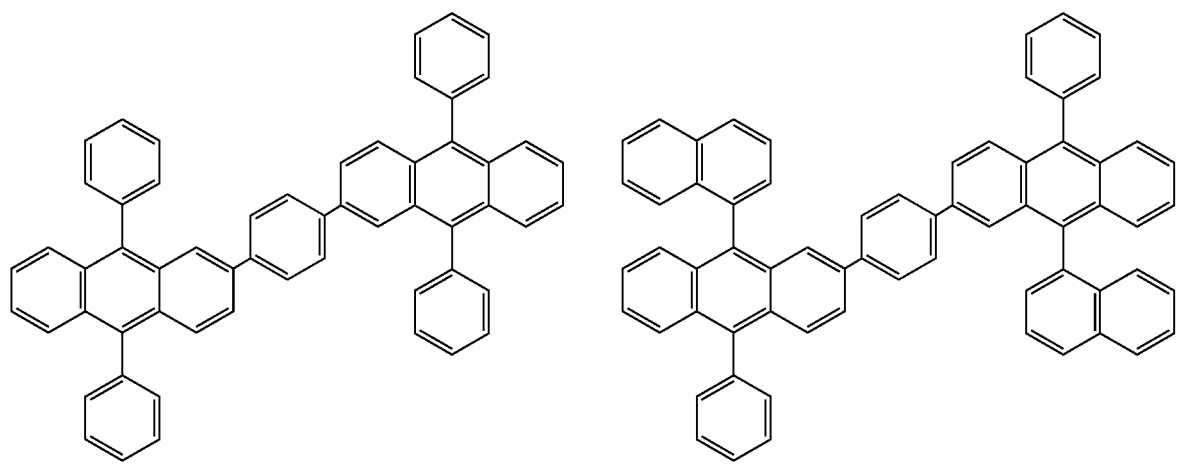
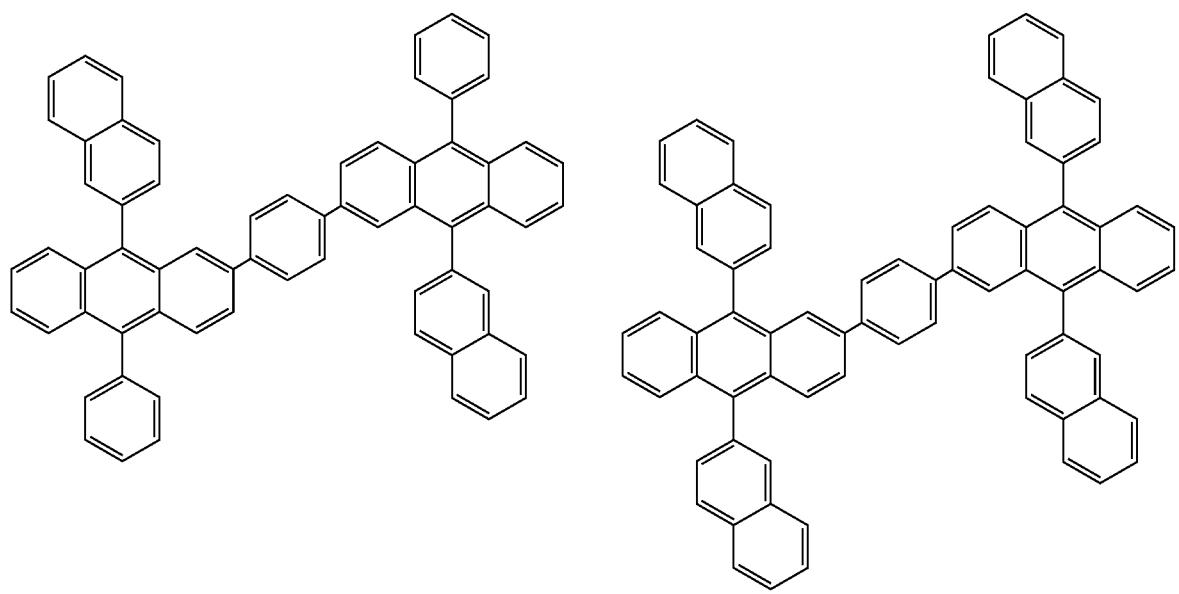

2a-29
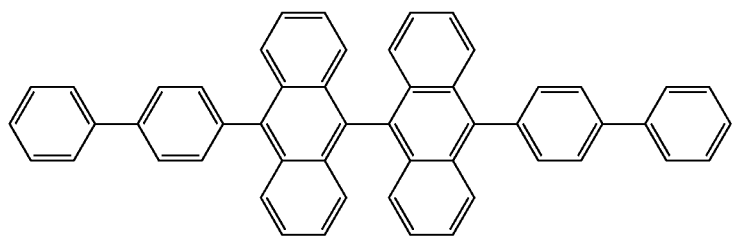
2a-30
2a-31
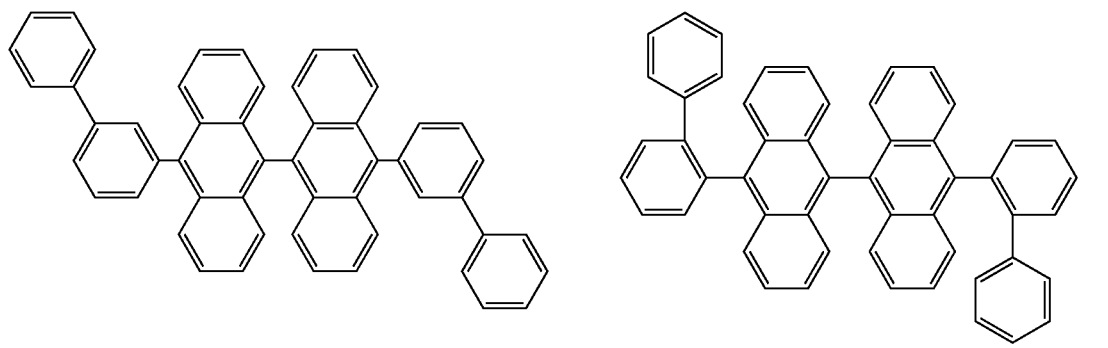
2a-32
2a-33
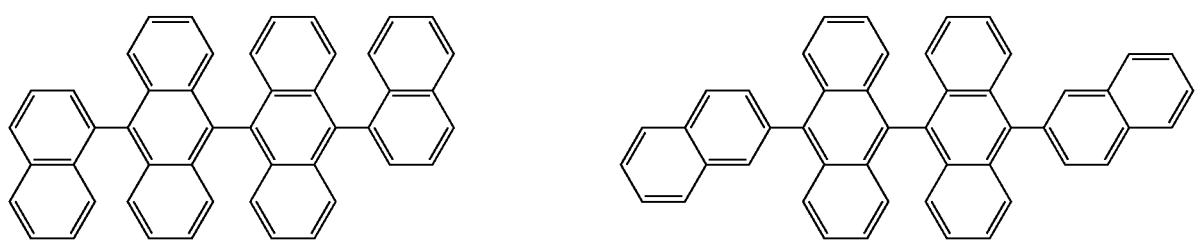
2a-34
2a-35
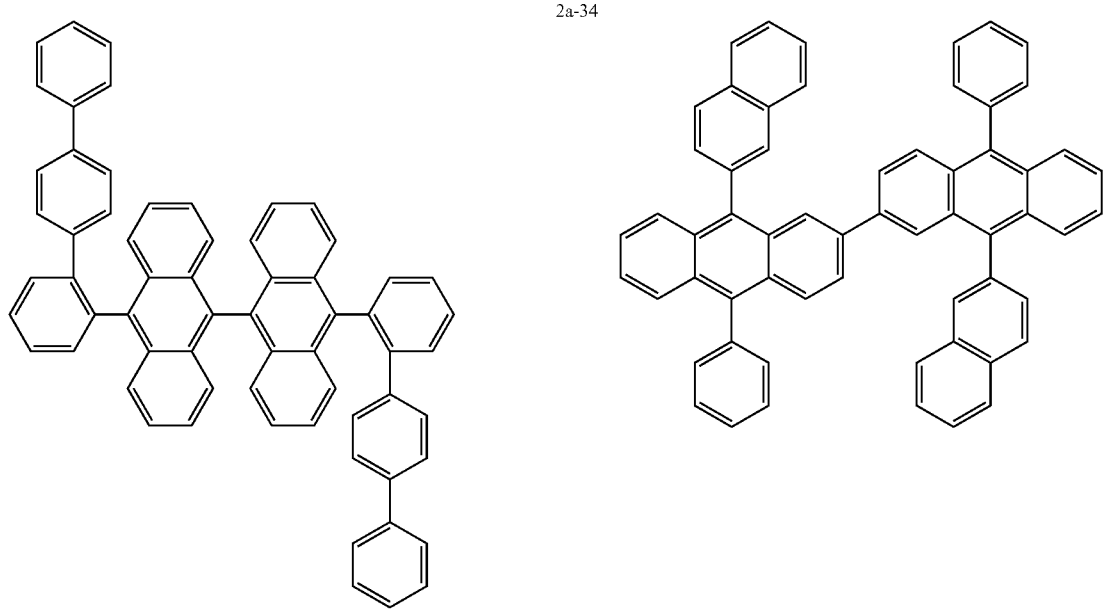

-continued
2a-36
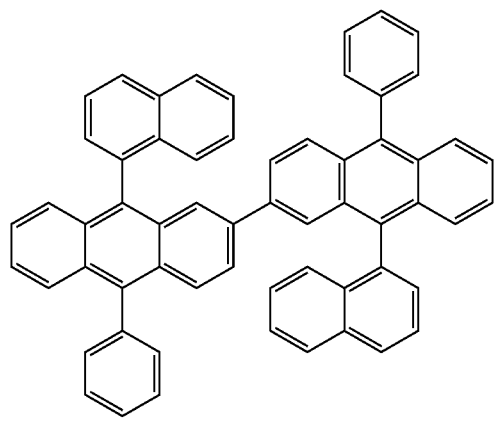
2a-37
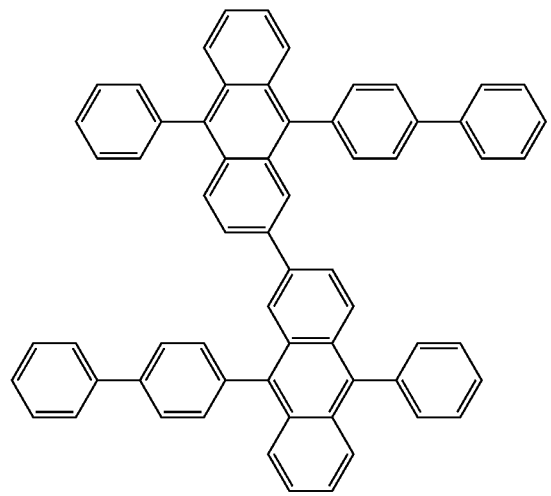
2a-38
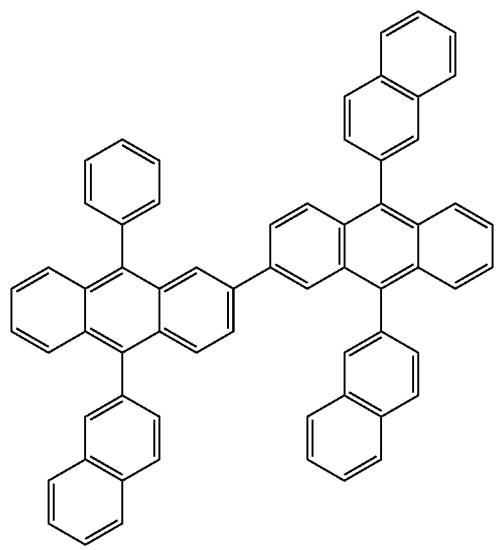
2a-39
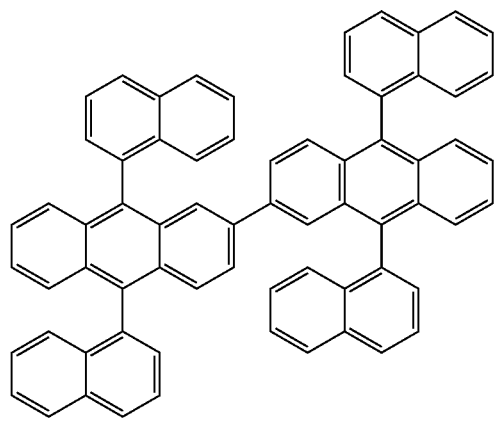
2a-40
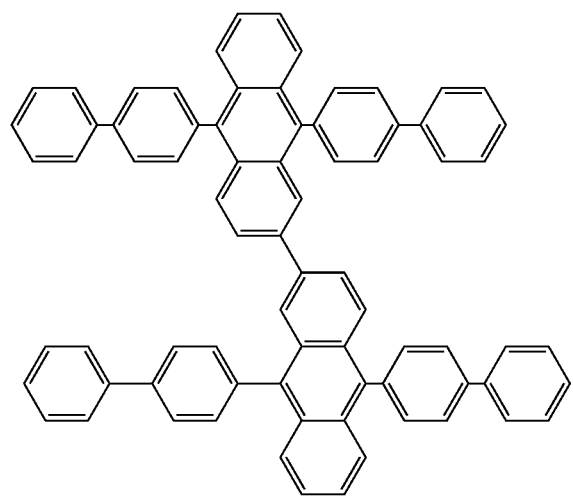
2a-41
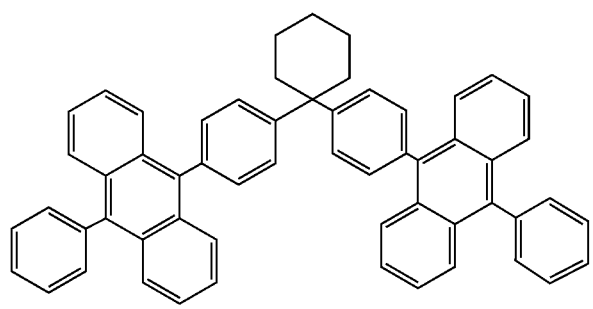

-continued
2a-42
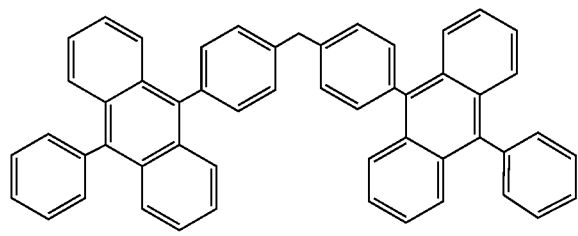
2a-43
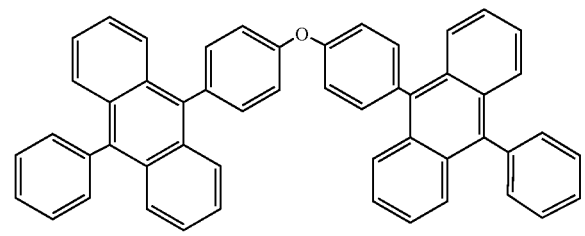
2a-44
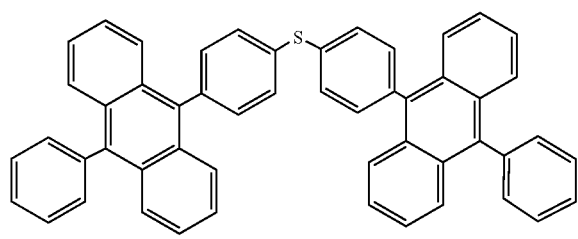
2a-45
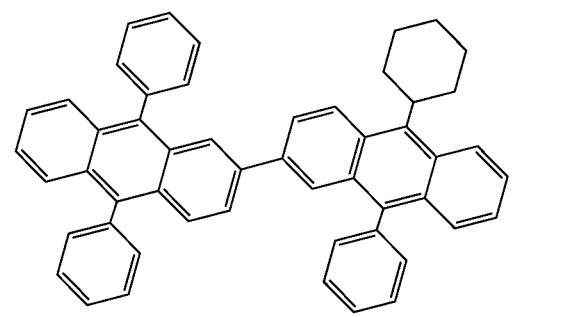
2a-46
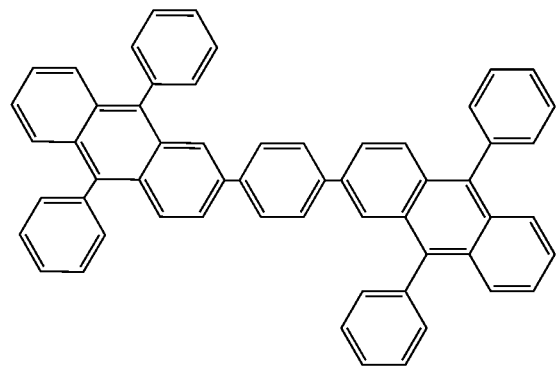
2a-47
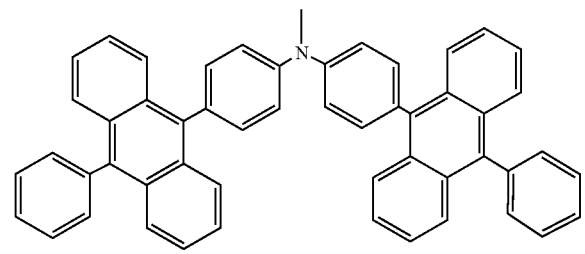
2a-48
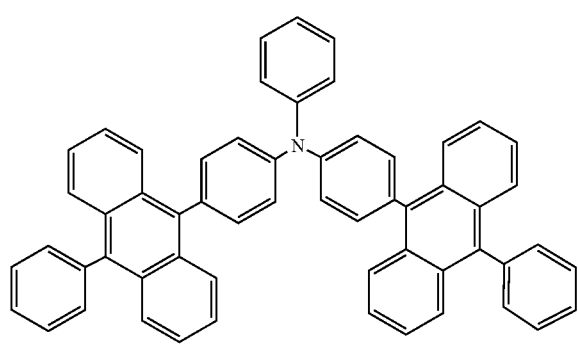
2a-49
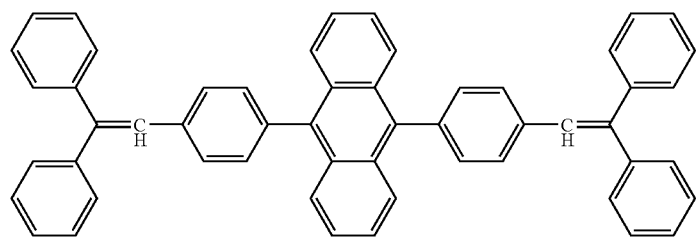

-continued
2a-50
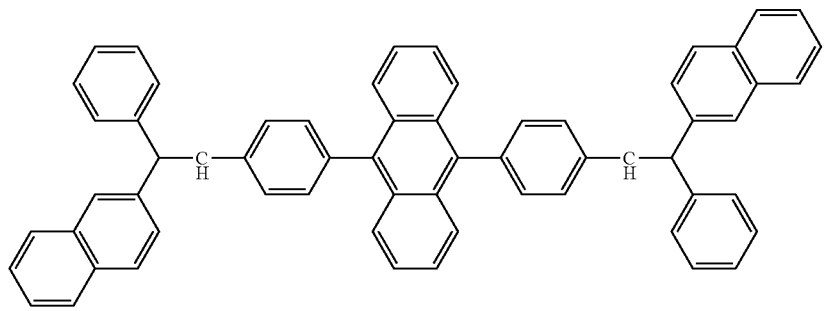
2a-51
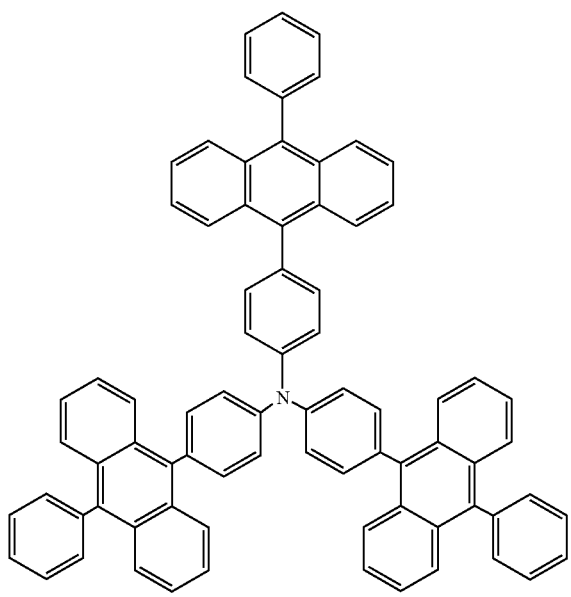
2a'-52
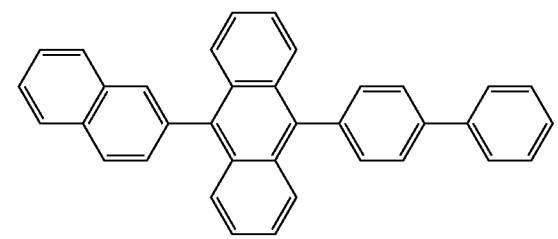
2a'-53
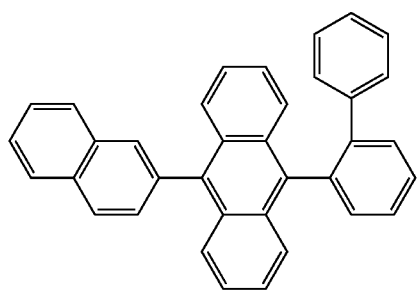
2a'-54
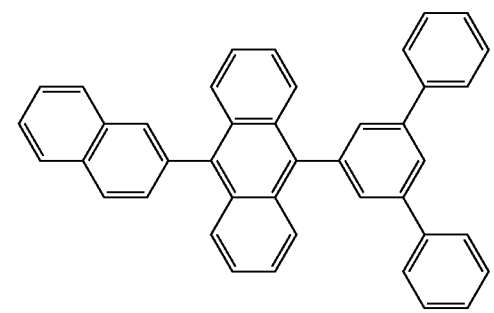
2a'-55
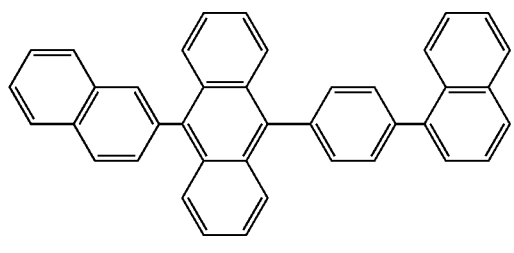
2a'-56
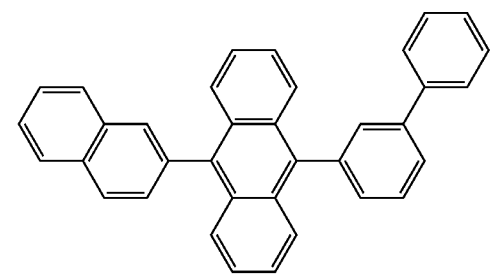

-continued
2a'-57
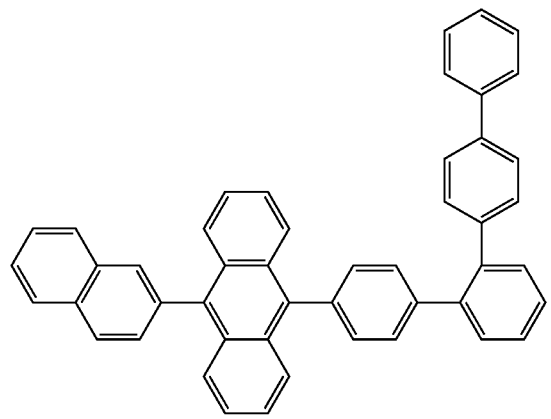
2a'-58
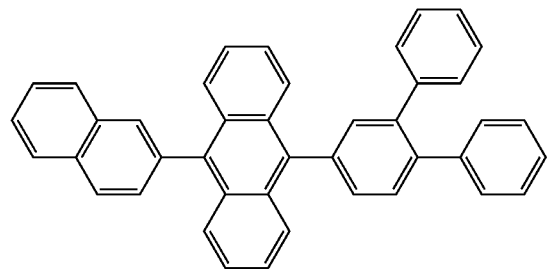
2a'-59
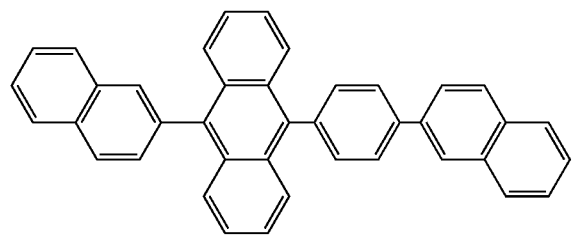
2a'-60
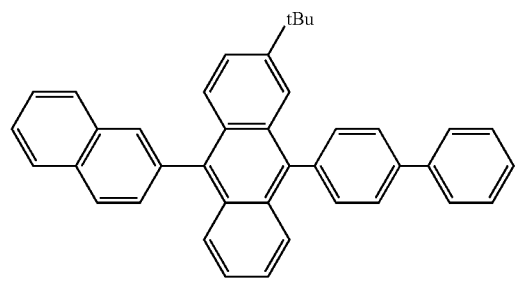
2a'-61
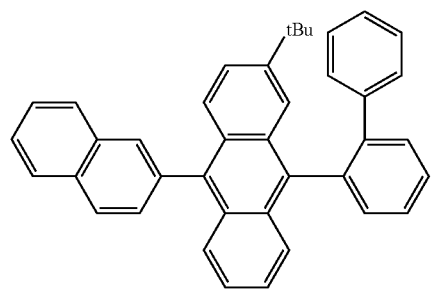
2a'-62
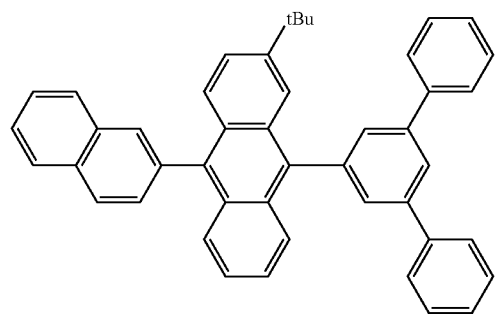
2a'-63
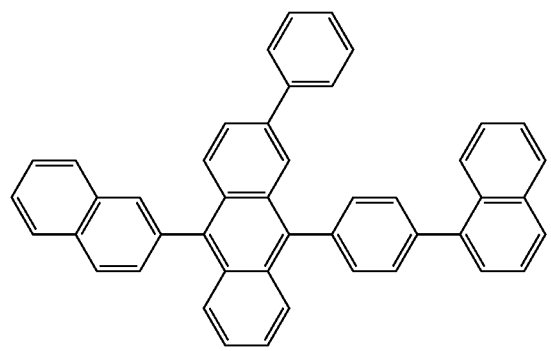
2a'-64
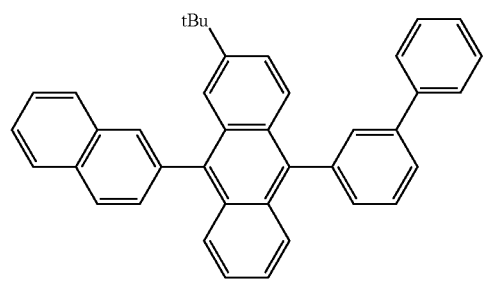

-continued
2a'-65
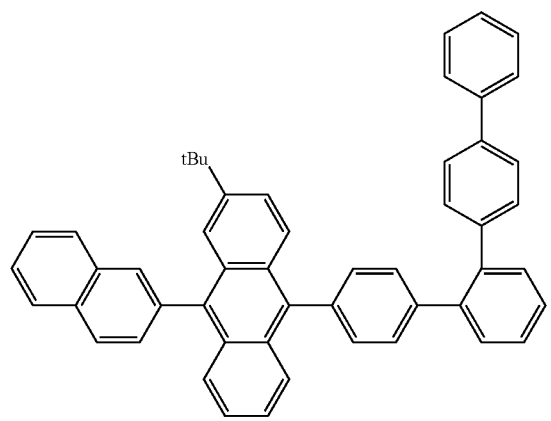
2a'-66
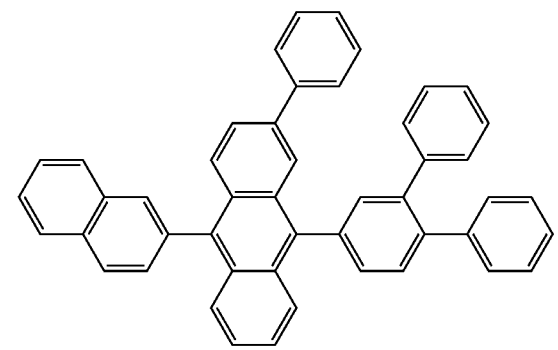
2a'-67
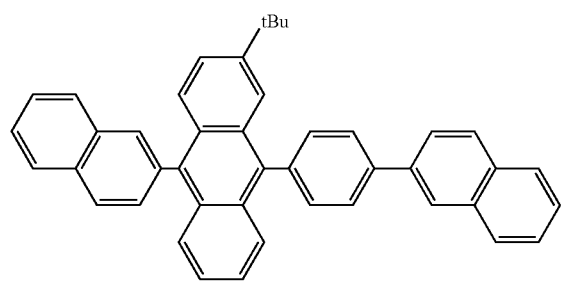
2a'-68
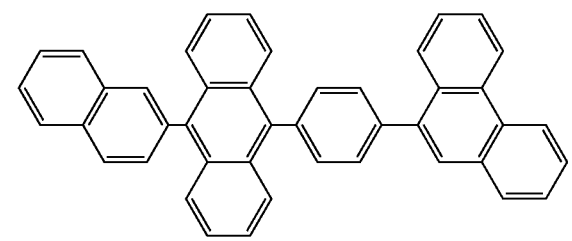
2a'-69
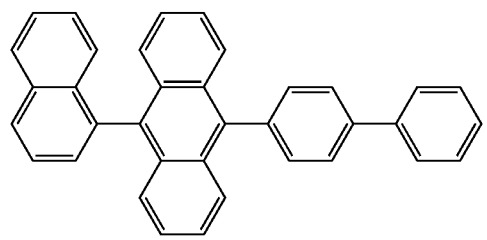
2a'-70
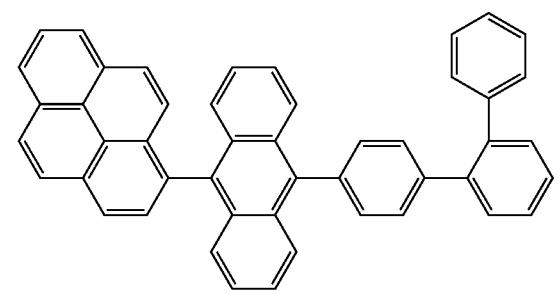
2a'-71
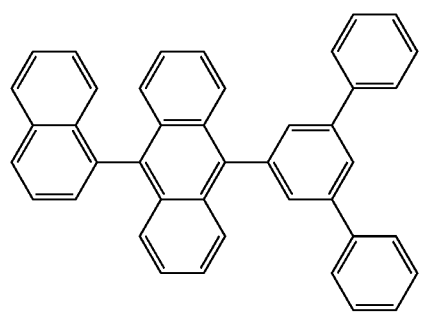
2a'-72
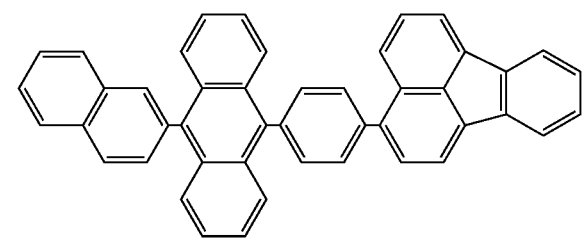

-continued
2a'-73
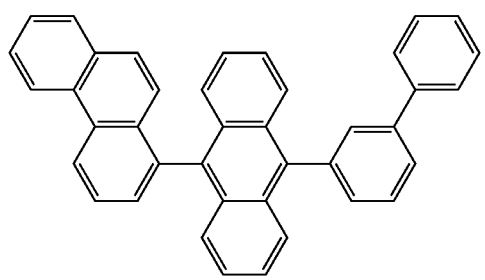
2a'-74
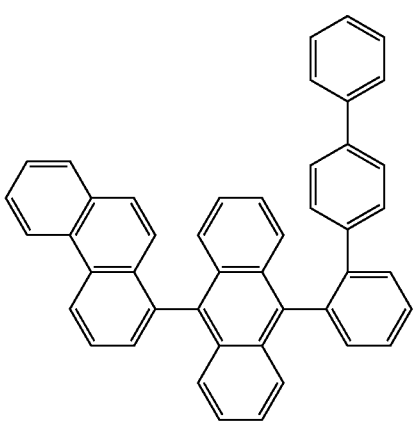
2a'-75
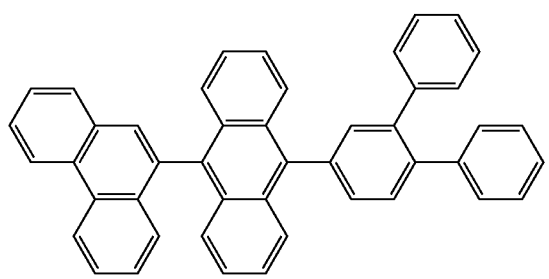
2a'-76
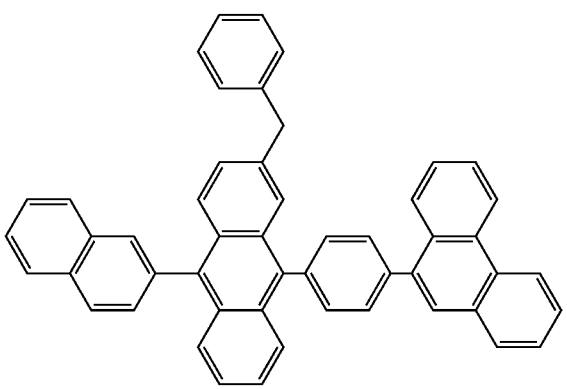
2a'-77
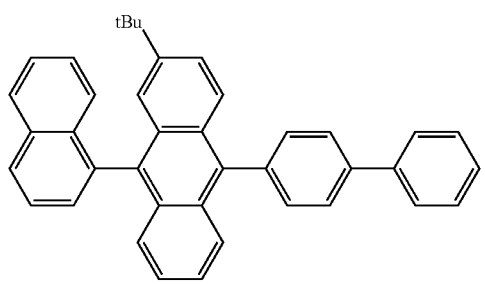
2a'-78
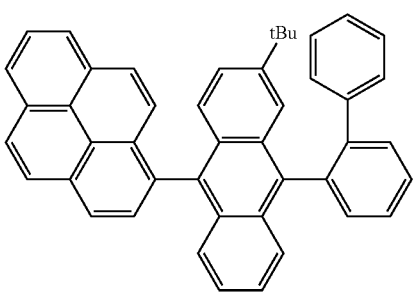
2a'-79
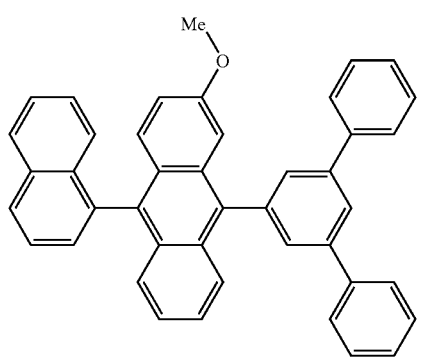
2a'-80
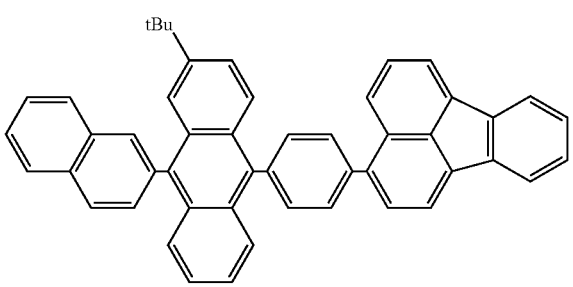

2a'-81
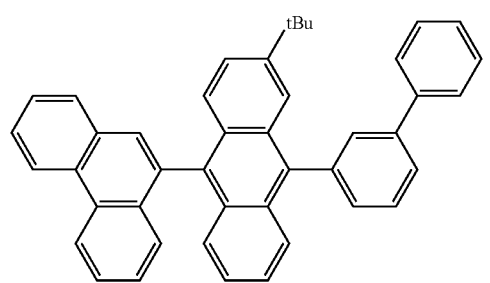
2a'-82
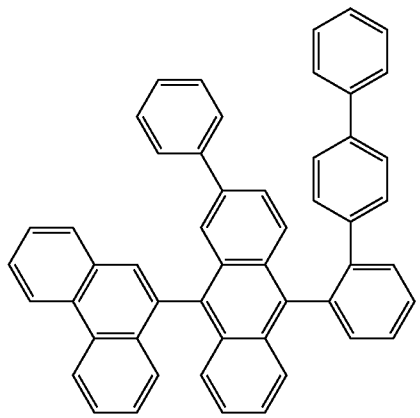
2a'-83
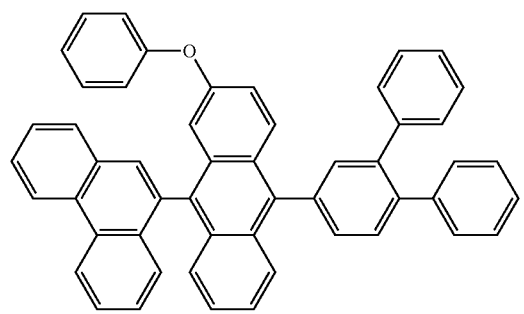
2a'-84
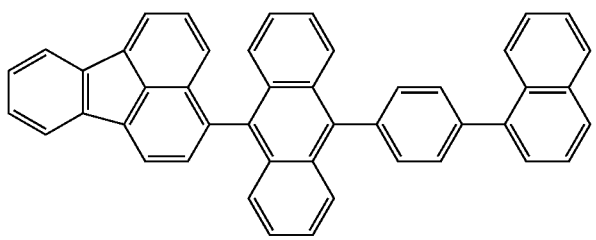
2a'-85
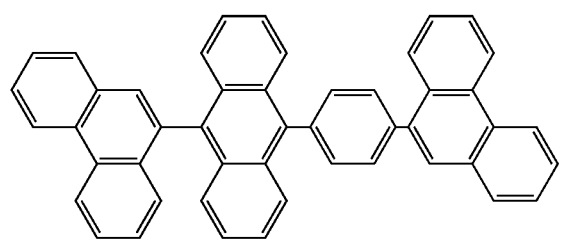
2a'-86
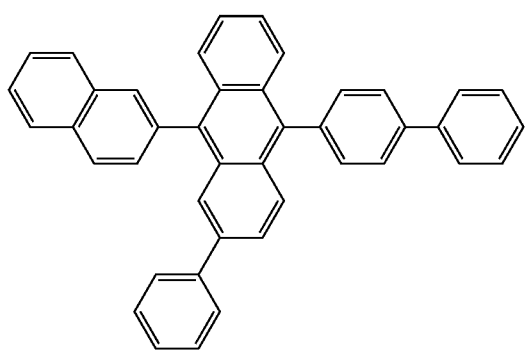
2a'-87
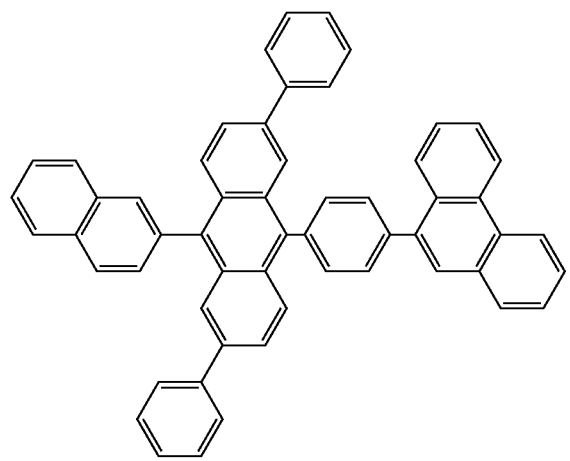
2a'-88
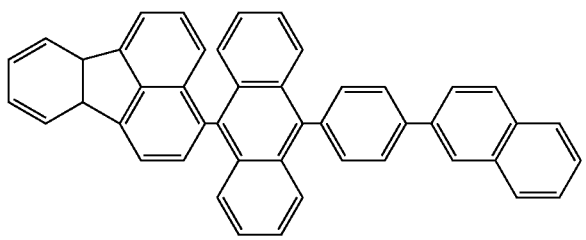

2a'-89
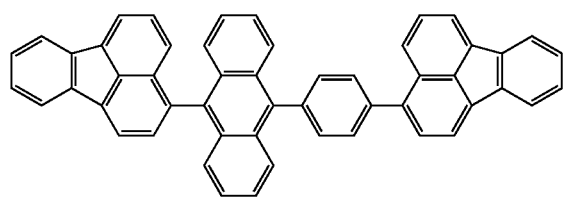
2a'-90
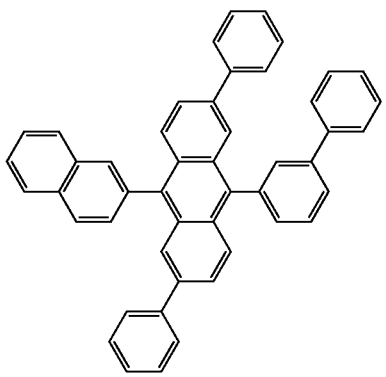
2a'-91
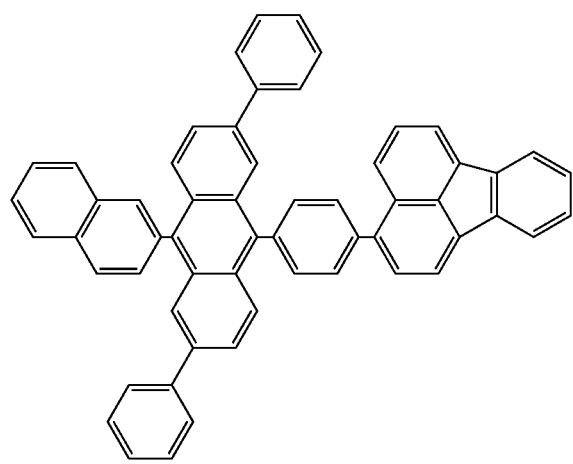
2a'-92
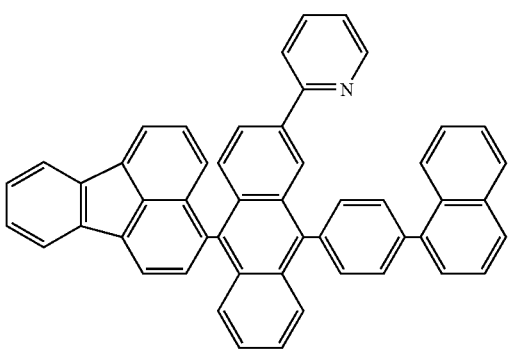
2a'-93
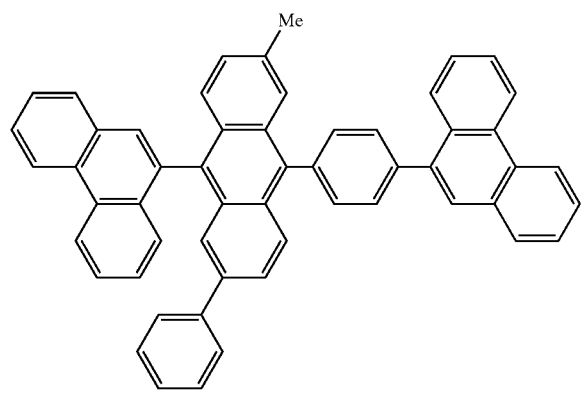
2a'-94
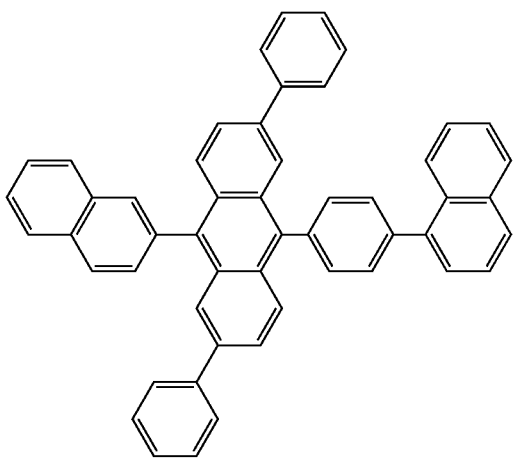

-continued
2a'-95
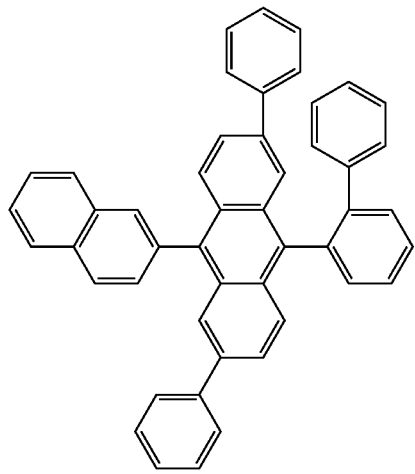
2a'-96
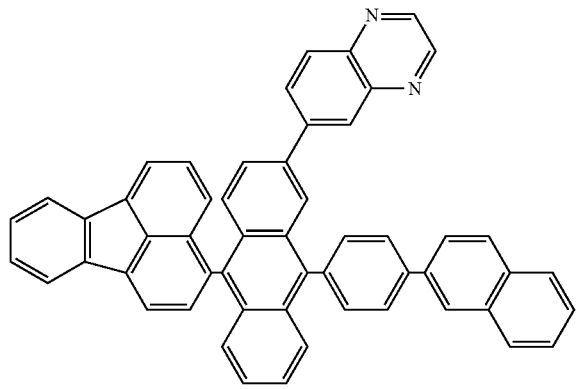
2a'-97
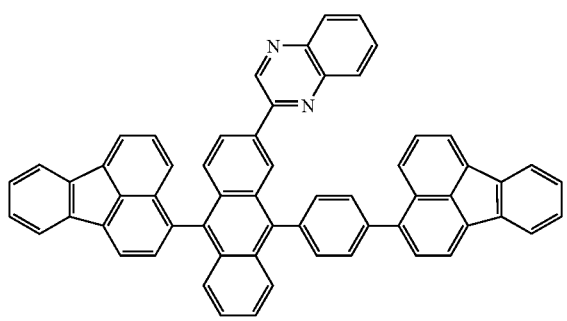
2a'-98
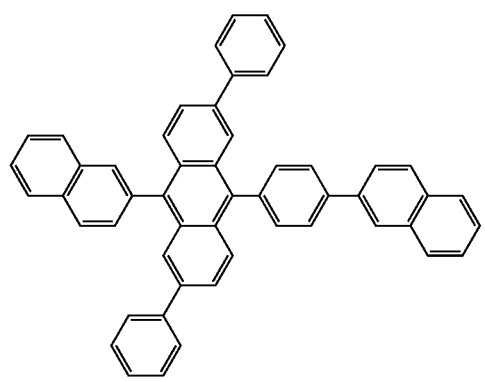
2a'-99
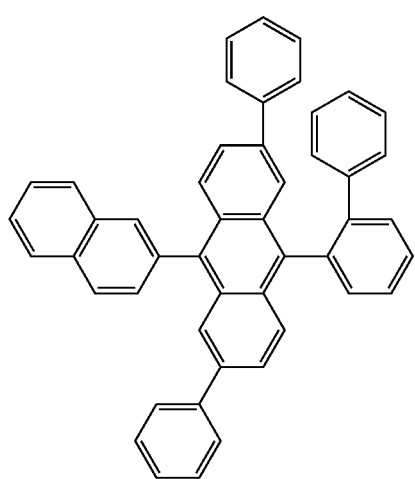
2a'-100
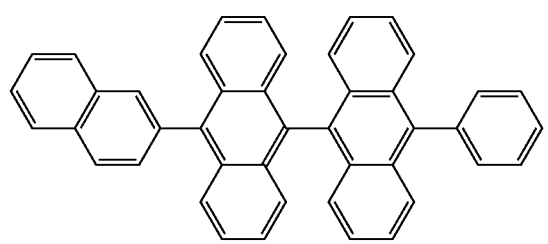

-continued
2a′-101
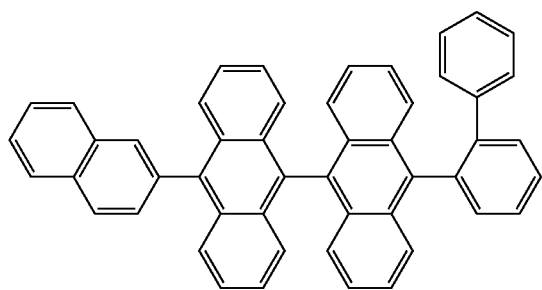
2a′-102
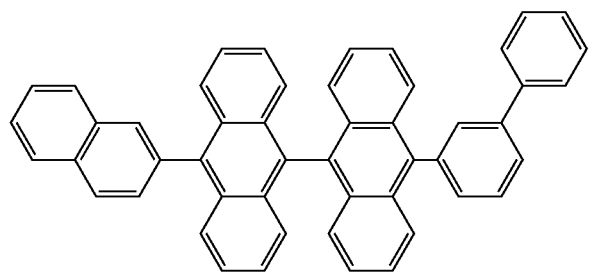
2a′-103
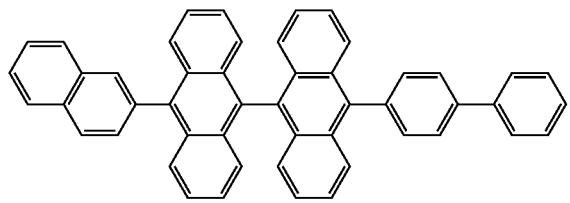
2a′-104
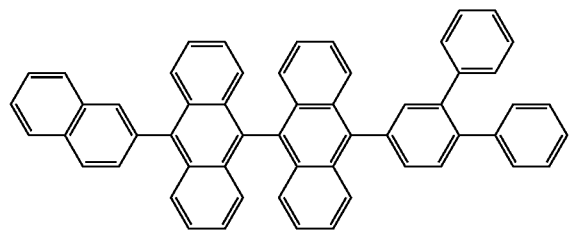
2a′-105
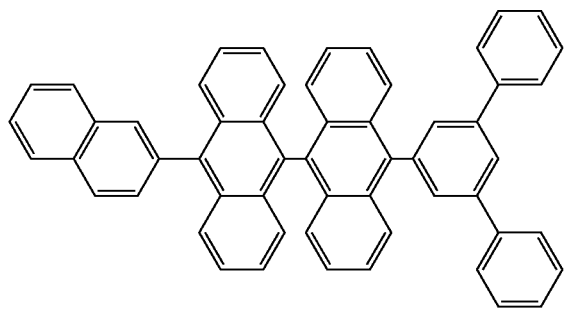
2a′-106
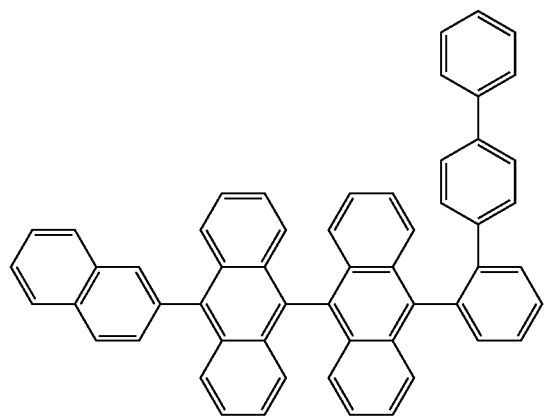
2a′-107
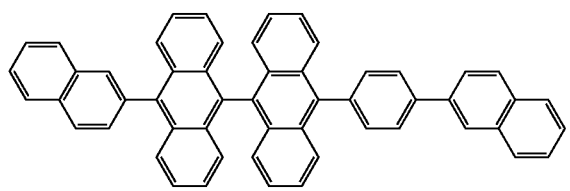
2a′-108
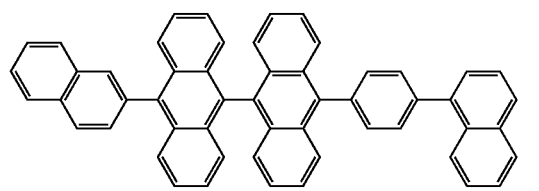
2a′-109
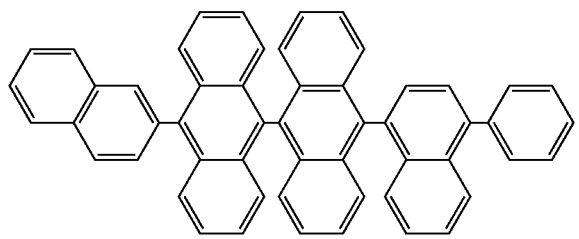
2a′-110
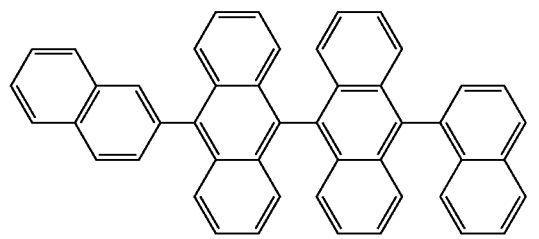

-continued
2a′-111
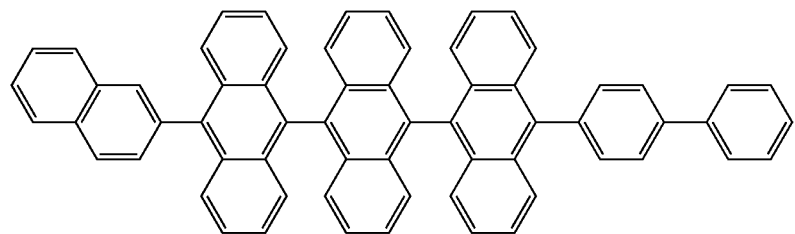
2a′-112
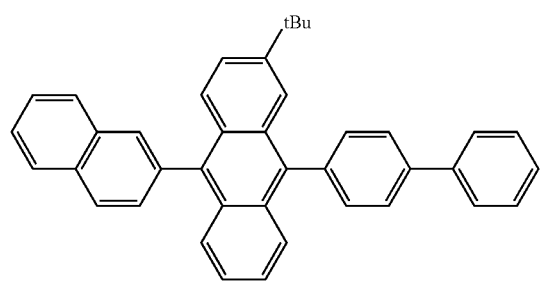
2a′-113
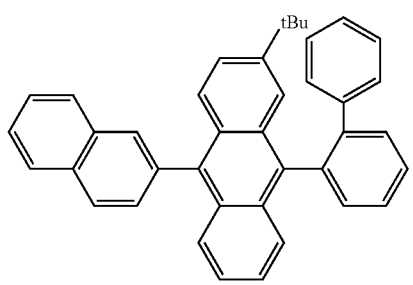
2a′-114
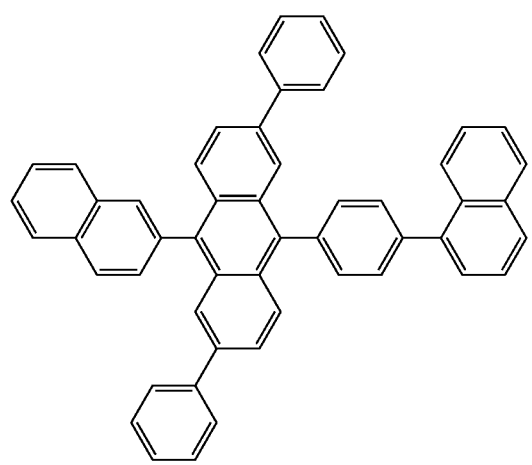
2a′-115
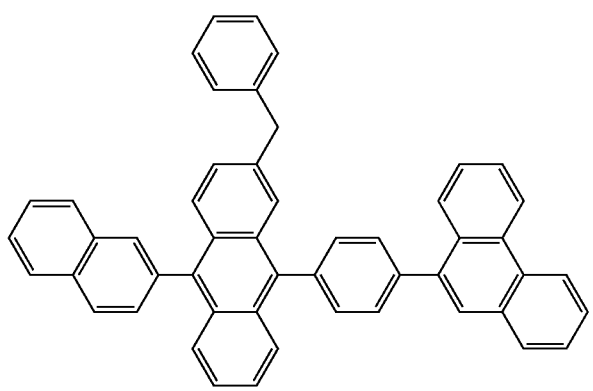
2a′-116
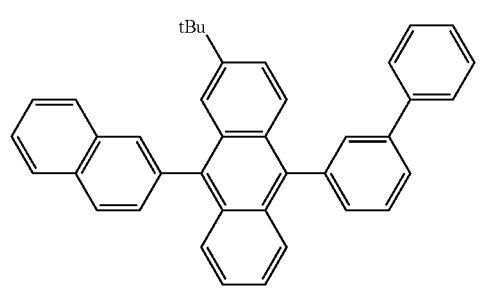
2a′-117
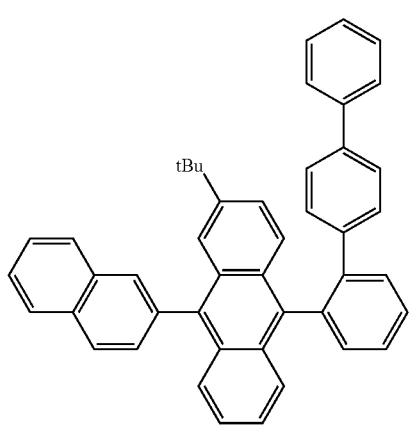

-continued
2a′-118
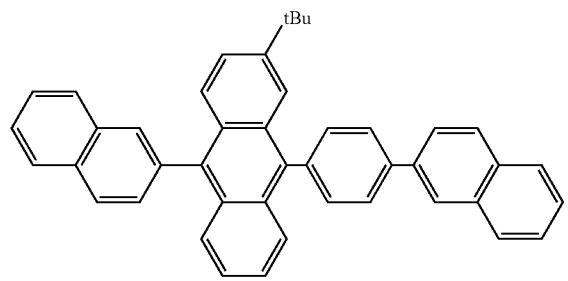
2a′-119
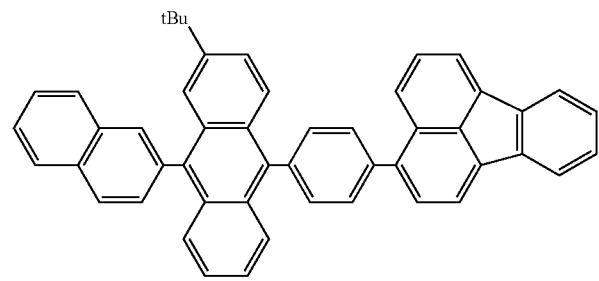
2a′-120
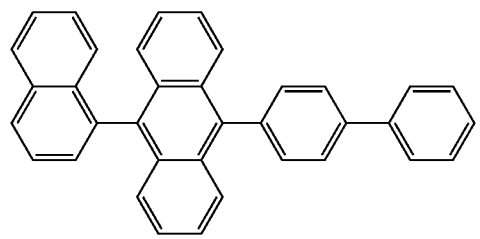
2a′-121
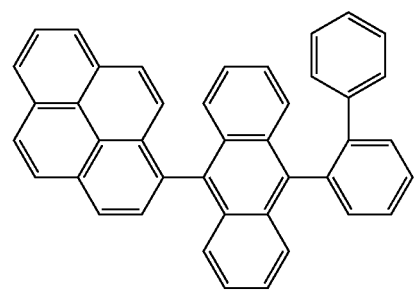
2a′-122
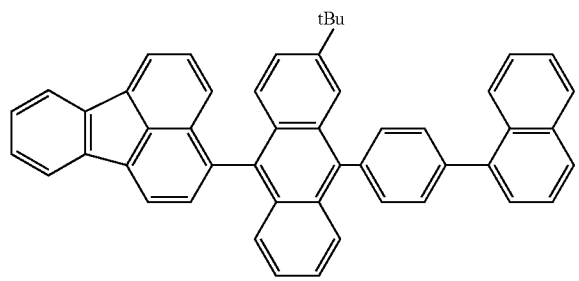
2a′-123
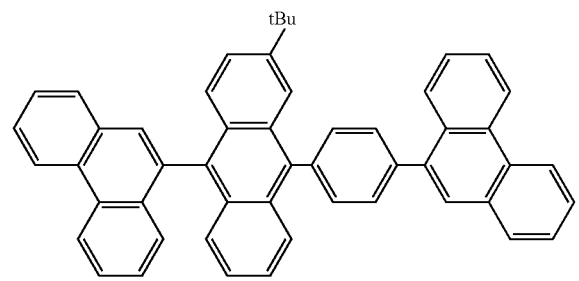
2a′-124
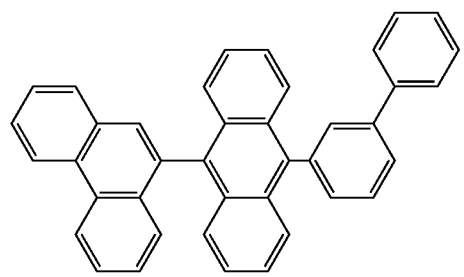
2a′-125
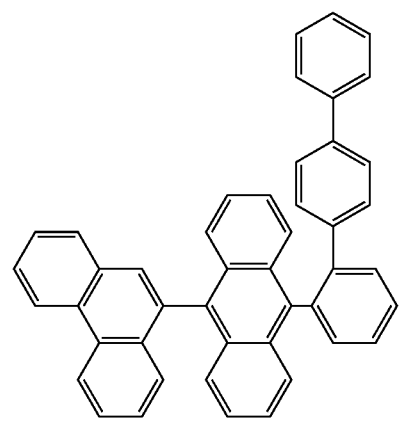
2a′-126
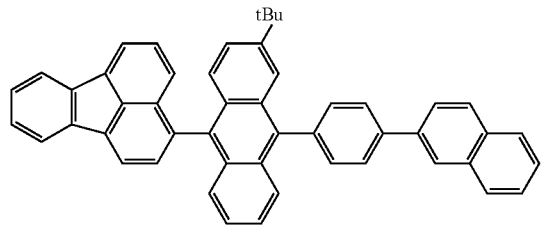
2a′-127
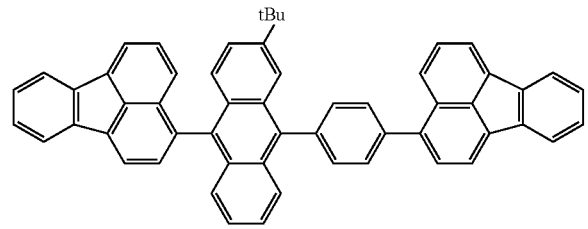

-continued
| 2a'-128 | 2a'-129 |
|---|---|
| 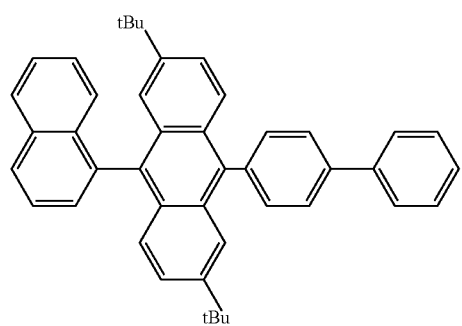 | 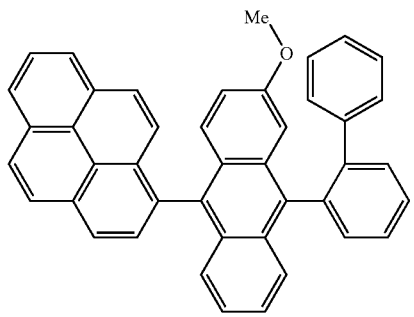 |
| 2a'-130 | 2a'-131 |
|---|---|
| 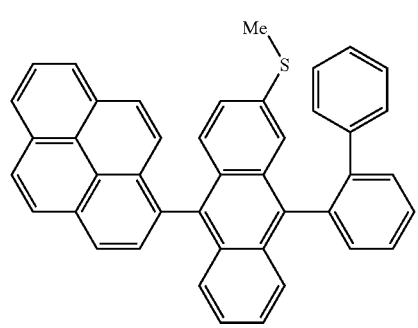 | 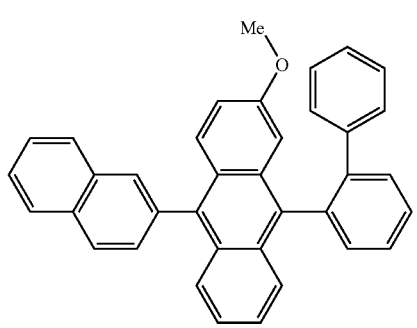 |
| 2a'-132 | 2a'-133 |
|---|---|
| 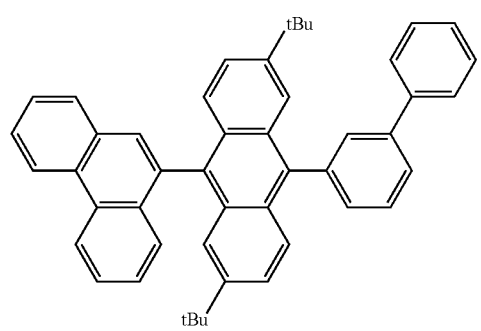 | 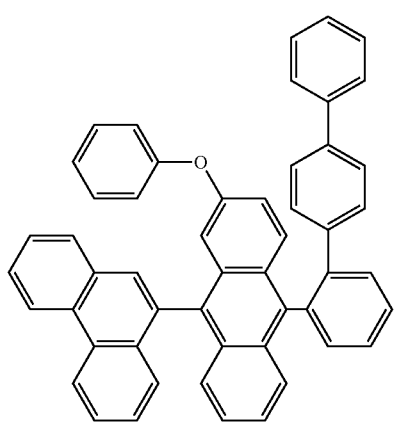 |
| 2a'-134 | 2a'-135 |
|---|---|
| 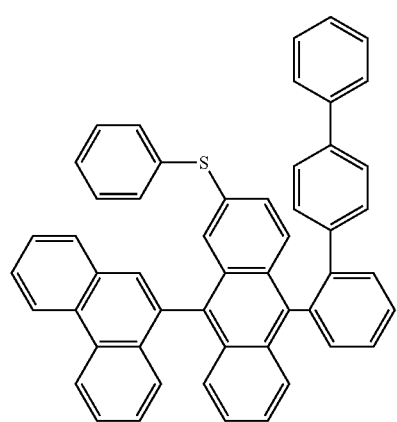 | 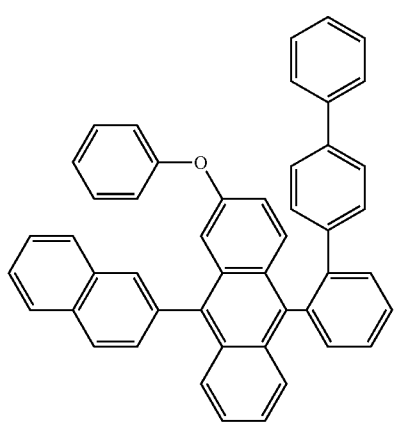 |

-continued
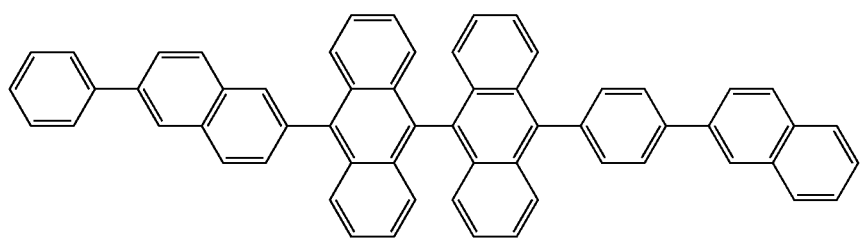
2a'-136
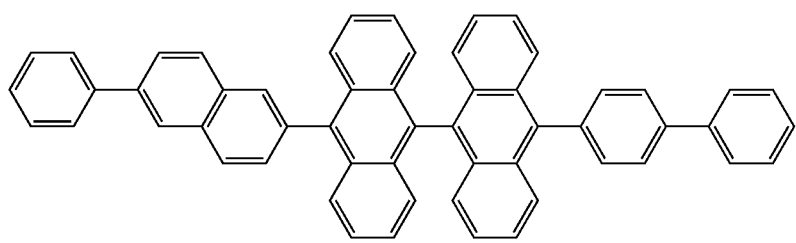
2a'-137
2a'-138
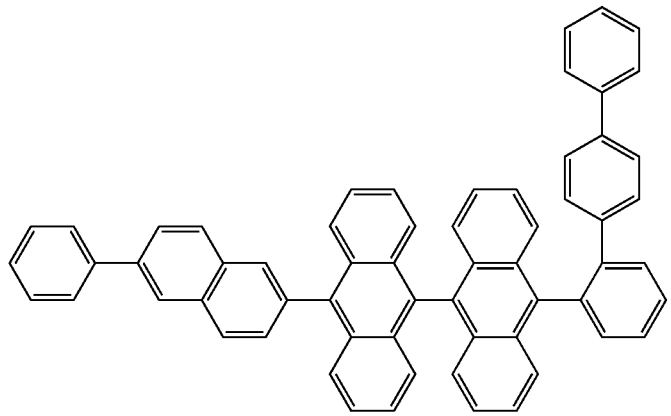
2a'-139
2a'-140
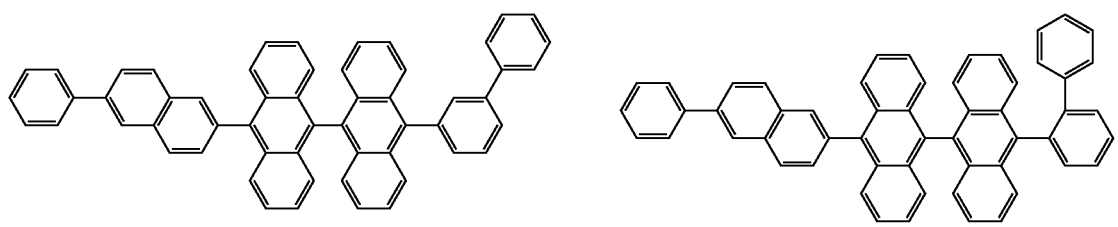
2a'-141
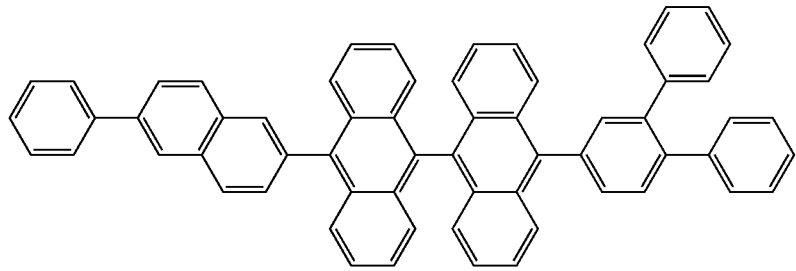

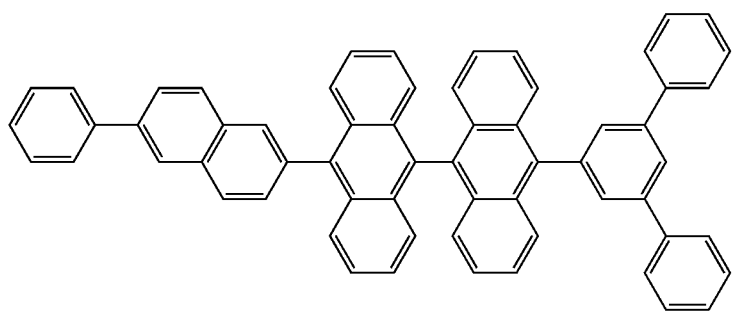

2a'-142

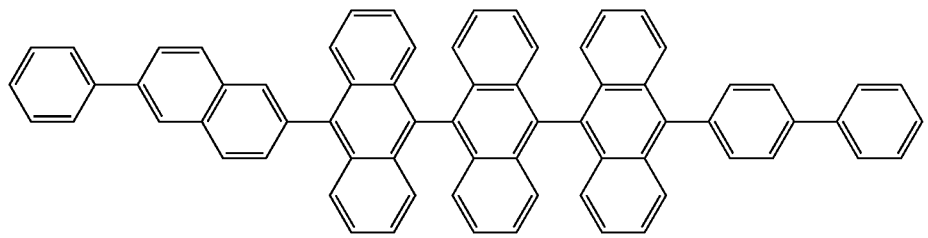

2a'-143

General Formula (2b):

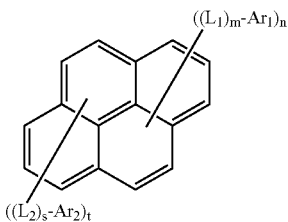

(2b)

(In the formula (2b), $Ar_1$ and $Ar_2$ each independently represents a substituted or unsubstituted aryl group having 6 to 50 carbon atoms forming a ring.

$L_1$ and $L_2$ each independently represents one member selected from a substituted or unsubstituted phenylene group, a substituted or unsubstituted naphthalenylene group, a substituted or unsubstituted fluorenylene group and a substituted or unsubstituted dibenzosilolylene group.

m represents an integer of 0 to 2, n represents an integer of 1 to 4, s represents an integer of 0 to 2 and t represents an integer of 0 to 4; Further, $L_1$ or $Ar_1$ is bonded to any one of 1- to 5-positions of pyrene ring; and $L_2$ or $Ar_2$ is bonded to any one of 6- to 10-positions of pyrene ring.)

Examples of the aryl group having 6 to 50 carbon atoms forming a ring represented by $Ar_1$ and $Ar_2$ in the general formula (2b) include phenyl group, 1-naphthyl group, 2-naphthyl group, 1-anthryl group, 2-anthryl group, 9-anthryl group, 9-(10-phenyl)anthryl, 9-(10-naphthyl-1-yl)anthryl, 9-(10-naphthyl-2-yl)anthryl, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, 3-methyl-2-naphthyl group, 4-methyl-1-naphthyl group, 4-methyl-1-anthryl group, etc. Preferable examples are the aromatic ring group having 6 to 16 carbon atoms forming a ring including particularly phenyl group, 1-naphthyl group, 2-naphthyl group, 9-(10-phenyl)anthryl group, 9-(10-naphthyl-1-yl)anthryl group, 9-(10-naphthyl-2-yl)anthryl group, 9-phenanthryl group, 1-pyrenyl group, 2-pyrenyl group, 4-pyrenyl group, 2-biphenyl group, 3-biphenylyl group, 4-biphenylyl group, o-tolyl group, m-tolyl group, p-tolyl group, p-t-butylphenyl group.

Further, the aryl group may be further substituted with a substituent, and examples of the substituent include alkyl group (methyl group, ethyl group, propyl group, isopropyl group, n-butyl group, s-butyl group, isobutyl group, t-butyl group, n-pentyl group, n-hexyl group, n-heptyl group, n-octyl group, hydroxymethyl group, 1-hydroxyethyl group, 2-hydroxyethyl group, 2-hydroxyisobutyl group, 1,2-dihydroxyethyl group, 1,3-dihydroxyisopropyl group, 2,3-dihydroxy-t-butyl group, 1,2,3-trihydroxypropyl group, chloromethyl group, 1-chloroethyl group, 2-chloroethyl group, 2-chloroisobutyl group, 1,2-dichloroethyl group, 1,3-dichloroisopropyl group, 2,3-dichloro-t-butyl group, 1,2,3-trichloropropyl group, bromomethyl group, 1-bromoethyl group, 2-bromoethyl group, 2-bromoisobutyl group, 1,2-dibromoethyl group, 1,3-dibromoisopropyl group, 2,3-dibromo-t-butyl group, 1,2,3-tribromopropyl group, iodomethyl group, 1-iodoethyl group, 2-iodoethyl group, 2-iodoisobutyl group, 1,2-diiodoethyl group, 1,3-diiodoisopropyl group, 2,3-diiodo-t-butyl group, 1,2,3-triiodopropyl group, aminomethyl group, 1-aminoethyl group, 2-aminoethyl group, 2-aminoisobutyl group, 1,2-diaminoethyl group, 1,3-diaminoisopropyl group, 2,3-diamino-t-butyl group, 1,2,3-triaminopropyl group, cyanomethyl group, 1-cyanoethyl group, 2-cyanoethyl group, 2-cyanoisobutyl group, 1,2-dicyanoethyl group, 1,3-dicyanoisopropyl group, 2,3-dicyano-t-butyl group, 1,2,3-tricyanopropyl group, nitromethyl group, 1-nitroethyl group, 2-nitroethyl group, 2-nitroisobutyl group, 1,2-dinitroethyl group, 1,3-dinitroisopropyl group, 2,3-dinitro-t-butyl group, 1,2,3-trinitropropyl group, cyclopropyl group, cyclobutyl group, cyclopentyl group, cyclohexyl group, 4-methylcyclohexyl group, 1-adamanthyl group, 2-adamanthyl group, 1-norbornyl group, 2-norbornyl group, etc.), an alkoxy group having 1 to 6 carbon atoms (ethoxy group, methoxy group, i-propoxy group, n-propoxy group, s-butoxy group, t-butoxy group, pentoxy group, hexyloxy group, cyclopentoxy group, cyclohexyloxy group, etc.), an aryl group having 5 to 40 atoms forming a ring, an amino group substituted with aryl group having 5 to 40 atoms forming a ring, an ester group with aryl group having 5 to 40 atoms forming a ring, an ester group with alkyl group having 1 to 6 carbon atoms, a cyano group, a nitro group, a halogen atom, etc.

It is preferable for $L_1$ and $L_2$ in the general formula (2b) that they each independently represents one member selected from a substituted or unsubstituted phenylene group and a substituted or unsubstituted fluorenylene group.

Further, examples of the substituent are the same as described about the substituents for the above aromatic groups.

In the general formula (2b), m is preferably an integer of 0 or 1. In the general formula (2b), n is preferably an integer of 1 or 2. In the general formula (2b), s is preferably an integer of 0 or 1. In the general formula (2b), t is preferably an integer of 0 to 2.

Specific examples of the pyrene derivative represented by the general formula (2b) employed for the organic EL device of the present invention include an asymmetric pyrene derivative which is shown in paragraphs [0020] to [0023] of International PCT publication WO 2005/115950 pamphlet. Besides, a symmetric pyrene derivative is also employable as a material for the organic EL device of the present invention. Typical examples are shown below.

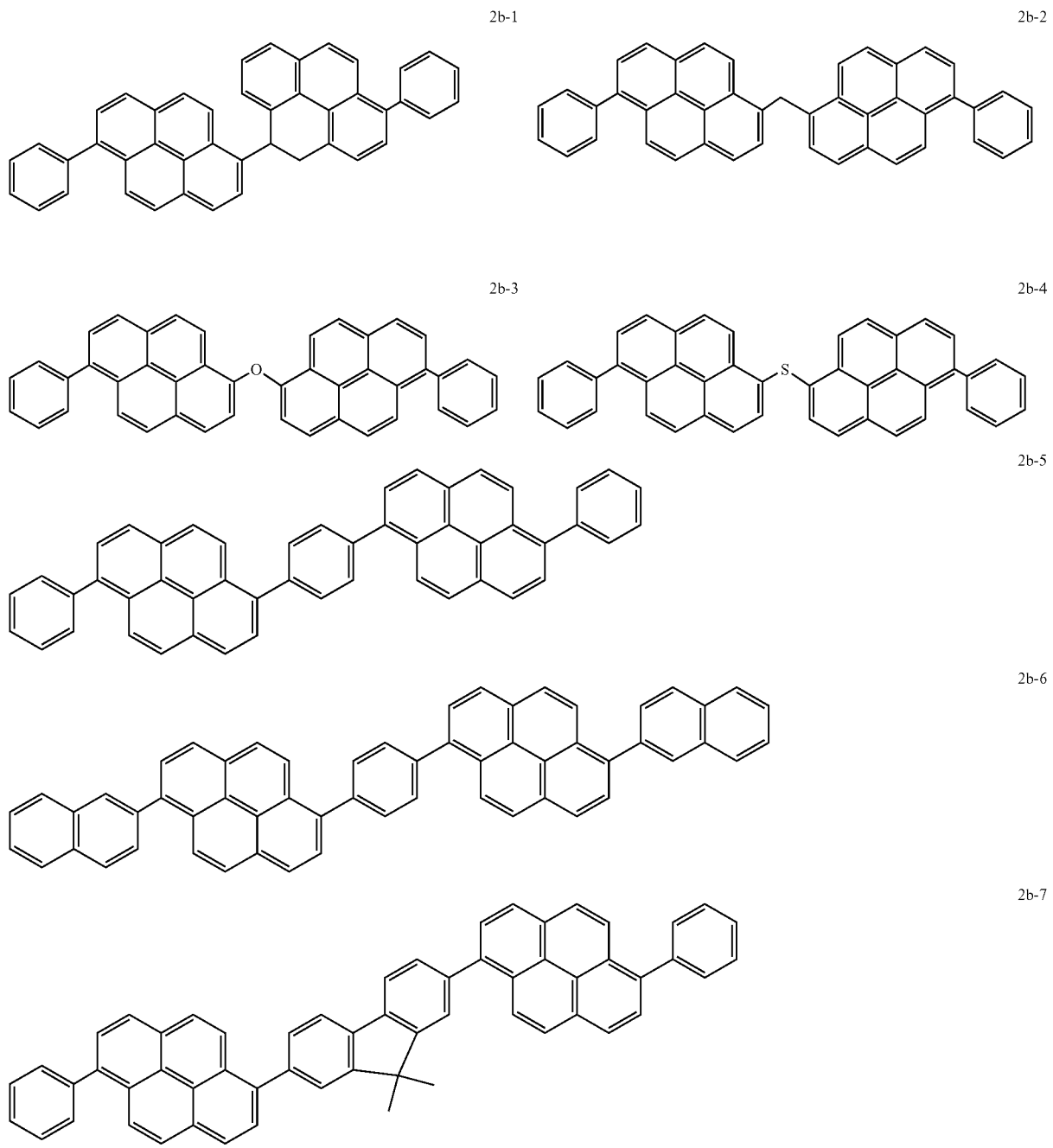

-continued
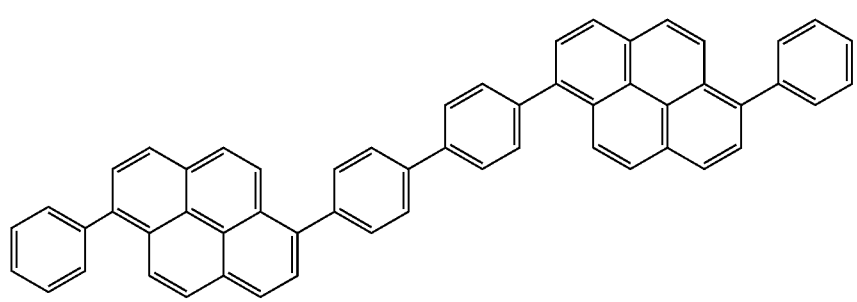
2b-8
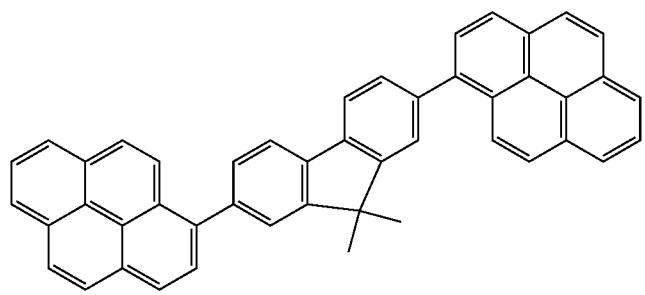
2b-9
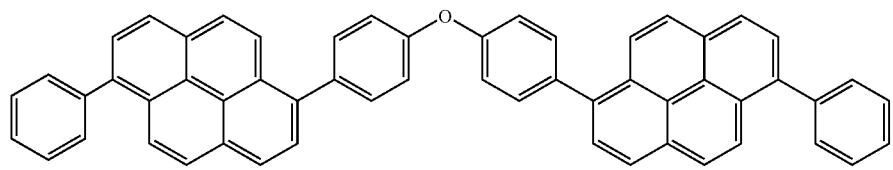
2b-10
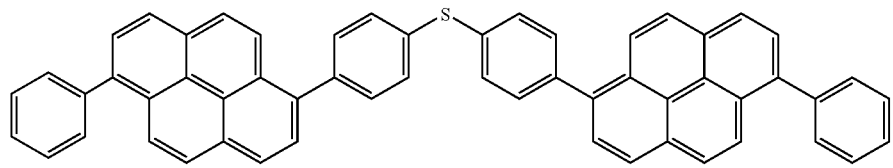
2b-11
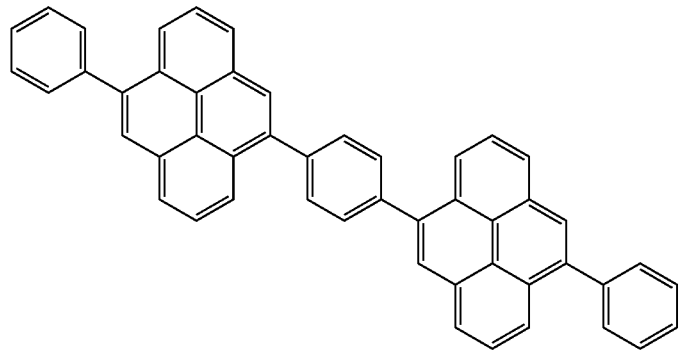
2b-12

-continued
2b-13
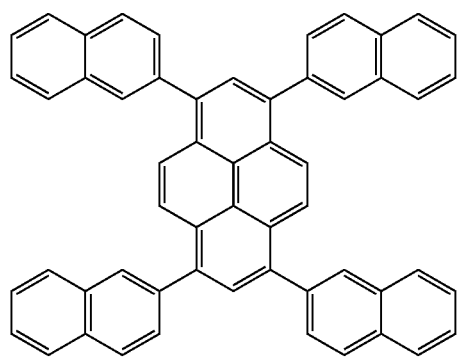
2b-14
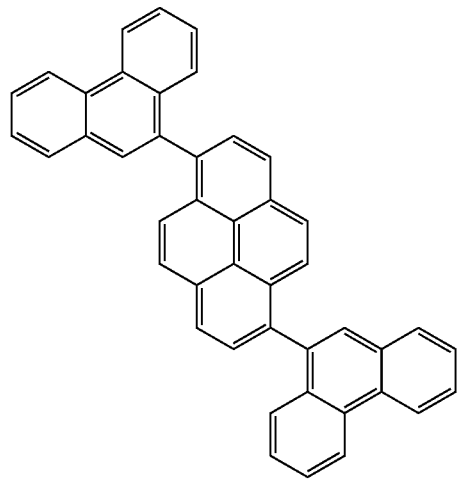
2b-15
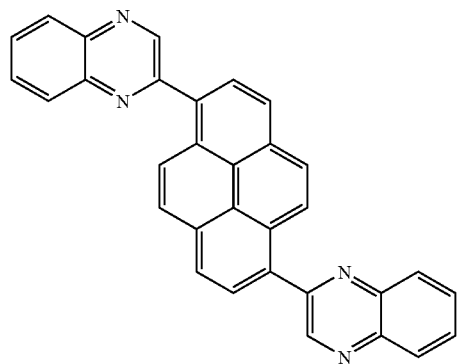
2b-16
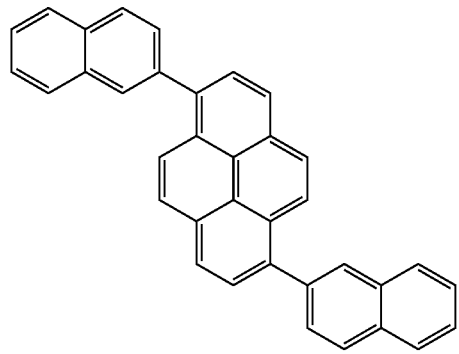
2b-17
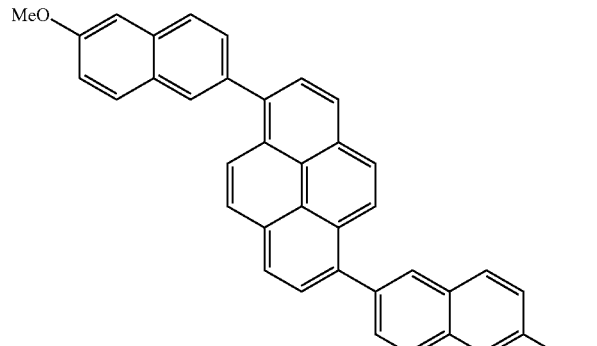
2b-18
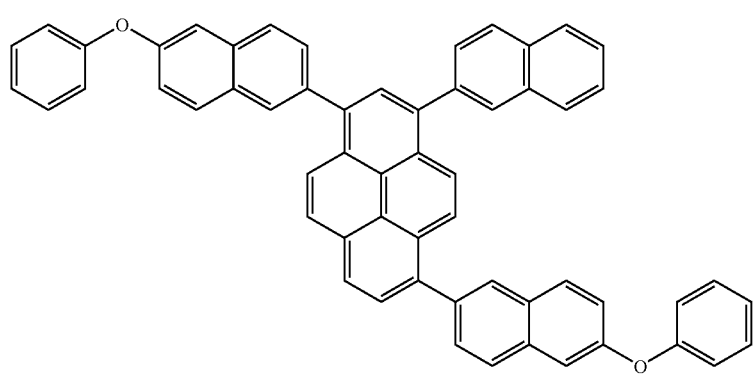
2b-19

-continued
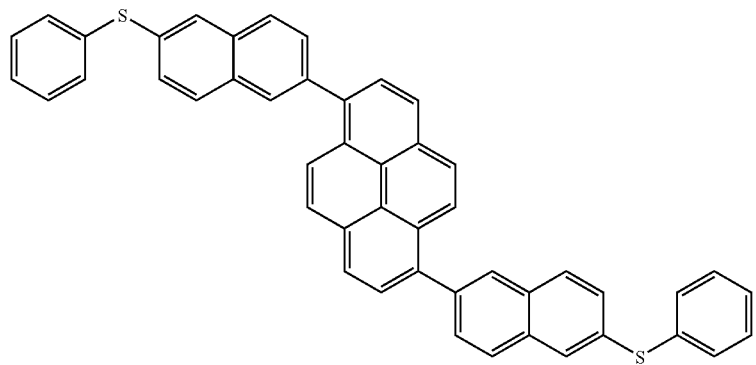
2b-20
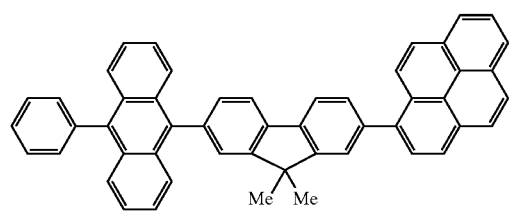
2b-21
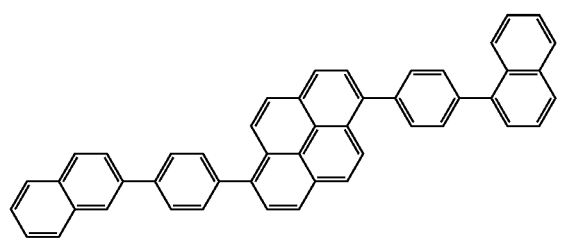
2b-22
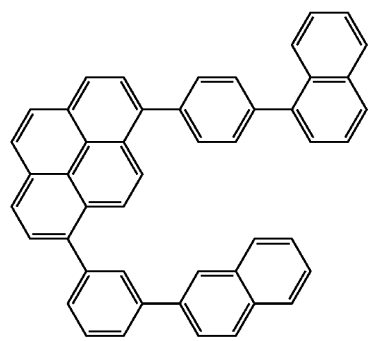
2b-23
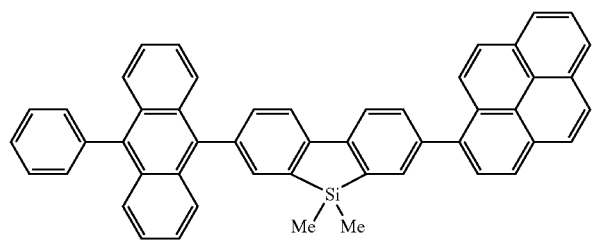
2b-24
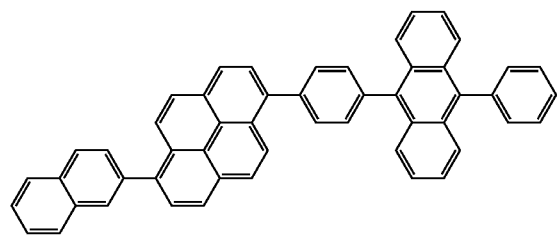
2b-25
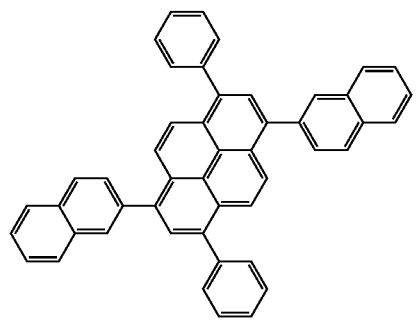
2b-26
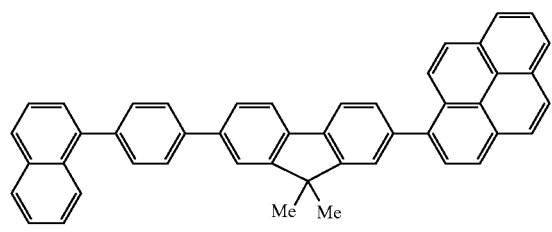
2b-27
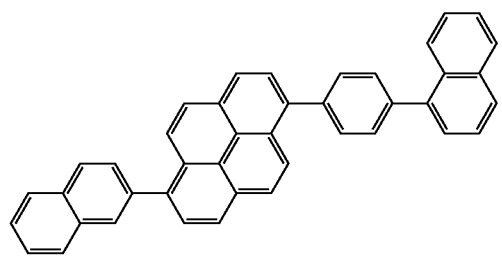
2b-28

-continued
2b-29
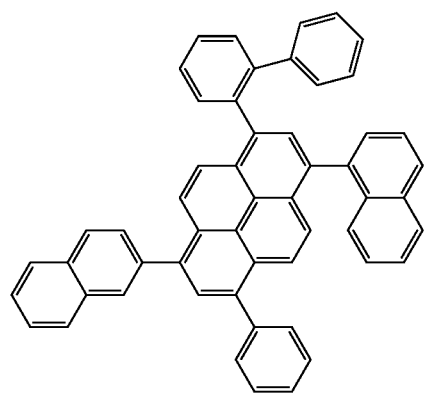
2b-30
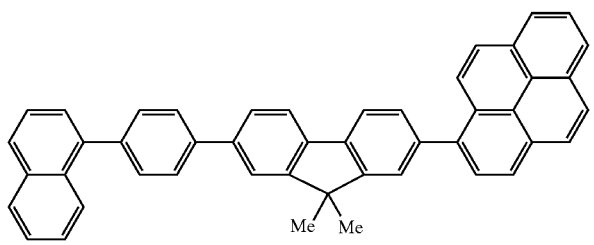
2b-31
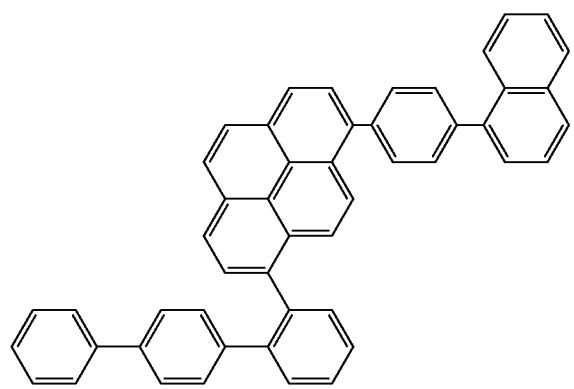
2b-32
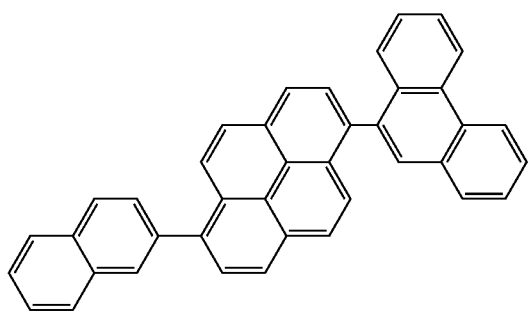
2b-33
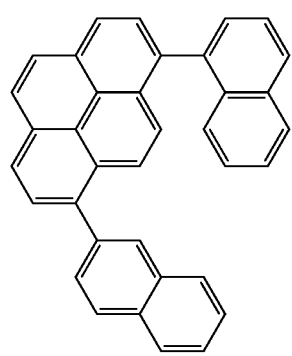
2b-34
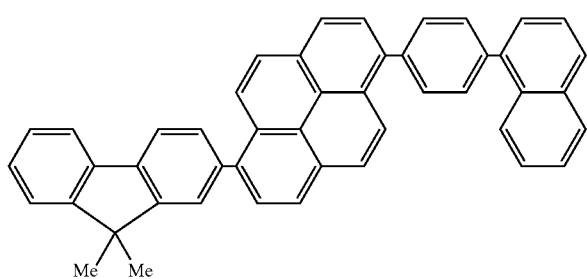
2b-35
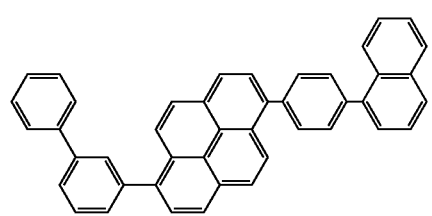
2b-36
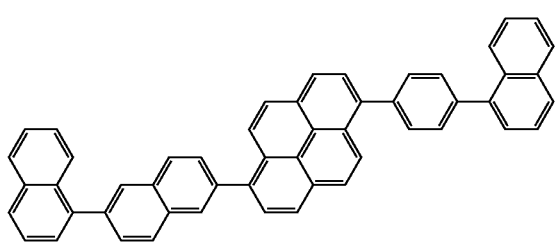

-continued
2b-37
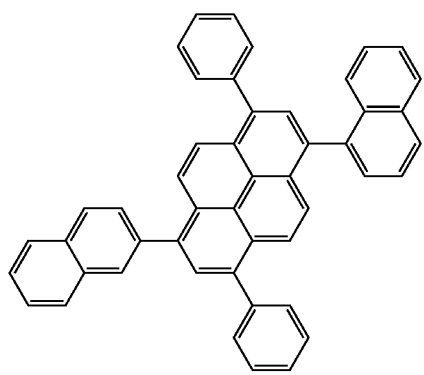
2b-38
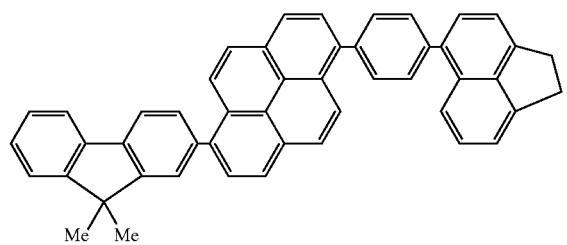
2b-39
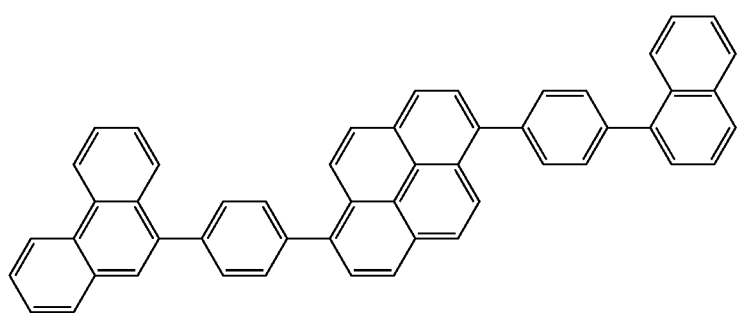
2b-40
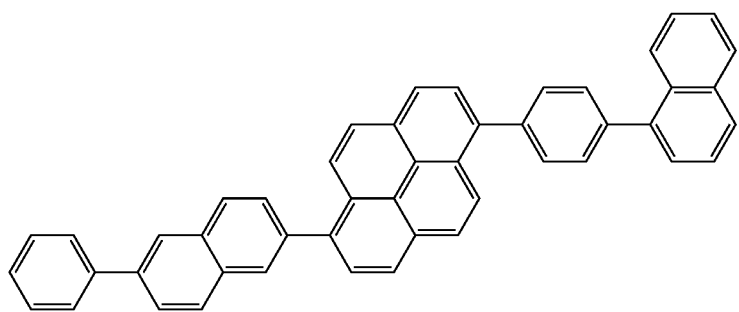
2b-41
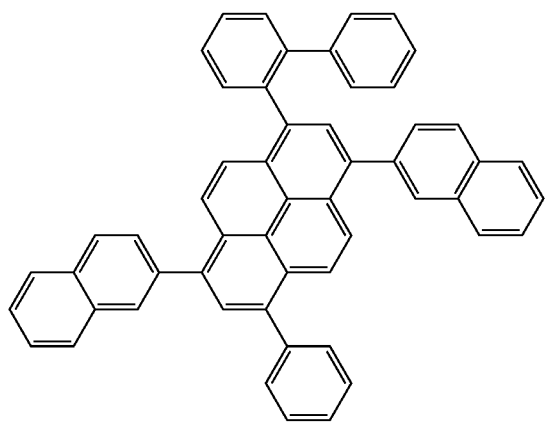

-continued 2b-42

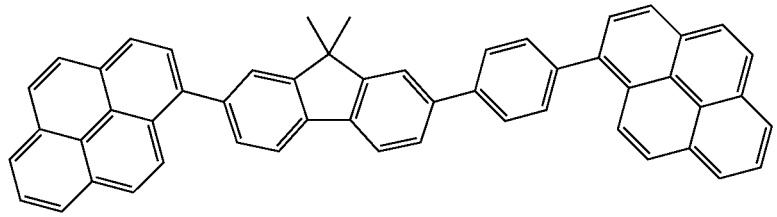

General Formula (2c);

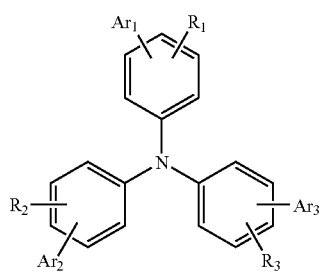

(2c)

(In the formula (2c), $Ar_1$, $Ar_2$ and $Ar_3$ each independently represents one member selected from a group having an anthracene structure, a group having a phenanthrene structure and a group having a pyrene structure respectively.

$R_1$, $R_2$ and $R_3$ each independently represents a hydrogen atom or a substituent.)

It is preferable for $Ar_1$, $Ar_2$ and $Ar_3$ in the general formula (2c) that they each independently represents one member selected from a substituted or unsubstituted anthrylphenyl group, an anthryl group, a phenanthrenyl group, a perilenyl group and a pyrenyl group; more preferably selected from an anthrylphenyl group substituted by alkyl group, an unsubstituted anthrylphenyl group, phenanthryl group and a pyrenyl group; particularly preferably selected from a pyrenyl group and a phenanthryl group.

Examples of $R_1$, $R_2$ and $R_3$ in the general formula (2c) include a hydrogen atom, alkyl group (alkyl group preferably having 1 to 30 carbon atoms, more preferably having 1 to 20 carbon atoms and particularly preferably having 1 to 10 carbon atoms; examples include methyl, ethyl, isopropyl, tert-butyl, n-octyl, n-decyl, n-hexadecyl, cyclopropyl, cyclopentyl, cyclohexyl, etc.); alkenyl group (alkenyl group preferably having 2 to 30 carbon atoms, more preferably having 2 to 20 carbon atoms and particularly preferably having 2 to 10 carbon atoms; examples include vinyl, allyl, 2-butenyl, 3-pentenyl, etc.); alkynyl group (alkynyl group preferably having 2 to 30 carbon atoms, more preferably having 2 to 20 carbon atoms and particularly preferably having 2 to 10 carbon atoms; examples include propargyl, 3-pentynyl, etc.); aryl group (aryl group having 6 to 30 carbon atoms, more preferably having 6 to 20 carbon atoms and particularly preferably having 6 to 12 carbon atoms; examples include phenyl, p-methylphenyl, naphthyl, anthranyl, etc.); amino group (amino group preferably having 0 to 30 carbon atoms, more preferably having 0 to 20 carbon atoms and particularly preferably having 0 to 10 carbon atoms; examples include amino, methylamino, dimethylamino, diethylamino, dibenzylamino, diphenylamino, ditolylamino, etc.); alkoxy group (alkoxy group preferably having 1 to 30 carbon atoms, more preferably having 1 to 20 carbon atoms and particularly preferably having 1 to 10 carbon atoms; examples include methoxy, ethoxy, butoxy, 2-ethylhexyloxy, etc.); aryloxy group (aryloxy group preferably having 6 to 30 carbon atoms, more preferably having 6 to 20 carbon atoms and particularly preferably having 6 to 12 carbon atoms; examples include phenyloxy, 1-naphthyloxy, 2-naphthyloxy, etc.); heteroaryloxy group (heteroaryloxy group preferably having 1 to 30 carbon atoms, more preferably having 1 to 20 carbon atoms and particularly preferably having 1 to 12 carbon atoms; examples include pyridyloxy, pyrazyloxy, pyrimidyloxy, quinolyloxy, etc.); acyl group (acyl group preferably having 1 to 30 carbon atoms, more preferably having 1 to 20 carbon atoms and particularly preferably having 1 to 12 carbon atoms; examples include acetyl, benzoyl, formyl, pivaloyl, etc.); alkoxycarbonyl group (alkoxycarbonyl group preferably having 2 to 30 carbon atoms, more preferably having 2 to 20 carbon atoms and particularly preferably having 2 to 12 carbon atoms; examples include methoxycarbonyl, ethoxycarbonyl, etc.); aryloxycarbonyl group (aryloxycarbonyl group preferably having 7 to 30 carbon atoms, more preferably having 7 to 20 carbon atoms and particularly preferably having 7 to 12 carbon atoms; examples include phenyloxycarbonyl, etc.); acyloxy group (acyloxy group preferably having 2 to 30 carbon atoms, more preferably having 2 to 20 carbon atoms and particularly preferably having 2 to 10 carbon atoms; examples include acetoxy, benzoyloxy, etc.); acylamino group (acylamino group preferably having 2 to 30 carbon atoms, more preferably having 2 to 20 carbon atoms and particularly preferably having 2 to 10 carbon atoms; examples include acetylamino, benzoylamino, etc.); alkoxycarbonylamino group (alkoxycarbonylamino group preferably having 2 to 30 carbon atoms, more preferably having 2 to 20 carbon atoms and particularly preferably having 2 to 12 carbon atoms; examples include methoxycarbonylamino, etc.); aryloxycarbonylamino group (aryloxycarbonylamino group preferably having 7 to 30 carbon atoms, more preferably having 7 to 20 carbon atoms and particularly preferably having 7 to 12 carbon atoms; examples include phenyloxycarbonylamino, etc.); sulfonylamino group (sulfonylamino group preferably having 1 to 30 carbon atoms, more preferably having 1 to 20 carbon atoms and particularly preferably having 1 to 12 carbon atoms; examples include methanesulfonylamino, benzenesulfonylamino, etc.); sulfamoyl group (sulfamoyl group preferably having 0 to 30 carbon atoms, more preferably having 0 to 20 carbon atoms and particularly preferably having 0 to 12 carbon atoms; examples include sulfamoyl, methylsulfamoyl, dimethylsulfamoyl, phenylsulfamoyl, etc.); carbamoyl group (carbamoyl group preferably having 1 to 30 carbon atoms, more preferably having 1 to 20 carbon atoms and particularly preferably having 1 to 12 carbon atoms; examples include carbamoyl, methylcarbamoyl, diethylcarbamoyl, phenylcarbamoyl, etc.); alkylthio group (alkylthio group preferably having 1 to 30 carbon atoms, more preferably having 1 to 20 carbon atoms and particularly preferably having 1 to 12 carbon atoms; examples include methylthio, ethylthio, etc.); arylthio group (arylthio group preferably having 6 to 30 carbon atoms, more preferably having 6 to 20 carbon atoms and particularly preferably having 6 to 12 carbon atoms; examples include phenylthio, etc.); heteroarylthio group (heteroarylthio group preferably having 1 to 30 carbon atoms, more preferably having 1 to 20 carbon atoms and particularly preferably having 1 to 12 carbon atoms; examples include pyridylthio, 2-benzimidazolylthio, 2-benzoxazolylthio, 2-benzothiazolylthio, etc.); sulfonyl group (sulfonyl group preferably having 1 to 30 carbon atoms, more preferably having 1 to 20 carbon atoms and particularly preferably having 1 to 12 carbon atoms; examples include mesyl, tosyl, etc.); sulfinyl group (sulfinyl group preferably having 1 to 30 carbon atoms, more preferably having 1 to 20 carbon atoms and particularly preferably having 1 to 12 carbon atoms; examples include methanesulfinyl, benzenesulfinyl, etc.); ureide group (ureide group preferably having 1 to 30 carbon atoms, more preferably having 1 to 20 carbon atoms and particularly preferably having 1 to 12 carbon atoms; examples include ureide, methylureide, phenylureide, etc.); phosphoricamide group (phosphoricamide group preferably having 1 to 30 carbon atoms, more preferably having 1 to 20 carbon atoms and particularly preferably having 1 to 12 carbon atoms; examples include diethylphosphoricamide, phenylphosphoricamide, etc.); hydroxy group; mercapto group; halogen atoms (for example, a fluorine atom, a chlorine atom, a bromine atom and an iodine atom); cyano group; sulfo group; carboxy group; nitro group; hydroxamic acid group; sulfino group; hydrazino group; imino group; heterocyclic group (heterocyclic group preferably having 1 to 30 carbon atoms, more preferably having 1 to 12 carbon atoms; examples of hetero atoms include a nitrogen atom, an oxygen atom, a sulfur atom; specific examples of the heterocyclic group include imidazolyl, pyridyl, quinolyl, furyl, thienyl, piperidyl, morpholino, benzoxazolyl, benzimidazolyl, benzothiazolyl, etc.); silyl group (silyl group preferably having 3 to 40 carbon atoms, more preferably having 3 to 30 carbon atoms and particularly preferably having 3 to 24 carbon atoms; examples include trimethylsilyl, triphenylsilyl, etc.); etc. Those substituents may be further substituted.

The substituents of $R_1$, $R_2$ and $R_3$ in the general formula (2c) are preferably selected from alkyl group and aryl group.

Specific examples of the amine derivative represented by the general formula (2c) employed for the organic EL device of the present invention include various kinds of well-known amine derivatives which are shown in paragraphs [0079] to [0083] of JP 2002-324678A. Typical examples are shown below.

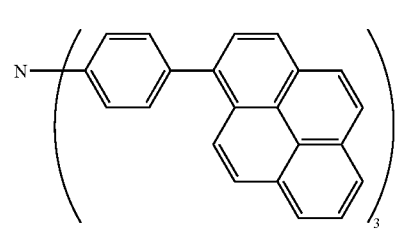

2c-1

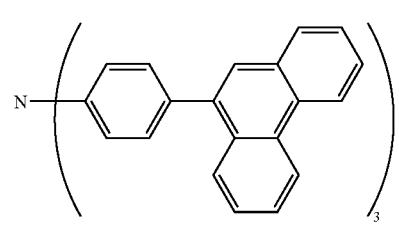

2c-2

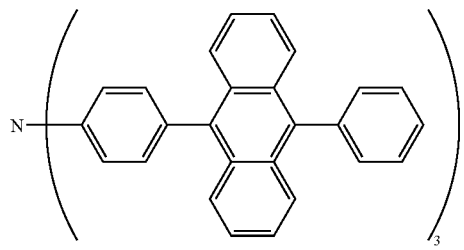

2c-3

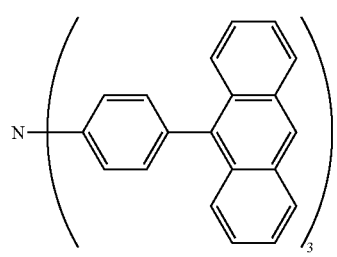

2c-4

-continued
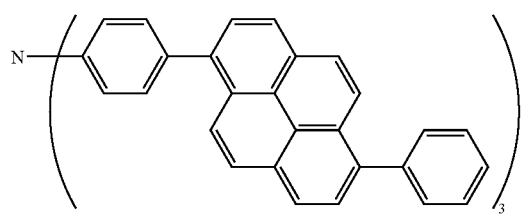
2c-5
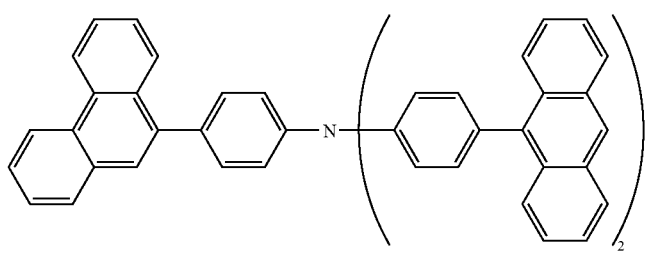
2c-6
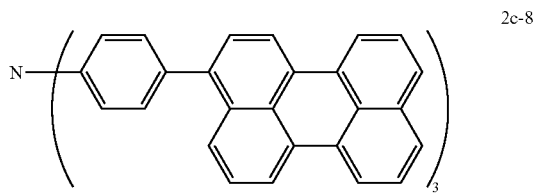
2c-8
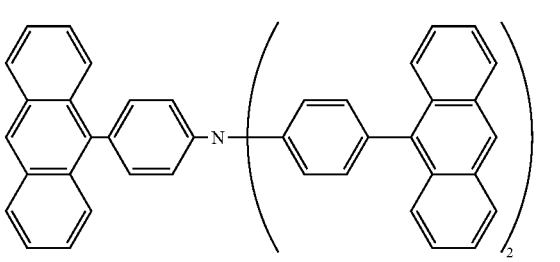
2c-10
2c-11
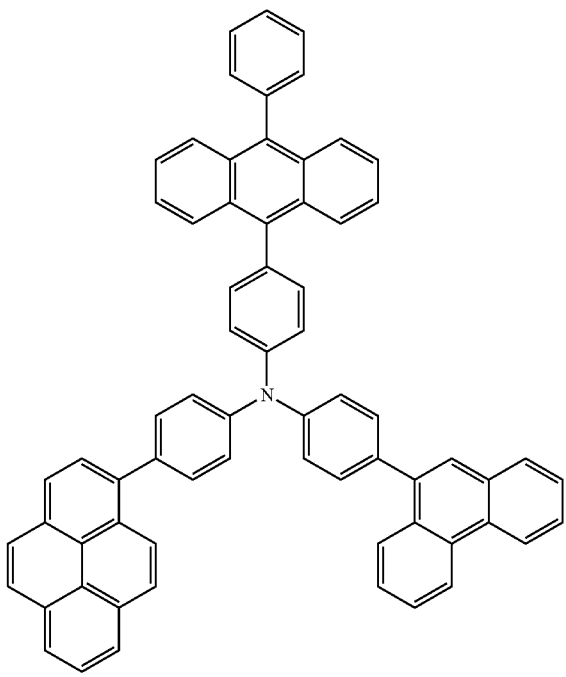

-continued
2c-12
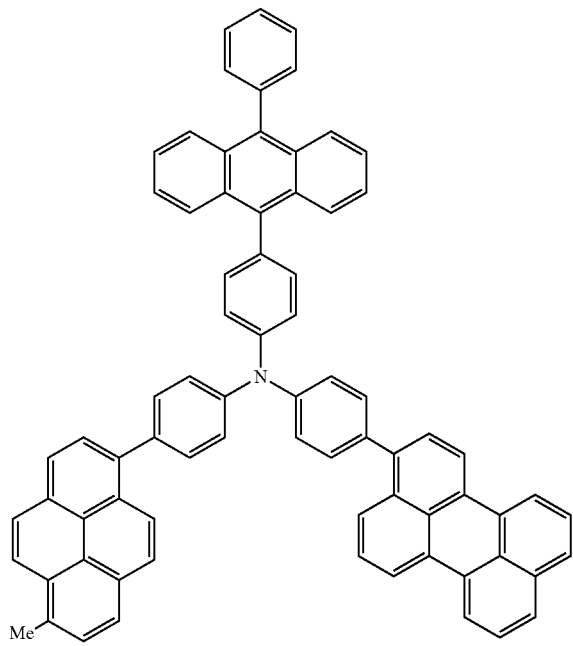
2c-13
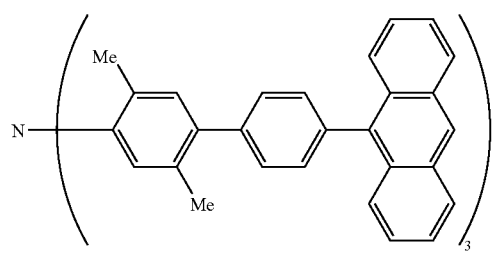
2c-15
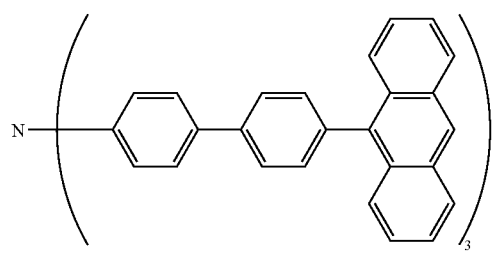
2c-17
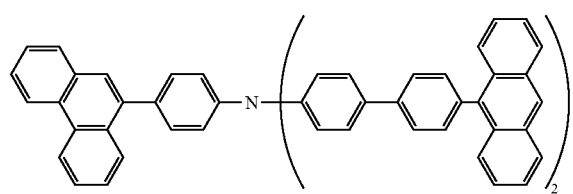

General Formula (2d):

(In the formula (2d), $Ar_{11}$, $Ar_{21}$ and $Ar_{31}$ each independently represents an aryl group having 6 to 50 carbon atoms forming a ring. The aryl group may be substituted by 1 or more substituents.

At least one of the aryl groups represented by $Ar_{11}$, $Ar_{21}$, $Ar_{31}$, and those substituents has a fused ring aryl structure having 10 to 20 carbon atoms forming a ring or a fused ring heteroaryl structure having 6 to 20 carbon atoms forming a ring.

Ar represents a trivalent group derived from an aromatic ring or a heteroaromatic ring.)

The aryl group having 6 to 50 carbon atoms forming a ring represented by $Ar_{11}$, $Ar_{21}$ and $Ar_{31}$ of the general formula (2d) has preferably 6 to 30, more preferably 6 to 20, and further preferably 6 to 16 carbon atoms forming a ring. Examples of the aryl group include phenyl group, naphthyl group, anthryl group, phenanthrenyl group, pyrenyl group, perilenyl group, fluorenyl group, biphenylyl group, terphenylyl group, rubrenyl group, crycenyl group, triphenylenyl group, benzanthryl group, benzophenanthrenyl group, diphenylanthryl group, etc., and those aryl groups may be further substituted.

Examples of the substituents on the aryl groups include alkyl group (alkyl group preferably having 1 to 30 carbon atoms, more preferably having 1 to 20 carbon atoms and particularly preferably having 1 to 10 carbon atoms; examples include methyl, ethyl, isopropyl, tert-butyl, n-octyl, n-decyl, n-hexadecyl, cyclopropyl, cyclopentyl, cyclohexyl, etc.); alkenyl group (alkenyl group preferably having 2 to 30 carbon atoms, more preferably having 2 to 20 carbon atoms and particularly preferably having 2 to 10 carbon atoms; examples include vinyl, allyl, 2-butenyl, 3-pentenyl, etc.); alkynyl group (alkynyl group preferably having 2 to 30 carbon atoms, more preferably having 2 to 20 carbon atoms and particularly preferably having 2 to 10 carbon atoms; examples include propargyl, 3-pentynyl, etc.); aryl group (aryl group having 6 to 30 carbon atoms, more preferably having 6 to 20 carbon atoms and particularly preferably having 6 to 12 carbon atoms; examples include phenyl, p-methylphenyl, naphthyl, anthranyl, etc.); amino group (amino group preferably having 0 to 30 carbon atoms, more preferably having 0 to 20 carbon atoms and particularly preferably having 0 to 10 carbon atoms; examples include amino, methylamino, dimethylamino, diethylamino, dibenzylamino, diphenylamino, ditolylamino, etc.); alkoxy group (alkoxy group preferably having 1 to 30 carbon atoms, more preferably having 1 to 20 carbon atoms and particularly preferably having 1 to 10 carbon atoms; examples include methoxy, ethoxy, butoxy, 2-ethylhexyloxy, etc.); aryloxy group (aryloxy group preferably having 6 to 30 carbon atoms, more preferably having 6 to 20 carbon atoms and particularly preferably having 6 to 12 carbon atoms; examples include phenyloxy, 1-naphthyloxy, 2-naphthyloxy, etc.); heteroaryloxy group (heteroaryloxy group preferably having 1 to 30 carbon atoms, more preferably having 1 to 20 carbon atoms and particularly preferably having 1 to 12 carbon atoms; examples include pyridyloxy, pyrazyloxy, pyrimidyloxy, quinolyloxy, etc.); acyl group (acyl group preferably having 1 to 30 carbon atoms, more preferably having 1 to 20 carbon atoms and particularly preferably having 1 to 12 carbon atoms; examples include acetyl, benzoyl, formyl, pivaloyl, etc.); alkoxycarbonyl group (alkoxycarbonyl group preferably having 2 to 30 carbon atoms, more preferably having 2 to 20 carbon atoms and particularly preferably having 2 to 12 carbon atoms; examples include methoxycarbonyl, ethoxycarbonyl, etc.); aryloxycarbonyl group (aryloxycarbonyl group preferably having 7 to 30 carbon atoms, more preferably having 7 to 20 carbon atoms and particularly preferably having 7 to 12 carbon atoms; examples include phenyloxycarbonyl, etc.); acyloxy group (acyloxy group preferably having 2 to 30 carbon atoms, more preferably having 2 to 20 carbon atoms and particularly preferably having 2 to 10 carbon atoms; examples include acetoxy, benzoyloxy, etc.); acylamino group (acylamino group preferably having 2 to 30 carbon atoms, more preferably having 2 to 20 carbon atoms and particularly preferably having 2 to 10 carbon atoms; examples include acetylamino, benzoylamino, etc.); alkoxycarbonylamino group (alkoxycarbonylamino group preferably having 2 to 30 carbon atoms, more preferably having 2 to 20 carbon atoms and particularly preferably having 2 to 12 carbon atoms; examples include methoxycarbonylamino, etc.); aryloxycarbonylamino group (aryloxycarbonylamino group preferably having 7 to 30 carbon atoms, more preferably having 7 to 20 carbon atoms and particularly preferably having 7 to 12 carbon atoms; examples include phenyloxycarbonylamino, etc.); sulfonylamino group (sulfonylamino group preferably having 1 to 30 carbon atoms, more preferably having 1 to 20 carbon atoms and particularly preferably having 1 to 12 carbon atoms; examples include methanesulfonylamino, benzenesulfonylamino, etc.); sulfamoyl group (sulfamoyl group preferably having 0 to 30 carbon atoms, more preferably having 0 to 20 carbon atoms and particularly preferably having 0 to 12 carbon atoms; examples include sulfamoyl, methylsulfamoyl, dimethylsulfamoyl, phenylsulfamoyl, etc.); carbamoyl group (carbamoyl group preferably having 1 to 30 carbon atoms, more preferably having 1 to 20 carbon atoms and particularly preferably having 1 to 12 carbon atoms; examples include carbamoyl, methylcarbamoyl, diethylcarbamoyl, phenylcarbamoyl, etc.); alkylthio group (alkylthio group preferably having 1 to 30 carbon atoms, more preferably having 1 to 20 carbon atoms and particularly preferably having 1 to 12 carbon atoms; examples include methylthio, ethylthio, etc.); arylthio group (arylthio group preferably having 6 to 30 carbon atoms, more preferably having 6 to 20 carbon atoms and particularly preferably having 6 to 12 carbon atoms; examples include phenylthio, etc.); heteroarylthio group (heteroarylthio group preferably having 1 to 30 carbon atoms, more preferably having 1 to 20 carbon atoms and particularly preferably having 1 to 12 carbon atoms; examples include pyridylthio, 2-benzimidazolylthio, 2-benzoxazolylthio, 2-benzothiazolylthio, etc.); sulfonyl group (sulfonyl group preferably having 1 to 30 carbon atoms, more preferably having 1 to 20 carbon atoms and particularly preferably having 1 to 12 carbon atoms; examples include mesyl, tosyl, etc.); sulfinyl group (sulfinyl group preferably having 1 to 30 carbon atoms, more preferably having 1 to 20 carbon atoms and particularly preferably having 1 to 12 carbon atoms; examples include methanesulfinyl, benzenesulfinyl, etc.); ureide group (ureide group preferably having 1 to 30 carbon atoms, more preferably having 1 to 20 carbon atoms and particularly preferably having 1 to 12 carbon atoms; examples include ureide, methylureide, phenylureide, etc.); phosphoricamide group (phosphoricamide group preferably having 1 to 30 carbon atoms, more preferably having 1 to 20 carbon atoms and particularly preferably having 1 to 12 carbon atoms; examples include diethylphosphoricamide, phenylphosphoricamide, etc.); hydroxy group; mercapto group; halogen atoms (for example, a fluorine atom, a chlorine atom, a bromine atom and an iodine atom); cyano group; sulfo group; carboxy group; nitro group; hydroxamic acid group; sulfino group; hydrazino group; imino group; heterocyclic group (heterocyclic group preferably having 1 to 30 carbon atoms, more preferably having 1 to 12 carbon atoms; examples of the hetero atoms include a nitrogen atom, an oxygen atom, a sulfur atom; specific examples of the heterocyclic group include imidazolyl, pyridyl, quinolyl, furyl, thienyl, piperidyl, morpholino, benzoxazolyl, benzimidazolyl, benzothiazolyl, carbazolyl group, azepinyl group, etc.); silyl group (silyl group preferably having 3 to 40 carbon atoms, more preferably having 3 to 30 carbon atoms and particularly preferably having 3 to 24 carbon atoms; examples include trimethylsilyl, triphenylsilyl, etc.); etc. Those substituents may be further substituted.

Examples of the fused ring aryl structure having 10 to 20 carbon atoms forming a ring held by at least one substituent of $Ar_{11}, Ar_{21}, Ar_{31}$ and those aryl groups in the general formula (2d) and those aryl groups include naphthalene structure, anthracene structure, phenanthrene structure, pyrene structure, perylene structure, etc.; preferably naphthalene structure, anthracene structure, pyrene structure and phenanthrene structure; more preferably phenanthrene structure and aryl structure having 4 or more rings; particularly preferably pyrene structure.

Examples of the fused ring heteroaryl structure having 6 to 20 carbon atoms forming a ring held by at least one substituent of $Ar_{11}, Ar_{21}$, and $Ar_{31}$ in the general formula (2d) and those aryl groups include quinoline structure, quinoxaline structure, quinazoline structure, acridine structure, phenanthridine structure, phthalazine structure, phenanthroline structure, etc.; preferably quinoline structure, quinoxaline structure, quinazoline structure, phthalazine structure and phenanthroline structure.

The trivalent group derived from the aromatic ring represented by Ar of the general formula (2d) has preferably 6 to 30, more preferably 6 to 20, and further preferably 6 to 16 carbon atoms. Specific examples include the trivalent group derived from benzene, naphthalene, anthracene, phenanthrene, pyrene, triphenylene, etc.

The trivalent group derived from the aromatic ring represented by Ar in the general formula (2d) preferably includes an atom selected from a nitrogen atom, a sulfur atom and an oxygen atom as hetero atoms, and more preferably includes a nitrogen atom. Moreover, it has preferably 2 to 30, more preferably 3 to 20, and further preferably 3 to 16 carbon atoms. Specific examples include the trivalent group derived from pyridine, pyrazine, thiopyran, quinoline, quinoxaline and triazine. Those trivalent groups derived from the aromatic ring or the heteroaromatic ring may have a substituent. Examples of the substituent include the groups described about the substituent on the aryl group represented by the substituent $Ar_{11}$. Ar is preferably benzenetriyl, naphthalenetriyl, anthracenetriyl, pyrenetriyl, or a trivalent group derived from triphenylene; more preferably benzenetriyl; and further preferably unsubstituted (with the proviso that $Ar_{11}, Ar_{21}$ and $Ar_{31}$ are substituted) benzenetriyl or benzenetriyl substituted by alkyl.

Specific examples of the benzene derivative represented by the general formula (2d) employed for the organic EL device of the present invention include various kinds of well-known benzene derivatives which are shown in paragraphs [0079] to [0083] of JP 2002-324678A. Typical examples are shown below.

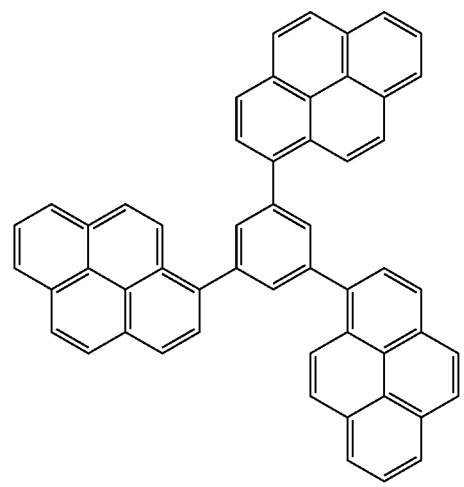

2d-1

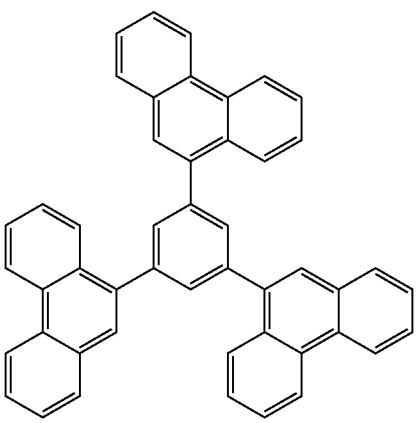

2d-2

2d-3
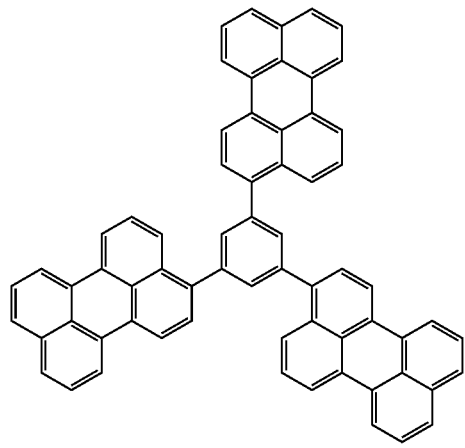
2d-4
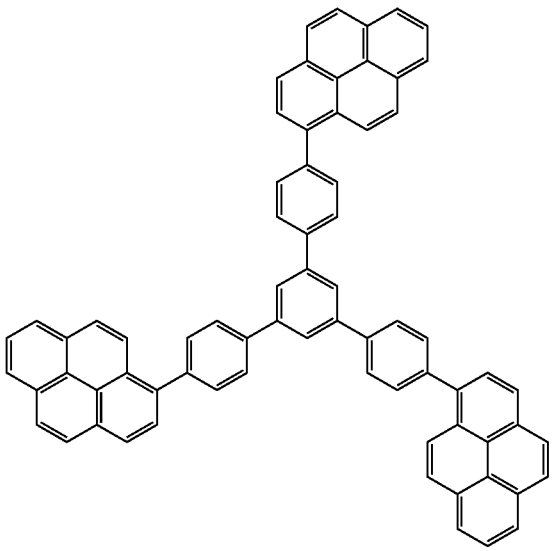
2d-5
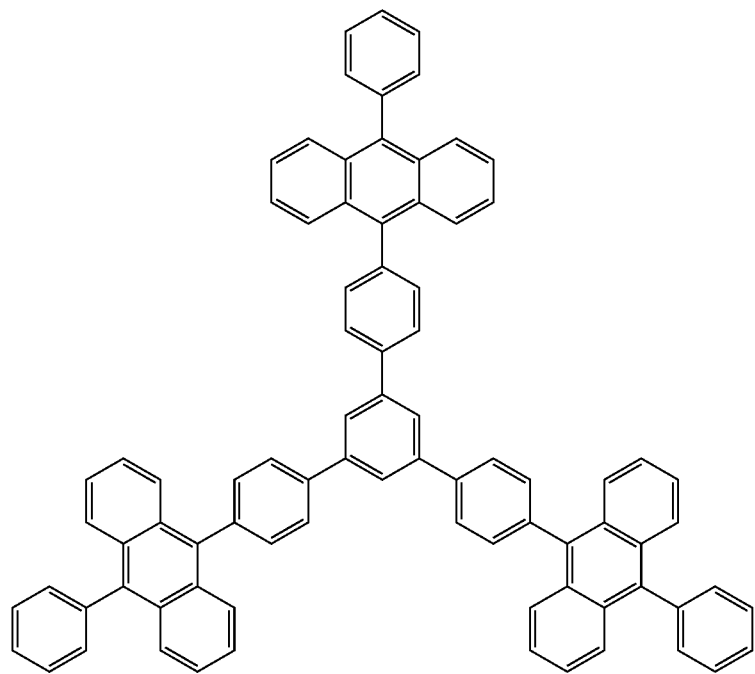

-continued
2d-6
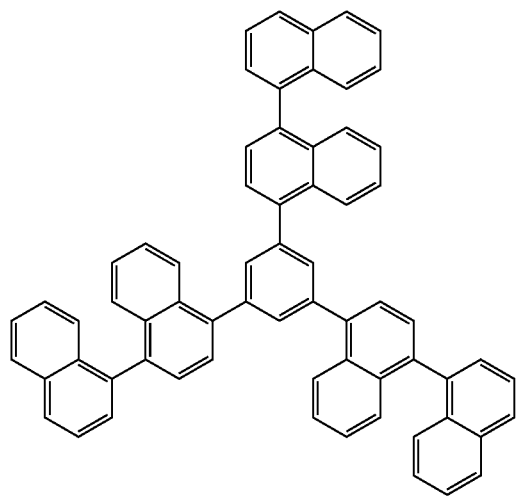
2d-7
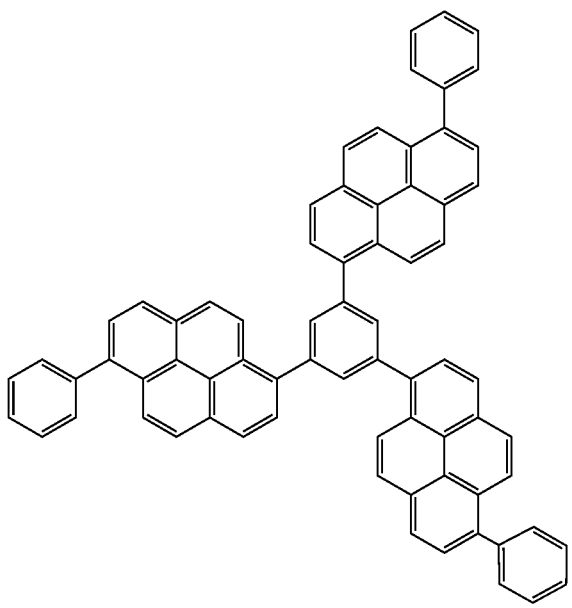
2d-8
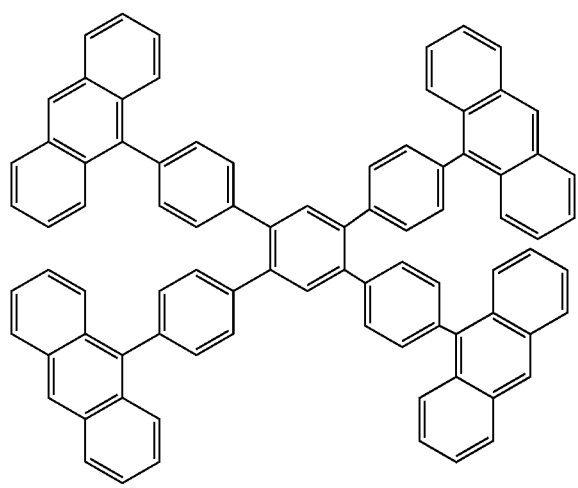
2d-9
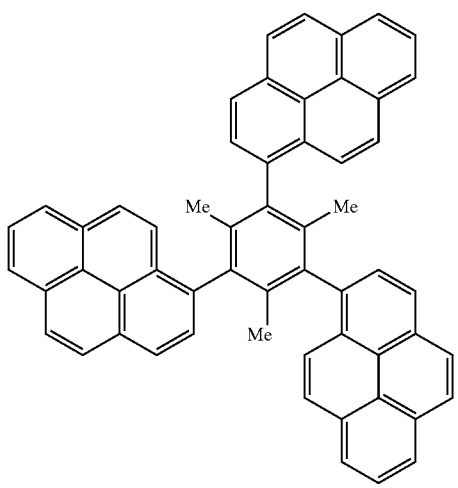
2d-10
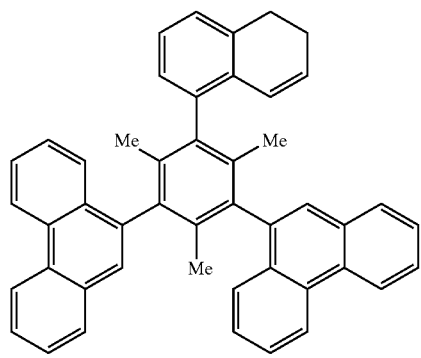
2d-11
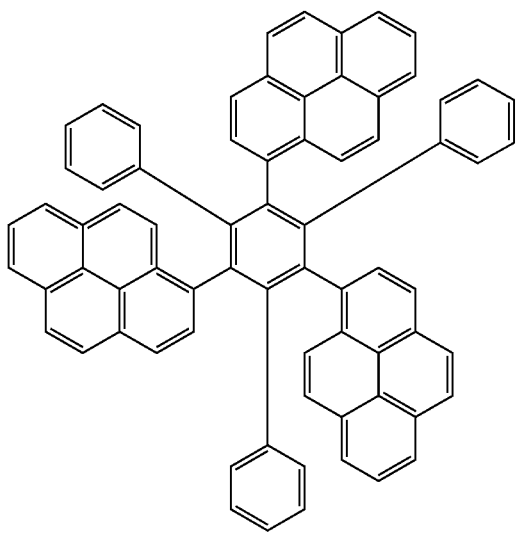

2d-12
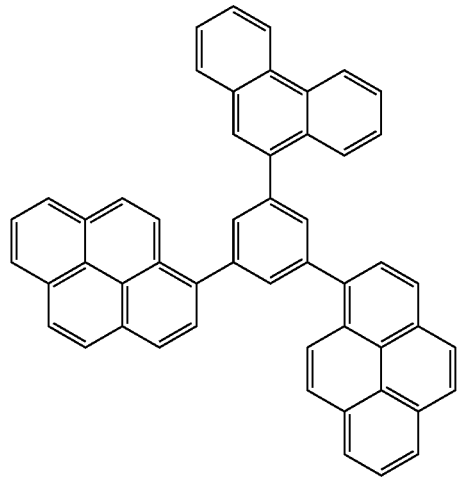
2d-13
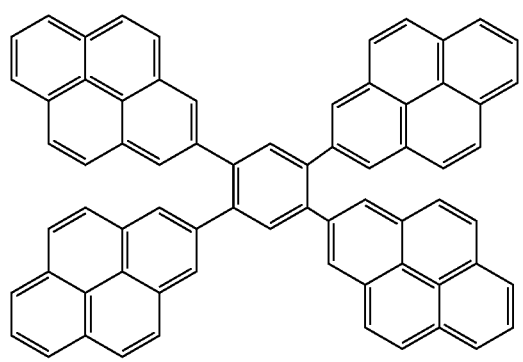
2d-14
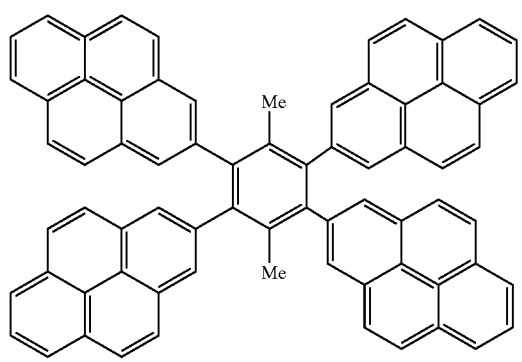
2d-15
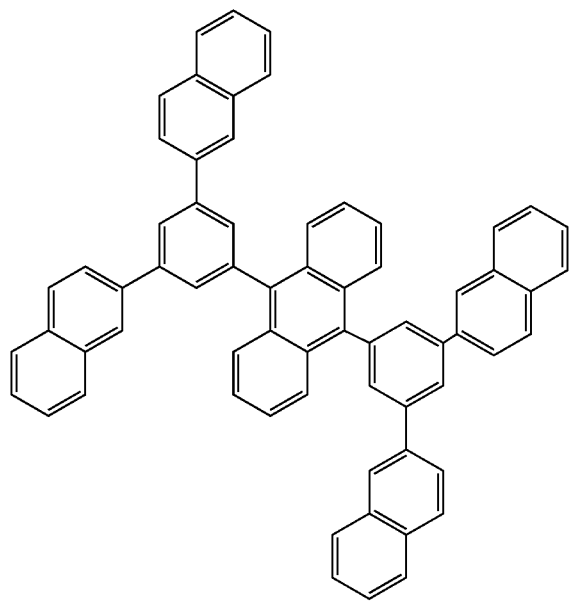
2d-16
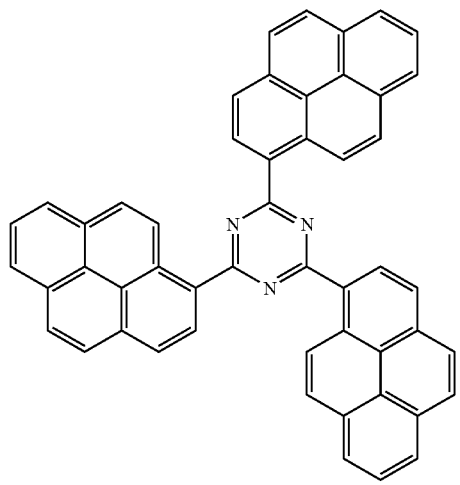

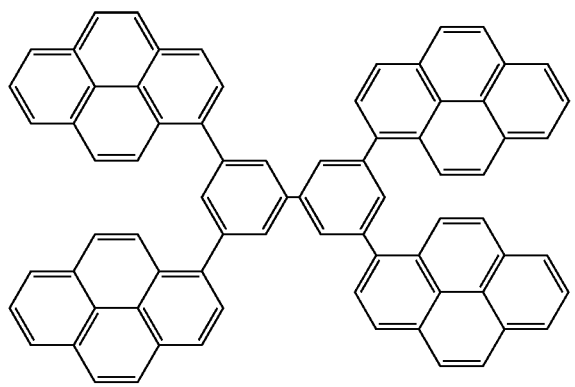

2d-17

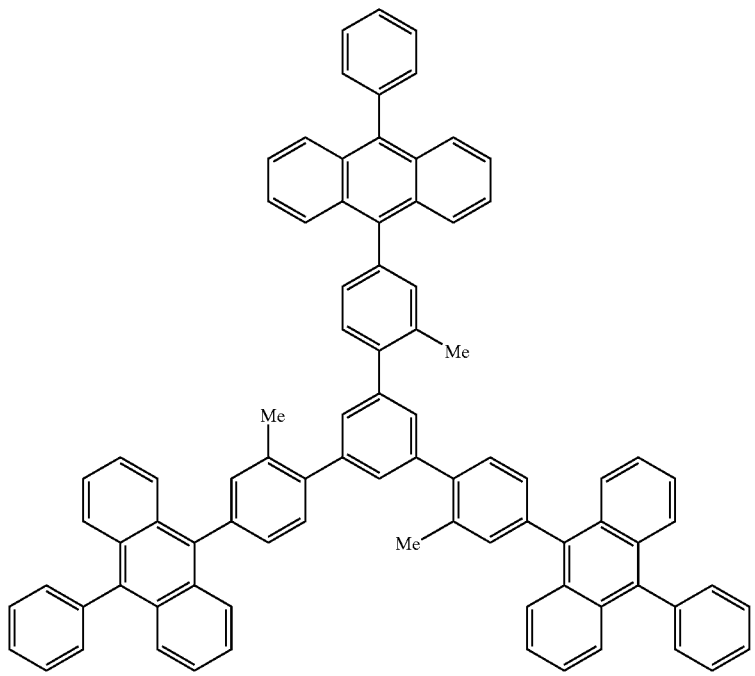

2d-18

Each organic layer such as the emitting layer or so in the organic EL device of the present invention may be formed in accordance with a dry-type film formation process such as the vacuum vapor deposition process, the molecular beam epitaxy process (MBE process), the sputtering process, the plasma process, the ion plating process and so on; or employing a coating process applying a solution made by dissolving the material into a solvent in accordance with such as the spin coating process, the dipping process, the casting process, the bar coating process, the roller coating process, the flow coating process, the ink-jet process, etc.

Particularly, in a case where the organic EL device is fabricated employing the fluoranthene compound of the present invention, the organic compound layer and the emitting layer are capable of being formed into a film in accordance with not only the vapor deposition process but also an wet process.

Although the film thickness of each organic compound layer is not particularly limited, it is necessary to predetermine the film thickness appropriately. Generally, when the film thickness is too thin, pinholes or so will occur causing a fear of failing in getting sufficient luminance of light emission despite applying an electric field. On the contrary, when the film thickness is too thick, a high applied voltage becomes necessary for getting a constant optical output thereby degrading the efficiency. Accordingly, it is appropriate that the thickness of the film is usually in the range of from 5 nm to 10 µm and more preferably in the range of from 10 nm to 0.2 µm.

In a case of the wet process of film formation, a solution containing materials for the organic EL including the fluoranthene compound of the present invention and the solvent is employable as the material for the organic EL device, and it is preferable that the solution containing materials for the organic EL contains at least one kind of the above fluoranthene compound and at least one kind selected from the compound represented by the foregoing general formulae (2a) to (2d).

In this occasion, the solution containing materials for the organic EL is prepared by dissolving or dispersing the materials for the organic EL forming each layers into an appropriate solvent, which is formed into a thin film, and any solvent may be employable. Examples of the solvent include halogen-based hydrocarbon-based solvent such as dichloromethane, dichloroethane, chloroform, tetrachloromethane, tetrachloroethane, trichloroethane, chlorobenzene, dichlorobenzene, chlorotoluene, trifluorotoluene, and so on; ether-based solvent such as dibutylether, tetrahydrofuran, tetrahydropyrane, dioxane, anisole, dimethoxyethane, and so on; alcohol-based solvent such as methanol, ethanol, propanol, isopropanol, butanol, pentanol, hexanol, cyclohexanol, methylcellosolve, ethylcellosolve, ethyleneglycol and so on; ketone-based solvent such as acetone, methylethylketone, diethylketone, 2-hexanone, methylisobutylketone, 2-heptanone, 4-heptanone, diisobutyl ketone, acetonylacetone, isophorone, cyclohexanone, methylhexanone, acetophenone, and so on; hydrocarbon-based solvent such as benzene, toluene, xylene, ethylbenzene, hexane, cyclohexane, octane, decane, tetralin and so on; ester-based solvent such as ethyl acetate, butyl acetate, amyl acetate and so on; chain carbonate ester-based solvent such as dimethyl carbonate, methylethyl carbonate, diethyl carbonate and so on; cyclic carbonate ester-based solvent such as ethylene carbonate, propylene carbonate and so on. Among those, hydrocarbon based solvent such as toluene or dioxane and ether based solvent are preferable. Further, the solvent may be used alone, or in combination of two or more kinds thereof. Additionally, the employable solvent is not limited to the above examples.

In any of the layers of the organic compound, suitable resins or additives may be used for improving the properties for forming the films and preventing formation of pinholes. Examples of the resin which can be used include insulating resins such as polystyrenes, polycarbonates, polyarylates, polyesters, polyamides, polyurethanes, polysulfones, polymethyl methacrylates, polymethyl acrylates, cellulose and copolymers of these resins; photoconductive resins such as poly-N-vinylcarbazoles and polysilanes; and electrically conductive resins such as polyanilines, polythiophenes and polypyrroles. Examples of the additive include antioxidants, ultraviolet light absorbents and plasticizers.

To improve the stability of the organic EL of the present invention to temperature, moisture and the atmosphere, a protective layer may be formed on the surface of the device or the entire device may be applied with silicone oil or a resin for protection.

It is preferable for the organic EL device of the present invention that a layer selected from a chalcogenide layer, a metal halide layer and a metal oxide layer is disposed on the surface of at least one of a pair of electrodes.

(Construction of the Organic EL Device)

Following is a description regarding a device structure about the organic EL device of the present invention.

(I) Construction of the organic EL device

Typical examples of the construction in the organic EL device of the present invention are shown below.
(1) An anode/an emitting layer/a cathode
(2) An anode/a hole injecting layer/an emitting layer/a cathode
(3) An anode/an emitting layer/an electron injecting layer/a cathode
(4) An anode/a hole injecting layer/an emitting layer/an electron injecting layer/cathode
(5) An anode/an organic semiconductor layer/an emitting layer/a cathode
(6) An anode/an organic semiconductor layer/an electron barrier layer/an emitting layer/a cathode
(7) An anode/an organic semiconductor layer/an emitting layer/an adhesion improving layer/a cathode
(8) An anode/a hole injecting layer/a hole transporting layer/an emitting layer/an electron injecting layer/a cathode
(9) An anode/an insulating layer/an emitting layer/an insulating layer/a cathode
(10) An anode/an inorganic semiconductor layer/an insulating layer/an emitting layer/an insulating layer/a cathode
(11) An anode/an organic semiconductor layer/an insulating layer/an emitting layer/an insulating layer/a cathode
(12) An anode/an insulating layer/a hole injecting layer/a hole transporting layer/an emitting layer/an insulating layer/a cathode
(13) An anode/an insulating layer/a hole injecting layer/a hole transporting layer/an emitting layer/an electron injecting layer/a cathode Among the above constructions, construction (8) is usually preferable.

Although the compound of the present invention may be used to any organic layer in the organic EL device, it is preferably employable in the light emitting region or the hole transporting region. The amount to be contained in the device is selected from 30 to 100% by mole.

(II) Substrate which Transmits Light

In general, the organic EL device is fabricated on a substrate which transmits light. The substrate which transmits light is a substrate for supporting the organic EL device and preferably a flat and smooth substrate having a light transmittance of 50% or greater to visible light of 400 to 700 nm.

As the substrate which transmits light, for example, glass plate and synthetic resin plate are advantageously employed. Specific examples of the glass plate include soda-lime glass, glass containing barium and strontium, lead glass, aluminosilicate glass, borosilicate glass, barium borosilicate glass and quartz. Specific examples of the synthetic resin plate include plate made of polycarbonate resins, acrylic resins, polyethylene terephthalate resins, polyether sulfide resins and polysulfone resins.

(III) Anode

The anode in the organic EL device of the present invention has a function of injecting holes into a hole transporting layer or an emitting layer, and it is effective that the anode has a work function of 4.5 eV or greater. Specific examples of the material for the anode in the present invention include indium tin oxide alloy (ITO), tin oxide (NESA), gold, silver, platinum, copper, etc. With regard to the anode, its material preferably has a small work function with the aim of injecting electrons into an electron transporting layer or into an emitting layer.

The anode can be prepared by forming a thin film of the electrode material described above in accordance with a process such as the vapor deposition process and the sputtering process.

When the light emitted from the emitting layer is obtained through the anode, it is preferable that the anode has a transmittance of the emitted light greater than 10%. It is also preferable that the sheet resistivity of the anode is several hundreds Ω/□ or smaller. Although the thickness of the anode depends on its material, it is usually selected in the range of from 10 nm to 1 µm and preferably in the range of from 10 to 200 nm.

(IV) Emitting Layer

In the organic EL device of the present invention, the emitting layer combines the following functions. That is,
(1) The injecting function: the function of injecting holes from the anode or the hole injecting layer and injecting electrons from the cathode or the electron injecting layer when an electric field is applied;
(2) The transporting function: the function of transporting the injected charges (electrons and holes) by the force of the electric field; and
(3) The light emitting function: the function of providing the field for recombination of electrons and holes and promote the recombination to emit light.

Although there may be a difference between the capability of the holes being injected and the capability of the electrons being injected, and although there may be a difference between the transporting functions expressed by mobilities of the holes and the electrons, either one of the charges is preferable to be transferred.

As the process for forming the emitting layer, a well-known process such as the vapor deposition process, the spin coating process and the LB process can be employed. It is particularly preferable for the emitting layer to be a molecular deposit film.

The molecular deposit film is a thin film formed by the deposition of a material compound in the gas phase or a thin film formed by the solidification of a material compound in a solution or liquid phase. In general, the molecular deposit film can be distinguished from the thin film formed in accordance with the LB process (the molecular accumulation film) based on the differences in the aggregation structure and higher order structures and functional differences caused by these structural differences.

In addition, as disclosed in JP 57-51781A, the emitting layer can also be formed by dissolving a binder such as a resin and the material compounds into a solvent to prepare a solution, followed by forming a thin film from the prepared solution in accordance with the spin coating process or the like.

In the present invention, any well-known light emitting material other than the compound having fluoranthene structure of the present invention and the compound containing fused ring may be contained in the emitting layer, or an emitting layer containing any other well-known light emitting material may be laminated with the emitting layer containing the light emitting material of the present invention, as long as the object of the present invention is not adversely affected.

The thickness of the emitting layer is, in general, selected in the range of from 5 to 50 nm, preferably in the range of from 7 to 50 nm and the most preferably in the range of from 10 to 50 nm. It is resulted in difficult to form the emitting layer and to control chromaticity thereof when the thickness is thinner than 5 nm, and it may be resulted in possibility of elevating driving voltage when it exceeds 50 nm.

(V) Hole Injecting and Transporting Layer (Hole Transporting Region)

The hole injecting and transporting layer is a layer which helps the injection of holes into the emitting layer and transports the holes to the light emitting region. The layer exhibits a great mobility of holes and, in general, has an ionization energy as small as 5.5 eV or smaller. For the hole injecting and transporting layer, a material which transports holes to the emitting layer at a small strength of the electric field is preferable. A material which exhibits, for example, a mobility of holes of at least $10^{-4}$ cm$^2$/V·sec under an electric field of from $10^4$ to $10^6$ V/cm is preferable.

When the fluoranthene compound of the present invention is employed in the hole transporting region, the hole injecting and transporting layer may be composed of only the fluoranthene compound of the present invention singly or may be composed of both the compound of the present invention and any other material in combination.

With regard to the material which may be employed for forming the hole injecting and transporting layer in combination with the fluoranthene compound of the present invention, any material having the foregoing preferable properties is employed without particularly restricted, any arbitrary material selected from conventional material commonly used as a charge transporting material for the holes in photoconductive materials and well-known material employed for the hole injecting and transporting layer in the EL device is employable.

Specific examples include triazole derivatives (refer to U.S. Pat. No. 3,112,197, etc.), oxadiazole derivatives (refer to U.S. Pat. No. 3,189,447, etc.), imidazole derivatives (refer to JP-B 37-16096, etc.), polyarylalkane derivatives (refer to U.S. Pat. Nos. 3,615,402; 3,820,989; 3,542,544, JP-B 45-555, JP-B 51-10983, JP 51-93224A, JP 55-17105A, JP 56-4148A, JP 55-108667A, JP 55-156953A, JP 56-36656A, etc.), pyrazoline derivatives and pyrazolone derivatives (refer to U.S. Pat. Nos. 3,180,729; 4,278,746; JP 55-88064A, JP 55-88065A, JP 49-105537A, JP 55-51086A, JP 56-80051A, JP 56-88141A, JP 57-45545A, JP 54-112637A, JP 55-74546A, etc.), phenylenediamine derivatives (refer to U.S. Pat. No. 3,615,404; JP-B 51-10105, JP-B 46-3712, JP-B 47-25336, JP 54-119925A, etc.), arylamine derivatives (refer to U.S. Pat. Nos. 3,567,450; 3,240,597; 3,658,520; 4,232,103; 4,175,961; 4,012,376; JP-B 49-35702, JP-B 39-27577, JP 55-144250A, JP 56-119132A, JP 56-22437A, German Patent No. 1,110,518, etc.), amino-substituted chalcone derivatives (refer to U.S. Pat. No. 3,526,501, etc.), oxazole derivatives (disclosed in U.S. Pat. No. 3,257,203, etc.), styrylanthracene derivatives (refer to JP 56-46234A, etc.), fluorenone derivatives (refer to JP 54-110837A, etc.), hydrazone derivatives (refer to U.S. Pat. No. 3,717,462, JP 54-59143A, JP 55-52063A, JP 55-52064A, JP 55-46760A, JP 57-11350A, JP 57-148749A, JP 2-311591A, etc.), stilbene derivatives (refer to JP 61-210363A, JP 61-228451A, JP 61-14642A, JP 61-72255A, JP 62-47646A, JP 62-36674A, JP 62-10652A, JP 62-30255A, JP 60-93455A, JP 60-94462A, JP 60-174749A, JP 60-175052A, etc.), silazane derivatives (U.S. Pat. No. 4,950,950), polysilane-based polymer (JP 2-204996A), aniline-based copolymer (JP 2-282263A), etc.

With regard to the material for the hole injecting and transporting layer, the above materials are also employable, and porphyrin compounds (disclosed in JP 63-295695A), aromatic tertiary amine compounds and styryl amine compounds (refer to U.S. Pat. No. 4,127,412, JP 53-27033A, JP 54-58445A, JP 55-79450A, JP 55-144250A, JP 56-119132A, JP 61-295558A, JP 61-98353A, JP 63-295695A, etc.) are preferable and the aromatic tertiary amine compounds are particularly preferable.

Further examples include, 4,4'-bis(N-(1-naphthyl)-N-phenylamino)biphenyl (hereinafter abbreviate as NPD) which has 2 fused aromatic rings in its molecule described in U.S. Pat. No. 5,061,569 and 4,4',4''-tris(N-(3-methylphenyl)-N-phenylamino)triphenylamine (hereinafter abbreviate as MTDATA) described in JP 4-308688A which includes three triphenylamine units connected in a star burst configuration.

In addition to the above-mentioned aromatic dimethylidene compound described as a material for the emitting layer, inorganic compound such as p-type Si and p-type SiC may be used as the material for the hole injecting layer.

To form the hole injecting and transporting layer, a thin film may be formed from the above compound in accordance with a well-known process such as the vacuum vapor deposition process, the spin coating process, the casting process and the LB process. Although the thickness of the hole injecting and transporting layer is not particularly limited, the thickness is usually from 5 nm to 5 μm.

(VI) Electron Injecting Layer

The electron injecting layer is a layer having a great electron mobility, which assists the injection of electrons into the emitting layer. Among the electron injecting layers, the adhesion improving layer is a layer made of a material exhibiting excellent adhesion to the cathode. As the material for the electron injecting layer, metal complexes of 8-hydroxyquinoline or derivatives thereof are preferable.

Examples of the metal complexes of 8-hydroxyquinoline and derivatives thereof include metal chelate oxinoid compounds including chelates of oxine (in general, 8-quinolinol or 8-hydroxyquinoline).

For example, Alq described in the above term about the light emitting material is employable as the electron injecting layer.

On the other hand, examples of the oxadiazole derivatives include an electron transfer compound represented by the following general formulae:

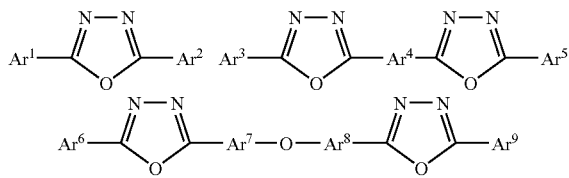

(In the formula, $Ar^1$, $Ar^2$, $Ar^3$, $Ar^5$, $Ar^6$ and $Ar^9$ may be the same or different and each independently represents a substituted or unsubstituted aryl group; $Ar^4$, $Ar^7$ and $Ar^8$ may be the same or different and each independently represents a substituted or unsubstituted arylene group.)

Examples of aryl group include a phenyl group, a biphenyl group, an anthracenyl group, a perilenyl group and a pyrenyl group. Examples of the arylene group include a phenylene group, a naphthylene group, a biphenylene group, an anthracenylene group, a perilenylene group, a pyrenylene group, etc. Furthermore, examples of the substituent include an alkyl group having 1 to 10 carbon atoms, an alkoxy group having 1 to 10 carbon atoms or a cyano group, etc. The electron transfer compound is preferably a thin-film forming compound.

Specific examples of the electron transfer compounds are shown below:

A preferred embodiment of the organic EL device of the present invention contains a reductive dopant in an electron transporting region or an interfacial region between a cathode and an organic compound layer. The reductive dopant is defined as the substance capable of reducing an electron transporting compound. Accordingly, various compounds having a specified reducing property may be employable and examples of the reductive dopant include at least one compound selected from alkali metals, alkaline earth metals, rare earth metals, oxides of alkali metals, halides of alkali metals, oxides of alkaline earth metals, halides of alkaline earth metals, oxides of rare earth metals, halides of rare earth metals, organic complexes of alkali metals, organic complexes of alkaline earth metals, and organic complexes of rare earth metals.

Examples of the preferable reductive dopant include at least one alkali metal selected from the group consisting of Li (the work function: 2.9 eV), Na (the work function: 2.36 eV), K (the work function: 2.28 eV), Rb (the work function: 2.16 eV) and Cs (the work function: 1.95 eV) or at least one alkaline earth metals selected from the group consisting of Ca (the work function: 2.9 eV), Sr (the work function: 2.0 to 2.5 eV) and Ba (the work function: 2.52 eV), and the compounds having work functions of 2.9 eV or smaller are particularly preferable. Among the above substances, at least one alkali metal selected from the group consisting of K, Rb and Cs is more preferable, Rb and Cs are still more preferable, and Cs is most preferable as the reducing dopant. Since those alkali metals have a particularly high reducing capability, the luminance is improved and the lifetime is prolonged by the addition thereof into an electron injection region in a relatively small amount. A combination of two or more alkali metals is also preferably used as the reductive dopant having a work function of 2.9 eV or smaller. A combination containing Cs such as Cs and Na, Cs and K, Cs and Rb and Cs, Na and K is particularly preferred. By combinedly containing Cs, the reducing capability is effectively performed, and the luminance is enhanced and the lifetime is prolonged in the organic EL device by the addition into the electron injection region.

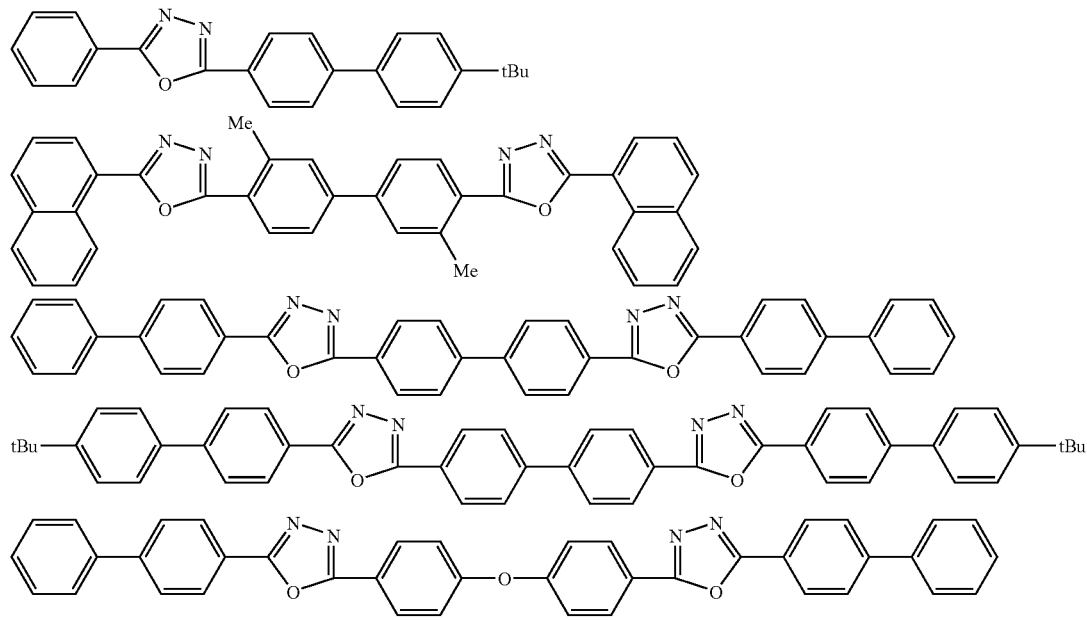

In the present invention, an electron injecting layer made of an electrically insulating material or a semiconductor may be further disposed between the cathode and the organic layer. The electron injecting layer enables to effectively prevent a leak of electric current and to improve the electron injection property. As the electrically insulating material, at least one metal compound selected from the group consisting of chalcogenides of alkali metals, chalcogenides of alkaline earth metals, halides of alkali metals and halides of alkaline earth metals is preferable. It is preferable that the electron injecting layer is constituted with the above metal compound since the electron injecting property can be further improved. Preferable examples of the chalcogenide of an alkali metal include $Li_2O$, $K_2O$, $Na_2S$, $Na_2Se$ and $Na_2O$. Preferable examples of the chalcogenide of an alkaline earth metal include CaO, BaO, SrO, BeO, BaS and CaSe. Further, preferable examples of the halide of an alkali metal include LiF, NaF, KF, LiCl, KCl and NaCl. Furthermore, preferable examples of the halide of an alkaline earth metal include fluoride such as $CaF_2$, $BaF_2$, $SrF_2$, $MgF_2$ and $BeF_2$ and halides other than the fluorides.

Examples of the semiconductor constituting the electron transporting layer include oxides, nitrides and oxide nitrides comprising at least one element selected from Ba, Ca, Sr, Yb, Al, Ga, In, Li, Na, Cd, Mg, Si, Ta, Sb and Zn used singly or in combination of two or more. It is preferable that the inorganic compound constituting the electron transporting layer forms a crystallite or amorphous insulating thin film. When the electron transporting layer is constituted with the above insulating thin film, a more uniform thin film can be formed and defective pixels such as dark spots can be decreased. Examples of the inorganic compound include chalcogenides of alkali metals, chalcogenides of alkaline earth metals, halides of alkali metals and halides of alkaline earth metals which are described above.

(VII) Cathode

The cathode is formed from an electrode substance such as metal, alloy, electrically conductive compound or a mixture thereof each having a small work function (4 eV or smaller) to ensure the electron injection into the electron injecting and transporting layer or the emitting layer. Examples of the electrode substance include sodium, sodium-potassium alloy, magnesium, lithium, magnesium-silver alloy, aluminum/aluminum oxide, aluminum-lithium alloy, indium, rare earth metal, etc.

The cathode is prepared by forming a thin film of the electrode material described above in accordance with a process such as the vapor deposition process and the sputtering process.

When the light emitted from the emitting layer is taken out of the cathode, it is preferable that the cathode has a transmittance of greater than 10% to the emitted light.

It is also preferable that the sheet resistivity of the cathode is several hundreds $\Omega/\square$ or smaller and the thickness of the cathode is, in general, selected from 10 nm to 1 μM and preferably from 50 to 200 nm.

(VIII) Insulating Layer

In general, an organic EL device tends to form defects in pixels due to leak and short circuit since an electric field is applied to ultra-thin films. To prevent the defects, a layer of an insulating thin film may be inserted between the pair of electrodes.

Examples of the material for the insulating layer include aluminum oxide, lithium fluoride, lithium oxide, cesium fluoride, cesium oxide, magnesium oxide, magnesium fluoride, calcium oxide, calcium fluoride, aluminum nitride, titanium oxide, silicon oxide, germanium oxide, silicon nitride, boron nitride, molybdenum oxide, ruthenium oxide and vanadium oxide.

Mixtures and laminates of the above compounds can also be employed.

(IX) Fabrication Process of the Organic EL Device

The organic EL device of the present invention is fabricated, for example, by forming an anode, an emitting layer, an optional hole injecting layer, an optional electron injecting layer, and a cathode in accordance with the process using the materials each being described above. Alternatively, each layer may be formed in a reverse order from the cathode to the anode.

An embodiment of the fabrication of an organic EL device having a construction of an anode/a hole injecting layer/an emitting layer/an electron injecting layer/a cathode in this order on a light-transmitting substrate will be described in the following.

First, on a suitable substrate which transmits light, a thin film of an anode substance is formed so as to have a film thickness of 1 μm or thinner, preferably from 10 nm to 200 nm in accordance with the vapor deposition process, the sputtering process, etc. Then, a hole injecting layer is formed on the anode. The hole injecting layer can be formed in accordance with the vacuum vapor deposition process, the spin coating process, the casting process or the LB process, as described above. The vacuum vapor deposition process is preferable because a uniform film can be easily obtained and pinhole is little formed. When the hole injecting layer is formed in accordance with the vacuum vapor deposition process, the conditions are preferably selected from the following ranges: temperature of vapor deposition source: 50 to 450° C.; degree of vacuum: $10^{-7}$ to $10^{-3}$ Torr; vapor deposition rate: 0.01 to 50 nm/s; temperature of the substrate: −50 to 300° C.; and film thickness: 5 nm to 5 μm; although depending on the employed compound (material for hole injecting layer), the crystal structure of the targeted hole injecting layer and the recombination structure thereof, etc.

Subsequently, the emitting layer is formed on the hole injecting layer by depositing a thin film of the organic light emitting material in accordance with the vacuum vapor deposition process, the sputtering process, the spin coating process or the casting process. The vacuum vapor deposition process is preferable because a uniform film can be easily obtained and pinhole is little formed. When the emitting layer is formed in accordance with the vacuum vapor deposition process, the conditions of the vacuum vapor deposition can be selected in the same ranges as in the deposition of the hole injecting layer, although depending on the compound to be used.

Next, the electron injecting layer is formed on the emitting layer formed above. Similarly to the formation of the hole injecting layer and emitting layer, the electron injecting layer is preferably formed in accordance with the vacuum vapor deposition process, because a uniform film is required. The conditions of the vacuum vapor deposition can be selected from the same ranges as in the formation of the hole injecting layer and the emitting layer.

Although the compound of the present invention depends on that they are contained in any layer among a light emitting region and a hole transporting region, it may be commonly vapor deposited together with other materials. In addition, when the spin coating process is employed, it may be contained therein by blending it with other materials.

Finally, the cathode is formed on the electron injecting layer, to obtain an organic EL device.

The cathode is made of a metal and can be formed in accordance with the vacuum vapor deposition process or the sputtering process. However, the vacuum vapor deposition process is preferably employed in order to prevent the underlying organic layers from being damaged during the formation of the film.

In the above fabrication of the organic EL device, the layers from the anode to the cathode are successively formed preferably in a single evacuation operation.

The thickness of each layer in the organic thin film layers in the organic EL device of the present invention is not particularly limited. In general, an excessively thin layer tends to have defects such as pinholes, and an excessively thick layer requires a high applied voltage and results in decreasing the efficiency. Therefore, the thickness is preferably from several nm to 1 μm.

The organic EL device emits light when a direct voltage of 5 to 40 V is applied with the anode being + terminal and the cathode being − terminal. In the reverse polarity, no electric current flows and no light is emitted upon the application of voltage. When an alternating voltage is applied, the uniform light emission is observed only in the polarity where the anode is + and the cathode is −. The wave shape of alternating voltage is not limited.

(Application of the Organic EL Device)

The organic EL device of the present invention is applicable to the product to which an enhanced luminance and efficiency of light emission are required under low driving voltage. Examples of the application include display devices, display panels, lighting systems, light sources for printer, backlight of liquid crystal display devices and so on; and the EL devices are applicable to the field such as beacon lights, signboards, and room interior goods. Examples of the display devices include flat panel display devices with energy-saving function and high visibility property. Further, the light source for the printer is employable as a light source for a laser beam printer. Furthermore, the use of the device of the present invention enables to excitingly reduce the volume of apparatuses. Regarding with the lighting system or the backlight, the use of the organic EL device of the present invention allows to expect energy-saving effect.

EXAMPLES

The present invention will be described in further detail with reference to Examples, which does not limit the scope of the present invention unless it goes beyond the gist of the invention.

Synthesis Example 1

Synthesis of Compound 1-2

(1) Synthesis of 5-bromoacenaphthylene

Adding 29.2 g (128.7 mmol) of 2,3-dichloro-5,6-dicyano-1,4-benzoquinone (DDQ) to 25.4 g (107.3 mmol) of 5-bromoacenaphthene and 500 ml of dry benzene, the resultant solution was stirred while refluxing under heating for 6 h. Further, adding 6.0 g (26.4 mmol) of DDQ into the reacted mixture, the resultant mixture was stirred under heating for 4 h. After the resultant mixture was cooled by being left standing, precipitates are separated by filtration and washed with chloroform. Gathering the filtrates together, it was washed with 10% sodium hydroxide aqueous solution and water. After the solution was separated, drying the organic layer through anhydrous magnesium sulfate, the solvent was distillated away. The resultant mixture was dried under reduced pressure to obtain 13.0 g (yield: 51.6%) of brown solid being 5-bromoacenaphthylene.

(2) Synthesis of 3-bromo-7,12-dibenzo[k]fluoranthene

A mixture prepared by adding 14.9 g (55.2 mmol) of 1,3-diphenylisobenzofuran and 12.8 g (55.2 mmol) of 5-bromoacenaphthylene into 50 ml of toluene was stirred while refluxing under heating for 16 h. After distillating away the solvent, adding 1200 ml of acetic acid and the resultant solution was heated up to 80° C. Adding 150 ml of 48% HBr aqueous solution into the mixture, stirred at 80° C. for 1 h. After cooling it down to a room temperature, precipitates were separated by filtration and washed with methanol. The resultant yellow solid was recrystallized through 200 ml of toluene. The crystal was separated by filtration to obtain 19.8 g (yield: 74%) of yellow solid being 3-bromo-7,12-dibenzo[k]fluoranthene.

(3) Synthesis of 3-(9,9-dimethyl-9H-fluorene-2-yl)-7,12-diphenylbenzo[k]-fluoranthene (Compound 1-2)

Under an atmospheric argon gas, adding 2M sodium carbonate aqueous solution (6.2 ml, 12.4 mmol) and 0.29 g (0.25 mmol) of tetrakis-(triphenylphosphino)palladium into a mixture of 4.00 g (8.27 mmol) of 3-bromo-7,12-dibenzo[k]fluoranthene, 2.36 g (9.92 mmol) of 9,9-dimethyl-9H-fluorene-2-yl boronic acid, 25 ml of toluene and 25 ml of dimethoxyethane, the resultant solution was stirred at 80° C. for 8 h. Further, adding 0.29 g (0.25 mmol) of tetrakis(triphenylphosphino)-palladium, the resultant solution was stirred at 80° C. for 11 h. After cooling it down to a room temperature, methanol was added, solids were separated by filtration and washed with methanol. The resultant solid was recrystallized through dichloromethane and methanol to obtain 4.78 g (yield: 96.8%) of 3-(9,9-dimethyl-9H-fluorene-2-yl)-7,12-diphenylbenzo[k]-fluoranthene as yellow solid.

The measured results of FDMS (Field Desorption Mass Spectrum) analysis, ultraviolet absorption peak wavelength λmax (molar absorption coefficient ε) in toluene solution and fluorescent light emission peak wavelength (FL) about the resultant compound are described below. Further, measured result of $^1$H-NMR spectrum is shown in FIG. 1. Additionally, the NMR measurement was conducted by means of FT-NMR apparatus AL400 manufactured by JEOL Ltd.

FDMS, calcd for $C_{47}H_{32}$=596. found m/z=596 (M$^+$).

UV(PhMe); λmax, 424 nm (ε 4.37), FL (PhMe, λex=320 nm); λmax, 444 nm

Synthesis Example 2

Synthesis of Compound 1-3

Synthesis Example 2 was carried out in a similar manner as Synthesis Example 1 except that 4-(naphthalen-1-yl)phenyl boronic acid was employed instead of 9,9-dimethyl-9H-fluorene-2-yl boronic acid to obtain 3-(4-(naphthalen-1-yl)phenyl)-7,12-diphenylbenzo[k]fluoranthene (Compound 1-3).

Figure 2:
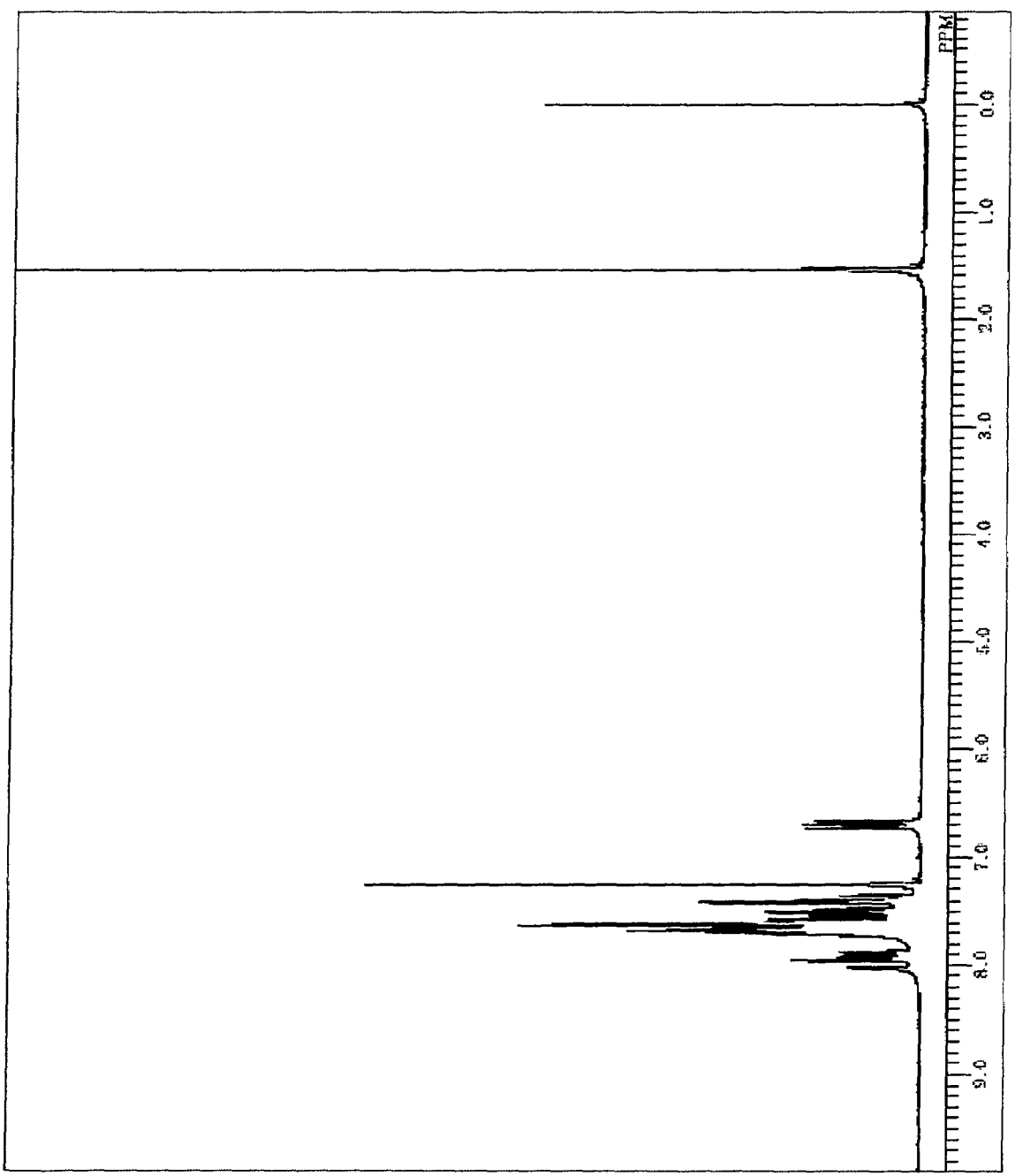
FIG. 2 is a diagram showing $^1$H-NMR spectrum of Compound 1-3, which is obtained in Synthesis Example 2.

The measured results of FDMS analysis, ultraviolet absorption peak wavelength λ max (molar absorption coefficient ε) in toluene solution and fluorescent light emission peak wavelength (FL) about the resultant compound are described below. Further, measured result of $^1$H-NMR spectrum is shown in FIG. 2.

FDMS, calcd for $C_{48}H_{30}$=606. found m/z=606 ($M^+$).
UV(PhMe); λmax, 422 nm (ε 4.35), FL (PhMe, λex=319 nm); λmax, 438 nm Synthesis Example 3

Synthesis of Compound 1-5

Synthesis Example 3 was carried out in a similar manner as Synthesis Example 1 except that 4-(10-naphthalen-2-ypanthracene-9-yl)-phenyl boronic acid was employed instead of 9,9-dimethyl-9H-fluorene-2-yl boronic acid to obtain 3-(4-(10-naphthalen-2-yl)anthracene-9-yl)phenyl)-7,12-diphenylbenzo[k]fluoranthene (Compound 1-5).

Figure 3:
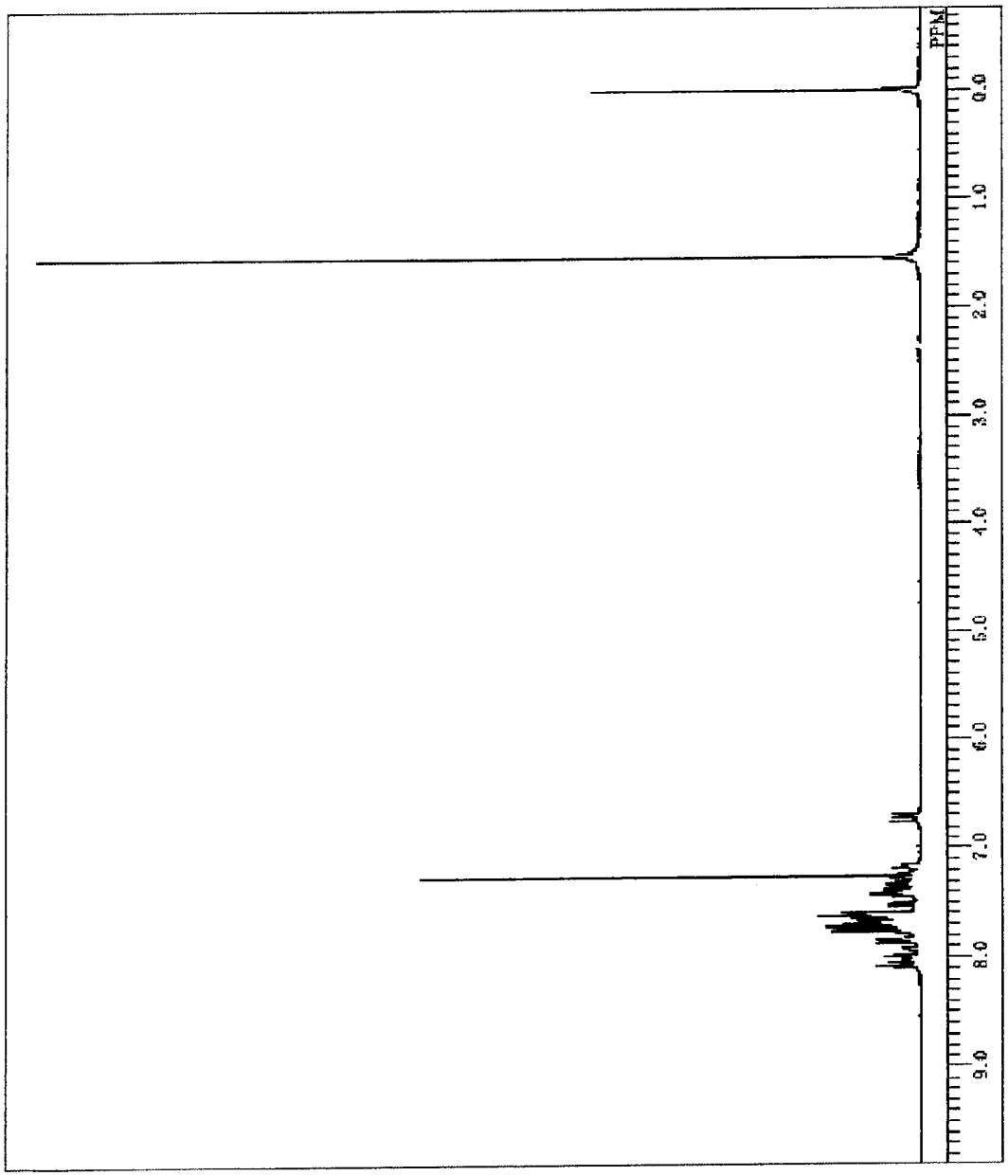
FIG. 3 is a diagram showing $^1$H-NMR spectrum of Compound 1-5, which is obtained in Synthesis Example 3.

The measured results of FDMS analysis, ultraviolet absorption peak wavelength λmax (molar absorption coefficient ε) in toluene solution and fluorescent light emission peak wavelength (FL) about the resultant compound are described below. Further, measured result of $^1$H-NMR spectrum is shown in FIG. 3.

FDMS, calcd for $C_{62}H_{38}$=782. found m/z=782 ($M^+$).
UV(PhMe); λmax, 422 nm (ε 4.37), FL (PhMe, λex=317 nm); λmax, 439 nm Synthesis Example 4

Synthesis of Compound 1-10

Synthesis Example 4 was carried out in a similar manner as Synthesis Example 1 except that 6-phenylnaphthalen-2-yl boronic acid was employed instead of 9,9-dimethyl-9H-fluorene-2-yl boronic acid to obtain 7,12-diphenyl-3-(6-phenyl naphthalen-2-yl)benzo[k]fluoranthene (Compound 1-10).

Figure 4:
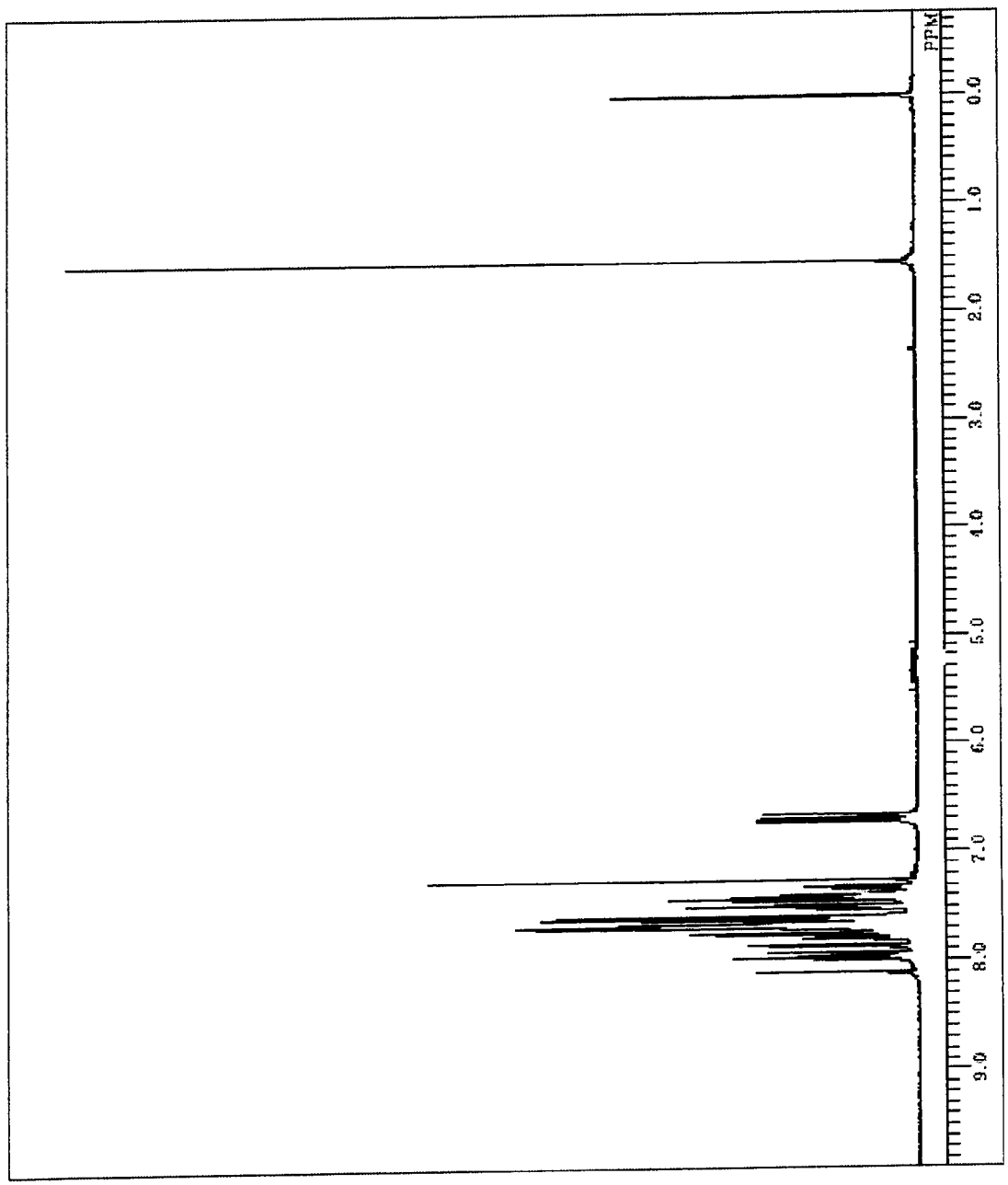
FIG. 4 is a diagram showing $^1$H-NMR spectrum of Compound 1.10, which is obtained in Synthesis Example 4.

The measured results of FDMS analysis, ultraviolet absorption peak wavelength λmax (molar absorption coefficient ε) in toluene solution and fluorescent light emission peak wavelength (FL) about the resultant compound are described below. Further, measured result of $^1$H-NMR spectrum is shown in FIG. 4.

FDMS, calcd for $C_{48}H_{30}$=606. found m/z=606 ($M^+$).
UV(PhMe); λmax, 424 (ε 4.24), FL (PhMe, λex=318 nm); λmax, 443 nm Synthesis Example 5

Synthesis of Compound 2-8

Synthesis Example 5 was carried out in a similar manner as Synthesis Example 1 except that 9,10-diphenylanthracene-2-yl boronic acid was employed instead of 9,9-dimethyl-9H-fluorene-2-yl boronic acid to obtain 3-(9,10-diphenylanthracene-2-yl)-7,12-diphenylbenzo[k]fluoranthene (Compound 2-8).

Figure 5:
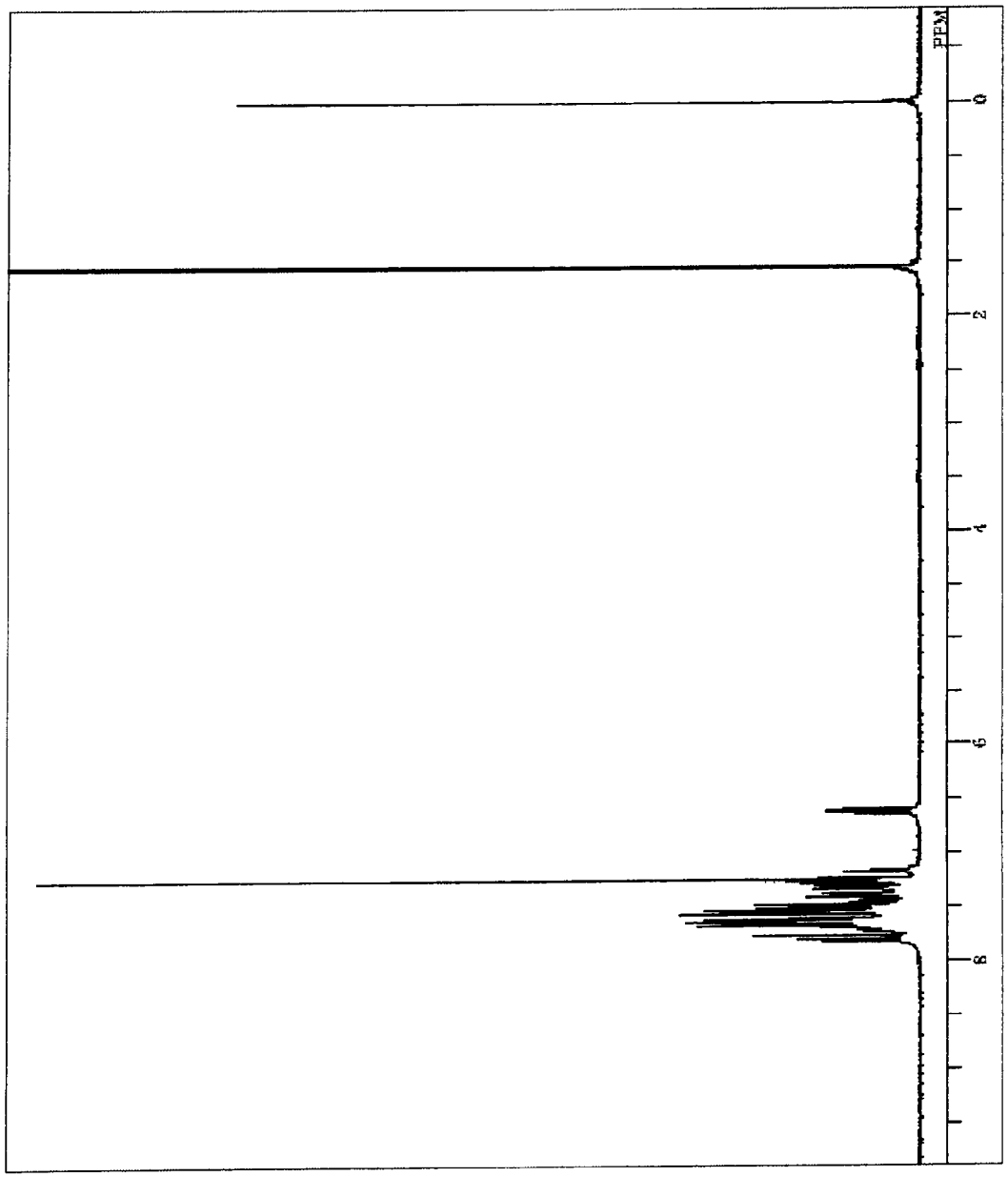
FIG. 5 is a diagram showing $^1$H•NMR spectrum of Compound 2-8, 15 which is obtained in Synthesis Example 5.

The measured results of FDMS analysis, ultraviolet absorption peak wavelength λmax (molar absorption coefficient ε) in toluene solution and fluorescent light emission peak wavelength (FL) about the resultant compound are described below. Further, measured result of $^1$H-NMR spectrum is shown in FIG. 5.

FDMS, calcd for $C_{58}H_{36}$=732. found m/z=732 ($M^+$).
UV(PhMe); λmax, 427 nm (ε 4.37), FL (PhMe, λex=315 nm); λmax, 455 nm Synthesis Example 6

Synthesis of Compound 2-9

Synthesis Example 6 was carried out in a similar manner as Synthesis Example 1 except that pyrene-1-yl boronic acid was employed instead of 9,9-dimethyl-9H-fluorene-2-yl boronic acid to obtain 7,12-diphenyl-3-(pyrene-4-yl)benzo[k]fluoranthene (Compound 2-9).

Figure 6:
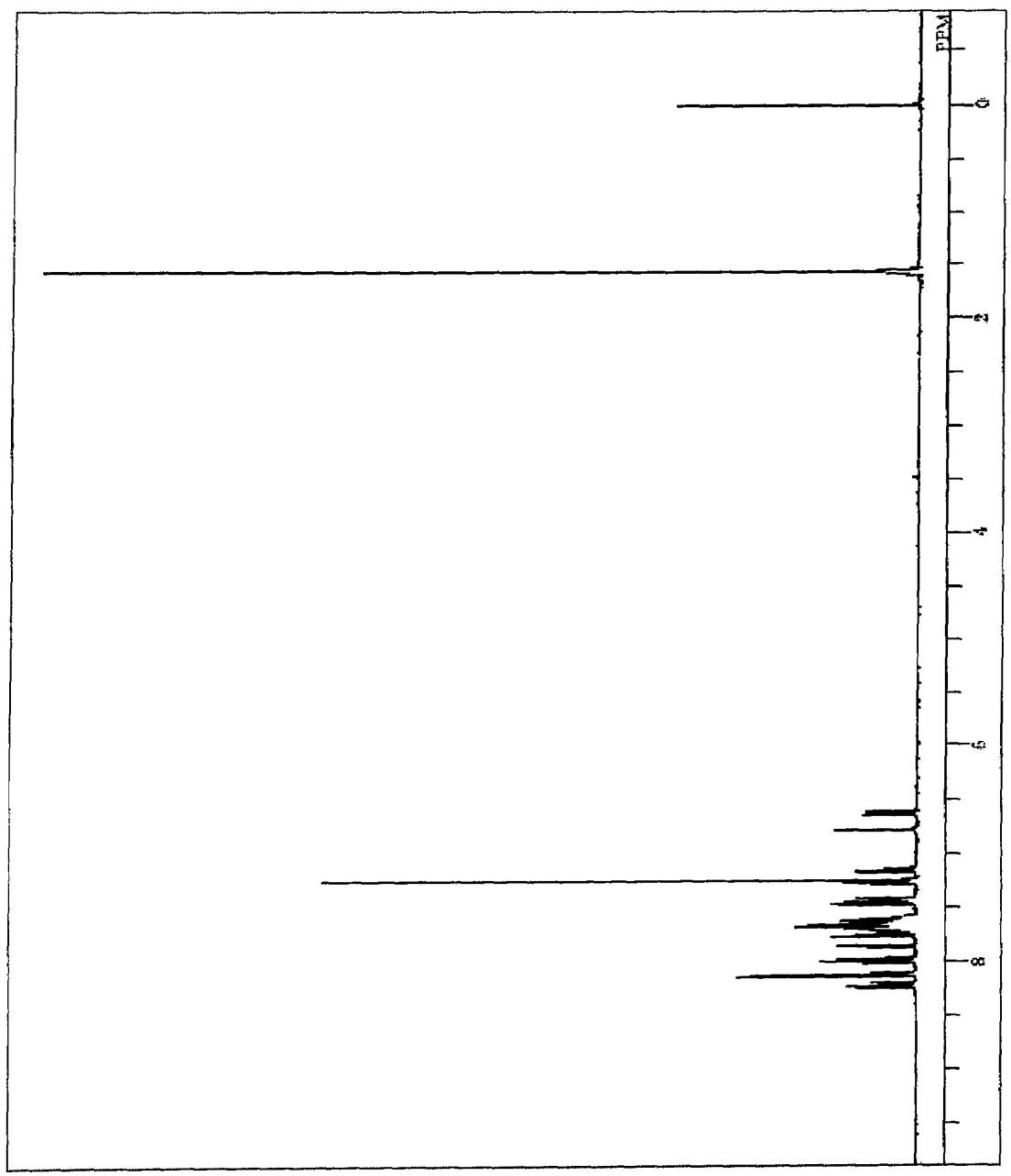
FIG. 6 is a diagram showing $^1$H-NMR spectrum of Compound 2-9, which is obtained in Synthesis Example 6.

The measured results of FDMS analysis, ultraviolet absorption peak wavelength λmax (molar absorption coefficient ε) in toluene solution and fluorescent light emission peak wavelength (FL) about the resultant compound are described below. Further, measured result of $^1$H-NMR spectrum is shown in FIG. 6.

FDMS, calcd for $C_{48}H_{28}$=604. found m/z=604 ($M^+$).
UV(PhMe); λmax, 419 nm (ε 4.45), FL (PhMe, λex=315 nm); λmax, 451 nm Synthesis Example 7

Synthesis of Compound 4-3

Under an atmospheric argon gas, adding 0.10 ml (62 mass %, 0.30 mmol) of tri-t-butylphosphine/toluene solution into a suspension made by throwing 3.50 g (6.26 mmol) of 3-(3-bromophenyl)-7,12-diphenylbenzo[k]-fluoranthene, 2.53 g (9.39 mmol) of dinaphthalen-2-ylamine, 0.17 g (0.19 mmol) of tris(dibenzylideneacetone)dipalladium(II) and 0.90 g (9.39 mmol) of t-butoxy sodium into 30 ml of anhydrous toluene; the reaction was allowed to proceed under refluxing while heating for 7 h. Methanol was added to the reacted mixture, precipitated solids were separated by filtration and washed with methanol. The resultant solid was purified through column chromatography (silicagel:toluene). Further, the solid was recrystallized through toluene and methanol to obtain 0.52 g (yield: 11%) of 3-(3-(dinaphthalen-2-ylamino)phenyl)-7,12-diphenylbenzo[k]fluoranthene (Compound 4-3).

Figure 7:
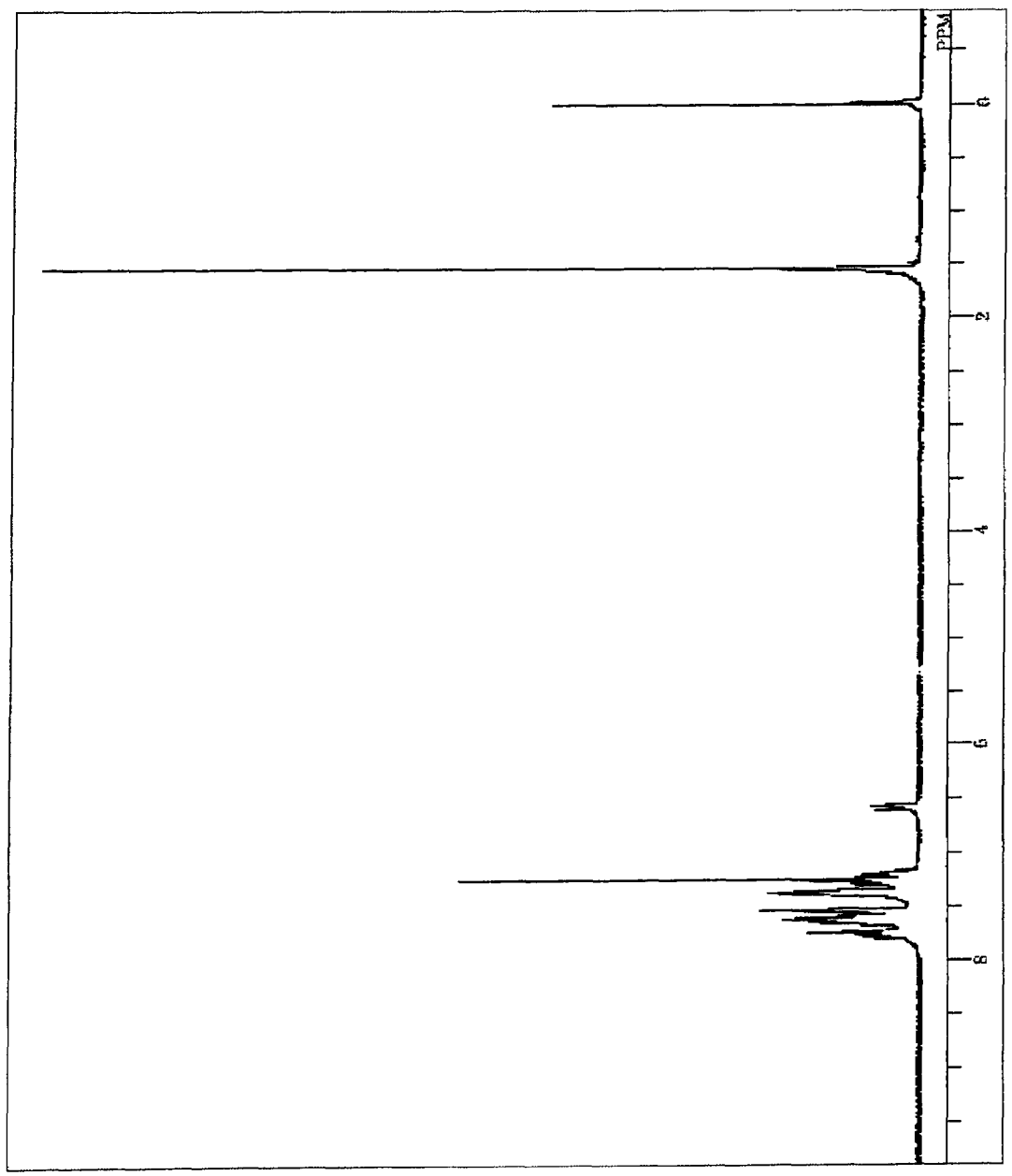
FIG. 7 is a diagram showing $^1$H•NMR. spectrum of Compound 4-3, which is obtained in Synthesis Example 7.

The measured results of FDMS analysis, ultraviolet absorption peak wavelength λmax (molar absorption coefficient ε) in toluene solution and fluorescent light emission peak wavelength (FL) about the resultant compound are described below. Further, measured result of $^1$H-NMR spectrum is shown in FIG. 7.

FDMS, calcd for $C_{58}H_{37}N$=747. found m/z=747 ($M^+$).
UV(PhMe); λmax, 422 nm (ε 4.28), FL (PhMe, λex=322 nm); λmax, 461 nm Synthesis Example 8

Synthesis of Compound 1-1

Synthesis Example 8 was carried out in a similar manner as Synthesis Example 1 except that phenyl boronic acid was employed instead of 9,9-dimethyl-9H-fluorene-2-yl boronic acid in Synthesis Example 1 to obtain 3-phenyl-7,12-diphenylbenzo[k]fluoranthene (Compound 1-1).

The measured results of FDMS analysis, ultraviolet absorption peak wavelength λmax (molar absorption coefficient ε) in toluene solution and fluorescent light emission peak wavelength about the resultant compound are described below.

FDMS, calcd for $C_{38}H_{24}$=481. found m/z=481 ($M^+$).
UV(PhMe); λmax, 420 (ε 4.31), FL (PhMe, λex=318 nm); λmax, 433 nm Synthesis Example 9

Synthesis of Compound 1-9

Synthesis Example 9 was carried out in a similar manner as Synthesis Example 1 except that 2-naphthyl boronic acid was employed instead of 9,9-dimethyl-9H-fluorene-2-yl boronic acid in Synthesis Example to obtain 3-(naphthalen-2-yl)-7,12-diphenylbenzo[k]fluoranthene (Compound 1-9).

The measured results of FDMS analysis, ultraviolet absorption peak wavelength λmax (molar absorption coefficient ε) in toluene solution and fluorescent light emission peak wavelength about the resultant compound are described below.

FDMS, calcd for $C_{42}H_{26}$=531. found m/z=531 ($M^+$).
UV(PhMe); λmax, 422 (ε 4.72), FL (PhMe, λex=319 nm); λmax, 439 nm

Synthesis Example 10

Synthesis of Compound 1-15

Synthesis Example 10 was carried out in a similar manner as Synthesis Example 1 except that 6-(naphthalen-2-yl)naphthalen-2-yl boronic acid was employed instead of 9,9-dimethyl-9H-fluorene-2-yl boronic acid in Synthesis Example 1 to obtain 3-(6-(naphthalen-2-yl-naphthalen-2-yl)-7,12-diphenylbenzo[k]fluoranthene (Compound 1-15).

The measured results of FDMS analysis, ultraviolet absorption peak wavelength λmax (molar absorption coefficient ε) in toluene solution and fluorescent light emission peak wavelength about the resultant compound are described below.

FDMS, calcd for $C_{52}H_{32}$=657. found m/z=657 ($M^+$).
UV(PhMe); λmax, 424 (ε 4.73), FL (PhMe, λex=332 nm); λmax, 443 nm

Synthesis Example 11

Synthesis of Compound 1-16

Synthesis Example 11 was carried out in a similar manner as Synthesis Example 1 except that 4-(diphenylamino)phenyl boronic acid was employed instead of 9,9-dimethyl-9H-fluorene-2-yl boronic in Synthesis Example 1 to obtain 3-(4-(diphenylamino)phenyl)-7,12-diphenylbenzo[k]-fluoranthene (Compound 1-16).

The measured results of FDMS analysis, ultraviolet absorption peak wavelength λmax (molar absorption coefficient c) in toluene solution and fluorescent light emission peak wavelength about the resultant compound are described below.

FDMS, calcd for $C_{50}H_{33}N$=648. found m/z=648 ($M^+$).
UV(PhMe); λmax, 426 (ε 4.41), FL (PhMe, λex=316 nm); λmax, 472 nm

Synthesis Example 12

Synthesis of Compound 2-12

Synthesis Example 12 was carried out in a similar manner as Synthesis Example 1 except that 4-(carbazole-9-yl)phenyl boronic acid was employed instead of 9,9-dimethyl-9H-fluorene-2-yl boronic acid in Synthesis Example 1 to obtain 3-(4-(carbazole-9-yl)phenyl)-7,12-diphenylbenzo[k]-fluoranthene (Compound 2-12).

The measured results of FDMS analysis, ultraviolet absorption peak wavelength λmax (molar absorption coefficient ε) in toluene solution and fluorescent light emission peak wavelength about the resultant compound are described below.

FDMS, calcd for $C_{50}H_{33}N$=646. found m/z=646 ($M^+$).
UV(PhMe); λmax, 422 (ε 4.35), FL (PhMe, λex=315 nm); λmax, 443 nm

Synthesis Example 13

Synthesis of Compound 4-14

Synthesis Example 13 was carried out in a similar manner as Synthesis Example 1 except that 1-biphenyl boronic acid was employed instead of 9,9-dimethyl-9H-fluorene-2-yl boronic acid in Synthesis Example 1 to obtain 3-(1-biphenyl)-7,12-diphenylbenzo[k]fluoranthene (Compound 4-14).

The measured results of FDMS analysis, ultraviolet absorption peak wavelength λmax (molar absorption coefficient ε) in toluene solution and fluorescent light emission peak wavelength about the resultant compound are described below.

FDMS, calcd for $C_{44}H_{28}$=557. found m/z=557 ($M^+$).
UV(PhMe); λmax, 419, FL (PhMe, λex=254 nm); λmax, 436 nm

Synthesis Example 14

Synthesis of Compound 5-3

Synthesis Example 14 was carried out in a similar manner as Synthesis Example 1 except that 4-cyanophenyl boronic acid was employed in stead of 9,9-dimethyl-9H-fluorene-2-yl boronic acid in Synthesis Example to obtain 3-(4-cyanophenyl)-7,12-diphenylbenzo[k]fluoranthene (Compound 5-3).

The measured results of FDMS analysis, ultraviolet absorption peak wavelength λmax (molar absorption coefficient ε) in toluene solution and fluorescent light emission peak wavelength about the resultant compound are described below.

FDMS, calcd for $C_{39}H_{23}N$=506. found m/z=506 ($M^+$).
UV(PhMe); λmax, 424 (ε 4.28), FL (PhMe, λex=318 nm); λmax, 443 nm

Synthesis Example 15

Synthesis of Compound 5-7

Synthesis Example 15 was carried out in a similar manner as Synthesis Example 1 except that 4-trifluoromethylphenyl boronic acid was employed instead of 9,9-dimethyl-911-fluorene-2-yl boronic acid in Synthesis Example 1 to obtain 3-(4-trifluoromethylphenyl)-7,12-diphenylbenzo[k]-fluoranthene (Compound 5-7).

The measured results of FDMS analysis, ultraviolet absorption peak wavelength λmax (molar absorption coefficient ε) in toluene solution and fluorescent light emission peak wavelength about the resultant compound are described below.

FDMS, calcd for $C_{39}H_{23}F_3$=549. found m/z=549 ($M^+$).
UV(PhMe); λmax, 421 (ε 4.28), FL (PhMe, λex=318 nm); λmax, 436 nm

Synthesis Example 16

Synthesis of Compound 5-16

Synthesis Example 16 was carried out in a similar manner as Synthesis Example 1 except that 3,5-difluorophenyl boronic acid was employed instead of 9,9-dimethyl-911- fluorene-2-yl boronic acid in Synthesis Example 1 to obtain 3-(3,5-difluorophenyl)-7,12-diphenylbenzo[k]-fluoranthene (Compound 5-16).

The measured results of FDMS analysis, ultraviolet absorption peak wavelength λmax (molar absorption coefficient ε) in toluene solution and fluorescent light emission peak wavelength about the resultant compound are described below.

FDMS, calcd for $C_{38}H_{22}F_2$=517. found m/z=517 ($M^+$).
UV(PhMe); λmax, 421 (ε 4.23), FL (PhMe, λex=318 nm); λmax, 437 nm Synthesis Example 17

Synthesis of Compound 6-1

Synthesis Example 17 was carried out in a similar manner as Synthesis Example 1 except that 9-phenylcarbazole-3-yl boronic acid was employed instead of 9,9-dimethyl-9H-fluorene-2-yl boronic acid in Synthesis Example 1 to obtain 3-(9-phenylcarbazole-3-yl)-7,12-diphenylbenzo[k]-fluoranthene (Compound 6-1).

The measured results of FDMS analysis, ultraviolet absorption peak wavelength λmax (molar absorption coefficient ε) in toluene solution and fluorescent light emission peak wavelength about the resultant compound are described below.

FDMS, calcd for $C_{50}H_{31}N$=646. found m/z=646 ($M^+$).
UV(PhMe); λmax, 424 (ε 4.33), FL (PhMe, λex=324 nm); λmax, 450 nm Synthesis Example 18

Synthesis of Compound 6-8

Synthesis Example 18 was carried out in a similar manner as Synthesis Example 1 except that 6-(10-phenylanthracene-9-yl)naphthyl-2-yl boronic acid was employed instead of 9,9-dimethyl-9H-fluorene-2-yl boronic acid in Synthesis Example 1 to obtain 3-(6-(10-phenylanthracene-9-yl)-naphthyl-2-yl)-7,12-diphenylbenzo[k]fluoranthene (Compound 6-8).

The measured results of FDMS analysis, ultraviolet absorption peak wavelength λmax (molar absorption coefficient ε) in toluene solution and fluorescent light emission peak wavelength about the resultant compound are described below.

FDMS, calcd for $C_{62}H_{38}$=783. found m/z=783 ($M^+$).
UV(PhMe); λmax, 423 (ε 4.42), FL (PhMe, λex=318 nm); λmax, 440 nm Synthesis Example 19

Synthesis of Compound 8-5

Synthesis Example 19 was carried out in a similar manner as Synthesis Example 1 except that trans-2-phenylvinyl boronic acid was employed instead of 9,9-dimethyl-9H-fluorene-2-yl boronic acid in Synthesis Example 1 to obtain 3-(trans-2-phenylvinyl)-7,12-diphenylbenzo[k]-fluoranthene (Compound 8-5).

The measured results of FDMS analysis, ultraviolet absorption peak wavelength λmax (molar absorption coefficient ε) in toluene solution and fluorescent light emission peak wavelength about the resultant compound are described below.

FDMS, calcd for $C_{40}H_{26}$=507. found m/z=507 ($M^+$).
UV(PhMe); λmax, 442 (ε 4.41), FL (PhMe, λex=345 nm); λmax, 460 nm Synthesis Example 20

Synthesis of Compound 8-6

Synthesis Example 20 was carried out in a similar manner as Synthesis Example 1 except that dibenzofuran-2-yl boronic acid was employed instead of 9,9-dimethyl-9H-fluorene-2-yl boronic acid in Synthesis Example 1 to obtain 3-(dibenzofuran-2-yl)-7,12-diphenylbenzo[k]-fluoranthene (Compound 8-6).

The measured results of FDMS analysis, ultraviolet absorption peak wavelength λmax (molar absorption coefficient ε) in toluene solution and fluorescent light emission peak wavelength about the resultant compound are described below.

FDMS, calcd for $C_{44}H_{26}O$=571. found m/z=571 ($M^+$).
UV(PhMe); λmax, 420 (ε 4.34), FL (PhMe, λex=376 nm); λmax, 435 nm Synthesis Example 21

Synthesis of Compound 8-8

Synthesis Example 21 was carried out in a similar manner as Synthesis Example 7 except that 3-bromo-7,12-dibenzo[k]fluoranthene was employed instead of 3-(3-bromophenyl)-7,12-diphenylbenzo[k]fluoranthene in Synthesis Example 7 to obtain 3-(bis-2-naphthylamino)-7,12-diphenylbenzo[k]fluoranthene (Compound 8-8).

The measured results of FDMS analysis, ultraviolet absorption peak wavelength λmax (molar absorption coefficient ε) in toluene solution and fluorescent light emission peak wavelength about the resultant compound are described below.

FDMS, calcd for $C_{52}H_{33}N$=672. found m/z=672 ($M^+$).
UV(PhMe); λmax, 445 (ε 4.26), FL (PhMe, λex=317 nm); λmax, 507 nm Synthesis Example 22

Synthesis of Compound 9-8

Synthesis Example 22 was carried out in a similar manner as Synthesis Example 7 except that 3-bromo-7,12-dibenzo[k]fluoranthene was employed instead of 3-(3-bromophenyl)-7,12-diphenylbenzo[k]fluoranthene and that bis(3,4-dimethylphenyl)amine was employed instead of dinaphthalen-2-ylamine in Synthesis Example 7 to obtain 3-(bis(3,4-dimethylphenyl)amino)-7,12-diphenylbenzo[k]fluoranthene (Compound 9-8).

The measured results of FDMS analysis, ultraviolet absorption peak wavelength λmax (molar absorption coefficient ε) in toluene solution and fluorescent light emission peak wavelength about the resultant compound are described below.

FDMS, calcd for $C_{48}H_{37}N$=628. found m/z=628 ($M^+$).
UV(PhMe); λmax, 453 (ε 4.20), FL (PhMe, λex=420 nm); λmax, 518 nm Synthesis Example 23

(1) Synthesis of 7,12-dibenzo[k]fluoranthene-3-yl boronic acid

Dissolving 30.8 g (64.0 mmol) of 3-bromo-7,12-dibenzo[k]fluoranthene into 400 ml of dry THF and 300 ml of dry toluene, the resultant solution was cooled down to −70° C. and further, chipping 44.6 ml (70.4 mmol) of n-butyllithium, stirring for 1 h, and adding 44.0 ml (192 mmol) of triisopropyl boronate, the temperature of the resultant solution was elevated up to a room temperature spending 2 h. The precipitate was separated by filtration, washed with toluene, and dried under a reduced pressure to obtain 25.14 g of 7,12-diphenylbenzo[k]fluoranthene-3-yl boronic acid as yellow solid (yield: 88%).

(2) Synthesis of 3-(6-bromonaphthalen-2-yl)-7,12-diphenylbenzo[k]-fluoranthene

It was carried out in a similar manner as Synthesis Example 1 except that 7,12-diphenylbenzo[k]fluoranthene-3-yl boronic acid was employed instead of 9,9-dimethyl-911-fluorene-2-yl boronic acid, and that 2,6-dibromo-naphthalene was employed instead of 3-bromo-7,12-dibenzo[k]fluoranthene in Synthesis Example 1 to obtain 3-(6-bromonaphthalen-2-yl)-7,12-diphenylbenzo[k]fluoranthene.

(3) Synthesis of 3-(6-(4-cyanophenyl)naphthalen-2-yl)-7,12-diphenylbenzo-[k]fluoranthene (Compound 5-12)

It was carried out in a similar manner as Synthesis Example 1 except that 4-cyanophenyl boronic acid was employed instead of 9,9-dimethyl-9H-fluorene-2-yl boronic acid, and that 3-(6-bromonaphthalen-2-yl)-7,12-diphenylbenzo[k] fluoranthene was employed instead of 3-bromo-7,12-dibenzo [k]fluoranthene in Synthesis Example 1 to obtain 3-(6-(4-cyanophenyl)naphthalen-2-yl)-7,12-diphenylbenzo[k] fluoranthene (Compound 5-12).

The measured results of FDMS analysis, ultraviolet absorption peak wavelength λmax (molar absorption coefficient ε) in toluene solution and fluorescent light emission peak wavelength about the resultant compound are described below.

FDMS, calcd for $C_{49}H_{29}N$=632. found m/z=632 ($M^+$).
UV(PhMe); λmax, 424 (ε 4.37), FL (PhMe, λex=420 nm); λmax, 444 nm Synthesis Example 24

Synthesis of Compound 8-4

Blending 4.8 g (10.0 mmol) of 3-bromo-7,12-dibenzo[k] fluoranthene, 1.5 g (15 mmol) of phenyl acetylene, 140 mg (0.2 mmol) of $(Ph3P)_2PdCl_2$ and 38 mg (0.2 mmol) of copper iodide, the resultant mixture was stirred under refluxing while heating for 8 h. After the resultant mixture was cooled by being left standing, precipitates were separated by filtration, washed 3 times with methanol and dimethoxyethane, recrystallized through toluene and ethanol, and dried under a reduced pressure to obtain 2.5 g of 3-(2-phenylacetinyl)-7,12-diphenylbenzo[k]fluoranthene-3-yl boronic acid as yellow solid (yield: 50%).

The measured results of FDMS analysis, ultraviolet absorption peak wavelength λmax (molar absorption coefficient ε) in toluene solution and fluorescent light emission peak wavelength about the resultant compound are described below.

FDMS, calcd for $C_{40}H_{24}$=505. found m/z=505 ($M^+$).
UV(PhMe); λmax, 437 (ε 4.50), FL (PhMe, λex=333 nm); λmax, 447 nm Example 1

(1) Fabrication of Organic EL Device

A 120 nm-thick transparent electrode made of indium tin oxide was formed on a glass substrate having a size of 25 mm×75 mm×1.1 mm. The glass substrate was cleaned by application of ultrasonic wave in isopropyl alcohol and then by exposure to ultraviolet ray and ozone.

Subsequently, the cleaned glass substrate having the transparent electrode line was attached to a substrate holder of a vacuum vapor deposition apparatus and degree of vacuum in the vacuum chamber was depressurized to $1\times10^{-3}$ Pa.

On the surface of the cleaned substrate at the side having the transparent electrode, a layer of N',N'''-bis[4-(diphenylamino)phenyl]-N',N'''-diphenylbiphenyl-4,4'-diamine having a thickness of 60 nm was formed with vapor deposition rate of 2 nm/s as to cover the transparent electrode. The formed film worked as the hole injecting layer.

Then, a layer of N,N,N',N'-tetra(4-biphenylyl)benzidine having a thickness of 20 nm was formed over the hole injecting layer at vapor deposition rate of 2 nm/s. The formed film worked as the hole transporting layer.

On the hole transporting layer, the above Compound (2a'-55) [light emitting material 1] and the above Compound (1-3) [light emitting material 2] obtained in Synthesis Example 1 were simultaneously vapor deposited at vapor deposition rate of 2 nm/s and 0.2 nm/s respectively in a weight ratio of (2a'-55):(1-3)=40:2 thereby getting a film thickness of 40 nm. The formed film worked as the emitting layer.

Thereupon, an electron transporting layer was formed by vapor depositing tris(8-hydroxyquinolinato)aluminum with vapor deposition rate of 2 nm/s, to obtain film thickness of 20 nm.

Further, an electron injecting layer was formed by vapor depositing lithium fluoride with vapor deposition rate of 0.1 nm/sec to obtain film thickness of 1 nm.

Finally, aluminum was vapor deposited at a vapor deposition rate of 2 nm/s to form a cathode layer having a thickness of 200 nm, thereby fabricating an organic EL device.

(2) Evaluation of the Organic EL Device

Then, the resultant device was evaluated by feeding an electric current, a luminance of light emission was 313 cd/m² at voltage of 6.3 V, and when a peak wavelength (EL λmax) of light emission and chromaticity were measured, the color of light emission was recognized as blue. Further, driving with a constant electric current starting from an initial luminance of 100 cd/m², a half lifetime of luminance was 10,000 h or longer, which was in a sufficiently practical range. The measurement results are shown in Table 1.

Examples 2 to 6

The organic EL devices were fabricated in the same manners as Example 1 except that Compound (2a'-55) and Compound (1-5) were employed in Example 2, that Compound (2a'-55) and Compound (1-10) were employed in Example 3, that Compound (2a'-59) and Compound (2-9) were employed in Example 4, that Compound (2b-42) and Compound (1-13) were employed in Example 5, and that Compound (2a'-59) and Compound (4-17) were employed in Example 6 each instead of Compound (2a'-55) and Compound (1-3) in Example 1.

The resultant organic EL devices were evaluated in the same manner as Example 1, and as a result, blue light emission was entirely observed, the luminance of light emission were from 280 to 550 cd/m² , and half lifetime were 10,000 h or longer as shown in Table 1.

Examples 7 and 8

The organic EL devices were fabricated in the same manners as Example 1 except that Compounds (2c-1) and (1-13) were employed in Example 7, Compounds (2d-1) and (1-13) were employed in Example 8 respectively instead of Compounds (2a'-55) and (1-3) in Example 1.

The resultant organic EL devices were evaluated in the same manner as Example 1, and as a result, blue light emission was entirely observed, a luminance of light emission were 180 cd/m² and 240 cd/m² respectively, and half lifetime were from 5,500 to 6,500 h as shown in Table 1.

Comparative Example 1

An organic EL device was fabricated in the same manner as Example 1 except that the fluoranthene compound (A) [UV(PhMe); λmax, 410, FL(PhMe); λmax, 424 nm] was employed in Comparative Example 1 instead of Compound (1-3) in Example 1.

The resultant organic EL device was evaluated in the same manner as Example 1, and as a result, although blue light emission was entirely observed, a luminance of light emission was 125 cd/m² and current efficiency of light emission was poor, and half lifetime was 2,000 h or shorter as shown in Table 1.

Compound (A)

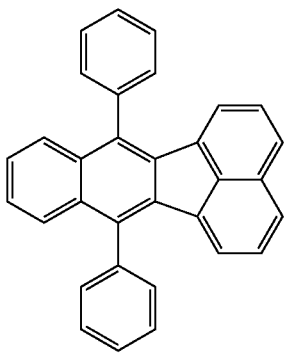

TABLE 1-1

|  | Examples | | | | |
|---|---|---|---|---|---|
|  | 1 | 2 | 3 | 4 | 5 |
| Light emitting material 1 | 2a'-55 | 2a'-55 | 2a'-55 | 2a'-59 | 2b-42 |
| Light emitting material 2 | 1-3 | 1-5 | 1-5 | 2-9 | 1-13 |
| Driving voltage | 6.3 | 6.3 | 6.3 | 6.3 | 6.3 |
| EL λmax | 445 | 445 | 449 | 458 | 445 |
| Luminance of emission (cd/m²) | 313 | 318 | 409 | 550 | 320 |
| Half lifetime (h) | >10,000 | >10,000 | >10,000 | >10,000 | >10,000 |

TABLE 1-2

|  | Examples | | | Comparative |
|---|---|---|---|---|
|  | 6 | 7 | 8 | Example 1 |
| Light emitting material 1 | 2a-7 | 2c-1 | 2d-1 | 2a'-55 |
| Light emitting material 2 | 4-17 | 1-13 | 1-13 | Compound (A) |
| Driving voltage | 6.3 | 6.3 | 6.3 | 6.3 |
| EL λmax | 443 | 445 | 446 | 448 |
| Luminance of emission (cd/m²) | 280 | 180 | 240 | 150 |
| Half lifetime (h) | 8,000 | 5,500 | 6,500 | 2,000 |

Example 9

A glass substrate (manufactured by GEOMATEC Company) of 25 mm×75 mm×1.1 mm thickness having an ITO transparent electrode was cleaned by application of ultrasonic wave in isopropyl alcohol for 5 min and then by exposure to ozone generated by ultraviolet light for 30 min.

Over the substrate, a hole injecting and transporting layer was formed in a laminated structure. First, a film of polyethylenedioxythiophene/polystyrene sulfonate (PEDOS/PSS) having a thickness of 100 nm was formed in accordance with the spin coating process. Subsequently, a toluene solution (0.6% by weight) of polymer 1 (molecular weight (Mw): 145000) shown below was formed into a film with a film thickness of 20 nm in accordance with the spin coating process and dried at 170° C. for 30 min.

Then, a film of an emitting layer was formed using a toluene solution containing 1% by weight of both the above Compound (2a'-55) and Compound (1-2) obtained in Synthesis Example 1 as the light emitting materials ((2a'-55):(1-2)=20:2 (weight ratio)) in accordance with the spin coating process. The film thickness of the emitting layer was 50 nm.

Subsequently, a film of tris(8-hydroxyquinolinato)aluminum (abbreviated as "Alq film" hereinafter) having a thickness of 10 nm was formed. The formed film of Alq worked as the electron transporting layer.

Thereafter, Li (the source of lithium: manufactured by SAES GETTERS Company) as a reductive dopant and Alq were binary vapor deposited and an Alq:Li film was formed as the electron injecting layer (cathode). On the Alq:Li film, aluminum was vapor deposited to form a metal cathode and an organic EL device was fabricated.

The device emitted blue light and the light emitting surface was uniform. The current efficiency of light emission was 2.9 cd/A.

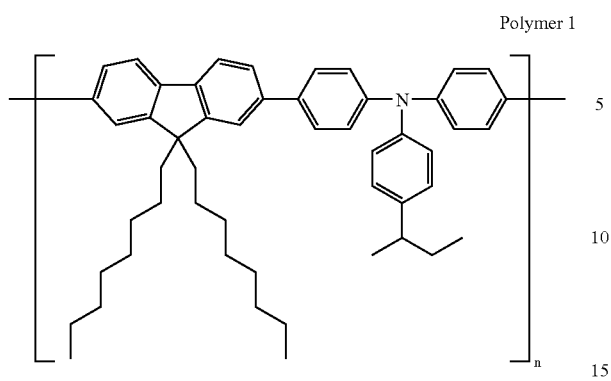

Polymer 1

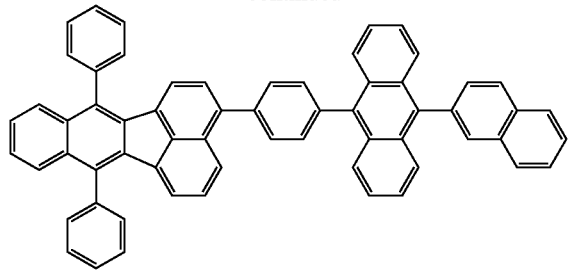

-continued

Example 10

An organic EL device was fabricated in the same manner as Example 9 except that the above Compound (1-3) obtained in Synthesis Example 2 was employed instead of Compound (1-2) in Example 9.

The device emitted blue light and the light emitting surface was uniform. The current deficiency of light emission was 2.5 cd/A.

INDUSTRIAL APPLICABILITY

As described in detail above, the organic EL device employing the fluoranthene compound of the present invention as the material for the organic EL device, particularly as the material for the light emitting of the organic EL device, has superior luminance of light emission, enhanced efficiency of light emission and prolonged lifetime. Further, the use of the solution containing materials for the organic EL including the fluoranthene compound of the present invention enables to form an organic compound layer of an organic EL device in accordance with a wet process.

Therefore, the organic EL device of the present invention is useful for a planar light emitting member for wall televisions and a light source for a backlight of displays. The fluoranthene compound of the present invention is usable as a hole injecting and transporting material for the organic EL device, and further, as a charge transporting material for an electrophotographic sensitizer or an organic semiconductor.

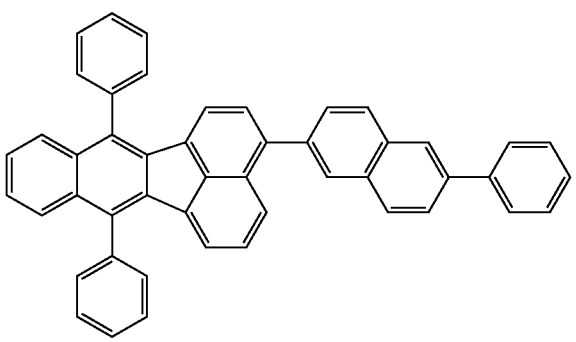

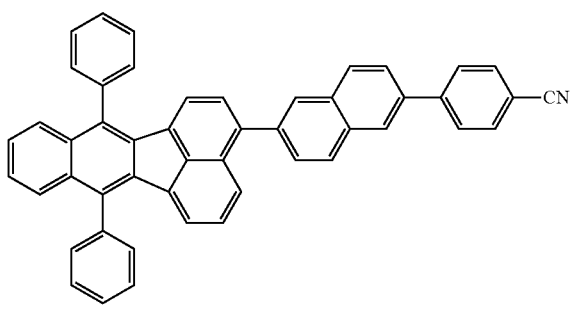

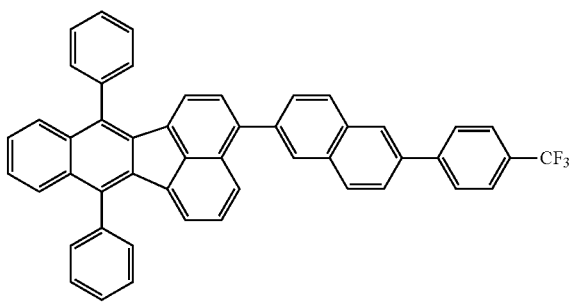

What is claimed is:

1. A light emitting material for an organic EL device, which emits blue light and comprises a fluoranthene compound selected from the group consisting of:

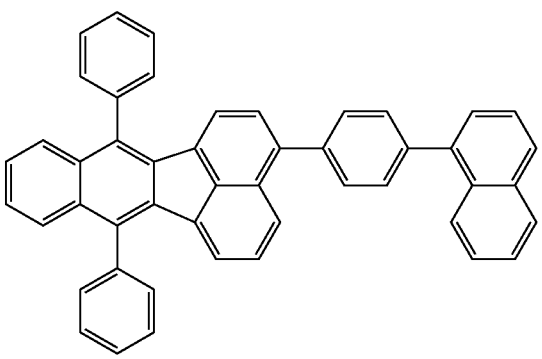

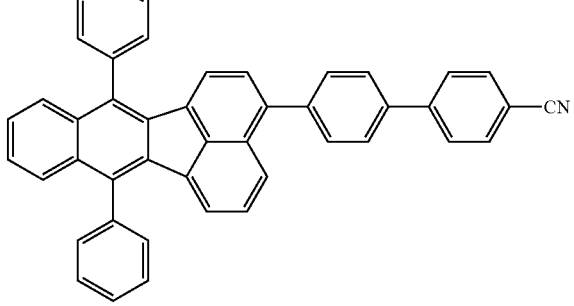

147
-continued
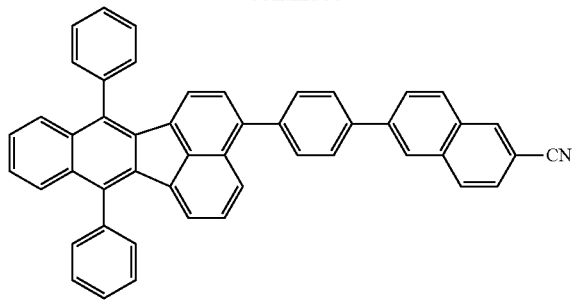
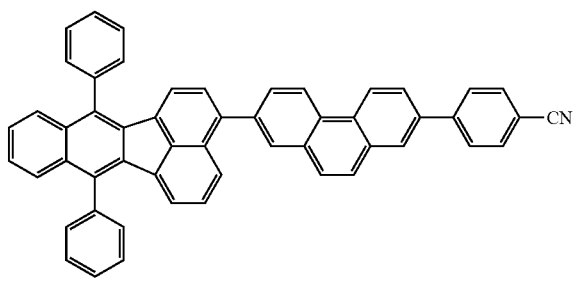
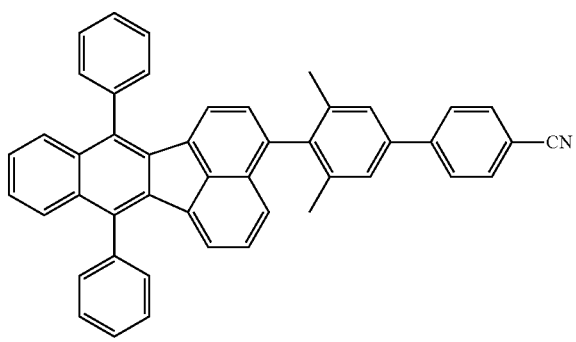
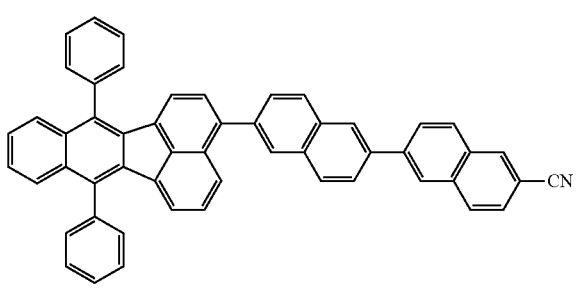
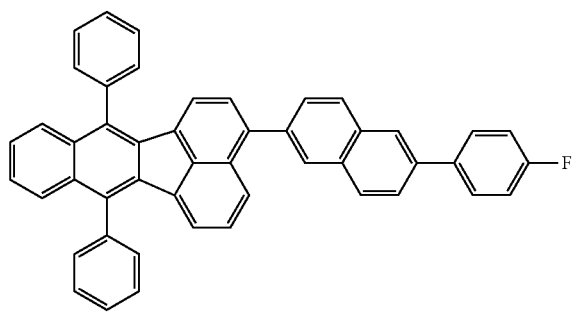
148
-continued
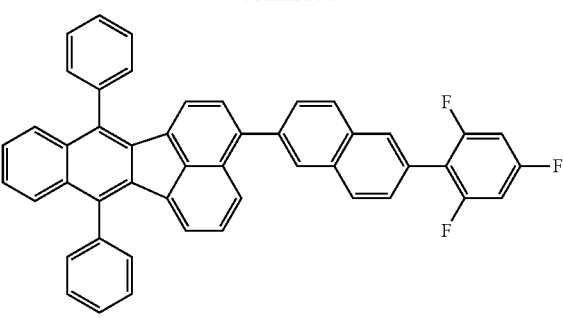
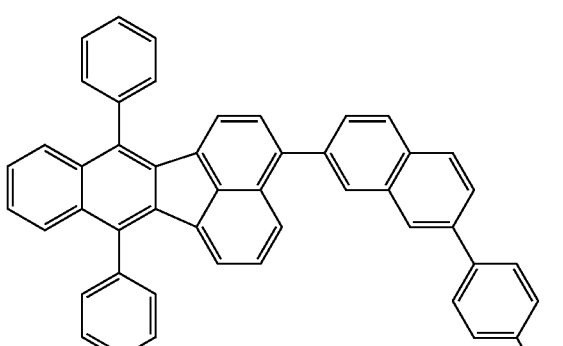
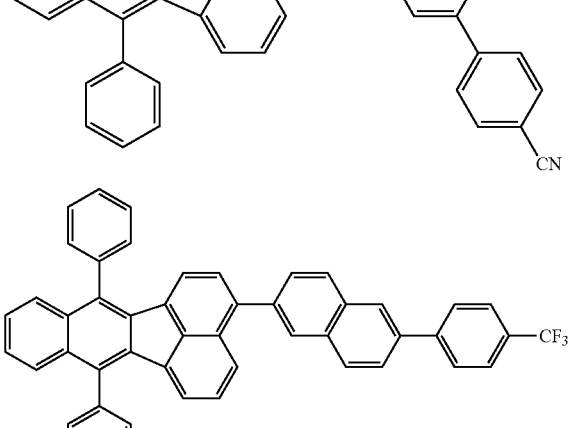
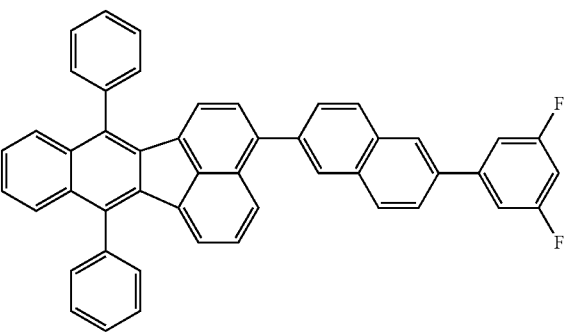
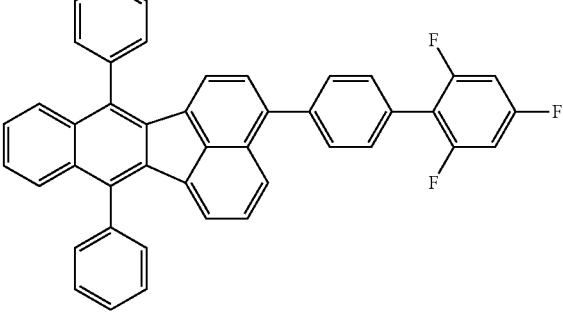

149
-continued
150
-continued
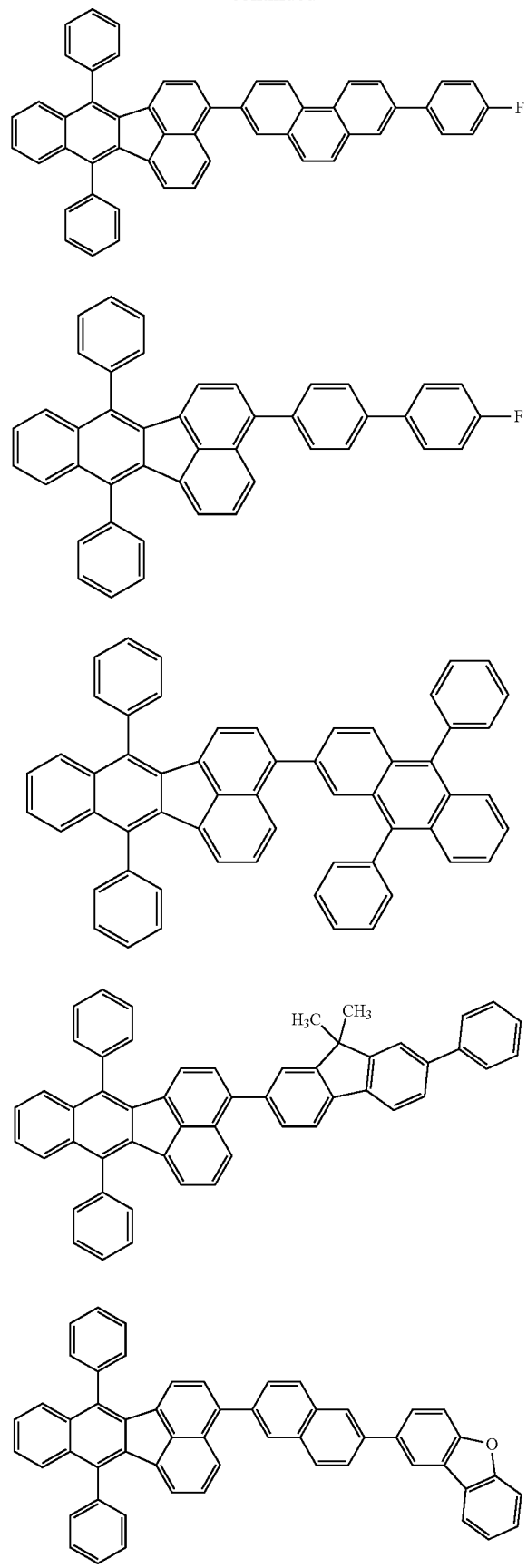
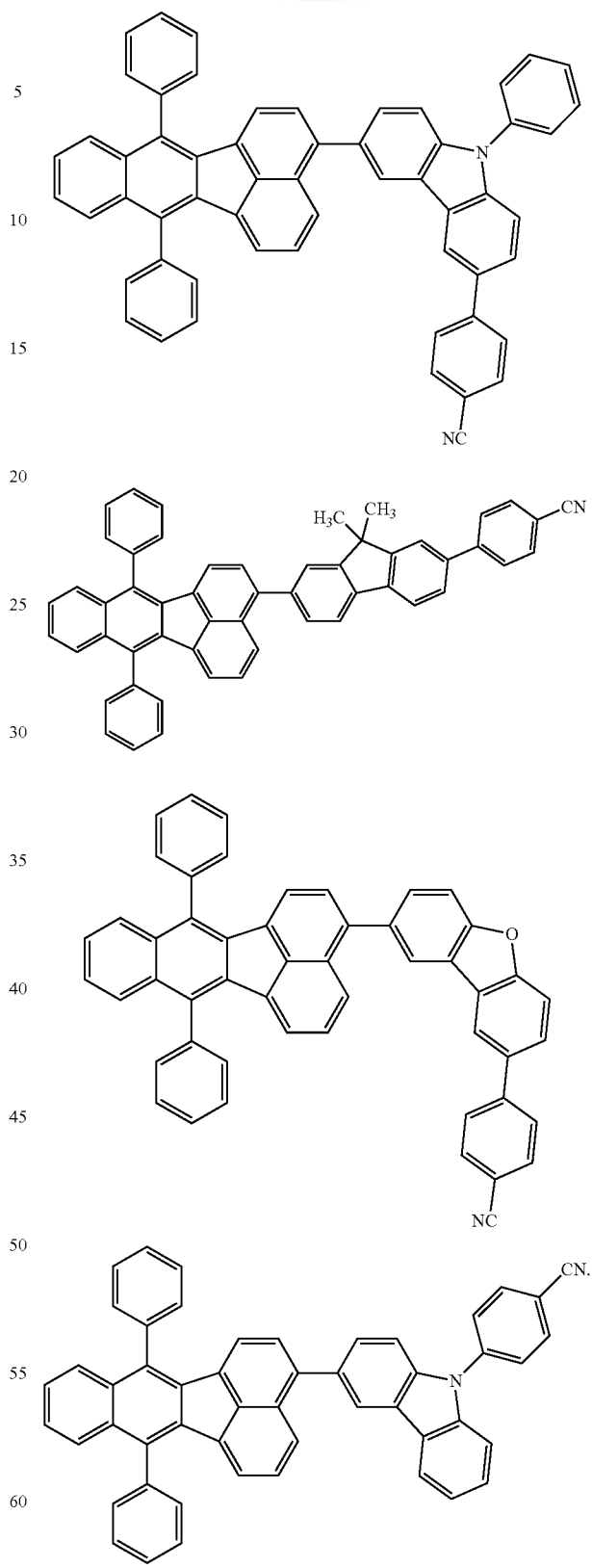
2. The light emitting material for an organic EL device according to claim 1, wherein said fluoranthene compound is selected from the group consisting of:

151
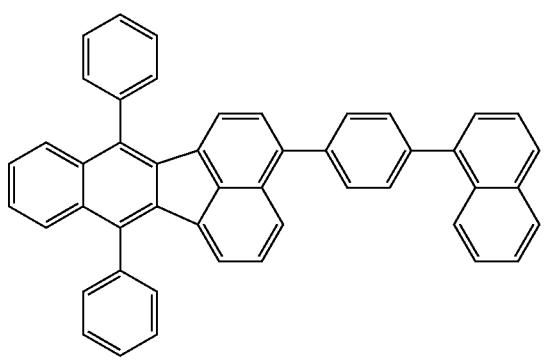
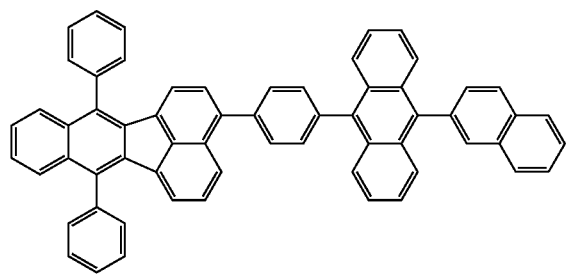
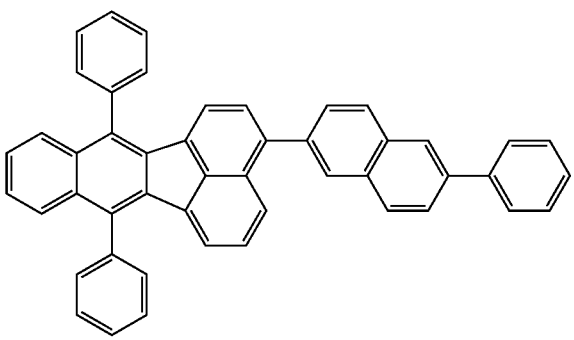
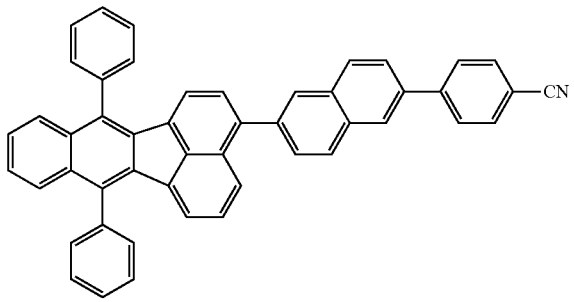
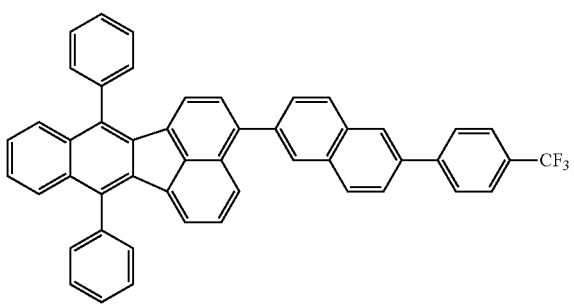
152
-continued

153
-continued
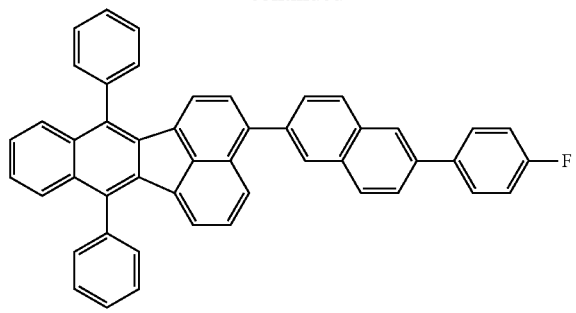
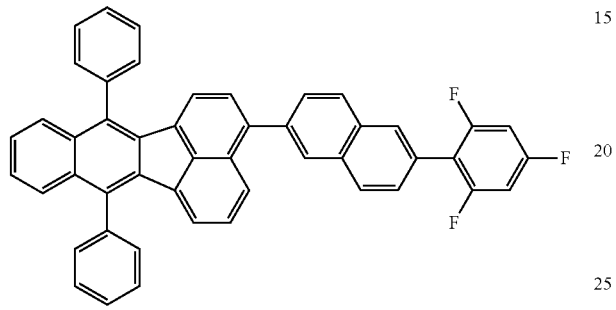
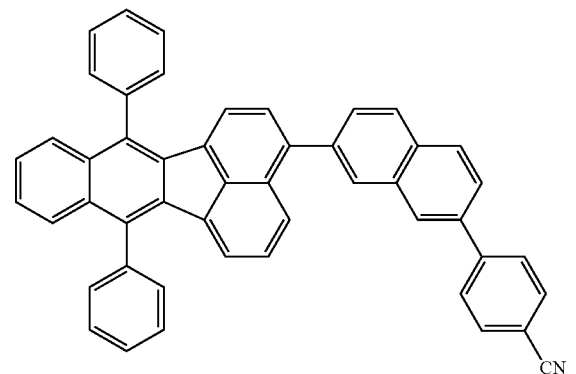
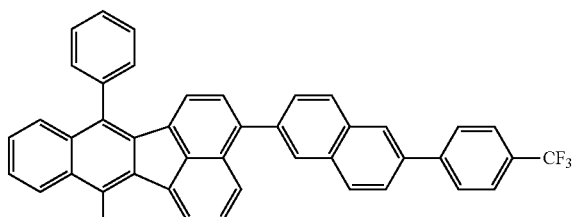
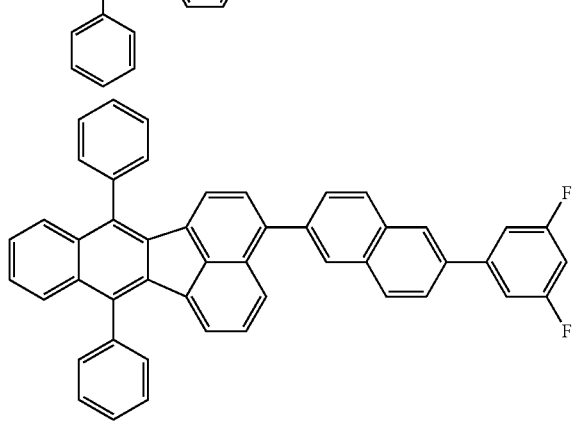
154
-continued
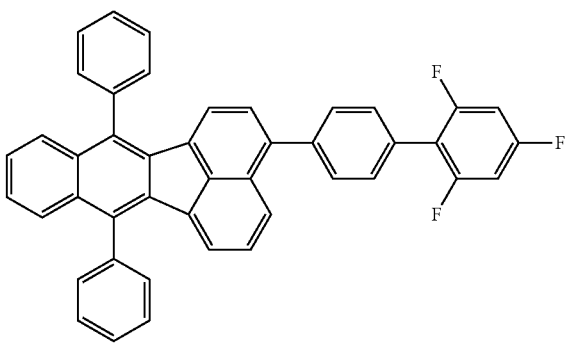
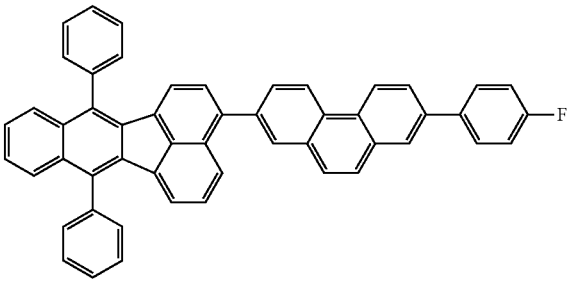
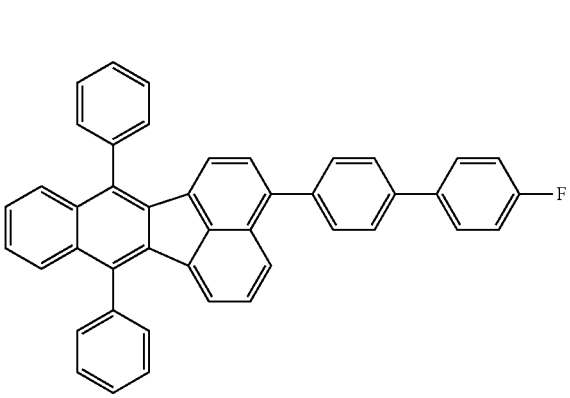
and
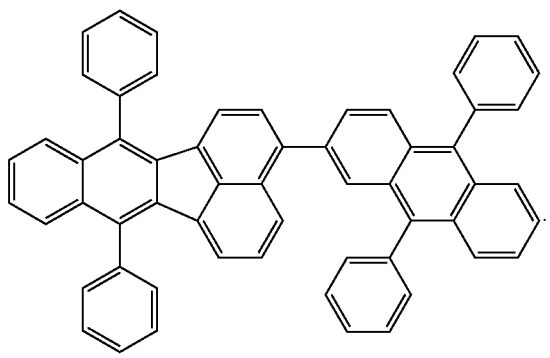

3. A fluoranthene selected from the group consisting of:
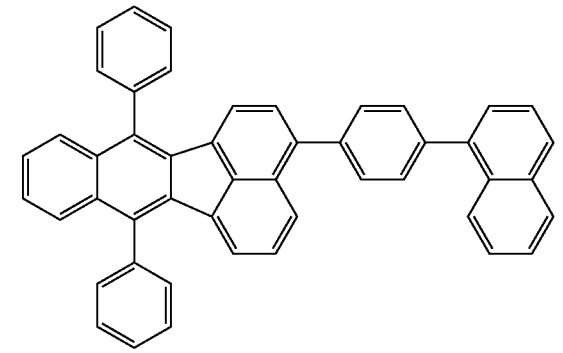
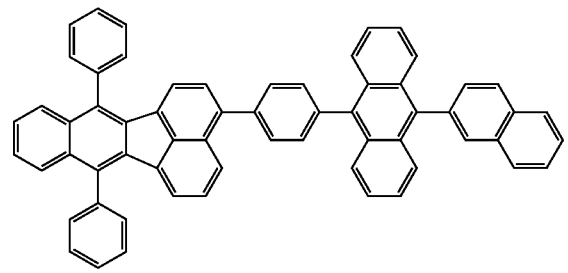
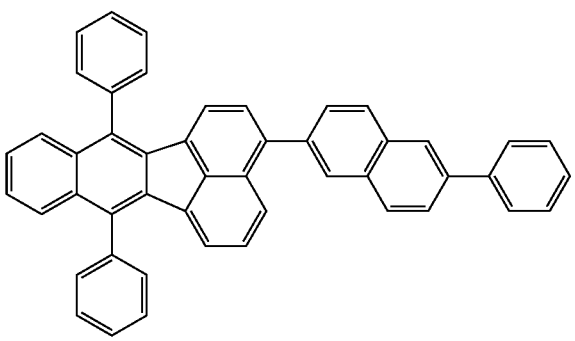
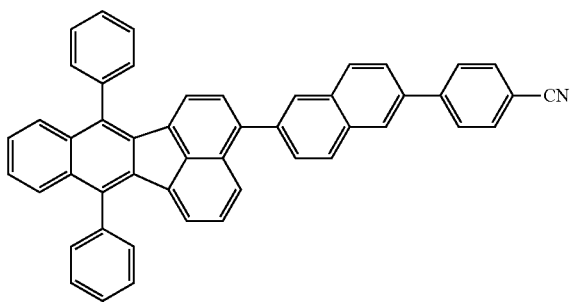
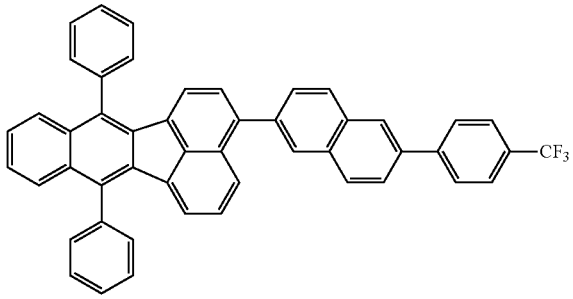
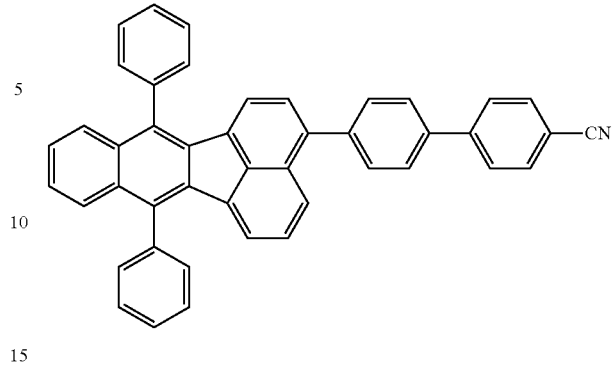
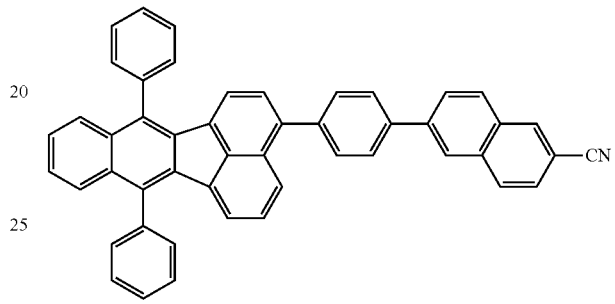
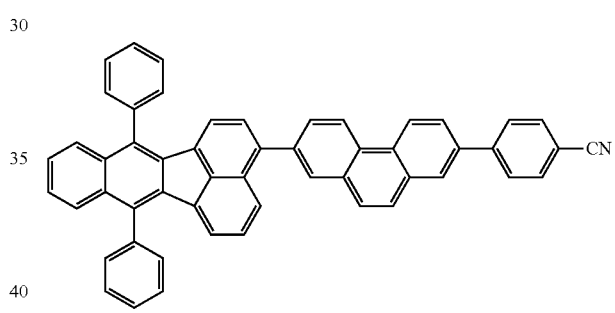
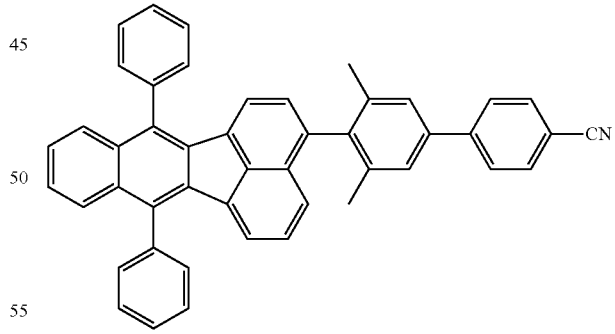
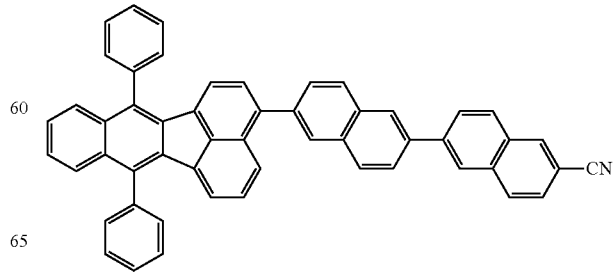

157
-continued
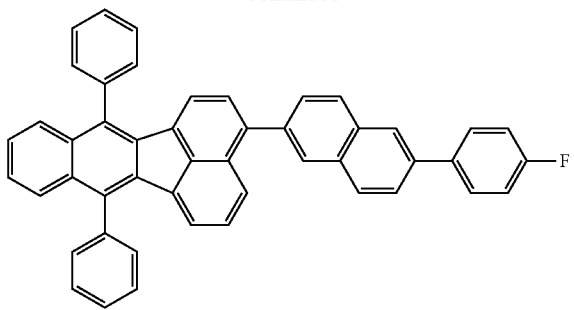
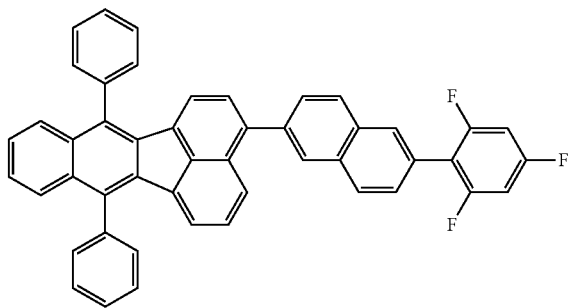
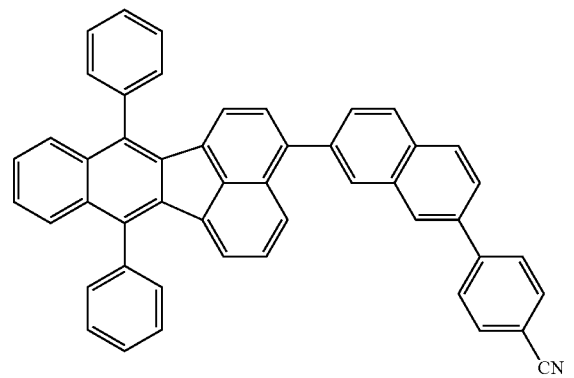
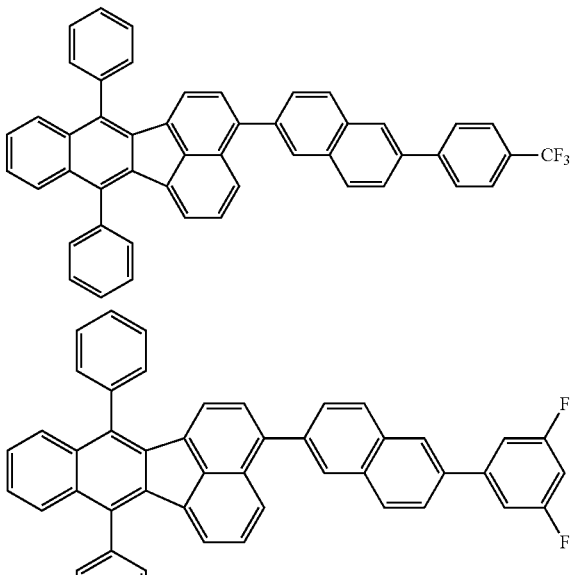
158
-continued
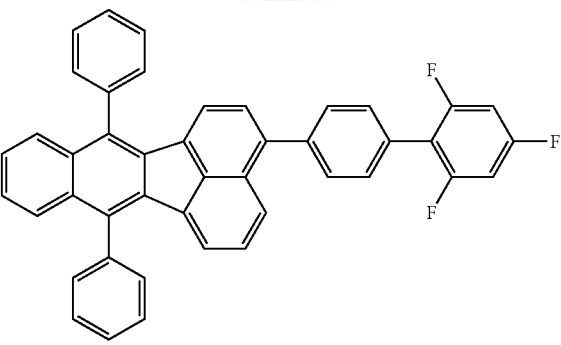
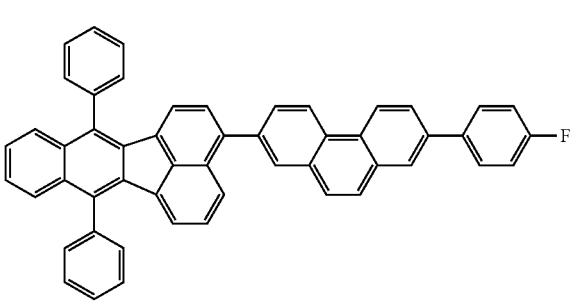
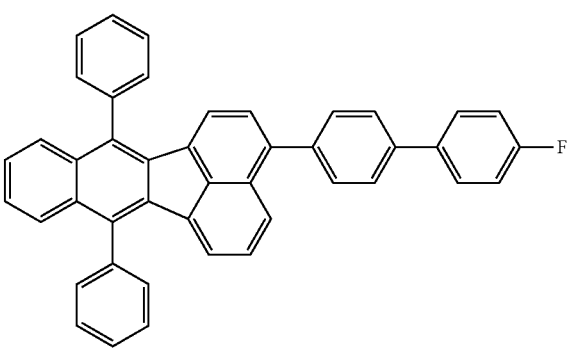
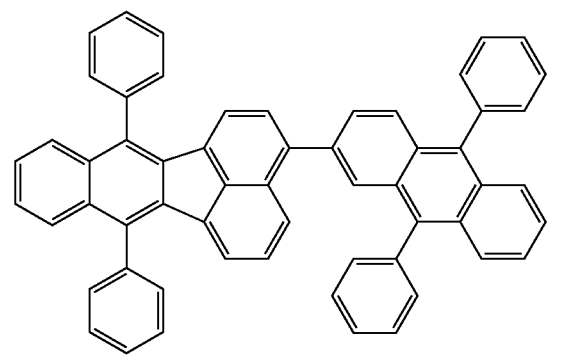
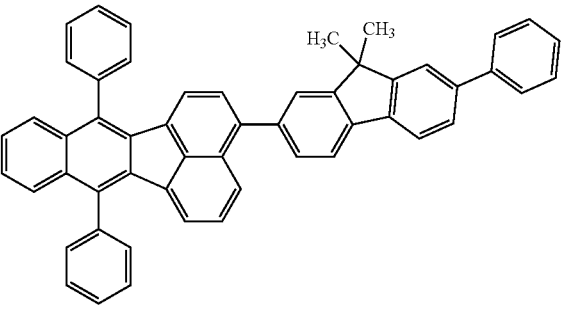

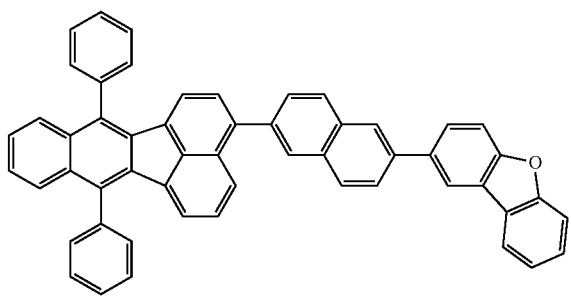

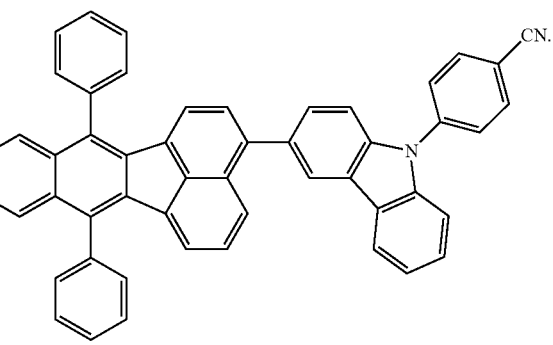

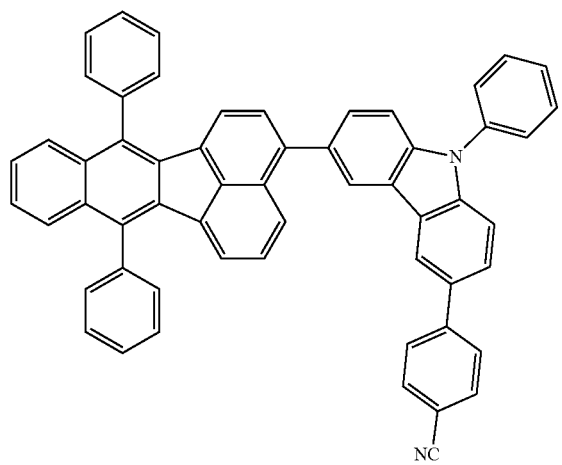

4. An organic electroluminescence device which comprises one or more organic compound layers including at least one emitting layer sandwiched between a pair of electrodes, wherein at least one of the organic compound layers comprises at least one kind of the fluoranthene compound according to claim 3.

5. An organic electroluminescence device which comprises one or more organic compound layers including at least one emitting layer sandwiched between a pair of electrodes, wherein at least one of the organic compound layers comprises the light emitting material according to claim 1.

6. The light emitting material for an organic EL device according to claim 1, wherein said fluoranthene compound is selected from the group consisting of:

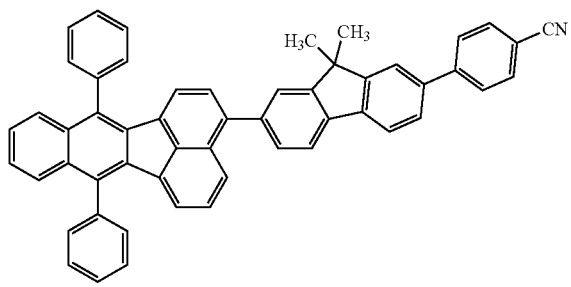

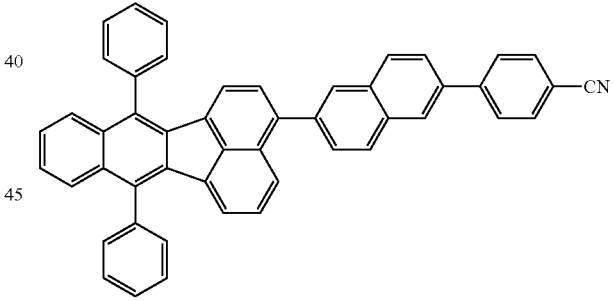

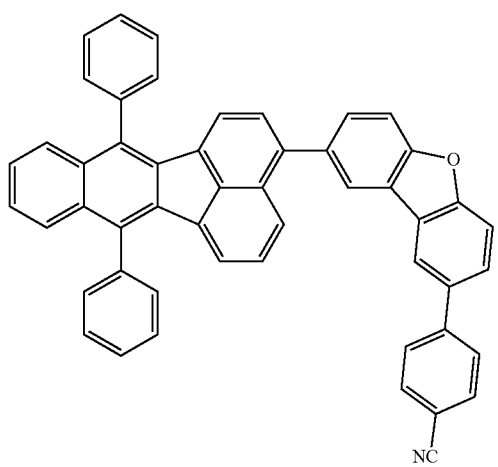

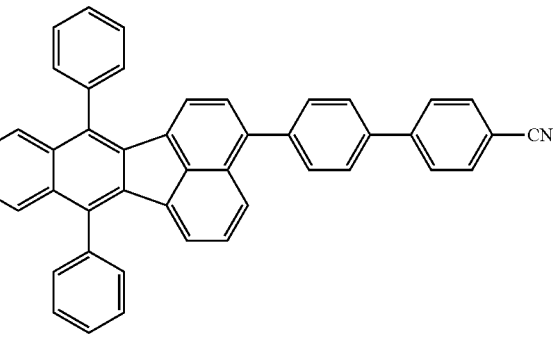

161
-continued
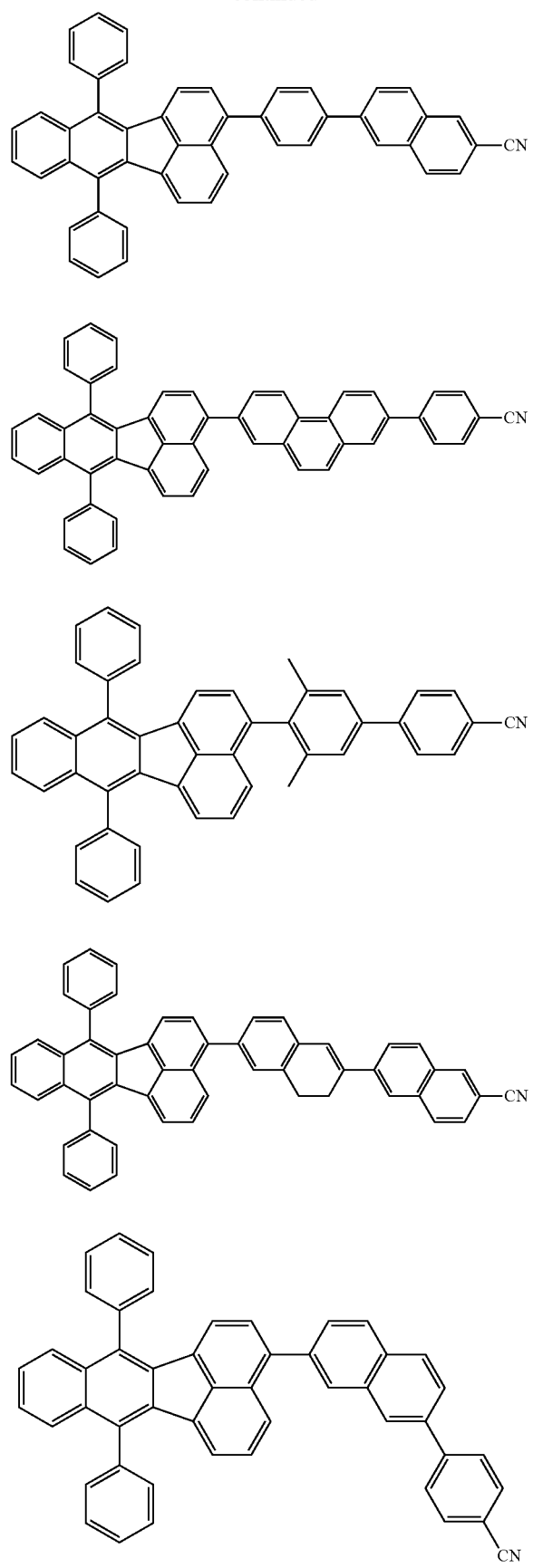
162
-continued
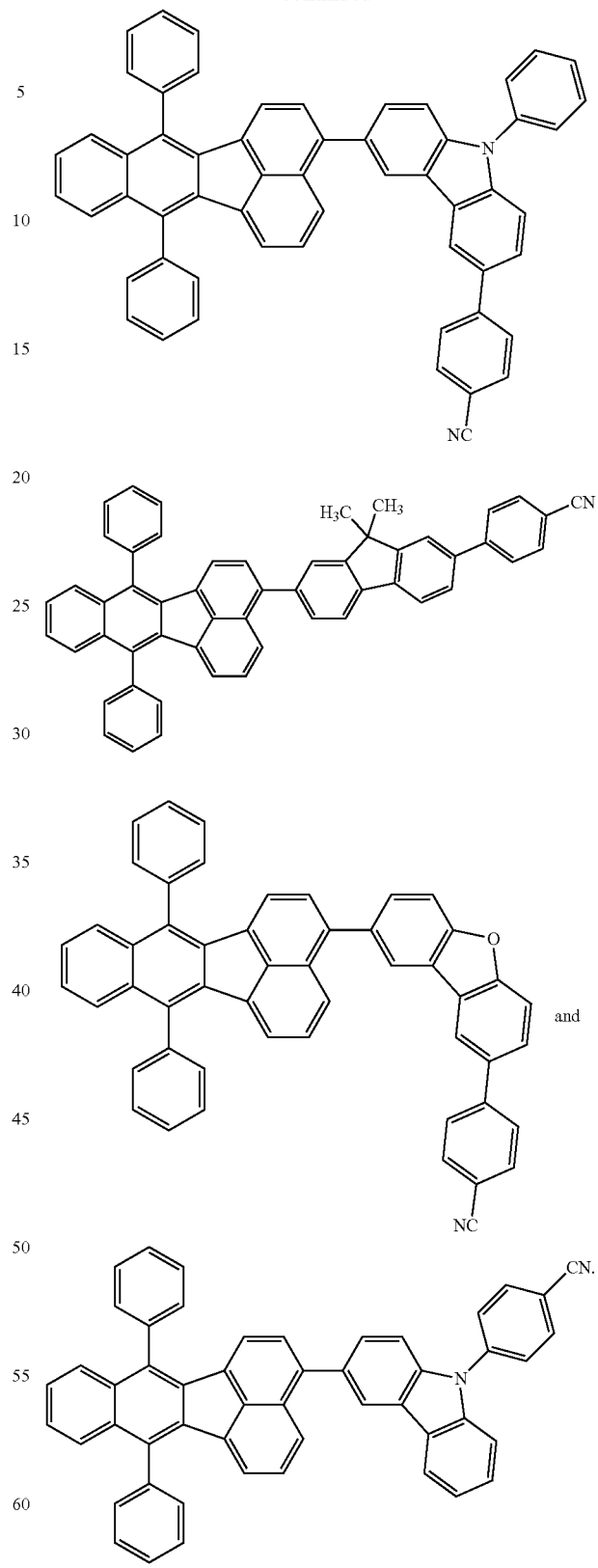
7. The fluoranthene compound according to claim 3, wherein said compound is selected from the group consisting of:

163
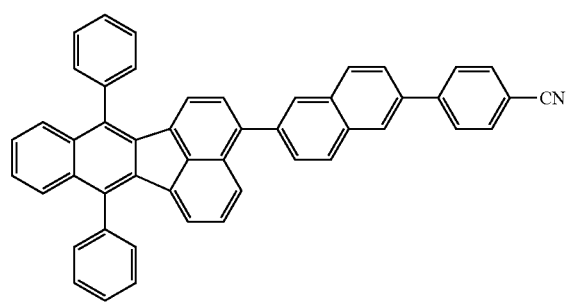
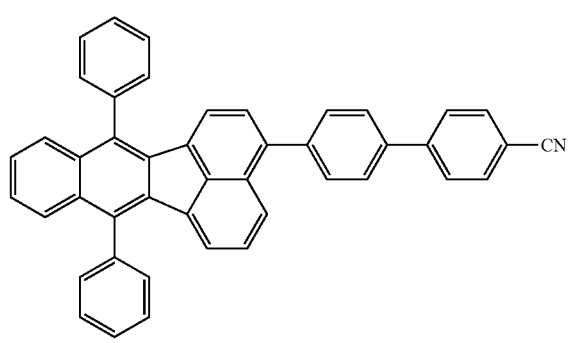
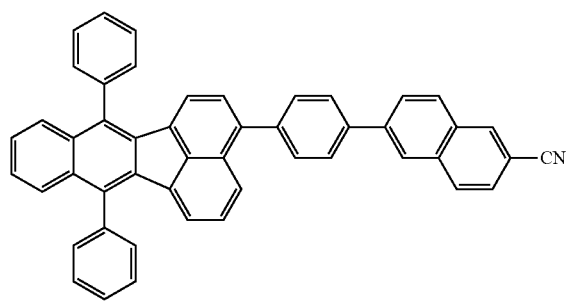
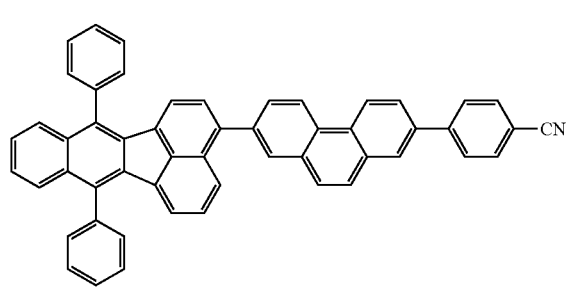
164
-continued
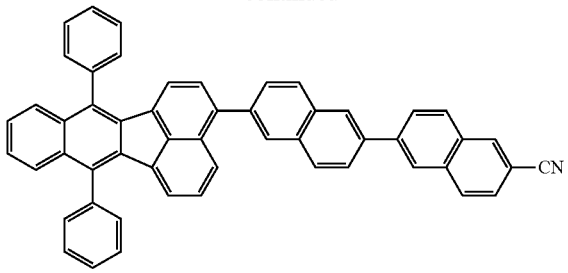
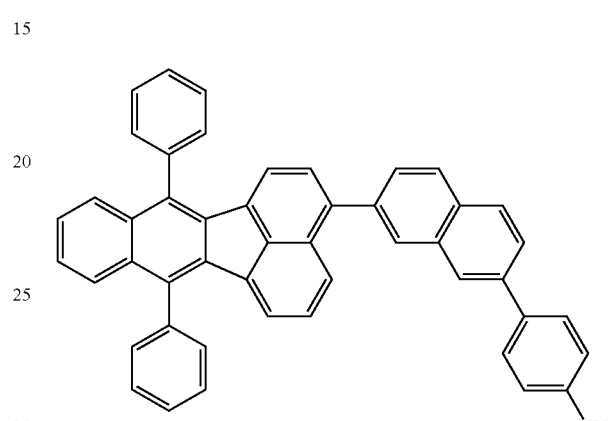
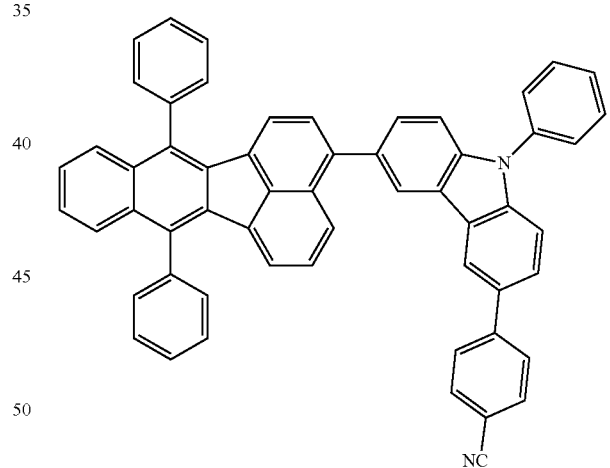
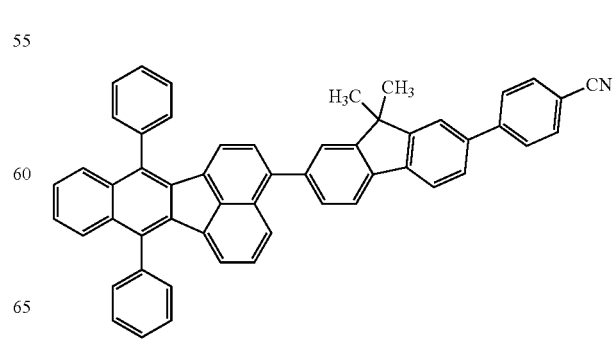

-continued
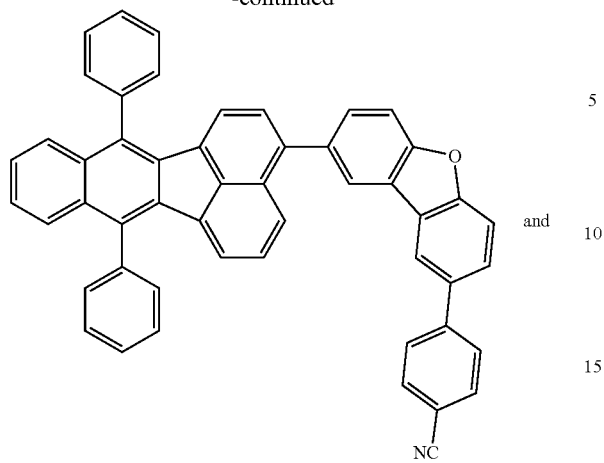
and
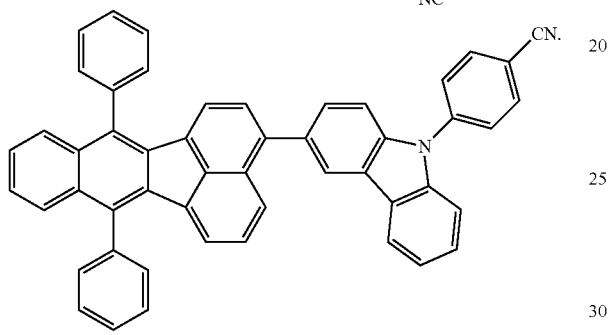
* * * * *